United States Patent
Fyfe et al.

(10) Patent No.: US 9,796,742 B2
(45) Date of Patent: Oct. 24, 2017

(54) KINASE INHIBITORS

(71) Applicants: Respivert Limited, High Wycombe, Buckinghamshire (GB); Topivert Pharma Limited, London (GB)

(72) Inventors: Matthew Colin Thor Fyfe, London (GB); Michael Knaggs, Burton-on-Trent (GB); Premji Meghani, Nottingham (GB); Stephen Malcolm Thom, Nottingham (GB)

(73) Assignees: Respivert Limited, High Wycombe, Buckinghamshire (GB); Topivert Pharma Limited, London (GB)

( * ) Notice: Subject to any disclaimer, the term of this patent is extended or adjusted under 35 U.S.C. 154(b) by 0 days.

(21) Appl. No.: 15/228,945

(22) Filed: Aug. 4, 2016

(65) Prior Publication Data

US 2016/0340375 A1    Nov. 24, 2016

Related U.S. Application Data

(63) Continuation of application No. 14/424,967, filed as application No. PCT/GB2013/052250 on Aug. 28, 2013, now abandoned.

(30) Foreign Application Priority Data

Aug. 29, 2012 (GB) .................................. 1215370.6
Mar. 15, 2013 (GB) .................................. 1304780.8

(51) Int. Cl.

| | | |
|---|---|---|
| C07F 9/6558 | (2006.01) | |
| C07F 9/6568 | (2006.01) | |
| A61K 31/675 | (2006.01) | |
| A61K 31/695 | (2006.01) | |
| C07D 213/68 | (2006.01) | |
| C07D 231/14 | (2006.01) | |
| C07D 239/22 | (2006.01) | |
| C07F 7/08 | (2006.01) | |
| C07F 9/28 | (2006.01) | |
| C07F 9/30 | (2006.01) | |
| C07F 9/6512 | (2006.01) | |
| C07F 9/6503 | (2006.01) | |

(52) U.S. Cl.
CPC ........ *C07F 9/65583* (2013.01); *A61K 31/675* (2013.01); *A61K 31/695* (2013.01); *C07D 213/68* (2013.01); *C07D 231/14* (2013.01); *C07D 239/22* (2013.01); *C07F 7/082* (2013.01); *C07F 9/28* (2013.01); *C07F 9/304* (2013.01); *C07F 9/65685* (2013.01); *C07F 9/6512* (2013.01); *C07F 9/65031* (2013.01)

(58) Field of Classification Search
CPC .... C07F 9/6512; C07F 9/65031; C07F 9/304; C07F 7/082; C07F 9/28; C07F 9/65583; C07F 9/65685; C07D 213/68; C07D 231/14; C07D 239/22; A61K 31/675; A61K 31/695

See application file for complete search history.

(56) References Cited

U.S. PATENT DOCUMENTS

| | | |
|---|---|---|
| 6,319,921 B1 | 11/2001 | Cirillo et al. |
| 6,492,393 B1 | 12/2002 | Breitfelder et al. |
| 6,492,529 B1 | 12/2002 | Kapadia et al. |
| 6,525,046 B1 | 2/2003 | Cirillo et al. |
| 6,852,717 B2 | 2/2005 | Cirillo et al. |
| 6,894,173 B2 | 5/2005 | Zhang et al. |
| 6,916,814 B2 | 7/2005 | Moss et al. |
| 7,241,758 B2 | 7/2007 | Hao et al. |
| 7,838,541 B2 | 11/2010 | Dumas et al. |
| 8,101,773 B2 | 1/2012 | Smith et al. |

(Continued)

FOREIGN PATENT DOCUMENTS

| | | | |
|---|---|---|---|
| CH | WO 2006072589 A2 * | 7/2006 | ........... C07D 401/12 |
| EP | 2 578 582 A1 | 4/2013 | |
| WO | WO 99/23091 | 5/1999 | |
| WO | WO 00/041698 | 7/2000 | |
| WO | WO 00/043384 | 7/2000 | |

(Continued)

OTHER PUBLICATIONS

Kinase Inhibitors, Methods in Molecular Biology 795 (B. Kuster ed., 2012).*

(Continued)

*Primary Examiner* — Alexander R Pagano
(74) *Attorney, Agent, or Firm* — Knobbe, Martens Olson & Bear, LLP

(57) ABSTRACT

There are provided compounds of formula I,

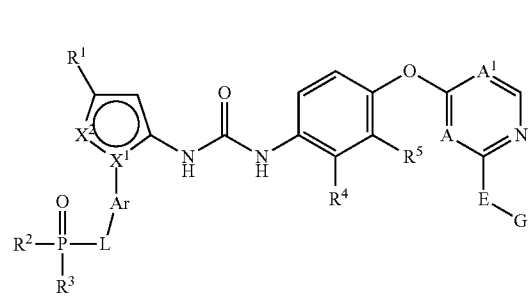

wherein $R^1$ to $R^5$, $X^1$, $X^2$, Ar, L, A, $A^1$, E and G have meanings given in the description, which compounds have antiinflammatory activity (e.g. through inhibition of one or more of members of: the family of p38 mitogen-activated protein kinase enzymes; Syk kinase; and members of the Src family of tyrosine kinases) and have use in therapy, including in pharmaceutical combinations, especially in the treatment of inflammatory diseases, including inflammatory diseases of the lung, eye and intestines.

23 Claims, No Drawings

(56) References Cited

U.S. PATENT DOCUMENTS

| | | | |
|---|---|---|---|
| 8,293,748 B2 | 10/2012 | Ito et al. |
| 8,293,771 B2 | 10/2012 | Ito et al. |
| 8,299,073 B2 | 10/2012 | Ito et al. |
| 8,299,074 B2 | 10/2012 | Ito et al. |
| 8,618,140 B2 | 12/2013 | Ito et al. |
| 8,642,773 B2 | 2/2014 | Ito et al. |
| 8,927,563 B2 | 1/2015 | Fyfe |
| 8,933,228 B2 | 1/2015 | Murray et al. |
| 8,975,285 B2 | 3/2015 | Ito et al. |
| 9,024,041 B2 | 5/2015 | King-Underwood |
| 9,079,893 B2 | 7/2015 | Cass |
| 9,108,950 B2 | 8/2015 | Ito et al. |
| 9,242,960 B2 | 1/2016 | Ito et al. |
| 9,249,125 B2 | 2/2016 | Duffy et al. |
| 9,481,648 B2 | 11/2016 | Baker et al. |
| 9,701,670 B2 | 7/2017 | Cariou |
| 2001/0011135 A1 | 8/2001 | Riedl et al. |
| 2004/0152725 A1 | 8/2004 | Moss et al. |
| 2012/0244120 A1 | 9/2012 | Charron et al. |
| 2013/0029990 A1 | 1/2013 | King-Underwood et al. |
| 2013/0040962 A1 | 2/2013 | King-Underwood et al. |
| 2013/0040995 A1 | 2/2013 | King-Underwood et al. |
| 2013/0102607 A1 | 4/2013 | Cass et al. |
| 2013/0123260 A1 | 5/2013 | Charron et al. |
| 2013/0150343 A1 | 6/2013 | Van Niel et al. |
| 2013/0156826 A1 | 6/2013 | Murray et al. |
| 2014/0057915 A1 | 2/2014 | Cariou et al. |
| 2014/0114061 A1 | 4/2014 | Kugimoto et al. |
| 2014/0228410 A1 | 8/2014 | Ito et al. |
| 2014/0249169 A1 | 9/2014 | Ito et al. |
| 2014/0296208 A1 | 10/2014 | Baker et al. |
| 2015/0166483 A1 | 6/2015 | Fyfe |
| 2015/0203475 A1 | 7/2015 | Duffy et al. |
| 2015/0218137 A1 | 8/2015 | Cariou et al. |
| 2015/0225373 A1 | 8/2015 | Fyfe et al. |
| 2015/0225427 A1 | 8/2015 | Fyfe et al. |
| 2015/0232450 A1 | 8/2015 | Longshaw et al. |
| 2015/0252024 A1 | 9/2015 | Ito et al. |
| 2015/0329523 A1 | 11/2015 | Frickel et al. |
| 2016/0009695 A1 | 1/2016 | Ito et al. |
| 2016/0016934 A1 | 1/2016 | Fyfe et al. |
| 2016/0039797 A1 | 2/2016 | Fyfe |
| 2016/0045482 A1 | 2/2016 | Charron |
| 2016/0045512 A1 | 2/2016 | Charron |
| 2016/0096805 A1 | 4/2016 | Fyfe |
| 2016/0102059 A1 | 4/2016 | Baker et al. |
| 2016/0115152 A1 | 4/2016 | King-Underwood et al. |
| 2016/0130256 A1 | 5/2016 | King-Underwood et al. |
| 2016/0318909 A1 | 11/2016 | Fyfe |
| 2016/0340343 A1 | 11/2016 | Fyfe et al. |
| 2016/0376232 A1 | 12/2016 | Thom |

FOREIGN PATENT DOCUMENTS

| | | |
|---|---|---|
| WO | WO 00/055139 | 9/2000 |
| WO | WO 01/04115 | 1/2001 |
| WO | WO 01/36403 | 5/2001 |
| WO | WO 02/083628 | 10/2002 |
| WO | WO 02/092576 | 11/2002 |
| WO | WO 03/005999 | 1/2003 |
| WO | WO 03/068223 | 8/2003 |
| WO | WO 03/068228 | 8/2003 |
| WO | WO 03/072569 | 9/2003 |
| WO | WO 2005/023761 | 3/2004 |
| WO | WO 2004/113352 | 12/2004 |
| WO | WO 2005/044825 | 5/2005 |
| WO | WO 2006/043090 | 4/2006 |
| WO | WO 2006/072589 | 7/2006 |
| WO | WO 2007/053394 | 5/2007 |
| WO | WO 2008/079968 | 7/2008 |
| WO | WO 2010/038085 | 4/2010 |
| WO | WO 2010/038086 | 4/2010 |
| WO | WO 2010/067130 | 6/2010 |
| WO | WO 2010/067131 | 6/2010 |
| WO | WO 2010/112936 | 10/2010 |
| WO | WO 2011/070368 | 6/2011 |
| WO | WO 2011/070369 | 6/2011 |
| WO | WO 2011/121366 | 10/2011 |
| WO | WO 2011/124923 | 10/2011 |
| WO | WO 2011/124930 | 10/2011 |
| WO | WO 2011/154738 | 12/2011 |
| WO | WO 2011/158039 | 12/2011 |
| WO | WO 2011/158042 | 12/2011 |
| WO | WO 2011/158044 | 12/2011 |
| WO | WO 2013/050756 | 4/2013 |
| WO | WO 2013/050757 | 4/2013 |
| WO | WO 2013/083604 A1 | 6/2013 |
| WO | WO 2014/027209 | 2/2014 |
| WO | WO 2014/033447 | 3/2014 |
| WO | WO 2014/033448 | 3/2014 |
| WO | WO 2014/033449 | 3/2014 |
| WO | WO 2014/140582 A1 | 9/2014 |
| WO | WO 2014/162121 A1 | 10/2014 |
| WO | WO 2015/121444 A1 | 8/2015 |
| WO | WO 2015/121660 A1 | 8/2015 |

OTHER PUBLICATIONS

R. Singh et al., 42 Annual Reports in Medicinal Chemistry, 379-391 (2007).*
M.E. Weinblatt et al., 363 The New England Journal of Medicine 1303-1312 (2010).*
N. Yamamoto et al., 306 The Journal of Pharmacology and Experimental Therapeutics, 1174-1181 (2003).*
E.S. Masuda et al., 21 Pulmonary Pharmacology & Therapeutics, 461-467 (2008).*
D. Singh et al., 50 The Journal of Clinical Pharmacology, 94-100 (2010).*
A.C. Brando et al., 63 Pharmacological Reports, 1029-1039 (2011).*
R.S. Jope et al., 32 Neurochemical Research, 577-595 (2007).*
M.P. Kim et al., 335 Cell and Tissue Research, 249-259 (2009).*
U. McDermott et al., 27 Journal of Clinical Oncology, 5650-5659 (2009).*
C.L. Sawyers, Nature, 548-552 (2008).*
C.M. Coughlin et al., Breast Cancer Research Treatment, 1-11 (2010).*
G. Liu et al., 31 Arteriosclerosis, Thrombosis and Vascular Biology, 1342-1350 (2011).*
U.S. Appl. No. 14/561,290, filed Dec. 5, 2014, Murray.
U.S. Appl. No. 15/105,912, filed Jun. 17, 2016, Fyfe, et al.
U.S. Appl. No. 15/207,915, filed Jul. 12, 2016, Fyfe.
Badrinarayan, et al. 2011 "Sequence, structure, and active site analyses of p38 MAP kinase: Exploiting DFG-out conformation as a strategy to design new type II leads" *Journal of Chemical Information and Modeling* 51; 115-129.
Barnes, et al. 2007 "Trimethylsilylpyrazoles as novel inhibitors of p38 MAP kinase: A new use of silicon bioisosteres in medicinal chemistry" *Bioorganic & Medicinal Chemistry* 17; 354-357.
Biancheri, et al. 2016 "Effect of Narrow Spectrum Versus Selective Kinase Inhibitors on the Intestinal Proinflammatory Immune Response in Ulcerative Colitis" *Inflamm Bowel Dis* 22: 1306-1315.
Boehm, et al. 2000 "New inhibitors of p38 kinase" *Expert Opinion on Therapeutic Patents* 10(1): 25-37.
Brando, et al. 2011 "Anti-inflammatory effects of LASSBio-998, a new drug candidate designed to be a p38 MAPK inhibitor, in an experimental model of acute lung inflammation" *Pharmacological Reports* 63: 1029-1039.
CAS Registry No. 1379397-83-7, 2012 American Chemical Society.
CAS Registry No. 1384608-34-7, 2012 American Chemical Society.
Coughlin, et al. 2010 "Approaches and limitations of phosphatidylinositol-3-kinase pathway activation status as a predictive biomarker in the clinical development of targeted therapy" *Breast Cancer Res Treat* 124: 1-11.

(56) References Cited

OTHER PUBLICATIONS

Dietrich, et al. 2010 "The design, synthesis, and evaluation of 8 hybrid DFG-out allosteric kinase inhibitors: A structural analysis of the binding interactions of Gleevec ®, Nexavar®, and BIRB-796" *Bioorganic & Medicinal Chemistry* 18; 5738-5748.

Dodeller, et al. 2006 "The p38 mitogen-activated protein kinase signaling cascade in CD4 T cells" *Arthritis Research & Therapy* 8(2): 1-11.

Dumas, et al. 2004 "Recent developments in the discovery of protein kinase inhibitors from the urea class" *Current Opinion in Drug Discovery & Development* 7(5); 600-616.

Jope, et al. 2007 "Glycogen synthase kinase-3 (GSK3): Inflammation, diseases, and therapeutics" *Neurochem Res* 32: 577-595.

Kim, et al. 2009 "Src family kinases as mediators of endothelial permeability: effects on inflammation and metastasis" *Cell Tissue Res* 335: 249-259.

Kuster 2012 "Kinase Inhibitors" *Methods in Molecular Biology* 795: 1-44.

Liu, et al. 2011 "Src phosphorylation of endothelial cell surface intercellular adhesion molecule-1 mediates neutrophil adhesion and contributes to the mechanism of lung inflammation" *Arteriosclerosis, Thrombosis and Vascular Biology* 31: 1342-1350.

Masuda, et al. 2008 "Syk inhibitors as treatment for allergic rhinitis" *Pulmonary Pharmacology & Therapeutics* 21: 461-467.

McDermott, et al. 2009 "Personalized cancer therapy with selective kinase inhibitors: An emerging paradigm in medical oncology" *Journal of Clinical Oncology* 27(33): 5650-5659.

Onions, et al. 2016 "The discovery of narrow spectrum kinase inhibitors: New therapeutic agents for the treatment of COPD and steroid-resistant asthma" *Journal of Medicinal Chemistry*; 59: 1727-1746.

Patterson, et al. 2013 "Protein kinase inhibitors in the treatment of inflammatory and autoimmune diseases" *Clinical and Experimental Immunology* 176; 1-10.

Pettus, et al. 2008 "Small Molecule p38 MAP Kinase Inhibitors for the Treatment of Inflammatory Diseases: Novel Structures and Developments During 2006-2008" *Current Topics in Medicinal Chemistry* 8; 1452-1467.

Sawyers 2008 "The cancer biomarker problem" *Nature* 452: 548-552.

Singh, et al. 2007 "Spleen tyrosine kinase (Syk) biology, inhibitors and therapeutic applications" *Annual Reports in Medicinal Chemistry* 42: 379-391.

Singh, et al 2010 "A randomized, placebo-controlled study of the effects of the p38 MAPK inhibitor SB-681323 on blood biomarkers of inflammation in COPD patients" *The Journal of Clinical Pharmacology* 50: 94-100.

To, et al. 2015 "Potent anti-inflammatory effects of the narrow spectrum kinase inhibitor RV1088 on rheumatoid arthritis synovial membrane cells" *Britch Journal of Pharmacology* 172: 3805-3816.

Weinblatt, et al. 2010 "An oral spleen tyrosine kinase (Syk) inhibitor for rheumatoid arthritis" *The New England Journal of Medicine* 363(14): 1303-1312.

Yamamoto, et al. 2003 "The orally available spleen tyrosine kinase inhibitor 2-[7-(3,4-Dimethoxyphenyl)-imidazo[1,2-c]pyrimidin-5-ylamino]-nicotinamide Dihydrocholoride (BAY 61-3606) Blacks antigen-induced airway inflammation in rodents" *The Journal of Pharmacology and Experimental Therapeutics* 306(3): 1174-1181.

Zambon, et al. 2010 "Novel hinge binder improves activity and pharmacokinetic properties of BRAF inhibitors" *Journal of Medicinal Chemistry* 53; 5639-5655.

Brinkmann, et al. 2010 "Fingolimod (FTY720): discovery and development of an oral drug to treat multiple sclerosis" *Nature Reviews* 9: 883-897.

Judge, et al. 2006 "Potassium channel blockers in multiple sclerosis: Neuronal K channels and effects of symptomatic treatment" *Pharmacology & Therapeutics* 111: 224-259.

Sutherland, et al. 2004 "Management of chronic obstructive pulmonary disease" *The New England Journal of Medicine* 350: 2689-2697.

\* cited by examiner

KINASE INHIBITORS

FIELD OF THE INVENTION

This invention relates, inter alia, to compounds which are antiinflammatory agents (e.g. through inhibition of one or more of members of: the family of p38 mitogen-activated protein kinase enzymes (referred to herein as p38 MAP kinase inhibitors), for example the alpha kinase sub-type thereof; Syk kinase; and the Src family of tyrosine kinases). The invention also relates to the use of such compounds in therapy, including in mono- and combination therapies, especially in the treatment of inflammatory diseases, including inflammatory diseases of the lung (such as asthma and chronic obstructive pulmonary disease (COPD)), eye (such as uveitis) and gastrointestinal tract (such as Crohn's disease and ulcerative colitis).

BACKGROUND OF THE INVENTION

The listing or discussion of an apparently prior-published document in this specification should not necessarily be taken as an acknowledgement that the document is part of the state of the art or is common general knowledge.

Four p38 MAPK isoforms (alpha, beta, gamma and delta respectively) have been identified, each displaying different patterns of tissue expression. The p38 MAPK alpha and beta isoforms are found ubiquitously throughout the body; are present in many different cell types and are inhibited by a number of previously described small molecular weight compounds. Early classes of inhibitors were highly toxic due to the broad tissue distribution of these isoforms which resulted in off-target effects of the compounds. Some of the more recently identified inhibitors show improved selectivity for p38 MAPK alpha and beta isoforms and have wider safety margins.

p38 MAP kinase is believed to play a pivotal role in many of the signalling pathways that are involved in initiating and maintaining chronic, persistent inflammation in human disease, for example, in severe asthma, COPD and inflammatory bowel disease (IBD). There is now an abundant literature which demonstrates that p38 MAP kinase is activated by a range of pro-inflammatory cytokines and that its activation results in the recruitment and release of further pro-inflammatory cytokines. Indeed, data from some clinical studies demonstrate beneficial changes in disease activity in patients during treatment with p38 MAP kinase inhibitors. For instance Smith describes the inhibitory effect of p38 MAP kinase inhibitors on TNFα (but not IL-8) release from human PBMCs (Smith, S. J., *Br. J. Pharmacol.*, 2006, 149:393-404).

The use of inhibitors of p38 MAP kinase in the treatment of COPD and IBD has also been proposed. Small molecule inhibitors targeted to p38 MAPKα/β have proved to be effective in reducing various parameters of inflammation in:
- cells and tissues obtained from patients with COPD, who are generally corticosteroid insensitive (Smith, S. J., *Br. J. Pharmacol.*, 2006, 149:393-404);
- biopsies from IBD patients (Docena, G. et al., *J. of Trans. Immunol.*, 2010, 162:108-115); and
- in vivo animal models (Underwood, D. C. et al., *Am. J. Physiol.*, 2000, 279:L895-902; Nath, P. et al., *Eur. J. PharmacoL*, 2006, 544:160-167).

Irusen and colleagues also suggested the possibility of involvement of p38 MAPKα/β on corticosteroid insensitivity via the reduction of binding affinity of the glucocorticoid receptor (GR) in nuclei (Irusen, E. et al., *J. Allergy Clin. Immunol.*, 2002, 109:649-657). Clinical investigations in inflammatory diseases with a range of p38 MAP kinase inhibitors, including AMG548, BIRB 796, VX702, SCIO469 and SCIO323, has been described (Lee, M. R. and Dominguez, C., *Current Med. Chem.*, 2005, 12:2979-2994.). However, the major obstacle hindering the utility of p38 MAP kinase inhibitors in the treatment of human chronic inflammatory diseases has been the toxicity observed in patients. This has been sufficiently severe to result in the withdrawal from clinical development of many of the compounds progressed, including all those specifically mentioned above.

COPD is a condition in which the underlying inflammation is reported to be substantially resistant to the anti-inflammatory effects of inhaled corticosteroids. Consequently, a superior strategy for treating COPD would be to develop an intervention which has both inherent anti-inflammatory effects and the ability to increase the sensitivity of the lung tissues of COPD patients to inhaled corticosteroids. The recent publication of Mercado et al. (2007; *American Thoracic Society Abstract A56*) demonstrates that silencing p38 MAPK gamma has the potential to restore sensitivity to corticosteroids. Thus, there may be a dual benefit for patients in the use of a p38 MAP kinase inhibitor for the treatment of COPD.

Many patients diagnosed with asthma or with COPD continue to suffer from uncontrolled symptoms and from exacerbations of their medical condition that can result in hospitalisation. This occurs despite the use of the most advanced, currently available treatment regimens, comprising of combination products of an inhaled corticosteroid and a long acting β-agonist. Data accumulated over the last decade indicates that a failure to manage effectively the underlying inflammatory component of the disease in the lung is the most likely reason that exacerbations occur. Given the established efficacy of corticosteroids as anti-inflammatory agents and, in particular, of inhaled corticosteroids in the treatment of asthma, these findings have provoked intense investigation. Resulting studies have identified that some environmental insults invoke corticosteroid-insensitive inflammatory changes in patients' lungs. An example is the response arising from virally-mediated upper respiratory tract infections (URTI), which have particular significance in increasing morbidity associated with asthma and COPD.

It has been disclosed previously that compounds that inhibit the activity of both the c-Src and Syk kinases are effective agents against rhinovirus replication (Charron, C. E. et al., WO 2011/158042) and that compounds that inhibit p59-HCK are effective against influenza virus replication (Charron, C. E. et al., WO 2011/070369). Taken together with inhibition of p38 MAPK, these are particularly attractive properties for compounds to possess that are intended to treat patients with chronic respiratory diseases.

Certain p38 MAPK inhibitors have also been described as inhibitors of replication of respiratory syncytial virus (Cass L. et al., WO 2011/158039).

The precise etiology of IBD is uncertain, but is believed to be governed by genetic and environmental factors that interact to promote an excessive and poorly controlled mucosal inflammatory response directed against components of the luminal microflora. This response is mediated through infiltration of inflammatory neutrophils, dendritic cells and T-cells from the periphery. Due to the ubiquitous expression of p38 in inflammatory cells it has become an obvious target for investigation in IBD models. Studies investigating the efficacy of p38 inhibitors in animal models of IBD and human biopsies from IBD patients indicated that p38 could be a target for the treatment of IBD (Hove, T. ten et al., *Gut,* 2002, 50:507-512, Docena, G. et al., *J. of Trans. Immunol.,* 2010, 162:108-115). However, these findings are not completely consistent with other groups reporting no effect with p38 inhibitors (Malamut G. et al., *Dig. Dis. Sci,* 2006, 51:1443-1453). A clinical study in Crohn's patients using the p38 alpha inhibitor BIRB796 demonstrated potential clinical benefit with an improvement in C-reactive protein levels. However this improvement was transient, returning to baseline by week 8 (Schreiber, S. et al., *Clin. Gastro. Hepatology,* 2006, 4:325-334). A small clinical study investigating the efficacy of CNI-1493, a P38 and Jnk inhibitor, in patients with severe Crohn's disease showed significant improvement in clinical score over 8 weeks (Hommes, D. et al. *Gastroenterology.* 2002 122:7-14).

T cells are known to play key role in mediating inflammation of the gastrointestinal tract. Pioneering work by Powrie and colleagues demonstrated that transfer of naive CD4+ cells into severely compromised immunodeficient (SCID) animals results in the development of colitis which is dependent on the presence of commensal bacteria (Powrie F. et al. *Int Immunol.* 1993 5:1461-71). Furthermore, investigation of mucosal membranes from IBD patients showed an upregulation of CD4+ cells which were either Th1 (IFNγ/IL-2) or Th2 (IL5/TGFβ) biased depending on whether the patient had Crohn's disease or ulcerative colitis (Fuss I J. et al. *J Immunol.* 1996 157:1261-70.). Similarly, T cells are known to play a key role in inflammatory disorders of the eye with several studies reporting increased levels of T cell associated cytokines (IL-17 and IL-23) in sera of Behcets patients (Chi W. et al. *Invest Ophthalmol Vis Sci.* 2008 49:3058-64). In support, Direskeneli and colleagues demonstrated that Behçets patients have increased Th17 cells and decreased Treg cells in their peripheral blood (Direskeneli H. et al. J Allergy Clin Immunol. 2011 128: 665-6).

One approach to inhibit T cell activation is to target kinases which are involved in activation of the T cell receptor signalling complex. Syk and Src family kinases are known to play a key role in this pathway, where Src family kinases, Fyn and Lck, are the first signalling molecules to be activated downstream of the T cell receptor (Barber E K. et al. *PNAS* 1989 86:3277-81). They initiate the tyrosine phosphorylation of the T cell receptor leading to the recruitment of the Syk family kinase, ZAP-70. Animal studies have shown that ZAP-70 knockout results in a SCID phenotype (Chan A C. et al. *Science.* 1994 10; 264(5165):1599-601).

A clinical trial in rheumatoid arthritis patients with the Syk inhibitor Fostamatinib demonstrated the potential of Syk as an anti-inflammatory target with patients showing improved clinical outcome and reduced serum levels of IL-6 and MMP-3 (Weinblatt M E. et al. *Arthritis Rheum.* 2008 58:3309-18). Syk kinase is widely expressed in cells of the hematopoietic system, most notably in B cells and mature T cells. Through interaction with immunoreceptor tyrosine-based activation (ITAM) motifs it plays an important role in regulating T cell and B cell expansion as well as mediating immune-receptor signalling in inflammatory cells. Syk activation leads to IL-6 and MMP release—inflammatory mediators commonly found upregulated in inflammatory disorders including IBD and rheumatoid arthritis (Wang Y D. et al *World J Gastroenterol* 2007; 13: 5926-5932, Litinsky I et al. *Cytokine.* 2006 January 33:106-10).

In addition to playing key roles in cell signalling events which control the activity of pro-inflammatory pathways, kinase enzymes are now also recognised to regulate the activity of a range of cellular functions, including the maintenance of DNA integrity (Shilo, Y. *Nature Reviews Cancer,* 2003, 3: 155-168) and co-ordination of the complex processes of cell division. Indeed, certain kinase inhibitors (the so-called "Olaharsky kinases") have been found to alter the frequency of micronucleus formation in vitro (Olaharsky, A. J. et al., *PLoS Comput. Biol.,* 2009, 5(7)). Micronucleus formation is implicated in, or associated with, disruption of mitotic processes and is therefore undesirable. Inhibition of glycogen synthase kinase 3α (GSK3α) was found to be a particularly significant factor that increases the likelihood of a kinase inhibitor promoting micronucleus formation. Also, inhibition of the kinase GSK3β with RNAi has been reported to promote micronucleus formation (Tighe, A. et al., *BMC Cell Biology,* 2007, 8:34).

Whilst it may be possible to attenuate the adverse effects of inhibition of Olaharsky kinases such as GSK3α by optimisation of the dose and/or by changing the route of administration of a molecule, it would be advantageous to identify further therapeutically useful molecules with low or negligible inhibition of Olaharsky kinases, such as GSK 3α and/or have low or negligible disruption of mitotic processes (e.g. as measured in a mitosis assay).

Various urea derivatives are disclosed as having anti-inflammatory properties (see, for example, WO 01/36403, WO 01/4115, WO 02/092576, WO 2003/068228, WO 2003/072569, WO 2004/113352, WO 2007/053394 and *Bioorg. Med. Chem. Lett.* 2007, 17, 354-357). Nevertheless, there remains a need to identify and develop alternative p38 MAP kinase inhibitors, and particularly inhibitors that have improved therapeutic potential over currently available treatments or, in particular, that exhibit a superior therapeutic index (e.g. inhibitors that are at least equally efficacious and, in one or more respects, are less toxic at the relevant therapeutic dose than previous agents).

SUMMARY OF THE INVENTION

We have now discovered, surprisingly, that certain phosphoryl (P=O)-containing diaryl ureas inhibit one or more of p38 MAP kinase, Syk and Src family kinases and therefore possess good anti-inflammatory properties.

Thus, according to a first aspect of the invention, there is provided a compound of formula I,

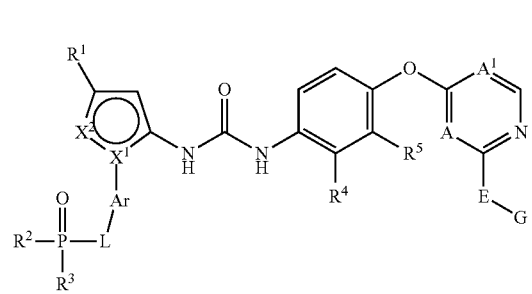

wherein
$R^1$ represents $C_{2-6}$ alkyl, $Si(R^{1a})(R^{1b})(R^{1c})$, $C_{3-7}$ cycloalkyl, phenyl or a 5- or 6-membered heteroaryl group containing one or more heteroatoms selected from N, O and S, which alkyl, cycloalkyl, phenyl and heteroaryl groups are optionally substituted by one or more substituents selected from halo, $C_{1-4}$ alkyl, $C_{2-3}$ alkynyl, $C_{3-4}$ cycloalkyl, $C_{1-4}$ haloalkyl, $C_{1-4}$ alkoxy, hydroxy, amino and cyano;

$R^{1a}$ and $R^{1b}$ independently represent $C_{1-4}$ alkyl or $C_{3-6}$ cycloalkyl, or $R^{1a}$ and $R^{1b}$ together combine to form $C_{2-6}$ alkylene;

$R^{1c}$ represents $C_{1-2}$ alkyl;

$X^1$ and $X^2$ are both N, or $X^1$ is C and $X^2$ is either O or S;

Ar is phenyl or a 5- or 6-membered heteroaryl group containing one or more heteroatoms selected from N, O and S, which phenyl and heteroaryl groups are optionally substituted by one or more substituents selected from halo, $C_{1-4}$ alkyl, $C_{1-4}$ haloalkyl, $C_{1-4}$ alkoxy, hydroxy, amino and cyano;

L is a direct bond or $C_{1-2}$ alkylene;

$R^2$ represents $C_{1-4}$ alkyl;

$R^3$ represents $C_{1-4}$ alkyl, $C_{3-6}$ cycloalkyl, $C_{1-4}$ alkoxy or hydroxy;

or $R^2$ and $R^3$ together combine to form $C_{3-6}$ alkylene;

$R^4$ and $R^5$ are each independently $C_{1-3}$ alkyl, $C_{1-3}$ haloalkyl, cyano or halo, or $R^4$ and $R^5$ together combine to form $C_{3-5}$ alkylene or $C_{3-5}$ alkenylene, which latter two groups are optionally substituted by one or more substituents selected from $C_{1-3}$ alkyl, $C_{1-3}$ haloalkyl, cyano and halo, or $R^4$ and $R^5$, together with the C-atoms to which they are attached, form a fused phenyl or $Het^1$ ring, which latter two rings are optionally substituted by one or more substituents selected from $C_{1-3}$ alkyl, $C_{1-3}$ haloalkyl, cyano and halo;

$Het^1$ represents a 5- to 7-membered heterocyclic group that is fully saturated, partially unsaturated or fully aromatic, which heterocyclic group contains one or more heteroatoms selected from N, O and S;

one of A and $A^1$ represents N and the other represents CH, or both A and $A^1$ represent CH;

E represents $N(G^1)$, O or S;

G represents
  phenyl optionally substituted by one or more $Y^1$,
  $Het^2$ optionally substituted by one or more $Y^2$,
  $R^{6a}$ or
  $C(O)R^{6b}$;

$G^1$ represents H or $C_{1-3}$ alkyl;

or G and $G^1$ together combine to form $C_{3-6}$ alkylene optionally substituted by one or more substituents selected from halo, hydroxy and $C_{1-3}$ alkyl, which latter group is optionally substituted by one or more halo atoms or by hydroxy;

each $Y^1$ is independently selected from the group consisting of
  halo, hydroxy, cyano, $SF_5$, $-OC(O)NH_2$,
  $P(O)R^{6c}R^{6d}$,
  $E^1$-$N(R^{6e})R^{6f}$,
  $E^2$-$S(O)_2R^{6g}$,
  $E^3$-$[CH_2(CH_2)_{0-1}CH_2-O]_{2-8}-R^{6h}$,
  $-C\equiv C-R^{6i}$,
  $-N=S(O)R^{6j}R^{6k}$,
  $Het^a$,
  $C_{1-6}$ alkyl, $C_{3-6}$ cycloalkyl, $C_{1-6}$ alkoxy, $C_{3-6}$ cycloalkoxy, $-S(O)_{0-1}-C_{1-6}$ alkyl and $-S(O)_{0-1}-C_{3-6}$ cycloalkyl which latter six groups are optionally substituted by one or more substituents selected from halo, hydroxy, $C_{1-3}$ alkyl, $C_{1-3}$ alkoxy and $C_{3-6}$ cycloalkyl;

each $Y^2$ independently represents oxo or $Y^1$;

$E^1$ represents
  a direct bond,
  $-C(O)-$
  $-[C(O)]_p-C_{1-8}$ alkylene,
  $-C(O)NR^{7a}-CH_2-[C_{1-7}$ alkylene]-,
  $-Q^1-CH_2-[C_{1-5}$ alkylene]-,
  the alkylene parts of which latter four groups are optionally substituted by one or more substituents selected from halo, $C_{1-3}$ alkyl and hydroxy;

$E^2$ represents
  a direct bond,
  $-O-$,
  $-NH-$
  $C_{1-6}$ alkylene or
  $-Q^2-CH_2-[C_{1-5}$ alkylene]-,
  the alkylene parts of which latter two groups are optionally substituted by one or more substituents selected from halo, $C_{1-3}$ alkyl and hydroxy;

$E^3$ represents $-O-$ or $S(O)_{0-2}$;

$Q^1$ and $Q^2$ independently represent O or $S(O)_{0-2}$;

p represents 0 or 1;

$R^{6a}$ represents $C_{1-8}$ alkyl, wherein one or two non-adjacent C-atoms of the alkyl group, that are not linked directly to E, are optionally replaced by heteroatoms independently selected from O and N and/or wherein the alkyl group is substituted by one or more $R^8$ substituents;

$R^{6b}$ represents $C_{1-8}$ alkyl, wherein one C-atom of the alkyl group is, or two non-adjacent C-atoms of the alkyl group are, optionally replaced by heteroatoms independently selected from O and N and/or wherein the alkyl group is substituted by one or more $R^8$ substituents;

$R^{6c}$ and $R^{6d}$ independently represent $C_{1-3}$ alkyl or $C_{1-3}$ alkoxy, or $R^{6c}$ and $R^{6d}$ together combine to form $C_{4-6}$ alkylene;

$R^{6e}$ and $R^{6f}$ independently represent H or $C_{1-8}$ alkyl, which latter group is optionally substituted by $R^{7b}$ and/or one or more substituents selected from halo and hydroxy or $R^{6e}$ and $R^{6f}$, together with the N-atom to which they are attached, form a 4- to 7-membered heterocyclic group that is fully saturated, partially unsaturated or fully aromatic and which heterocyclic group contains one N atom (the atom to which $R^{6e}$ and $R^{6f}$ are attached) and, optionally, one or more further heteroatoms selected from 0, S and N, and which heterocyclic group is optionally substituted by one or more substituents selected from halo, hydroxy, oxo, $C_{1-4}$ alkyl and $C_{1-4}$ alkoxy;

$R^{6g}$ represents $C_{1-6}$ alkyl, $C_{3-6}$ cycloalkyl or phenyl, which latter three groups are optionally substituted by one or more substituents selected from halo, hydroxy, $C_{1-3}$ alkyl, $C_{1-3}$ alkoxy and $C_{3-6}$ cycloalkyl;

$R^{6h}$, $R^{6i}$, $R^{6j}$ and $R^{6k}$ independently represent $C_{1-4}$ alkyl optionally substituted by one or more halo atoms, or $R^{6h}$ and $R^{6i}$ independently represent H;

$R^{7a}$ represents H or $C_{1-3}$ alkyl optionally substituted by one or more halo atoms;

$R^{7b}$ represents $C_{1-4}$ alkoxy, $S-C_{1-4}$ alkyl, phenyl or $Het^4$, which latter two groups are optionally substituted by one or more substituents selected from halo, $C_{1-4}$ alkyl, $C_{1-4}$ haloalkyl, $C_{1-4}$ alkoxy, hydroxy, amino and cyano;

$R^8$ represents, independently on each occurrence, halo, hydroxy, $C_{1-4}$ alkoxy, oxo, $C_{3-8}$ cycloalkyl, $Het^3$ or phenyl, which latter three groups are optionally substituted by one or more substituents selected from halo, $C_{1-4}$ alkyl, $C_{1-4}$ haloalkyl, $C_{1-4}$ alkoxy, hydroxy, amino and cyano;

$Het^2$ represents a 5- to 10-membered heteroaromatic group, which group is monocyclic or bicyclic and contains at least one carbocyclic or heterocyclic ring that is fully aromatic, and which group contains one or more heteroatoms selected from N, O and S;

$Het^3$ and $Het^4$ independently represent 4- to 10-membered heterocyclic groups that are fully saturated, partially unsaturated or fully aromatic, which heterocyclic groups contain one or more heteroatoms selected from N, O and S; and Het$^a$ represents a 5- or 6-membered heterocyclic group that is fully saturated, partially unsaturated or fully aromatic, which group contains one or more heteroatoms selected from N, O and S, and which group is optionally substituted by one or more substituents selected from halo, hydroxy, $C_{1-3}$ alkyl, $C_{1-3}$ alkoxy and $C_{3-6}$ cycloalkyl;
or a pharmaceutically acceptable salt, solvate or isotopic derivative thereof,
which compounds may be referred to hereinafter as "the compounds of the invention".

DETAILED DESCRIPTION

Pharmaceutically acceptable salts that may be mentioned include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of formula I in the form of a salt with another counter-ion, for example using a suitable ion exchange resin.

Examples of pharmaceutically acceptable salts include acid addition salts derived from mineral acids and organic acids, and salts derived from metals.

For the avoidance of doubt, compounds of formula I may contain the stated atoms in any of their natural or non-natural isotopic forms. In this respect, embodiments of the invention that may be mentioned include those in which:
(a) the compound of formula I is not isotopically enriched or labelled with respect to any atoms of the compound; and
(b) the compound of formula I is isotopically enriched or labelled with respect to one or more atoms of the compound.

References herein to an "isotopic derivative" relate to the second of these two embodiments. In particular embodiments of the invention, the compound of formula I is isotopically enriched or labelled (with respect to one or more atoms of the compound) with one or more stable isotopes. Thus, the compounds of the invention that may be mentioned include, for example, compounds of formula I that are isotopically enriched or labelled with one or more atoms such as deuterium or the like.

Compounds of formula I may exhibit tautomerism. All tautomeric forms and mixtures thereof are included within the scope of the invention. In particular, the invention includes the keto-enol tautomerism existing between indolin-2-one and 2-hydroxyindole.

Unless otherwise specified, alkyl groups and alkoxy groups as defined herein may be straight-chain or, when there is a sufficient number (i.e. a minimum of three) of carbon atoms, be branched. Particular alkyl groups that may be mentioned include, for example, methyl, ethyl, n-propyl, iso-propyl, butyl, n-butyl and tert-butyl. Particular alkoxy groups that may be mentioned include, for example, methoxy, ethoxy, propoxy, and butoxy.

Unless otherwise specified, cycloalkyl groups as defined herein may, when there is a sufficient number (i.e. a minimum of four) of carbon atoms, be part cyclic/acyclic.

Unless otherwise specified, alkylene groups as defined herein may be straight-chain or, when there is a sufficient number (i.e. a minimum of two) of carbon atoms, be branched. In particular embodiments of the invention, alkylene refers to straight-chain alkylene.

Unless otherwise stated, the point of attachment of aryl groups may be via any atom of the ring system. However, when aryl groups are bicyclic or tricyclic, they are linked to the rest of the molecule via an aromatic ring. $C_{6-14}$ aryl groups include phenyl, naphthyl and the like. Embodiments of the invention that may be mentioned include those in which aryl is phenyl.

Values of Het$^a$ that may be mentioned include imidazolyl (e.g. imidazol-2-yl), isothiazolyl (e.g. isothiazol-3-yl), isoxazolyl (e.g. isoxazol-3-yl), 1,2,4-oxadiazolyl (e.g. 1,2,4-oxadiazol-3-yl or 1,2,4-oxadiazol-5-yl), 1,3,4-oxadiazolyl, oxazolyl (e.g. oxazol-2-yl), pyridinyl (e.g. pyridin-2-yl), pyrimidinyl (e.g. pyrimidin-2-yl), 1,2,4-thiadiazolyl (e.g. 1,2,4-thiadiazol-3-yl or 1,2,4-thiadiazol-5-yl), 1,3,4-thiadiazolyl, thiazolyl (e.g. thiazol-2-yl), 1,2,3-triazolyl (e.g. 1,2,3-triazol-1-yl, 1,2,3-triazol-4-yl or 1,2,3-triazol-5-yl) and 1,2,4-triazolyl (e.g. 1,2,4-triazol-1-yl, 1,2,4-triazol-3-yl or 1,2,4-triazol-5-yl).

Unless otherwise specified, the term "halo" includes references to fluoro, chloro, bromo or iodo, in particular to fluoro, chloro or bromo, especially fluoro or chloro.

Embodiments of the invention that may be mentioned include those in which one or more of the following definitions apply to the compound of formula I:
$R^1$ represents $C_{2-6}$ alkyl optionally substituted by halo or $C_{3-6}$ cycloalkyl optionally substituted by $C_{1-4}$ alkyl, $C_{1-4}$ haloalkyl or $C_{1-4}$ alkoxy, or $R^1$ represents $Si(R^{1a})(R^{1b})(R^{1c})$;
$R^{1a}$ and $R^{1b}$ independently represent $C_{1-4}$ alkyl (e.g. $C_{1-2}$ alkyl), or $R^{1a}$ and $R^{1b}$ together combine to form $C_{2-6}$ alkylene;
$R^{1c}$ represents $C_{1-2}$ alkyl;
$X^1$ and $X^2$ are both N;
Ar is phenyl or pyridyl;
L is a direct bond or $C_{1-2}$ alkylene (e.g. a direct bond or —$CH_2$—);
$R^2$ represents $C_{1-4}$ alkyl (e.g. $C_{1-2}$ alkyl);
$R^3$ represents $C_{1-4}$ alkyl (e.g. $C_{1-2}$ alkyl), $C_{1-4}$ alkoxy (e.g. $C_{1-2}$ alkoxy) or hydroxy;
or $R^2$ and $R^3$ together combine to form $C_{3-6}$ alkylene;
$R^4$ and $R^5$ are each independently $C_{1-3}$ alkyl, $C_{1-3}$ haloalkyl, cyano or halo,
or, particularly, $R^4$ and $R^5$, together with the C-atoms to which they are attached, form a fused phenyl ring, which ring is optionally substituted by one or more substituents selected from $C_{1-3}$ alkyl, $C_{1-3}$ haloalkyl, cyano or halo;
either A represents N and $A^1$ represents CH, or both A and $A^1$ represent CH;
E represents $N(G^1)$ or S;
G represents $R^{ha}$, $C(O)R^{6b}$, phenyl optionally substituted by one or more $Y^1$ or Het$^2$ optionally substituted by one or more $Y^2$;
$G^1$ represents H or $C_{1-3}$ alkyl (e.g. H or $C_1$ alkyl);
or G and $G^1$ together combine to form $C_{3-6}$ alkylene optionally substituted by one or more substituents selected from halo, hydroxy and $C_{1-3}$ alkyl, which latter group is optionally substituted by one or more halo atoms or by hydroxy;
$R^{6a}$ represents $C_{1-8}$ alkyl, wherein one or two non-adjacent C-atoms of the alkyl group, that are not linked directly to E, are optionally replaced by heteroatoms independently selected from O and N and/or wherein the alkyl group is substituted by one or more $R^8$ substituents;
$R^{6b}$ represents $C_{1-8}$ alkyl, wherein one C-atom of the alkyl group is, or two non-adjacent C-atoms of the alkyl group are, optionally replaced by heteroatoms independently selected from O and N and/or wherein the alkyl group is substituted by one or more $R^8$ substituents;

each $Y^1$ is independently selected from the group consisting of halo, hydroxy, cyano, $P(O)R^{6c}R^{6d}$, $SF_5$, —C≡CH, $E^1$-N$(R^{6e})R^{6f}$, —S(O)$_2R^{6g}$, —O—[CH$_2$CH$_2$O]$_{2-7}$—$R^{6h}$, $C_{1-4}$ alkyl, —S—$C_{1-4}$ alkyl and $C_{1-4}$ alkoxy, which latter three groups are optionally substituted by hydroxy or by one or more halo atoms;

each $Y^2$ is independently oxo or $Y^1$;

$E^1$ represents
a direct bond,
—C(O)—,
$C_{1-4}$ alkylene,
—C(O)NH—CH$_2$—[$C_{1-3}$ alkylene]-,
-$Q^1$-CH$_2$—[$C_{1-3}$ alkylene]-,
the alkylene parts of which latter three groups are optionally substituted by one or more substituents selected from halo and hydroxy;

$R^{6c}$ and $R^{6d}$ independently represent $C_{1-3}$ alkyl (e.g. methyl), or $R^{6c}$ and $R^{6d}$ together combine to form $C_{4-5}$ alkylene;

$R^{6e}$ and $R^{6f}$, independently on each occurrence, represent H or $C_{1-4}$ alkyl, which latter group is optionally substituted by one or more substituents selected from halo and hydroxy, or, together with the N-atom to which they are attached, $R^{6e}$ and $R^{6f}$ form a 4- to 7-membered heterocyclic group that is fully saturated, partially unsaturated or fully aromatic and which heterocyclic group contains one N atom (the atom to which $R^{6e}$ and $R^{6f}$ are attached) and, optionally, one or more further heteroatoms selected from O, S and N, and which heterocyclic group is optionally substituted by one or more substituents selected from halo, hydroxy, oxo, $C_{1-4}$ alkyl and $C_{1-4}$ alkoxy;

$R^{6g}$ represents $C_{1-2}$ alkyl or $C_{3-5}$ cycloalkyl, which latter two groups are optionally substituted by one or more halo atoms;

$R^{6h}$ represents H or $C_{1-2}$ alkyl;

$R^8$ represents, independently on each occurrence, halo, hydroxy, $C_{1-4}$ alkoxy, oxo, $C_{3-8}$ cycloalkyl, Het$^3$ or phenyl, which latter three groups are optionally substituted by one or more substituents selected from halo, $C_{1-4}$ alkyl, $C_{1-4}$ haloalkyl, $C_{1-4}$ alkoxy, hydroxy, amino and cyano;

Het$^2$ represents a 5- to 10-membered heteroaromatic group, which group is monocyclic or bicyclic and contains at least one carbocyclic or heterocyclic ring that is fully aromatic, and which group contains one or more heteroatoms selected from N, O and S;

Het$^3$ represents a 4- to 10-membered heterocyclic group that is fully saturated, partially unsaturated or fully aromatic, which heterocyclic group contains one or more heteroatoms selected from N, O and S.

Particular embodiments that may be mentioned include compounds of formula I (or any embodiment thereof, such as that defined directly above) wherein:

L is a direct bond or, particularly, —CH$_2$—;

$R^2$ represents $C_{1-4}$ alkyl (e.g. $C_{1-2}$ alkyl), and $R^3$ represents hydroxy or, particularly, $C_{1-4}$ alkyl (e.g. $C_{1-2}$ alkyl) or $C_{1-4}$ alkoxy (e.g. $C_{1-2}$ alkoxy).

Further embodiments of the invention that may be mentioned include those in which the compound of formula I is a compound of formula Ia,

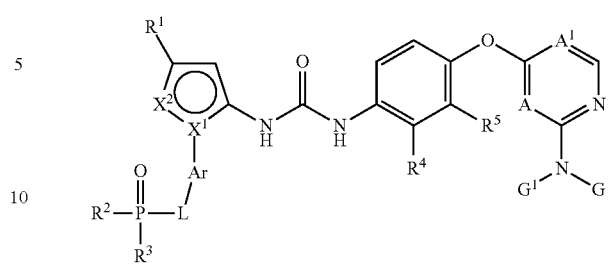

Ia wherein $R^1$ to $R^5$, A, $A^1$, G, $G^1$, $X^1$, $X^2$, Ar and L are as defined above in respect of compounds of formula I.

Particular embodiments of the invention that may be mentioned include those in which one or more of the following definitions apply to the compound of formula I or Ia:

$R^1$ represents $C_{1-4}$ alkyl or Si(CH$_3$)$_3$;

$R^2$ and $R^3$ independently represent $C_{1-2}$ alkyl or $C_{1-2}$ alkoxy, or $R^2$ and $R^3$ together combine to form $C_{3-6}$ alkylene (e.g. $C_{4-5}$ alkylene, such as $C_4$ alkylene);

$X^1$ and $X^2$ are both N;

Ar is pyrimidinyl, pyridinyl or, particularly, phenyl, which three groups are optionally substituted by one or more substituents selected from halo, $C_{1-3}$ alkyl and $C_{1-3}$ alkoxy;

L is a direct bond or —CH$_2$—;

$R^4$ and $R^5$ are each independently cyano or halo, or $R^4$ and $R^5$, together with the C-atoms to which they are attached, form a fused phenyl ring;

either A represents N and $A^1$ represents CH, or both A and $A^1$ represent CH;

G represents
$C_{1-4}$ alkyl (e.g. $C_3$ alkyl), which latter group is optionally substituted with one or more hydroxy substituents,
phenyl optionally substituted by one or more $Y^1$ or
Het$^3$ optionally substituted by one or more $Y^2$;

$G^1$ represents H or methyl;

or G and $G^1$ together combine to form $C_4$ alkylene optionally substituted by one or more $C_{1-2}$ alkyl (e.g. methyl), which latter group is optionally substituted by hydroxy;

each $Y^1$ is independently selected from the group consisting of halo, hydroxy, cyano, $P(O)R^{6c}R^{6d}$, $SF_5$, —C≡CH, —C(O)NH—CH$_2$—[$C_{1-3}$ alkylene]-N$(R^{6e})R^{6f}$ and -$Q^1$-CH$_2$—[$C_{1-3}$ alkylene]-N$(R^{6e})R^{6f}$, —S(O)$_2R^{6g}$, —O—[CH$_2$CH$_2$O]$_{2-7}$—$R^{6h}$, $C_{1-4}$ alkyl, —S—$C_{1-4}$ alkyl, $C_{1-4}$ alkoxy and C(O)NHC$_{1-4}$ alkyl, which latter four groups are optionally substituted by hydroxy or by one or more halo atoms;

each $Y^2$ is independently selected from $Y^1$ and oxo;

$R^{6e}$ and $R^{6f}$, independently on each occurrence, represent $C_{1-4}$ alkyl, or, together with the N-atom to which they are attached, form a 5- or 6-membered heterocyclic group that is fully saturated and which heterocyclic group contains one N atom (the atom to which $R^{6e}$ and $R^{6f}$ are attached) and, optionally, one further heteroatom selected from O, S and N, and which heterocyclic group is optionally substituted by one or more substituents selected from halo, hydroxy, oxo, $C_{1-4}$ alkyl and $C_{1-4}$ alkoxy;

$R^{6g}$ represents $C_{1-2}$ alkyl or cyclopropyl, which latter two groups are optionally substituted by one or more halo atoms;

$R^{6h}$ represents H or, particularly, methyl;

$R^{6c}$ and $R^{6d}$ independently represent $C_{1-3}$ alkyl (e.g. methyl);

Het$^3$ represents a 6- to 10-membered heteroaromatic group, which group is monocyclic or bicyclic and contains at least one carbocyclic or heterocyclic ring that is fully aromatic, and which group contains one to four heteroatoms selected from N, O and S.

Further embodiments of the invention that may be mentioned include those in which the compound of formula I is a compound of formula Ib,

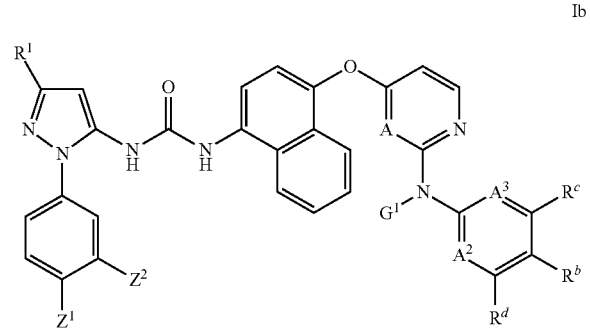

wherein
one of $Z^1$ and $Z^2$ represents the structural fragment

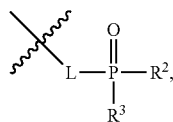

and the other of $Z^1$ and $Z^2$ represents H;
$R^1$ represents $C_{1-4}$ alkyl (e.g. $C_{3-4}$ alkyl) or $Si(CH_3)_3$;
$R^2$ and $R^3$ independently represent $C_{1-2}$ alkyl (e.g. methyl) or $C_{1-2}$ alkoxy (e.g. ethoxy); or $R^2$ and $R^3$ together combine to form $C_{3-6}$ alkylene (e.g. $C_{4-5}$ alkylene, such as $C_4$ alkylene);
L is a direct bond or, particularly, —$CH_2$—;
A represents CH or N;
$G^1$ represents H or methyl;
$A^2$ and $A^3$ both represent $C(R^a)$, or one of $A^2$ and $A^3$ represents N and the other represents $C(R^a)$;
$R^a$, $R^b$, $R^c$ and $R^d$ independently represent (or, particularly, one or two (e.g. one) of $R^a$, $R^b$, $R^c$ and $R^d$ represents) H, halo, hydroxy, or particularly, cyano, $P(O)R^{6c}R^{6d}$, $SF_5$, —C≡CH, —O—$CH_2CH_2$—N($R^{6e}$)$R^{6f}$, —C(O)NHC$_{1-2}$ alkyl, —C(O)NHCH$_2$CH$_2$—N($R^{6e}$)$R^{6f}$, —S(O)$_2$R$^{6g}$, —O—[CH$_2$CH$_2$O]$_{2-7}$—CH$_3$, —S—C$_{1-4}$ alkyl, —S—C$_{2-4}$ hydroxyalkyl, C$_{1-4}$ hydroxyalkyl, C$_{1-4}$ alkyl or C$_{1-4}$ alkoxy, which latter two groups are optionally substituted by one or more halo atoms (e.g. $R^a$, $R^b$, $R^c$ and $R^d$ independently represent H, halo, hydroxy, or particularly, $P(O)R^{6c}R^{6d}$, $SF_5$, —C≡CH, —O—$CH_2CH_2$—N($R^{6e}$)$R^{6f}$, —C(O)NHCH$_2$, —C(O)NHCH$_2$CH$_2$—N($R^{6e}$)$R^{6f}$, —S(O)$_2$R$^{6g}$, —O—[CH$_2$CH$_2$O]$_{2-7}$—CH$_3$, —S—C$_{1-4}$ alkyl, —S—C$_{2-4}$ hydroxyalkyl, C$_{1-4}$ hydroxyalkyl, C$_{1-4}$ alkyl or C$_{1-4}$ alkoxy, which latter two groups are optionally substituted by one or more halo atoms);
or $R^b$ and $R^c$, together with the C-atoms to which they are attached, form a fused, 5- or 6-membered aromatic, heteroaromatic or heterocyclic ring, which ring:
(i) when heteroaromatic or heterocyclic contains one to three heteroatoms selected from N, O and S; and
(ii) is optionally substituted by one or more substituents selected from H, halo, hydroxy, oxo, amino, $C_{1-2}$ alkyl and $C_{1-2}$ alkoxy, which latter two groups are optionally substituted by one or more halo atoms;

$R^{6c}$ and $R^{6d}$ both represent methyl;
$R^{6e}$ and $R^{6f}$ both represent $C_{1-2}$ alkyl or, together with the N-atom to which they are attached, form a 5- or 6-membered heterocyclic group that is fully saturated and which heterocyclic group contains one N atom (the atom to which $R^{6e}$ and $R^{6f}$ are attached) and, optionally, one further heteroatom selected from O, S and N, and which heterocyclic group is optionally substituted by one or more substituents selected from halo, hydroxy, oxo, $C_{1-4}$ alkyl and $C_{1-4}$ alkoxy; and
$R^{6g}$ represents $C_{1-2}$ alkyl or cyclopropyl, which latter two groups are optionally substituted by one or more halo atoms,
or a pharmaceutically acceptable salt, solvate or isotopic derivative thereof.

Particular compounds of formula Ib that may be mentioned include those in which:
$R^a$ to $R^d$ are all H;
$R^a$ to $R^c$ are all H and $R^d$ is other than H; or
$R^a$ and $R^b$ are both H and $R^c$ and $R^d$ are both other than H.

Particular embodiments of the invention that may be mentioned include those in which the compound of formula Ia or Ib is a compound of formula Ic,

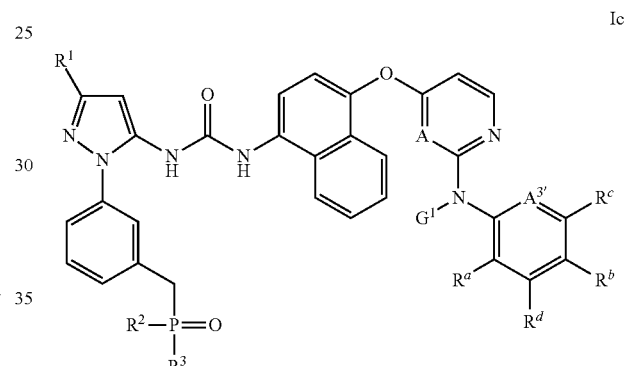

or a pharmaceutically acceptable salt, solvate or isotopic derivative thereof,
wherein $R^1$ to $R^3$, A, $G^1$ and $R^a$ to $R^d$ are as defined above in respect of compounds of formula Ib and $A^{3'}$ represents CH or N.

Particular compounds of formula Ic that may be mentioned include those in which:
$R^a$ to $R^d$ are all H;
$R^a$ to $R^c$ are all H and $R^d$ is other than H; or
$R^a$ and $R^b$ are both H and $R^c$ and $R^d$ are both other than H.

Embodiments of the invention that may be mentioned include those in which one or more of the following definitions apply to the compound of formula Ib or Ic:
(1) $R^1$ represents $C_{3-4}$ alkyl (e.g. isopropyl or tert-butyl) or $Si(CH_3)_3$;
(2) $R^2$ and $R^3$ independently represent $C_{1-2}$ alkoxy (e.g. ethoxy) or, particularly, $C_{1-2}$ alkyl (e.g. methyl), or $R^2$ and $R^3$ together combine to form $C_4$ alkylene;
(3) $G^1$ represents methyl or, particularly, H;
(4) either
(i) $R^a$, $R^b$, $R^c$ and $R^d$ are all H,
(ii) one of $R^a$, $R^b$, $R^c$ and $R^d$ is —S—CH$_2$CH$_2$—OH, $P(O)R^{6c}R^{6d}$, $SF_5$, —OCH$_3$, —O—CH$_2$CH$_2$—N($R^{6e}$)$R^{6f}$, —C(O)NHCH$_2$CH$_2$—N($R^{6e}$)$R^{6f}$, —S(O)$_2$R$^{6g}$ or —O—[CH$_2$CH$_2$O]$_{2-7}$—CH$_3$, and the other three of $R^a$, $R^b$, $R^c$ and $R^d$ are H,
(iii) one of $R^c$ and $R^d$ is —C(O)NHCH$_2$CH$_2$—N($R^{6e}$)$R^{6f}$, —O—CH$_2$CH$_2$—N($R^{6e}$)$R^{6f}$, —S(O)$_2$R$^{6g}$ or —O—

[CH₂CH₂O]₂₋₇—CH₃ and the other of $R^c$ and $R^d$ is —C≡CH or, particularly, cyano, $C_{1-3}$ alkyl (e.g. methyl) or $C_{1-3}$ alkoxy (e.g. methoxy), which alkyl or alkoxy groups are optionally substituted by one or more fluoro atoms (e.g. the other of $R^c$ and $R^d$ is —C≡CH or, particularly, $C_{1-3}$ alkyl (e.g. methyl) or $C_{1-3}$ alkoxy (e.g. methoxy), which alkyl or alkoxy groups are optionally substituted by one or more fluoro atoms), and $R^a$ and $R^b$ are both H, or (iv) $R^a$ is H, $R^d$ is H or methyl and $R^b$ and $R^c$, together with the C-atoms to which they are attached, form a fused ring selected from pyrrolidinone, pyrazole and isoxazole, wherein the latter ring is optionally substituted with amino;

(5) $R^{6c}$ and $R^{6d}$ are both methyl;
(6) $N(R^{6e})R^{6f}$ represents dimethylamino or, particularly, morpholin-4-yl;
(7) $R^{6g}$ represents methyl or, particularly, cyclopropyl, which latter two groups are optionally substituted by one or more halo atoms.

Particular embodiments of the compounds of formula I, Ia, Ib and Ic that may be mentioned include those in which the structural fragment

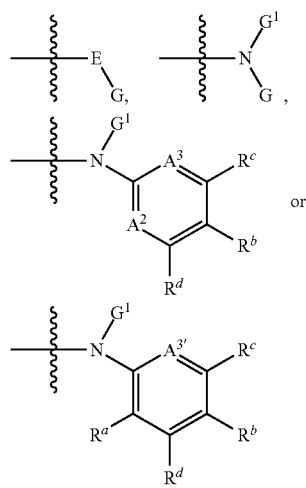

represents a group selected from:

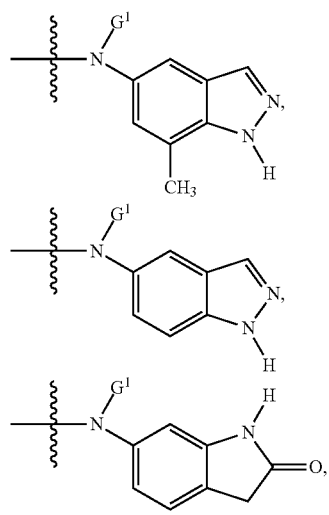

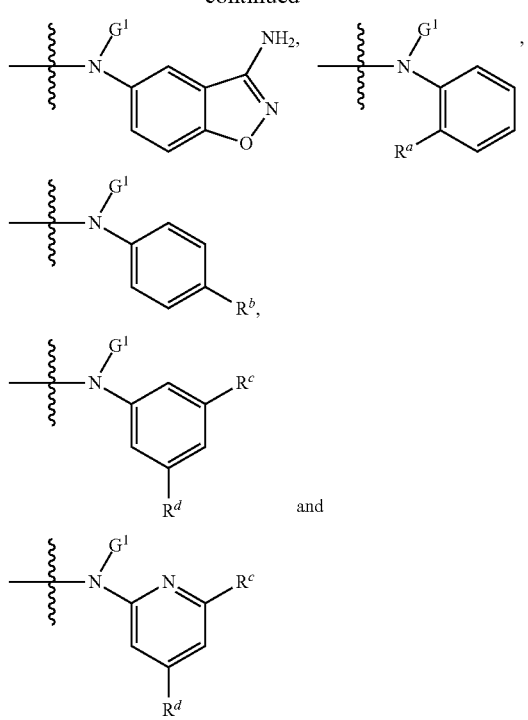

wherein $G^1$ and $R^a$ to $R^d$ are as defined above in respect of compounds of formula Ib or Ic.

In this regard, particular embodiments of the invention that may be mentioned include those in which the compound of formula I, Ia, Ib or Ic is a compound of formula Id, Ie or If.

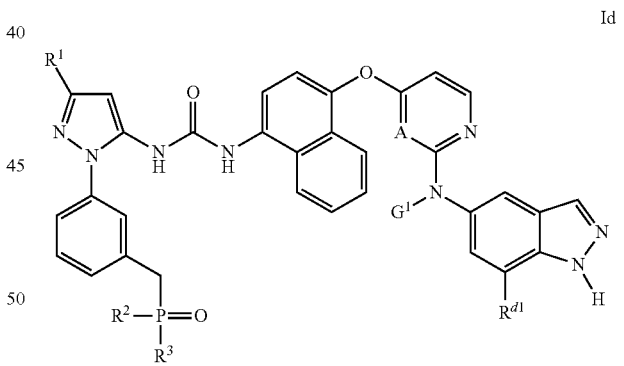

Id

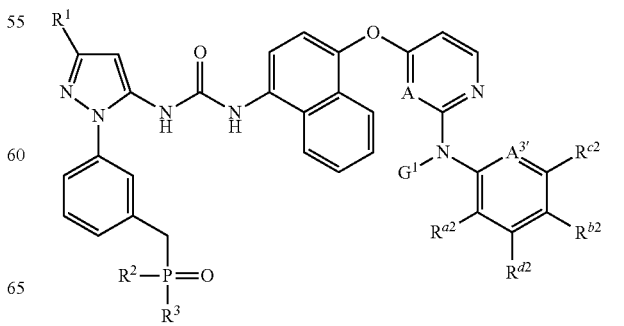

Ie

-continued

If

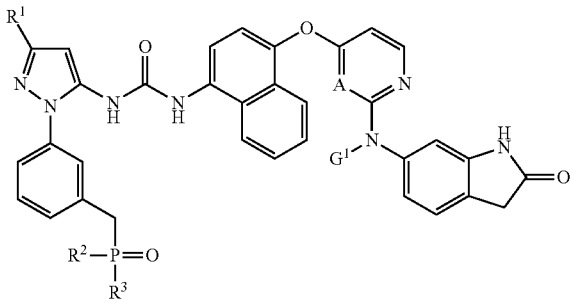

or a pharmaceutically acceptable salt, solvate or isotopic derivative thereof,
wherein
$R^1$ to $R^3$, A, $A^{3'}$ and $G^1$ are as defined above in respect of compounds of formula I, Ia, Ib or Ic;
$R^{d1}$ is as defined above for $R^d$ in respect of compounds of formula Ib and Ic; and
$R^{a2}$ to $R^{d2}$ are as defined above for $R^a$ to $R^d$, respectively, in respect of compounds of formula Ib and Ic.

Embodiments of the invention that may be mentioned include those in which one or more of the following definitions apply to the compound of formula Id, Ie or If:
(1) $R^1$ represents $C_{3-4}$ alkyl (e.g. tert-butyl or iso-propyl);
(2) $R^2$ and $R^3$ independently represent $C_{1-2}$ alkyl (e.g. methyl) or $R^2$ and $R^3$ together combine to form $C_4$ alkylene;
(3) $G^1$ represents H;
(4) $A^{3'}$ represents N or, particularly, CH;
(5) either
  (i) $R^{a2}$, $R^{b2}$, $R^{c2}$ and $R^{d2}$ and are all H,
  (ii) one of $R^{c2}$ and $R^{d2}$ is —O—CH$_2$CH$_2$—N($R^{6e}$)$R^{6f}$, —C(O)NHCH$_2$CH$_2$—N($R^{6e}$)$R^{6f}$ or —O—[CH$_2$CH$_2$O]$_{2-7}$—CH$_3$, and the other three of $R^{a2}$, $R^{b2}$, $R^{c2}$ and $R^{d2}$ are H,
  (iii) one of $R^{c2}$ and $R^{d2}$ is —C≡CH, —CH$_3$ or, particularly, cyano, —CF$_3$, —OCH$_3$ or —OCF$_3$ (e.g. one of $R^{c2}$ and $R^{d2}$ is —C≡CH, —CH$_3$ or, particularly, —CF$_3$, —OCH$_3$ or —OCF$_3$), the other of $R^{c2}$ and $R^{d2}$ is —C(O)NHCH$_2$CH$_2$—N($R^{6e}$)$R^{6f}$, —O—CH$_2$CH$_2$—N($R^{6e}$)$R^{6f}$, —S(O)$_2$$R^{6g}$ or —O—[CH$_2$CH$_2$O]$_{2-7}$—CH$_3$, and $R^{a2}$ and $R^{b2}$ are both H,
  (iv) $R^{b2}$ is P(O)$R^{6c}$$R^{6d}$, SF$_5$, or —S—CH$_2$CH$_2$—OH, and $R^{a2}$, $R^{c2}$ and $R^{d2}$ are all H, or
  (v) $R^{d1}$ is H or methyl;
(6) $R^{6c}$ and $R^{6d}$ are both methyl;
(7) N($R^{6e}$)$R^{6f}$ represents morpholin-4-yl;
(8) $R^{6g}$ represents methyl or, particularly, cyclopropyl.

Other compounds of formula I, Ia, Ib, Ic, Id, Ie or If that may be mentioned include the compounds of the examples described hereinafter. Thus, embodiments of the invention that may be mentioned include those in which the compound of formula I (or, where applicable, Ia, Ib, Ic, Id or Ie) is a compound selected from the list:

1-(3-(tert-Butyl)-1-(4-(dimethylphosphoryl)phenyl)-1H-pyrazol-5-yl)-3-(4-((2-(phenylamino)pyrimidin-4-yl)oxy)naphthalen-1-yl)urea;
1-(3-(tert-Butyl)-1-(3-(dimethylphosphoryl)phenyl)-1H-pyrazol-5-yl)-3-(4-((2-(phenylamino)pyrimidin-4-yl)oxy)naphthalen-1-yl)urea;
N-(4-((4-(3-(3-(tert-Butyl)-1-(4-(dimethylphosphoryl)phenyl)-1H-pyrazol-5-yl)ureido)naphthalen-1-yl)oxy)pyridin-2-yl)-2-methoxyacetamide;
1-(1-(4-(Dimethylphosphoryl)phenyl)-3-isopropyl-1H-pyrazol-5-yl)-3-(4-((2-(phenylamino)pyrimidin-4-yl)oxy)naphthalen-1-yl)urea;
1-(1-(4-(Dimethylphosphoryl)phenyl)-3-(trimethylsilyl)-1H-pyrazol-5-yl)-3-(4-((2-(phenylamino)pyrimidin-4-yl)oxy)naphthalen-1-yl)urea;
1-(3-(tert-Butyl)-1-(4-((dimethylphosphoryl)methyl)phenyl)-1H-pyrazol-5-yl)-3-(4-((2-(phenylamino)pyrimidin-4-yl)oxy)naphthalen-1-yl)urea;
1-(4-((2-((1H-Indazol-5-yl)amino)pyrimidin-4-yl)oxy)naphthalen-1-yl)-3-(3-(tert-butyl)-1-(4-(dimethylphosphoryl)phenyl)-1H-pyrazol-5-yl)urea;
1-(3-(tert-Butyl)-1-(4-(1-oxidophospholan-1-yl)phenyl)-1H-pyrazol-5-yl)-3-(4-((2-(phenylamino)pyrimidin-4-yl)oxy)naphthalen-1-yl)urea;
Ethyl (4-(3-(tert-butyl)-5-(3-(4-((2-(phenylamino)pyrimidin-4-yl)oxy)naphthalen-1-yl)ureido)-1H-pyrazol-1-yl)phenyl)(methyl)phosphinate;
1-(4-((2-((1H-Indazol-5-yl)amino)pyrimidin-4-yl)oxy)naphthalen-1-yl)-3-(3-(tert-butyl)-1-(3-(dimethylphosphoryl)phenyl)-1H-pyrazol-5-yl)urea;
1-(3-(tert-Butyl)-1-(3-(dimethylphosphoryl)phenyl)-1H-pyrazol-5-yl)-3-(4-((2-((2-oxoindolin-6-yl)amino)pyrimidin-4-yl)oxy)naphthalen-1-yl)urea;
1-(4-((2-((3-Aminobenzo[d]isoxazol-5-yl)amino)pyrimidin-4-yl)oxy)naphthalen-1-yl)-3-(3-(tert-butyl)-1-(3-(dimethylphosphoryl)phenyl)-1H-pyrazol-5-yl)urea;
1-(3-(tert-Butyl)-1-(3-(dimethylphosphoryl)phenyl)-1H-pyrazol-5-yl)-3-(4-((2-((7-methyl-1H-indazol-5-yl)amino)pyrimidin-4-yl)oxy)naphthalen-1-yl)urea;
1-(3-(tert-Butyl)-1-(4-(dimethylphosphoryl)phenyl)-1H-pyrazol-5-yl)-3-(4-((2-((2-oxoindolin-6-yl)amino)pyrimidin-4-yl)oxy)naphthalen-1-yl)urea;
1-(3-(tert-Butyl)-1-(4-(dimethylphosphoryl)phenyl)-1H-pyrazol-5-yl)-3-(4-((2-(methyl(phenyl)amino)pyrimidin-4-yl)oxy)naphthalen-1-yl)urea;
3-((4-((4-(3-(3-(tert-Butyl)-1-(3-(dimethylphosphoryl)phenyl)-1H-pyrazol-5-yl)ureido)naphthalen-1-yl)oxy)pyrimidin-2-yl)amino)-N-(2-morpholinoethyl)benzamide;
1-(3-(tert-Butyl)-1-(4-(dimethylphosphoryl)phenyl)-1H-pyrazol-5-yl)-3-(4-((2-((3-(2-morpholinoethoxy)phenyl)amino)pyrimidin-4-yl)oxy)naphthalen-1-yl)urea;
1-(3-(tert-Butyl)-1-(4-(dimethylphosphoryl)phenyl)-1H-pyrazol-5-yl)-3-(4-((2-((4-((2-hydroxyethyl)thio)phenyl)amino)pyrimidin-4-yl)oxy)naphthalen-1-yl)urea;
(4-(3-(tert-Butyl)-5-(3-(4-((2-(phenylamino)pyrimidin-4-yl)oxy)naphthalen-1-yl)ureido)-1H-pyrazol-1-yl)phenyl)(methyl)phosphinic acid;
1-(4-((2-((3-Aminobenzo[d]isoxazol-5-yl)amino)pyrimidin-4-yl)oxy)naphthalen-1-yl)-3-(3-(tert-butyl)-1-(4-(dimethylphosphoryl)phenyl)-1H-pyrazol-5-yl)urea;
1-(3-(tert-Butyl)-1-(4-(dimethylphosphoryl)phenyl)-1H-pyrazol-5-yl)-3-(4-((2-((7-methyl-1H-indazol-5-yl)amino)pyrimidin-4-yl)oxy)naphthalen-1-yl)urea;
1-(3-(tert-Butyl)-1-(4-(diethylphosphoryl)phenyl)-1H-pyrazol-5-yl)-3-(4-((2-(phenylamino)pyrimidin-4-yl)oxy)naphthalen-1-yl)urea;
1-(3-(tert-Butyl)-1-(3-((dimethylphosphoryl)methyl)phenyl)-1H-pyrazol-5-yl)-3-(4-((2-(phenylamino)pyrimidin-4-yl)oxy)naphthalen-1-yl)urea;
3-((4-((4-(3-(3-(tert-Butyl)-1-(4-(dimethylphosphoryl)phenyl)-1H-pyrazol-5-yl)ureido)naphthalen-1-yl)oxy)pyrimidin-2-yl)amino)-N-(2-morpholinoethyl)benzamide;
1-(3-(tert-Butyl)-1-(4-(dimethylphosphoryl)phenyl)-1H-pyrazol-5-yl)-3-(4-((2-((4-(dimethylphosphoryl)phenyl)amino)pyrimidin-4-yl)oxy)naphthalen-1-yl)urea;

(S)-1-(3-(tert-Butyl)-1-(4-(dimethylphosphoryl)phenyl)-1H-pyrazol-5-yl)-3-(4-((2-(2-(hydroxymethyl)pyrrolidin-1-yl)pyrimidin-4-yl)oxy)naphthalen-1-yl)urea;

(R)-1-(3-(tert-Butyl)-1-(4-(dimethylphosphoryl)phenyl)-1H-pyrazol-5-yl)-3-(4-((2-(2-(hydroxymethyl)pyrrolidin-1-yl)pyrimidin-4-yl)oxy)naphthalen-1-yl)urea;

1-(3-(tert-Butyl)-1-(4-(dimethylphosphoryl)phenyl)-1H-pyrazol-5-yl)-3-(4-((2-((4-(pentafluorothio)phenyl)amino)pyrimidin-4-yl)oxy)naphthalen-1-yl)urea;

1-(3-(tert-Butyl)-1-(4-(dimethylphosphoryl)phenyl)-1H-pyrazol-5-yl)-3-(4-((2-(phenylthio)pyrimidin-4-yl)oxy)naphthalen-1-yl)urea;

1-(3-(tert-Butyl)-1-(4-(dimethylphosphoryl)phenyl)-1H-pyrazol-5-yl)-3-(4-((2-((3-hydroxypropyl)(methyl)amino)pyrimidin-4-yl)oxy)naphthalen-1-yl)urea;

1-(3-(tert-Butyl)-1-(4-(dimethylphosphoryl)phenyl)-1H-pyrazol-5-yl)-3-(4-((2-((3-hydroxypropyl)amino)pyrimidin-4-yl)oxy)naphthalen-1-yl)urea;

1-(3-(tert-Butyl)-1-(3-((dimethylphosphoryl)methyl)phenyl)-1H-pyrazol-5-yl)-3-(4-((2-((7-methyl-1H-indazol-5-yl)amino)pyrimidin-4-yl)oxy)naphthalen-1-yl)urea;

1-(3-(tert-Butyl)-1-(3-((dimethylphosphoryl)methyl)phenyl)-1H-pyrazol-5-yl)-3-(4-((2-((2-oxoindolin-6-yl)amino)pyrimidin-4-yl)oxy)naphthalen-1-yl)urea;

1-(3-(tert-Butyl)-1-(3-((dimethylphosphoryl)methyl)phenyl)-1H-pyrazol-5-yl)-3-(4-((2-((3-(2-morpholinoethoxy)phenyl)amino)pyrimidin-4-yl)oxy)naphthalen-1-yl)urea;

1-(1-(3-((Dimethylphosphoryl)methyl)phenyl)-3-(trimethylsilyl)-1H-pyrazol-5-yl)-3-(4-((2-(phenylamino)pyrimidin-4-yl)oxy)naphthalen-1-yl)urea;

1-(3-(tert-Butyl)-1-(3-((diethylphosphoryl)methyl)phenyl)-1H-pyrazol-5-yl)-3-(4-((2-((7-methyl-1H-indazol-5-yl)amino)pyrimidin-4-yl)oxy)naphthalen-1-yl)urea;

1-(1-(3-((Dimethylphosphoryl)methyl)phenyl)-3-isopropyl-1H-pyrazol-5-yl)-3-(4-((2-((7-methyl-1H-indazol-5-yl)amino)pyrimidin-4-yl)oxy)naphthalen-1-yl)urea;

3-((4-((4-(3-(1-(3-((Dimethylphosphoryl)methyl)phenyl)-3-isopropyl-1H-pyrazol-5-yl)ureido)naphthalen-1-yl)oxy)pyrimidin-2-yl)amino)-5-methoxy-N-(2-morpholino ethyl)benzamide;

1-(1-(3-((Dimethylphosphoryl)methyl)phenyl)-3-isopropyl-1H-pyrazol-5-yl)-3-(4-((2-((3-methoxy-5-(2-morpholinoethoxy)phenyl)amino)pyrimidin-4-yl)oxy)naphthalen-1-yl)urea;

1-(1-(3-((dimethylphosphoryl)methyl)phenyl)-3-isopropyl-1H-pyrazol-5-yl)-3-(4-((2-((2-methoxyphenyl)amino)pyrimidin-4-yl)oxy)naphthalen-1-yl)urea;

1-(3-(tert-butyl)-1-(3-((dimethylphosphoryl)methyl)phenyl)-1H-pyrazol-5-yl)-3-(4-((2-(phenylamino)pyridin-4-yl)oxy)naphthalen-1-yl)urea;

1-(1-(3-((dimethylphosphoryl)methyl)phenyl)-3-isopropyl-1H-pyrazol-5-yl)-3-(4-((2-(phenylamino)pyridin-4-yl)oxy)naphthalen-1-yl)urea;

3-((4-((4-(3-(1-(3-((Dimethylphosphoryl)methyl)phenyl)-3-isopropyl-1H-pyrazol-5-yl)ureido)naphthalen-1-yl)oxy)pyrimidin-2-yl)amino)-5-ethynyl-N-(2-morpholinoethyl)benzamide;

1-(3-(tert-Butyl)-1-(3-((1-oxidophospholan-1-yl)methyl)phenyl)-1H-pyrazol-5-yl)-3-(4-((2-(phenylamino)pyridin-4-yl)oxy)naphthalen-1-yl)urea;

1-(1-(3-((Dimethylphosphoryl)methyl)phenyl)-3-isopropyl-1H-pyrazol-5-yl)-3-(4-((2-((3-methoxy-5-(2-(2-(2-methoxyethoxy)ethoxy)ethoxy)phenyl)amino)pyrimidin-4-yl)oxy)naphthalen-1-yl)urea;

1-(4-((2-((3-(Cyclopropylsulfonyl)-5-methoxyphenyl)amino)pyrimidin-4-yl)oxy)naphthalen-1-yl)-3-(1-(3-((dimethylphosphoryl)methyl)phenyl)-3-isopropyl-1H-pyrazol-5-yl)urea;

3-((4-((4-(3-(3-(tert-butyl)-1-(3-((dimethylphosphoryl)methyl)phenyl)-1H-pyrazol-5-yl)ureido)naphthalen-1-yl)oxy)pyrimidin-2-yl)amino)-5-methoxy-N-(2-morpholinoethyl)-benzamide;

1-(1-(3-((dimethylphosphoryl)methyl)phenyl)-3-isopropyl-1H-pyrazol-5-yl)-3-(4-((2-((3-(2-morpholinoethoxy)-5-(trifluoromethoxy)phenyl)amino)pyrimidin-4-yl)oxy)naphthalen-1-yl)urea;

1-(1-(3-((dimethylphosphoryl)methyl)phenyl)-3-isopropyl-1H-pyrazol-5-yl)-3-(4-((2-((3-(2-morpholinoethoxy)-5-(trifluoromethyl)phenyl)amino)pyrimidin-4-yl)oxy)naphthalen-1-yl)urea;

3-((4-((4-(3-(1-(3-((dimethylphosphoryl)methyl)phenyl)-3-isopropyl-1H-pyrazol-5-yl)ureido)naphthalen-1-yl)oxy)pyridin-2-yl)amino)-5-methoxy-N-(2-morpholinoethyl)-benzamide;

1-(1-(3-((dimethylphosphoryl)methyl)phenyl)-3-isopropyl-1H-pyrazol-5-yl)-3-(4-((2-((3-methoxy-5-(2-morpholinoethoxy)phenyl)amino)pyridin-4-yl)oxy)naphthalen-1-yl)urea;

1-(4-((2-((3-(2,5,8,11-tetraoxatridecan-13-yloxy)-5-methoxyphenyl)amino)pyrimidin-4-yl)oxy)naphthalen-1-yl)-3-(1-(3-((dimethylphosphoryl)methyl)phenyl)-3-isopropyl-1H-pyrazol-5-yl)urea;

1-(1-(3-((dimethylphosphoryl)methyl)phenyl)-3-isopropyl-1H-pyrazol-5-yl)-3-(4-((2-((3-(methylsulfonyl)-5-(2-morpholinoethoxy)phenyl)amino)pyrimidin-4-yl)oxy)naphthalen-1-yl)urea;

1-(1-(3-((dimethylphosphoryl)methyl)phenyl)-3-isopropyl-1H-pyrazol-5-yl)-3-(5-((2-((3-methoxy-5-(2-morpholinoethoxy)phenyl)amino)pyrimidin-4-yl)oxy)quinolin-8-yl) urea;

1-(4-((2-((3-(2,5,8,11,14-pentaoxahexadecan-16-yloxy)-5-methoxyphenyl)amino)-pyrimidin-4-yl)oxy)naphthalen-1-yl)-3-(1-(3-((dimethylphosphoryl)methyl)phenyl)-3-isopropyl-1H-pyrazol-5-yl)urea;

1-(1-(3-((dimethylphosphoryl)methyl)phenyl)-3-isopropyl-1H-pyrazol-5-yl)-3-(4-((2-((3-ethynyl-5-(2-morpholinoethoxy)phenyl)amino)pyrimidin-4-yl)oxy)naphthalen-1-yl)urea;

1-(4-((2-((3-cyano-5-(2-morpholinoethoxy)phenyl)amino)pyrimidin-4-yl)oxy)naphthalen-1-yl)-3-(1-(3-((dimethylphosphoryl)methyl)phenyl)-3-isopropyl-1H-pyrazol-5-yl)urea;

3-((4-((4-(3-(3-(tert-butyl)-1-(3-((dimethylphosphoryl)methyl)phenyl)-1H-pyrazol-5-yl)-ureido)naphthalen-1-yl)oxy)pyrimidin-2-yl)amino)-N-(2-morpholinoethyl)-5-(trifluoromethyl)benzamide;

3-((4-((4-(3-(3-(tert-butyl)-1-(3-((dimethylphosphoryl)methyl)phenyl)-1H-pyrazol-5-yl)-ureido)naphthalen-1-yl)oxy)pyrimidin-2-yl)amino)-N-(2-morpholinoethyl)-5-(trifluoromethoxy)benzamide;

1-(3-(tert-butyl)-1-(3-((dimethylphosphoryl)methyl)phenyl)-1H-pyrazol-5-yl)-3-(4-((2-((3-methoxy-5-(2-(2-(2-methoxyethoxy)ethoxy)ethoxy)phenyl)amino)pyrimidin-4-yl)oxy)-naphthalen-1-yl)urea; and 1-(3-(tert-Butyl)-1-(3-((dimethylphosphoryl)methyl)phenyl)-1H-pyrazol-5-yl)-3-(4-((2-((3-(2-morpholinoethoxy)-5-(trifluoromethyl)phenyl)amino)pyrimidin-4-yl)oxy)naphthalen-1-yl)urea, or a pharmaceutically acceptable salt, solvate or isotopic derivative thereof.

Examples of salts of compounds of formula I, Ia, Ib, Ic, Id, Ie or If include all pharmaceutically acceptable salts, such as, without limitation, acid addition salts of strong mineral acids such as HCl and HBr salts and addition salts of strong organic acids such as methanesulfonic acid.

References herein to a compound of the invention (a compound of formula I, Ia, Ib, Ic, Id, Ie or If) are intended to include references to the compound and to all pharmaceutically acceptable salts, solvates and/or tautomers of said compound, unless the context specifically indicates otherwise. In this respect, solvates that may be mentioned include hydrates.

The compounds of the invention (compounds of formula I, Ia, Ib, Ic, Id, Ie or If) are p38 MAP kinase inhibitors (especially of the alpha subtype) and are therefore useful in medicine, in particular for the treatment of inflammatory diseases. Further aspects of the invention that may be mentioned therefore include the following.

(a) A pharmaceutical formulation comprising compound of formula I, Ia, Ib, Ic, Id, Ie or If, as hereinbefore defined, or pharmaceutically acceptable salt, solvate or isotopic derivative thereof, in admixture with a pharmaceutically acceptable adjuvant, diluent or carrier.

(b) A combination product comprising
  (A) a compound of formula I, Ia, Ib, Ic, Id, Ie or If, as hereinbefore defined, or pharmaceutically acceptable salt, solvate or isotopic derivative thereof, and
  (B) another therapeutic agent,
  wherein each of components (A) and (B) is formulated in admixture with a pharmaceutically-acceptable adjuvant, diluent or carrier.

In this aspect of the invention, the combination product may be either a single (combination) pharmaceutical formulation or a kit-of-parts.

Thus, this aspect of the invention encompasses a pharmaceutical formulation including a compound of formula I, Ia, Ib, Ic, Id, Ie or If, as hereinbefore defined, or pharmaceutically acceptable salt, solvate or isotopic derivative thereof, and another therapeutic agent, in admixture with a pharmaceutically acceptable adjuvant, diluent or carrier (which formulation is hereinafter referred to as a "combined preparation").

It also encompasses a kit of parts comprising components:
  (i) a pharmaceutical formulation including a compound of formula I, Ia, Ib, Ic, Id, Ie or If, as hereinbefore defined, or pharmaceutically acceptable salt, solvate or isotopic derivative thereof, in admixture with a pharmaceutically acceptable adjuvant, diluent or carrier; and
  (ii) a pharmaceutical formulation including another therapeutic agent, in admixture with a pharmaceutically-acceptable adjuvant, diluent or carrier,
  which components (i) and (ii) are each provided in a form that is suitable for administration in conjunction with the other.

Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier.

(c) A process for preparing the pharmaceutical formulation of aspect (a) above, sad process comprising the step of admixing the compound of formula I, Ia, Ib, Ic, Id, Ie or If, as hereinbefore defined, or pharmaceutically acceptable salt, solvate or isotopic derivative thereof, with a pharmaceutically acceptable adjuvant, diluent or carrier.
  Embodiments of this aspect of the invention that may be mentioned include those in which the pharmaceutically acceptable adjuvant, diluent or carrier is a topically acceptable adjuvant, diluent or carrier (and/or wherein the process is for preparing a topical pharmaceutical formulation, i.e. a pharmaceutical formulation that is adapted for topical administration).

(d) A compound of formula I, Ia, Ib, Ic, Id, Ie or If, as hereinbefore defined, or pharmaceutically acceptable salt, solvate or isotopic derivative thereof, for use in medicine (or for use as a medicament or as a pharmaceutical).

(e) A compound of formula I, Ia, Ib, Ic, Id, Ie or If, as hereinbefore defined, or pharmaceutically acceptable salt, solvate or isotopic derivative thereof, or a pharmaceutical formulation or combination product as defined in connection with aspect (a) or (b) of the invention, for use in the treatment or prevention of an inflammatory disease.

(f) The use of
  a compound of formula I, Ia, Ib, Ic, Id, Ie or If, as hereinbefore defined, or pharmaceutically acceptable salt, solvate or isotopic derivative thereof, or
  a pharmaceutical formulation or combination product as defined in connection with aspect (a) or (b) of the invention,
for the preparation of a medicament for the treatment or prevention of an inflammatory disease.

(g) A method of treating or preventing an inflammatory disease, said method comprising administering to a subject an effective amount of
  a compound of formula I, Ia, Ib, Ic, Id, Ie or If, as hereinbefore defined, or pharmaceutically acceptable salt, solvate or isotopic derivative thereof, or
  a pharmaceutical formulation or combination product as defined in connection with aspect (a) or (b) of the invention.

(h) A method of sensitizing a subject to the anti-inflammatory effects of a corticosteroid, said method comprising administering to the subject an effective amount of
  a compound of formula I, Ia, Ib, Ic, Id, Ie or If, as hereinbefore defined, or pharmaceutically acceptable salt, solvate or isotopic derivative thereof, or
  a pharmaceutical formulation or combination product as defined in connection with aspect (a) or (b) of the invention.
  Embodiments of this aspect of the invention that may be mentioned include those in which the subject is one who has become refractory to the anti-inflammatory effects of a corticosteroid.

Formulations

In relation to aspects (a) and (b) above, diluents and carriers that may be mentioned include those suitable for parenteral, oral, topical, mucosal and rectal administration.

The pharmaceutical formulations and combination products of aspects (a) and (b) above may be prepared e.g. for parenteral, subcutaneous, intramuscular, intravenous, intraarticular, intravitreous, periocular, retrobulbar, subconjunctival, sub-Tenon, topical ocular or peri-articular administration, particularly in the form of liquid solutions, emulsions or suspensions; for oral administration, particularly in the form of tablets or capsules, and especially involving technologies aimed at furnishing colon-targeted drug release (Patel, M. M. *Expert Opin. Drug Deliv.* 2011, 8 (10), 1247-1258); for topical e.g. pulmonary or intranasal administration, particularly in the form of powders, nasal drops or aerosols and transdermal administration; for topical ocular administration, particularly in the form of solutions, emulsions, suspensions, ointments, implants/inserts, gels, jellies or liposomal microparticle formulations (Ghate, D.; Edelhauser, H. F. *Expert Opin. Drug Deliv.* 2006, 3 (2), 275-287);

for ocular administration, particularly in the form of biodegradable and non-biodegradable implants, liposomes and nanoparticles (Thrimawithana, T. R. et al. *Drug Discov. Today* 2011, 16 (5/6), 270-277); for mucosal administration e.g. to buccal, sublingual or vaginal mucosa, and for rectal administration e.g. in the form of a suppository or enema.

The pharmaceutical formulations and combination products of aspects (a) and (b) above may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered sprays. For buccal administration typical excipients include sugars, calcium stearate, magnesium stearate, pregelatinated starch, and the like.

Pharmaceutical formulations and combination products suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrrolidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules.

A dry shell formulation typically comprises of about 40% to 60% w/w concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

A compound of the invention may be administered topically (e.g. to the lung, eye or intestines). Thus, embodiments of aspects (a) and (b) above that may be mentioned include pharmaceutical formulations and combination products that are adapted for topical administration. Such formulations include those in which the excipients (including any adjuvant, diluent and/or carrier) are topically acceptable.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Aerosol formulations are packaged in canisters and a suitable dose is delivered by means of a metering valve (e.g. as supplied by Bespak, Valois or 3M).

Topical administration to the lung may also be achieved by use of a non-pressurised formulation such as an aqueous solution or suspension. This may be administered by means of a nebuliser. Topical administration to the lung may also be achieved by use of a dry-powder formulation. A dry powder formulation will contain the compound of the disclosure in finely divided form, typically with a mass mean aerodynamic diameter (MMAD) of 1-10 μm. The formulation will typically contain a topically acceptable diluent such as lactose, usually of large particle size e.g. an MMAD of 100 μm or more. Examples of dry powder delivery systems include SPINHALER, DISKHALER, TURBOHALER, DISKUS and CLICKHALER.

The compounds of the present invention may also be administered rectally, for example in the form of suppositories or enemas, which include aqueous or oily solutions as well as suspensions and emulsions. Such compositions are prepared following standard procedures, well known by those skilled in the art. For example, suppositories can be prepared by mixing the active ingredient with a conventional suppository base such as cocoa butter or other glycerides. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the inhibitor will be about 0.0001 to less than 4.0% (w/w).

Preferably, for topical ocular administration, the compositions administered according to the present invention will be formulated as solutions, suspensions, emulsions and other dosage forms. Aqueous solutions are generally preferred, based on ease of formulation, as well as a patient's ability to administer such compositions easily by means of instilling one to two drops of the solutions in the affected eyes. However, the compositions may also be suspensions, viscous or semi-viscous gels, or other types of solid or semi-solid compositions. Suspensions may be preferred for compounds that are sparingly soluble in water.

The compositions administered according to the present invention may also include various other ingredients, including, but not limited to, tonicity agents, buffers, surfactants, stabilizing polymer, preservatives, co-solvents and viscosity building agents. Preferred pharmaceutical compositions of the present invention include the inhibitor with a tonicity agent and a buffer. The pharmaceutical compositions of the present invention may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars such as dextrose, fructose, galactose, and/or simply polyols such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will be present in the range of 2 to 4% w/w. Preferred tonicity agents of the invention include the simple sugars or the sugar alcohols, such as D-mannitol.

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7.

Surfactants may optionally be employed to deliver higher concentrations of inhibitor. The surfactants function to solubilise the inhibitor and stabilise colloid dispersion, such as micellar solution, microemulsion, emulsion and suspension. Examples of surfactants which may optionally be used include polysorbate, poloxamer, polyosyl 40 stearate, polyoxyl castor oil, tyloxapol, triton, and sorbitan monolaurate. Preferred surfactants to be employed in the invention have a hydrophile/lipophile/balance "HLB" in the range of 12.4 to 13.2 and are acceptable for ophthalmic use, such as TritonX114 and tyloxapol.

Additional agents that may be added to the ophthalmic compositions of the present invention are demulcents which function as a stabilising polymer. The stabilizing polymer should be an ionic/charged example with precedence for topical ocular use, more specifically, a polymer that carries negative charge on its surface that can exhibit a zeta-potential of (−)10-50 mV for physical stability and capable of making a dispersion in water (i.e. water soluble). A preferred stabilising polymer of the invention would be polyelectrolyte, or polyelectrolytes if more than one, from the family of cross-linked polyacrylates, such as carbomers and Pemulen(R), specifically Carbomer 974p (polyacrylic acid), at 0.1-0.5% w/w.

Other compounds may also be added to the ophthalmic compositions of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edentate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

The medical practitioner, or other skilled person, will be able to determine a suitable dosage for the compounds of the invention, and hence the amount of the compound of the invention that should be included in any particular pharmaceutical formulation (whether in unit dosage form or otherwise).

Embodiments of the invention that may be mentioned in connection with the combination products described at (b) above include those in which the other therapeutic agent is one or more therapeutic agents that are known by those skilled in the art to be suitable for treating inflammatory diseases (e.g. the specific diseases mentioned below).

For example, for the treatment of respiratory disorders (such as COPD or asthma), the other therapeutic agent is one or more agents selected from the list comprising:
  steroids (e.g. budesonide, beclomethasone dipropionate, fluticasone propionate, mometasone furoate, fluticasone furoate);
  beta agonists (e.g. terbutaline, salbutamol, salmeterol, formoterol); and
  xanthines (e.g. theophylline).

Further, for the treatment of gastrointestinal disorders (such as Crohn's disease or ulcerative colitis), the other therapeutic agent may be, for example, one or more agents selected from the list comprising:
  5-aminosalicylic acid, or a prodrug thereof (such as sulfasalazine, olsalazine or bisalazide);
  corticosteroids (e.g. prednisolone, methylprednisolone, or budesonide);
  immunosuppressants (e.g. cyclosporin, tacrolimus, methotrexate, azathioprine or 6-mercaptopurine);
  anti-TNFα antibodies (e.g., infliximab, adalimumab, certolizumab pegol or golimumab);
  anti-IL12/IL23 antibodies (e.g., ustekinumab) or small molecule IL12/IL23 inhibitors (e.g., apilimod);
  Anti-α487 antibodies (e.g., vedolizumab);
  MAdCAM-1 blockers (e.g., PF-00547659);
  antibodies against the cell adhesion molecule α4-integrin (e.g., natalizumab);
  antibodies against the IL2 receptor α subunit (e.g., daclizumab or basiliximab);
  JAK3 inhibitors (e.g., tofacitinib or R348);
  Syk inhibitors and prodrugs thereof (e.g., fostamatinib and R-406);
  Phosphodiesterase-4 inhibitors (e.g., tetomilast);
  HMPL-004;
  probiotics;
  Dersalazine;
  semapimod/CPSI-2364; and
  protein kinase C inhibitors (e.g. AEB-071).

For the treatment of eye disorders (such as uveitis), the other therapeutic agent may be, for example, one or more agents selected from the list comprising:
  corticosteroids (e.g. dexamethasone, prednisolone, triamcinolone acetonide, difluprednate or fluocinolone acetonide);
  immunosuppressants (e.g. cyclosporin, voclosporin, azathioprine, methotrexate, mycophenolate mofetil or tacrolimus);
  anti-TNFα antibodies (e.g., infliximab, adalimumab, certolizumab pegol, ESBA-105 or golimumab);
  anti-IL-17A antibodies (e.g., secukinumab);
  mTOR inhibitors (e.g., sirolimus);
  VGX-1027;
  JAK3 inhibitors (e.g., tofacitinib or R348); and
  protein kinase C inhibitors (e.g. AEB-071).

Medical Uses

The compounds of the invention may be used as monotherapies for inflammatory diseases, or in combination therapies for such diseases.

Thus, embodiments of aspects (e) to (g) above that may be mentioned include those in which the compound of formula I, Ia, Ib, Ic, Id, Ie or If (or pharmaceutically acceptable salt, solvate or isotopic derivative thereof) is the sole pharmacologically active ingredient utilised in the treatment.

However, in other embodiments of aspects (e) to (g) above, the compound of formula I, Ia, Ib, Ic, Id, Ie or If (or pharmaceutically acceptable salt, solvate or isotopic derivative thereof) is administered to a subject who is also administered one or more other therapeutic agents (e.g. wherein the one or more other therapeutic agents are as defined above in connection with combination products).

When used herein, the term "inflammatory disease" specifically includes references to any one or more of the following:

(i) lung diseases or disorders having an inflammatory component, such as cystic fibrosis, pulmonary hypertension, lung sarcoidosis, idiopathic pulmonary fibrosis or, particularly, COPD (including chronic bronchitis and emphysema), asthma or paediatric asthma;

(ii) skin diseases or disorders having an inflammatory component, such as atopic dermatitis, allergic dermatitis, contact dermatitis or psoriasis;

(iii) nasal diseases or disorders having an inflammatory component, such as allergic rhinitis, rhinitis or sinusitis;

(iv) eye diseases or disorders having an inflammatory component, such as conjunctivitis, allergic conjunctivitis, keratoconjunctivitis sicca (dry eye), glaucoma, diabetic retinopathy, macular oedema (including diabetic macular oedema), central retinal vein occlusion (CRVO), dry and/or wet age related macular degeneration (AMD), post-operative cataract inflammation, or, particularly, uveitis (including posterior, anterior and pan uveitis), corneal graft and limbal cell transplant rejection; and (v) gastrointestinal diseases or disorders having an inflammatory component, such as gluten sensitive enteropathy (coeliac disease), eosinophilic esophagitis, intestinal graft versus host disease or, particularly, Crohn's disease or ulcerative colitis.

References herein to diseases having an inflammatory component include references to diseases that involve inflammation, whether or not there are other (non-inflammatory) symptoms or consequences of the disease.

According to a further aspect of the invention there is provided a process for the preparation of a compound of formula I which process comprises:

(a) reaction of a compound of formula II,

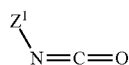

with a compound of formula III,

wherein one of $Z^1$ and $Z^2$ is a structural fragment of formula IV

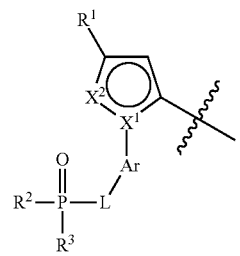

and the other of $Z^1$ and $Z^2$ is a structural fragment of formula V

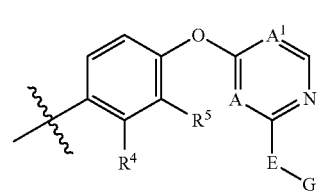

where E, L, Ar, $X^1$, $X^2$, $R^1$ to $R^5$, A, $A^1$, G and $G^1$ are as hereinbefore defined, for example under conditions known to those skilled in the art, for example at a temperature from ambient (e.g. 15 to 30° C.) to about 110° C. in the presence of a suitable organic solvent (e.g. a polar aprotic solvent such as DMF, THF, 1,4-dioxane, or mixtures thereof);

(b) reaction of a compound of formula IIa,

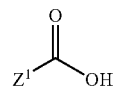

wherein $Z^1$ is as defined above, with a suitable azide-forming agent (i.e. a suitable source of a leaving group and activated azide ion, such as diphenyl phosphorazidate; see, for example, *Tetrahedron* 1974, 30, 2151-2157) under conditions known to those skilled in the art, such as at sub-ambient to ambient temperature (e.g. from an initial reaction temperature of about −5 to 5° C. to ambient temperature post-reaction) in the presence of an amine base (e.g. triethylamine or a sterically hindered base such as N,N-diisopropylethylamine) and a suitable organic solvent (e.g. a polar aprotic solvent such as DMF, THF, 1,4-dioxane, or mixtures thereof), which reaction is followed, without isolation, by thermal rearrangement (e.g. under heating) of the intermediate acyl azide (of formula $Z^1$—C(O)—$N_3$) to provide, in situ, a compound of formula II, which compound is then reacted with a compound of formula III, as defined above, to provide the compound of formula I;

(c) reaction of a compound of formula IIb,

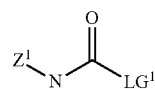

wherein $LG^1$ represents a suitable leaving group (e.g. imidazolyl, chloro, or aryloxy) and $Z^1$ is as defined above, with a compound of formula III, as defined above, for example under conditions known to those skilled in the art, such as at ambient temperature (e.g. from 15 to 30° C.), optionally in the presence of an amine base (e.g. a sterically hindered base like N,N-diisopropylethylamine) and a suitable organic solvent (e.g. an aprotic solvent, such as dichloromethane);

(d) reaction of a compound of formula VI,

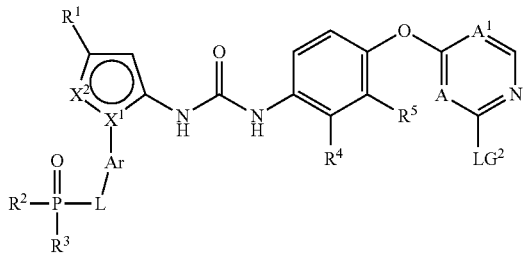

wherein LG² represents a suitable leaving group (e.g. a halo group such as fluoro, chloro, bromo or methanesulfonyl) and L, Ar, X¹, X², R¹ to R⁵, A and A¹ are as hereinbefore defined with a compound of formula VII,

wherein G and E are as hereinbefore defined, for example under conditions known to those skilled in the art (e.g. as described in *J. Am. Chem. Soc.* 2011, 133, 15686-15696), such as at elevated temperature (e.g. from 50 to 110° C.), in the presence of a suitable organic solvent (e.g. a polar aprotic solvent such as DMF, THF, 1,4-dioxane, or a protic solvent, such as trifluoroethanol or ethanol, or mixtures thereof) and, optionally, an acidic catalyst (e.g. a sulfonic acid such as para-toluenesulfonic acid, for example in the presence of approximately 0.5 to 1 equivalents of such an acid relative to the compound of formula VI or formula VII); or (e) deprotection of an protected derivative of a compound of formula I, under conditions known to those skilled in the art, wherein the protected derivative bears a protecting group on an O- or N-atom of the compound of formula I (and, for the avoidance of doubt, a protected derivative of one compound of formula I may or may not represent another compound of formula I).

Compounds of formula II may be prepared according to or by analogy with methods known to those skilled in the art, for example by reaction of a compound of formula IIa, as defined above, with an azide-forming agent, followed by rearrangement of the intermediate acyl azide (as described at (b) above; see, for example, *Tetrahedron* 1974, 30, 2151-2157).

Compounds of formula IIb may be prepared reaction of a compound of formula VIII,

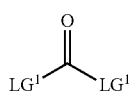

wherein LG¹ is as hereinbefore defined, with a compound of formula IX,

wherein Z¹ is as hereinbefore defined, for example under conditions known to those skilled in the art.

Amines of formula IX may be prepared from carboxylic acids of formula IIa through the route described in (b) above, where the intermediate isocyanate II is hydrolysed with water to give a carbamic acid that loses carbon dioxide to furnish IX. By the same token, the intermediate isocyanate II can be reacted with an alcohol, such as t-butanol, to generate a protected version of IX.

Certain carboxylic acids of formula IIa, where Z¹ is a structural fragment of formula IV, in which both X¹ and X² are nitrogen, may be synthesised employing the route outlined in Scheme 1 below (see also: *Bioorg. Med. Chem. Lett.* 2007, 17, 354-357). This route commences with cycloaddition of alkynes X with alkyl (Ak) diazoacetates XI to give pyrazoles XII. These pyrazoles are then coupled with aryl- or heteroaryl-boronic acids XIII, employing copper (II)-mediated ChanLam reactions (see, for example: *Tetrahedron Lett.* 1998, 39, 2941-2944), to furnish N-arylpyrazole esters XIV. Saponification of esters XIV, typically employing an alkali hydroxide, followed by acidification furnishes the desired carboxylic acids.

Scheme 1

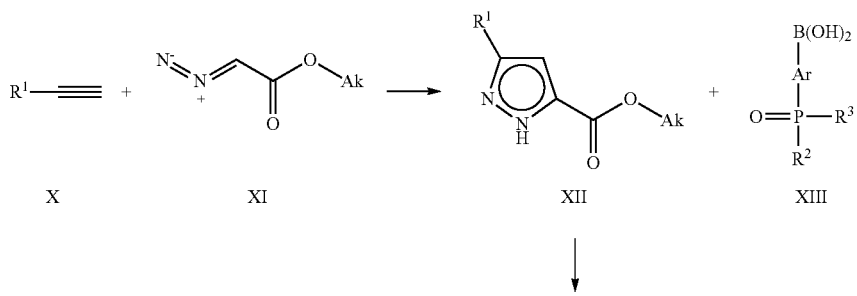

-continued

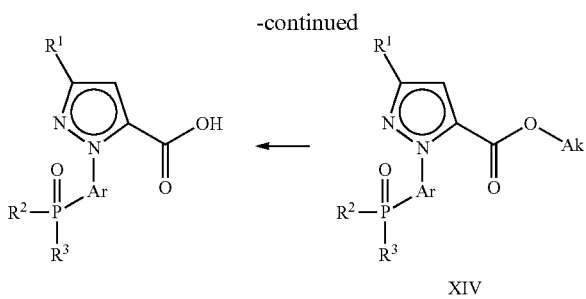

XIV

Alternatively, pyrazole XII may be subjected to a copper (II)-mediated Chan-Lam reaction with a boronic acid of formula XV—where W represents chlorine, bromine or iodine, or a latent halogen that can be revealed after the coupling step (Scheme 2)—to furnish a compound of formula XVI. The compounds of formula XVI where W is chlorine, bromine or iodine may be cross-coupled with compounds of the formula XVII, typically employing a palladium-containing catalyst (e.g. a Pd(II) catalytic species, such as Pd(II) acetate, optionally in the presence of a bidentate phosphine ligand such as 4,5-bis(diphenylphosphino)-9,9-dimethylxanthene (Xantphos); see, for example, WO 2009/143389) to furnish the phosphoryl-containing compounds XIV. Saponification of esters XIV, typically employing an alkali hydroxide, followed by acidification, furnishes the desired carboxylic acids of formula IIa, where $Z^1$ is a structural fragment of formula IV.

with compounds XVII (as defined in Scheme 2), for example by heating in a polar aprotic solvent (e.g. DMF) in the presence of a palladium-containing catalyst (e.g. a Pd(II) catalytic species, such as Pd(II) acetate, optionally in the presence of a bidentate phosphine ligand such as 4,5-bis (diphenylphosphino)-9,9-dimethylxanthene (Xantphos)) Alternatively, the compounds of formula XVIII are coupled, in an Arbuzov-type reaction (WO 2010/141406; *Bioorg. Med. Chem. Lett.* 2009, 19, 2053-2058), with compounds XIX. (The latter compounds are typically made in situ by reaction of the corresponding chlorophosphine (Cl—$PR^2R^3$) with a $C_{1-4}$ alkyl alcohol in the presence or a base (e.g. diisopropylethylamine), or with an alkali metal salt of a $C_{1-4}$ alkyl alcohol.)

Scheme 3

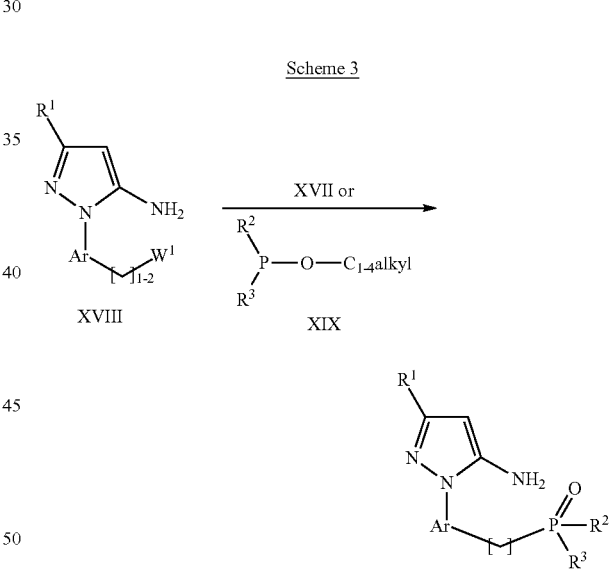

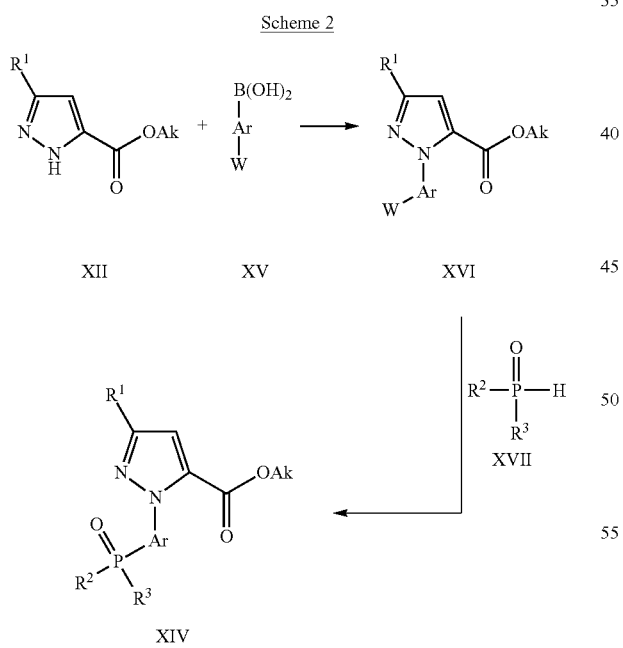

Certain amines of formula III, where $Z^2$ is a structural fragment of formula IV, in which both $X^1$ and $X^2$ are nitrogen and L is $C_1$ or $C_2$ alkylene, may be synthesised employing the route outlined in Scheme 3 below. The compounds of formula XVIII, in which $W^1$ is a leaving group, such as chlorine, bromine or iodine may be combined Arylamines of formula III in which $Z^2$ is a structural fragment of formula IV and $X^1$ and $X^2$ are N, as well as amines of formula XVIII, may be synthesised by adapting known strategies for preparing 1-aryl-5-aminopyrazoles. For example, as outlined in Scheme 4, arylhydrazine XX (in which $W^2$ is chloro, bromo or iodo, or a group that may be converted to $C_1$ alkylene-$W^1$ or $C_2$ alkylene-$W^1$, such as $C_{1-2}$ alkylene-OH or $C_{0-1}$ alkylene-COOH) may be condensed with β-ketonitrile XXI to furnish aminopyrazole XXII bearing a substituted aryl group in the 1-position (WO 2011/124930; US 20070191336).

When $W^2$ is chloro, bromo or iodo, the desired amine III is then produced via a cross-coupling reaction—typically utilising a transition metal, such as palladium(II) (see, for example, *Org. Lett.* 2011, 13, 3270-3273 and WO 2009/143389) or nickel (*Bioorg. Med. Chem. Lett.* 2009, 19, 2053-2058), catalyst—of XXII with phosphoryl compound XVII (as defined in Scheme 2) to generate the phosphoryl-aryl bond.

Alternatively, the $W^2$ group is converted to $C_1$ alkylene-$W^1$ or $C_2$ alkylene-$W^1$, for example by reduction (e.g. using diborane or borane:THF) of C(O)OH or $CH_2$C(O)OH to $CH_2$OH or $CH_2CH_2$OH, respectively, followed by reaction of the resulting compound with a halogenating agent, such as thionyl chloride. In some instances, the appropriate $C_{1-2}$ alkylene-OH-containing hydrazines, e.g., (3-hydrazinophenyl)methanol, are available from commercial sources.

protecting group (see, for example: Greene, T. W.; Wuts, P. G. M. *Protective Groups in Organic Synthesis*; Wiley, 4th revised edition, 2006; ISBN-10: 0471697540), e.g., a carbamate ester or carboxamide. The sequence starts with the base-mediated $S_NAr$ displacement of $LG^1$ in XXIV by the aroxides formed when XXIII is treated with base to generate ether XXV. The remaining halogen or methanesulfonyl substituents ($LG^2$) of the ether XXV is then displaced i) by an amine of formula VII in a second $S_NAr$ reaction or (ii) via a Buchwald coupling (see, for example, WO 2009/017838) with an amine of formula VII to furnish the desired compound (when FG is $NH_2$), or XXVI (when FG is nitro or NH—$PG^2$). When FG is nitro in XXVI, the $NH_2$ group may be revealed by a reduction reaction, typically done through

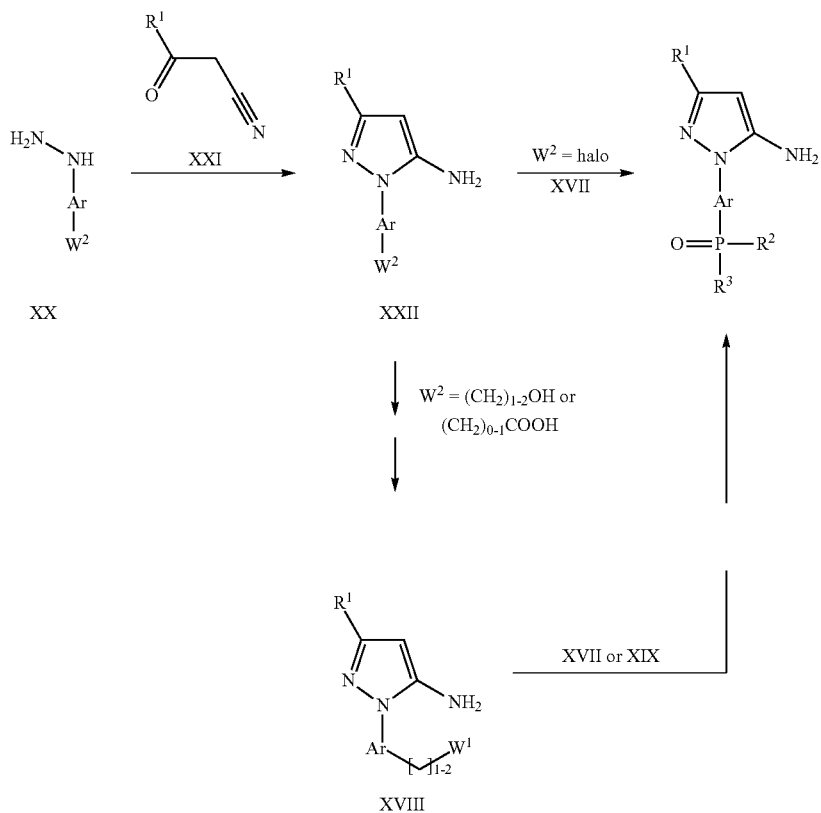

Scheme 4

Certain arylamines of formula III, in which $Z^2$ is a structural fragment of formula V, may be synthesised employing the route outlined in Scheme 5 (see, for example: WO 2003/072569; and WO 2008/046216), wherein $R^4$, $R^5$, A, $A^1$, G and $G^1$ are as hereinbefore defined, $LG^1$ and $LG^2$ represent leaving groups, e.g., halogen or methanesulfonyl, and FG represents a real or latent $NH_2$ group, i.e., a group that is readily transformed into an $NH_2$ group, such as nitro or a protected variant NH—$PG^2$, where $PG^2$ is a typical hydrogenation employing a suitable catalyst, e.g., palladium on carbon, or employing dissolving metal conditions, such as with iron in glacial acetic acid. Alternatively, when FG is a protecting group, the $NH_2$ group may be revealed by a deprotection reaction. Although only depicted as taking place in the final step of the sequence, it should be noted that the unmasking of the latent $NH_2$ group represented by FG can take place at any stage in the synthetic route shown in Scheme 5.

Scheme 5

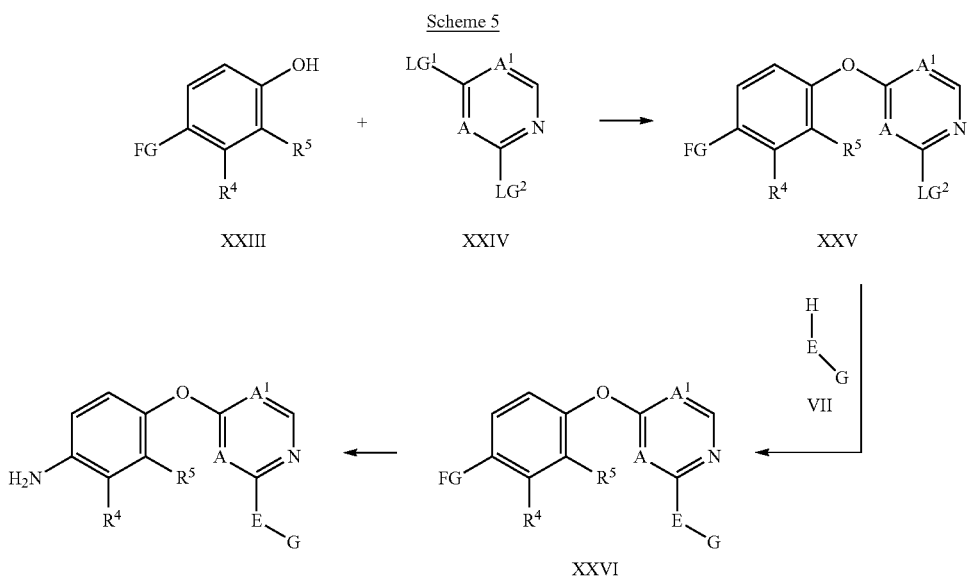

Compounds of formula VI may be synthesised by analogy with the compounds of formula I (see, for example, alternative processes (a) to (c) above). For example, compounds of formula VI can be prepared by reaction of a compound of formula IIx with a compound of formula IIIx, wherein the compounds of formulae IIx and IIIx take the same definitions as the compounds of formulae II and III, with the exception that one of $Z^1$ and $Z^2$ represents a structural fragment of formula IV, as hereinbefore defined, and the other of $Z^1$ and $Z^2$ represents a structural fragment of formula Va,

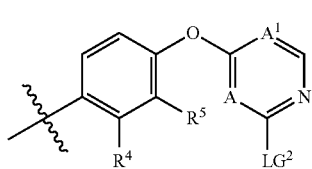

Va

It should be noted that the compounds of formula I where $R^3$ is $C_{1-4}$ alkoxy can be readily transformed into the compounds of formula I where $R^3$ is hydroxyl by a hydrolysis reaction, which is typically carried out with aqueous alkali.

It will be understood by persons skilled in the art that compounds represented by formulae II and IIb are generally reactive intermediates. These intermediates may be formed in situ and reacted directly, without isolation, with compounds of formula III to provide compounds of formula I. Furthermore, it will be understood by those skilled in the art that the use of appropriate protective groups may be required during the processes described above for any of the groups $Z^1$ and $Z^2$ which possess chemically-sensitive functional groups, for example, a hydroxyl group or an amino function.

Many of the compounds illustrated in the Schemes are either commercially available, or can be obtained using the cited procedures, or can be readily prepared by conventional methods by those skilled in the art. See for example Regan, J. et al.; *J. Med. Chem.* 2003, 46, 4676-4686, WO 2000/043384, WO 2007/087448 and WO 2007/089512.

Novel intermediates as described herein form an aspect of the invention. In this respect, further aspects of the invention relate to:

(i) a compound of formula II, IIa or IIb as hereinbefore defined, wherein $Z^1$ is a structural fragment of formula IV, as hereinbefore defined, or a salt or protected derivative thereof;

(ii) a compound of formula III, as hereinbefore defined, wherein $Z^2$ is a structural fragment of formula IV, as hereinbefore defined, or a salt or protected derivative thereof; and (iii) a compound of formula VI, as hereinbefore defined, or a salt or protected derivative thereof.

In the compounds of formulae II, IIa, IIb, III and VI, the groups L, Ar, $X^1$, $X^2$, $R^1$ to $R^5$, A, $A^1$ and $LG^2$, when present, take any of the definitions for those groups as hereinbefore defined.

Protected derivatives of the compound of formula IIa include esters (e.g. $C_{1-4}$ alkyl esters) thereof.

Protected derivatives of the compound of formula III include those in which the essential $NH_2$ group is protected. In this respect, such protected derivatives include amides or, particularly, carbamates of those compounds. For example, those protected derivatives include compounds in which a H-atom of the $NH_2$ group is replaced by:

R'—C(O)—, wherein R' is H, $C_{1-8}$ alkyl, phenyl or benzyl, which latter two groups are optionally substituted by one or more groups selected from halo, hydroxy, methyl and methoxy; or R"—O—C(O)—, wherein R" is tert-butyl, phenyl, benzyl or fluorenyl, which latter three groups are optionally substituted by one or more groups selected from halo, hydroxy, methyl and methoxy.

The aspects of the invention described herein (e.g. the above-mentioned compounds, combinations, methods and uses) may have the advantage that, in the treatment of the conditions described herein, they may be more convenient for the physician and/or patient than, be more efficacious than, be less toxic than, have better selectivity over, have a broader range of activity than, be more potent than, produce fewer side effects than, have a better pharmacokinetic and/or pharmacodynamic profile than, have more suitable solid state morphology than, have better stability (e.g. long term stability) than, or may have other useful pharmacological properties over, similar compounds, combinations, methods (treatments) or uses known in the prior art for use in the treatment of those conditions or otherwise.

The compounds of the invention may additionally (or alternatively):

exhibit a long duration of action and/or persistence of action (e.g. in comparison to other previously disclosed p38 MAP kinase inhibitors such as, for example, BIRB796);

not strongly inhibit GSK 3α (e.g. they may have an $IC_{50}$ against GSK 3α of 1500 nM or greater; such as 2,000, 3,000, 4,000, 5,000, 6,000, 7,000, 8,000, 9,000 or 10,000 nM or greater);

maintain a relatively high drug concentration between doses (e.g. a high concentration relative to other previously disclosed p38 MAP kinase inhibitors such as, for example, BIRB796);

establish and maintain a relatively high drug concentration in a target tissue following (e.g. topical) administration (e.g. a high concentration relative to other previously disclosed p38 MAP kinase inhibitors such as, for example, BIRB796);

exhibit little or no reversible inhibition of cytochrome enzymes (e.g. CYP3A4) and/or time-independent inhibition of such enzymes;

have anti-viral effects (e.g. against respiratory viruses);

exhibit properties that are particularly suited to topical/local administration (e.g. following topical/local administration, the generation of high target tissue concentrations but low plasma concentrations of the compounds of formula I and/or rapid clearance of the compounds of formula I from plasma);

have a reduced risk of extravascular exposure following intravenous administration (e.g. due to a low volume of distribution for the compounds of formula I);

exhibit superior potency with respect to selected kinases (e.g. Syk and/or a panel of kinases, such as Syk, Src and p38 MAPKα);

exhibit reduced β-catenin induction and/or inhibition of mitosis in cells;

exhibit no or less time-dependent inhibition of members of the cytochrome P450 superfamily; and/or produce less problematic (e.g. less toxic) metabolites, e.g. following administration to a patient.

Experimental Methods
General Procedures

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated or under a balloon of hydrogen. Microwave reactions were performed in a CEM Discover and Smithcreator microwave reactor, heating to a constant temperature using variable power microwave irradiation.

Normal phase column chromatography was routinely carried out on an automated flash chromatography system such as CombiFlash Companion or CombiFlash RF system using pre-packed silica (230-400 mesh, 40-63 μm) cartridges. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% $NH_3$ in MeOH.

Analytical Methods

Analytical HPLC was carried out using an Agilent Zorbax Extend C18, Rapid Resolution HT 1.8 μm column eluting with a gradient of either 0.1% formic acid in MeCN in 0.1% aqueous formic acid or a gradient of MeCN in 10 mM Ammonium Bicarbonate; a Waters Xselect CSH C18 3.5 μm eluting with a gradient of 0.1% formic acid in MeCN in 0.1% aqueous formic acid. UV spectra of the eluted peaks were measured using either a diode array or variable wavelength detector on an Agilent 1100 system.

Analytical LCMS was carried out using an Agilent Zorbax Extend C18, Rapid Resolution HT 1.8 μm column eluting with a gradient of either 0.1% formic acid in MeCN in 0.1% aqueous formic acid or a gradient of MeCN in 10 mM Ammonium Bicarbonate; a Waters Xselect CSH C18 3.5 μm eluting with a gradient of 0.1% formic acid in MeCN in 0.1% aqueous formic acid. UV and mass spectra of the eluted peaks were measured using a variable wavelength detector on either an Agilent 1100 with or an Agilent Infinity 1260 LC with 6120 quadrupole mass spectrometer with positive and negative ion electrospray.

Preparative HPLC was carried out using an Agilent Prep-C18 5 μm Preparative Cartridge using either a gradient of either 0.1% formic acid in MeCN in 0.1% aqueous formic acid or a gradient of MeCN in 10 mM Ammonium Bicarbonate; or a Waters Xselect CSH C18 5 μm column using a gradient 0.1% MeCN in 0.1% aqueous formic acid. Fractions were collected following detection by UV at 254 nm.

$^1$H NMR Spectroscopy: $^1$H NMR spectra were acquired on a Bruker Avance III spectrometer at 400 MHz. Either the central peaks of chloroform-d, dimethylsulfoxide-$d_6$ or an internal standard of tetramethylsilane were used as references.

Preparation of Compounds of the Invention

Example 1

1-(3-(tert-Butyl)-1-(4-(dimethylphosphoryl)phenyl)-1H-pyrazol-5-yl)-3-(4-((2-(phenylamino) pyrimidin-4-yl)oxy)naphthalen-1-yl)urea

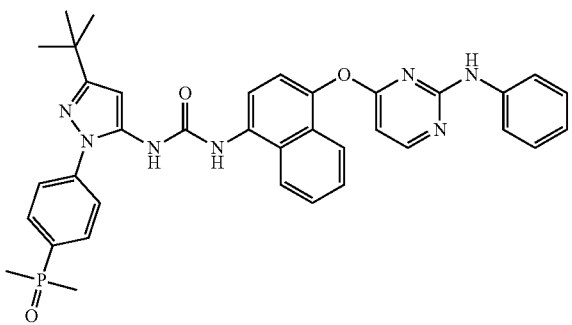 [SMILES: CC(C)(C)c1cc(NC(=O)Nc2ccc(Oc3ccnc(Nc4ccccc4)n3)c3ccccc23)n(-c2ccc(P(C)(C)=O)cc2)n1]

(i) 4-((4-Aminonaphthalen-1-yl)oxY)—N-Phenylpyrimidin-2-amine p-TSA monohydrate (2.80 g, 14.72 mmol) was added to a stirred mixture of 4-((2-chloropyrimidin-4-yl)oxy)naphthalen-1-amine (see, for example, Cirillo, P. F. et al., WO 2002/92576, 21 Nov. 2000; 8 g, 29.4 mmol) and aniline (6.71 mL, 73.6 mmol) in THF (50 mL) at rt under $N_2$. The mixture was heated under reflux for 2 h (reaction mixture solidified), a further 50 mL of THF was added and the mixture heated for a further 2 h. The mixture was cooled, diluted with THF (200 mL), the solid filtered and washed with THF (150 mL). The solid was suspended in DCM (100 mL) and 2M NaOH (35 mL) and the mixture stirred vigorously for 1 h, during which time the solid dissolved. The organic layer was separated, the aq. layer extracted with DCM (100 mL) and the organics combined, dried ($MgSO_4$) and evaporated under reduced pressure. The residue was triturated with ether and filtered to give the sub-title compound (4.18 g).

1H NMR (400 MHz; DMSO-d6) δ 9.46 (s, 1H), 8.32 (d, 1H), 8.18-8.15 (m, 1H), 7.64-7.62 (m, 1H), 7.45-7.40 (m, 2H), 7.35 (d, 2H), 7.11 (d, 1H), 7.03-6.99 (m, 2H), 6.80 (t, 1H), 6.72 (d, 1H), 6.42 (d, 1H), 5.79 (s, 2H).

LCMS m/z 329 (M+H)$^+$ (ES$^+$)

(ii) (4-(5-Amino-3-(tert-butyl)-1H-pyrazol-1-yl)phenyl)dimethylphosphine oxide

To a solution of 1-(4-bromophenyl)-3-(tert-butyl)-1H-pyrazol-5-amine (250 mg, 0.850 mmol) in DMF (3.4 mL) was added dimethylphosphine oxide (81 mg, 0.935 mmol), palladium(II) acetate (9.54 mg, 0.042 mmol), $K_3PO_4$ (198 mg, 0.935 mmol) and Xantphos (29.5 mg, 0.051 mmol) and the mixture purged with $N_2$ for 20 min. The reaction was heated in the microwave at 150° C. for 20 min after which time LCMS showed complete conversion to product. The reaction was duplicated then the reaction mixtures were quenched with acetic acid (~0.5 mL), combined and loaded onto SCX resin (~20 g), washing with methanol (4 CV) and then eluting with 1N $NH_3$ in MeOH (3 CV). Solvent removed under reduced pressure afforded 700 mg of a yellow oil. The crude product was purified by chromatography on the Companion (40 g column, 0-10% MeOH in DCM) to afford the sub-title compound (300 mg) as a pale yellow foam.

1H NMR (400 MHz; DMSO-d6) δ 7.86-7.79 (m, 2H), 7.77-7.73 (m, 2H), 5.42 (s, 1H), 5.36 (br. s, 2H), 1.66 (d, 6H), 1.22 (s, 9H).

LCMS m/z 292 (M+H)$^+$ (ES$^+$)

(iii) 1-(3-(tert-Butyl)-1-(4-(dimethylphoshoryl)phenyl)-1H-pyrazol-5-yl)-3-(4-((2-(phenylamino)pyrimidin-4-yl)oxy)naphthalen-1-yl)urea A solution of CDI (175 mg, 1.079 mmol) in DCM (5 mL) was added to the product from step (ii) above (300 mg, 1.030 mmol) in DCM (1 mL) and the reaction stirred at ambient temperature. After 3.5 h further CDI was added (80 mg) and the reaction stirred overnight. Solvent was removed under reduced pressure and the product dissolved in THF (5 mL). The product from step (i) above (169 mg, 0.515 mmol) was added and the reaction stirred overnight at ambient temperature. The solvent was removed under reduced pressure and the crude product was purified by chromatography on the Companion (40 g column, 0-9% MeOH in DCM) to afford a pale yellow solid (230 mg). The product was further purified by preparative HPLC (Waters acidic method: Waters X-Select Prep-C18, 5 μm, 19×50 mm column, 30-60% MeCN in Water 0.1% Formic Acid) to afford the title compound (90 mg) as a white powder.

1H NMR (400 MHz; DMSO-d6) δ 9.53 (br. s, 1H), 9.20 (s, 1H), 8.97 (s, 1H), 8.40 (d, 1H), 8.11 (br. d, 1H), 7.99-7.90 (m, 3H), 7.83-7.77 (m, 3H), 7.64 (ddd, 1H), 7.57 (ddd, 1H), 7.40 (d, 1H), 7.27 (br. s, 2H), 6.97 (br. t, 2H), 6.77 (t, 1H), 6.59 (d, 1H), 6.49 (s, 1H), 1.70 (d, 6H), 1.31 (s, 9H).

LCMS m/z 646 (M+H)$^+$ (ES$^+$); 644 (M−H)$^−$ (ES$^−$)

Example 2

1-(3-(tert-Butyl)-1-(3-(dimethylphosphoryl)phenyl)-1H-pyrazol-5-yl)-3-(4-((2-(phenylamino)pyrimidin-4-yl)oxy)naphthalen-1-yl)urea

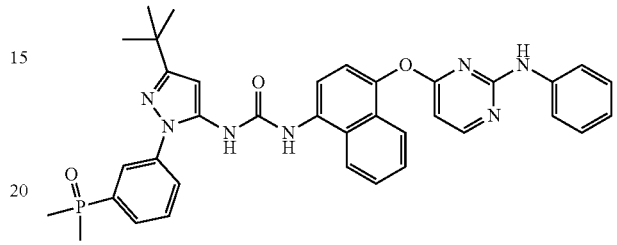

(i) (3-(5-Amino-3-(tert-butyl)-1H-pyrazol-1-yl)phenyl)dimethylphosphine oxide

To a solution of 1-(3-bromophenyl)-3-(tert-butyl)-1H-pyrazol-5-amine (250 mg, 0.850 mmol) in DMF (3.5 mL) was added dimethylphosphine oxide (81 mg, 0.935 mmol), palladium(II) acetate (10 mg, 0.045 mmol), Xantphos (32 mg, 0.055 mmol) and $K_3PO_4$ (198 mg, 0.935 mmol) and the mixture purged with $N_2$ for 5 min. The reaction was heated in the microwave at 120° C. for 40 min. Reaction was repeated twice. The combined reaction mixtures were partitioned between DCM (150 mL) and water (50 mL), the aqueous layer was extracted with DCM (2×100 mL) and the combined organic layers washed with brine (50 mL), dried ($MgSO_4$) and evaporated under reduced pressure. The crude product was purified by chromatography on silica gel (40 g column, 0-10% MeOH/DCM) to afford the sub-title compound (352 mg) as a solid.

1H NMR (400 MHz; CDCl$_3$) δ 7.96-7.92 (m, 1H), 7.79-7.75 (m, 1H), 7.70-7.65 (m, 1H), 7.61-7.56 (m, 1H), 5.56 (s, 1H), 3.75 (s, 2H), 1.77 (d, 6H), 1.31 (s, 9H).

LCMS m/z 292 (M+H)$^+$ (ES$^+$)

(ii) 1-(3-(tert-Butyl)-1-(3-(dimethylphosphoryl)phenyl)-1H-pyrazol-5-yl)-3-(4-((2-(phenylamino)pyrimidin-4-yl)oxy)naphthalen-1-yl)urea CDI (198 mg, 1.221 mmol) was added to a stirred solution of the product from step (i) above (348 mg, 1.183 mmol) in DCM (5 mL) at rt under $N_2$ and the mixture stirred for 18 h. A solution of 4-((4-aminonaphthalen-1-yl)oxy)-N-phenylpyrimidin-2-amine (see Example 1(i) above; 163 mg, 0.497 mmol) in THF (3 mL) was added, stirred for 18 h, the solvent was evaporated and the residue purified by chromatography on silica gel (40 g column, 0-10% MeOH/DCM) to give a solid which was triturated with ether, filtered and dried to afford the title compound (239 mg) as a white solid.

1H NMR (400 MHz; DMSO-d6) δ 9.50 (s, 1H), 9.10 (s, 1H), 8.85 (s, 1H), 8.40 (d, 1H), 8.07 (d, 1H), 8.01 (d, 1H), 7.91 (d, 1H), 7.85-7.79 (m, 3H), 7.75-7.71 (m, 1H), 7.64-7.54 (m, 2H), 7.39 (d, 1H), 7.28 (brd, 2H), 6.97 (t, 2H), 6.77 (t, 1H), 6.58 (d, 1H), 6.46 (s, 1H), 1.72 (d, 6H), 1.32 (s, 9H).

LCMS m/z 646 (M+H)$^+$ (ES$^+$); 644 (M−H)$^−$ (ES$^−$)

Example 3

N-(4-((4-(3-(3-(tert-Butyl)-1-(4-(dimethylphosphoryl)phenyl)-1H-pyrazol-5-yl)ureido)-naphthalen-1-yl)oxy)pyridin-2-yl)-2-methoxyacetamide

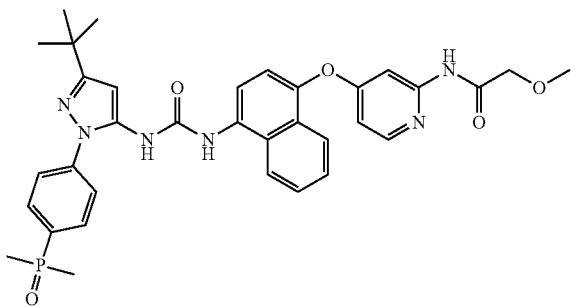

To (4-(5-amino-3-(tert-butyl)-1H-pyrazol-1-yl)phenyl)dimethylphosphine oxide (see Example 1(ii) above; 159 mg, 0.546 mmol) was added a solution of CDI (102 mg, 0.629 mmol) in DCM (1 mL) and the reaction stirred overnight at rt. Solvent was removed under reduced pressure, the residue dissolved in THF (3 mL), N-(4-((4-aminonaphthalen-1-yl)oxy)pyridin-2-yl)-2-methoxy acetamide (see, for example, King-Underwood, John et al. WO 2011/121366, 6 Oct. 2011; 88 mg, 0.273 mmol) added and the reaction stirred for 1 h at ambient temperature. The mixture was concentrated under reduced pressure and then purified by chromatography on the Companion (12 g column, 0-10% MeOH in DCM) to afford a pale yellow foam (220 mg). The crude product was dissolved in acetonitrile (2 mL) and ether (5 mL) added to precipitate a solid. Solvent was removed and the pale yellow solid triturated with acetonitrile (4×3 mL) to afford a white solid which was dried under vacuum at 45° C. over 16 h to afford the title compound (90 mg).

1H NMR (400 MHz; DMSO-d6) δ 10.02 (s, 1H), 9.13 (s, 1H), 8.96 (s, 1H), 8.19 (d, 1H), 8.11 (d, 1H), 7.98-7.92 (m, 3H), 7.85 (br. d, 1H), 7.77 (dd, 2H), 7.69-7.64 (m, 2H), 7.60-7.56 (m, 1H), 7.34 (d, 1H), 6.70 (dd, 1H), 6.47 (s, 1H), 3.99 (s, 2H), 3.32 (s, 3H), 1.70 (d, 6H), 1.30 (s, 9H).

LCMS m/z 641 (M+H)+ (ES+); 639 (M−H)− (ES−)

Example 4

1-(1-(4-(Dimethylphosphoryl)phenyl)-3-isopropyl-1H-pyrazol-5-yl)-3-(4-((2-(phenylamino)-pyrimidin-4-yl)oxy)naphthalen-1-yl)urea

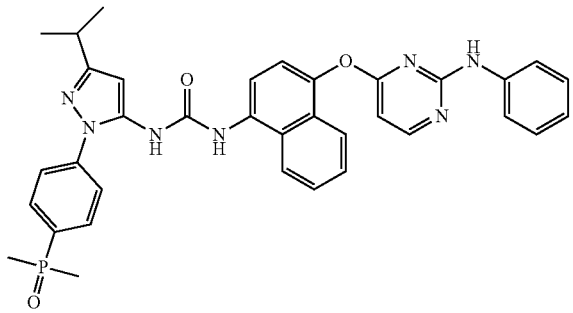 [SMILES: CC(C)c1cc(NC(=O)Nc2ccc(Oc3ccnc(Nc4ccccc4)n3)c3ccccc23)n(-c2ccc(P(C)(C)=O)cc2)n1]

(i) (4-(5-Amino-3-isopropyl-1H-pyrazol-1-yl)phenyl)dimethylphosphine oxide 1-(4-Bromophenyl)-3-isopropyl-1H-pyrazol-5-amine (0.75 g, 2.68 mmol), Xantphos (0.155 g, 0.268 mmol), palladium (II) acetate (0.030 g, 0.134 mmol) and K₃PO₄ (0.625 g, 2.94 mmol) were combined in a microwave tube under nitrogen. Dimethylphosphine oxide (0.225 mL, 3.21 mmol) was dissolved in anhydrous DMF (7 mL) and the mixture degassed before combining with the other reactants. The reaction was heated under N₂ at 150° C. in a microwave (300 W) for 40 min. The reaction was cooled to ambient temperature and filtered on Glass fibre pad (Whatmans GF/C). Solvents evaporated and the residue was preadsorbed onto silica (ca. 4 g) and purified by chromatography on the Companion (40 g column, DCM to 10% MeOH:DCM) to afford the sub-title compound (450 mg) as a pale yellow glass.

1H NMR (400 MHz, DMSO-d6) δ 7.77 (m, 4H), 5.38 (s, 3H), 2.76 (hept, 1H), 1.66 (d, 6H), 1.17 (d, 6H).

LCMS m/z 278 (M+H)+ (ES+)

(ii) 1-(1-(4-(Dimethylphosphoryl)phenyl)-3-isopropyl-1H-pyrazol-5-yl)-3-(4-((2-(phenylamino)pyrimidin-4-yl)oxy)naphthalen-1-yl)urea CDI (270 mg, 1.666 mmol) was dissolved in DCM (5 mL) and the product from step (i) above (440 mg, 1.587 mmol) in DCM (5 mL) added in one portion and the reaction mixture stirred for 16 h. 4-((4-Aminonaphthalen-1-yl)oxy)-N-phenylpyrimidin-2-amine (see Example 1(i) above; 391 mg, 1.190 mmol) was added in one portion. After stirring for 3 h, the product had precipitated from reaction mixture and was filtered off. The solid was washed with ice cold DCM (2 mL), dried to give the product (300 mg) as a colourless solid. Liquors were purified by chromatography on the Companion (40 g column, DCM to 10% MeOH:DCM) to afford a second batch (220 mg). Batches were combined to afford the title compound (520 mg).

1H NMR (400 MHz, DMSO-d6) δ 9.50 (s, 1H), 9.16 (s, 1H), 8.94 (s, 1H), 8.39 (d, 1H), 8.10 (d, 1H), 7.94 (m, 3H), 7.80 (m, 3H), 7.63 (ddd, 1H), 7.56 (m, 1H), 7.40 (d, 1H), 7.28 (d, 2H), 6.97 (t, 2H), 6.77 (t, 1H), 6.57 (d, 1H), 6.44 (s, 1H), 2.93 (hept, 1H), 1.69 (d, 6H), 1.26 (d, 6H).

LCMS m/z 632 (M+H)+ (ES+); 630 (M−H)− (ES−)

Example 5

1-(1-(4-(Dimethylphosphoryl)phenyl)-3-(trimethylsilyl)-1H-pyrazol-5-yl)-3-(4-((2-(phenyl-amino)pyrimidin-4-yl)oxy)naphthalen-1-yl)urea

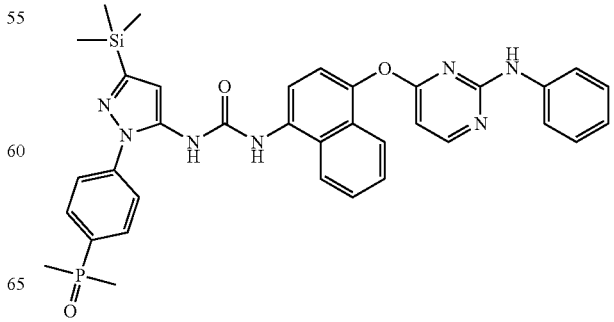

(i) Ethyl 1-(4-bromophenyl)-3-(trimethylsilyl)-1H-pyrazole-5-carboxylate

Pyridine (0.381 mL, 4.71 mmol) followed by activated 4A molecular sieves (1.5 g) were added to a stirred mixture of (4-bromophenyl)boronic acid (0.946 g, 4.71 mmol), ethyl 3-(trimethylsilyl)-1H-pyrazole-5-carboxylate (see, for example, *Bioorg. & Med. Chem. Lett.*, 17(2), 354-357 (2007); 0.5 g, 2.355 mmol) and copper (II) acetate (0.642 g, 3.53 mmol) in DCM (40 mL) at rt. The mixture was stirred for 18 h then filtered through Celite, and the cake washed with DCM (200 mL). The organics were evaporated under reduced pressure and ether (80 mL) added and the solid copper salts filtered. The filtrate was evaporated under reduced pressure and the residue purified by chromatography on silica gel (40 g column, 0-10% Et$_2$O/isohexane) to afford the sub-title compound (847 mg) as a colourless oil.

1H NMR (400 MHz; CDCl$_3$) δ 7.57 (d, 2H), 7.32 (d, 2H), 7.12 (s, 1H), 4.24 (q, 2H), 1.28 (t, 3H), 0.33 (s, 9H).

LCMS m/z 367/9 (M+H)$^+$ (ES$^+$)

(ii) Ethyl 1-(4-(dimethylphosphoryl)phenyl)-3-(trimethylsilyl)-1H-pyrazole-5-carboxylate The product from step (i) above (0.5 g, 1.361 mmol), Xantphos (0.079 g, 0.136 mmol), palladium(II) acetate (0.015 g, 0.068 mmol) and K$_3$PO$_4$.H$_2$O (0.318 g, 1.361 mmol) were combined under N$_2$ in a microwave tube containing a magnetic stirrer. Dimethylphosphine oxide (0.114 mL, 1.633 mmol) was dissolved in anhydrous DMF (7 mL) and the mixture degassed before addition of the other reagents under N$_2$. The reaction was heated under N$_2$ at 150° C. in a microwave (300 W) for 40 min. The reaction was cooled to ambient temperature and filtered on Glass fibre pad (Whatmans GF/C), solvents evaporated and the residue was preadsorbed onto silica (ca. 4 g) and purified by chromatography on the Companion (12 g column, DCM to 10% MeOH:DCM) to afford the sub-title compound (250 mg) as a brown solid.

1H NMR (400 MHz, DMSO-d6) δ 7.73 (m, 2H), 7.47 (m, 2H), 7.10 (s, 1H), 4.05 (q, 2H), 1.56 (d, 6H), 1.04 (t, 3H), 0.15 (s, 9H).

LCMS m/z 365 (M+H)$^+$ (ES$^+$)

(iii) 1-(4-(Dimethylphosphoryl)phenyl)-3-(trimethylsilyl)-1H-pyrazole-5-carboxylic acid The product from step (ii) above (250 mg, 0.686 mmol) was dissolved in ethanol (2 mL), 2N NaOH (514 µL, 1.029 mmol) added and stirred for 72 h. Solvent evaporated and the residue partitioned between water (10 mL) and EtOAc (10 mL). Aqueous separated and acidified with 1N HCl. Product extracted with EtOAc (2×10 mL), organics bulked and washed with 20% w/w brine (10 mL). Organic layer separated, dried (MgSO$_4$) filtered and solvent evaporated to give the sub-title compound (220 mg) as a pale yellow solid.

1H NMR (400 MHz, DMSO-d6) δ 13.31 (s, 1H), 7.86 (m, 2H), 7.60 (m, 2H), 7.19 (s, 1H), 1.70 (d, 6H), 0.29 (s, 9H).

LCMS m/z 337 (M+H)$^+$ (ES$^+$); 335 (M−H)$^-$ (ES$^-$)

(iv) 1-(1-(4-(Dimethylphosphoryl)phenyl)-3-(trimethylsilyl)-1H-pyrazol-5-yl)-3-(4-((2-(phenylamino)pyrimidin-4-yl)oxy)naphthalen-1-yl)urea DPPA (138 µL, 0.639 mmol) was added to a stirred solution of the product from step (iii) above (215 mg, 0.639 mmol) and Et$_3$N (223 µL, 1.598 mmol) in DMF (7 mL) under N$_2$ at 0-5° C. After 30 min the mixture was warmed to rt and stirred for a further 1 h. 4-((4-Aminonaphthalen-1-yl)oxy)-N-phenylpyrimidin-2-amine (see Example 1(i) above; 199 mg, 0.607 mmol) was added and the mixture heated at 100° C. for 1 h. Cooled and partitioned between EtOAc (50 mL) and water (50 mL). The organic layer was separated, washed with water (50 mL), 20% w/w brine (50 mL), dried (MgSO$_4$) filtered and evaporated under reduced pressure to a brown solid. Preadsorbed on silica (ca. 4 g) and purified by chromatography on the Companion (12 g column, DCM, to 10% MeOH:DCM) to afford a brown solid. Triturated with EtOAc:isohexane (1:1) to give the title compound (150 mg) as a beige solid.

1H NMR (400 MHz, DMSO-d6) δ 9.50 (s, 1H), 9.17 (s, 1H), 8.92 (s, 1H), 8.39 (d, 1H), 8.09 (d, 1H), 7.98 (dd, 2H), 7.91 (d, 1H), 7.80 (dq, 3H), 7.63 (m, 1H), 7.56 (m, 1H), 7.39 (d, 1H), 7.28 (d, 2H), 6.96 (t, 2H), 6.77 (t, 1H), 6.67 (s, 1H), 6.57 (d, 1H), 1.70 (d, 6H), 0.29 (s, 9H).

LCMS m/z 662 (M+H)$^+$ (ES$^+$)

Example 6

1-(3-(tert-Butyl)-1-(4-((dimethylphosphoryl)methyl)phenyl)-1H-pyrazol-5-yl)-3-(4-((2-(phenylamino)pyrimidin-4-yl)oxy)naphthalen-1-yl)urea

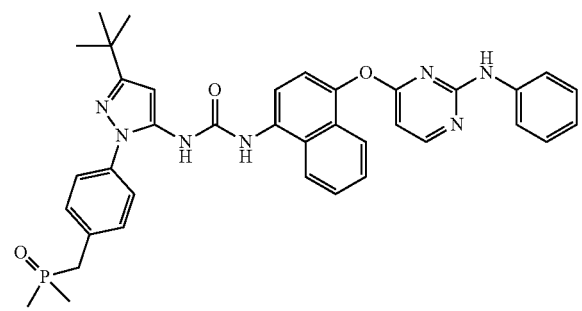 [SMILES: CC(C)(C)c1cc(NC(=O)Nc2ccc(Oc3ccnc(Nc4ccccc4)n3)c3ccccc23)n(-c2ccc(CP(C)(C)=O)cc2)n1]

(i) 3-(tert-Butyl)-1-(4-(chloromethyl)phenyl)-1H-pyrazol-5-amine, HCl (4-(5-Amino-3-(tert-butyl)-1H-pyrazol-1-yl)phenyl)methanol (see, for example, Charron, Catherine Elisabeth et al. WO 2011/070369, 16 Jun. 2011; 1275 mg, 5.20 mmol) and thionyl chloride (759 µL, 10.39 mmol) were heated to reflux in THF (20 mL) for 2 h. The mixture was concentrated under reduced pressure and the residue was co-evaporated with toluene (3×20 mL). The residue was triturated in diethyl ether:iso-hexane (25:75, 10 mL). The solid was collected by filtration to yield the sub-title compound (950 mg) as an orange brown solid.

LCMS m/z 264 (M+H)$^+$ (ES$^+$)

(ii) (4-(5-Amino-3-(tert-butyl)-1H-pyrazol-1-yl)benzyl)dimethylphosphine oxide To a solution of the product from step (i) above (656 mg, 2.363 mmol) in DMF (1 mL) was added dimethylphosphine oxide (203 mg, 2.60 mmol), palladium(II) acetate (26.5 mg, 0.118 mmol), Xantphos (82 mg, 0.142 mmol) and K$_3$PO$_4$.H$_2$O (1103 mg, 5.20 mmol) and the mixture purged with nitrogen for 20 min. The reaction mixture was heated in the microwave (Smith, 120° C.) for 30 min. The reaction mixture was diluted with water (10 mL) then filtered. The solvent was removed under reduced pressure and the residue was concentrated onto silica gel. The silicate was purified by chromatography on the Companion (40 g column, 0-50% ⁱPrOH:CH₂Cl₂) to afford the sub-title compound (395 mg) as a yellow oil.

1H NMR (400 MHz; DMSO-d6) δ 7.50 (d, 2H), 7.32 (dd, 2H), 5.38 (s, 1H), 5.17 (s, 2H), 3.17 (d, 2H), 1.36 (d, 6H), 1.22 (s, 9H).

LCMS m/z 306 (M+H)⁺ (ES⁺)

(iii) 1-(3-(tert-Butyl)-1-(4-((dimethylphosphoryl)methyl)phenyl)-1H-pyrazol-5-yl)-3-(4-((2-(phenylamino)pyrimidin-4-yl)oxy)naphthalen-1-yl)urea The product from step (ii) above (250 mg, 0.811 mmol) and CDI (145 mg, 0.892 mmol) were stirred in DCM (5 mL) for 6 h. 4-((4-Aminonaphthalen-1-yl)oxy)-N-phenylpyrimidin-2-amine (see Example 1(i) above; 253 mg, 0.770 mmol) was added and the mixture was stirred at rt overnight. The mixture was concentrated onto loose silica and the preadsorbed silicate was purified by chromatography on the Companion (40 g column, CH₂Cl₂:CH₃OH 95:5) to afford the title compound (142 mg) as a white solid.

1H NMR (400 MHz; DMSO-d6) δ 9.52 (s, 1H), 9.17 (s, 1H), 8.82 (s, 1H), 83.8 (d, 1H), 8.10 (d, 1H), 7.92 (d, 1H), 7.80 (d, 1H), 7.67-7.59 (m, 1H), 7.59-7.50 (m, 3H), 7.47-7.36 (m, 3H), 7.35-7.21 (m, 2H), 7.01-6.91 (m, 2H), 6.83-6.71 (m, 1H), 6.57 (d, 1H), 6.43 (s, 1H), 3.25 (d, 2H), 1.39 (d, 6H), 1.29 (s, 9H).

LCMS m/z 660 (M+H)⁺ (ES⁺); 658 (M−H)⁻ (ES⁻)

Example 7

1-(4-((2-((1H-Indazol-5-yl)amino)pyrimidin-4-yl)oxy)naphthalen-1-yl)-3-(3-(tert-butyl)-1-(4-(dimethylphosphoryl)phenyl)-1H-pyrazol-5-yl)urea

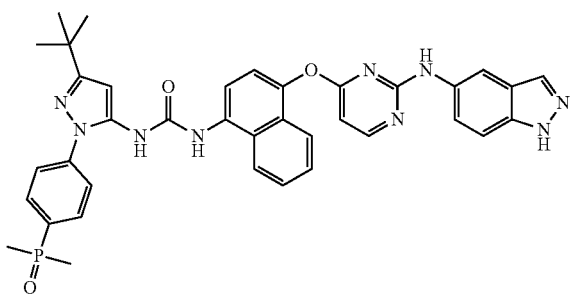 [SMILES: CC(C)(C)c1cc(NC(=O)Nc2ccc(Oc3ccnc(Nc4ccc5[nH]ncc5c4)n3)c3ccccc23)n(-c2ccc(P(C)(C)=O)cc2)n1]

(i) 1-(3-(tert-Butyl)-1-(4-(dimethylphosphoryl)phenyl)-1H-pyrazol-5-yl)-3-(4-((2-chloropyrimidin-4-yl)oxy)naphthalen-1-yl)urea To a solution of CDI (60.2 mg, 0.371 mmol) in DCM (2 mL) was added (4-(5-amino-3-(tert-butyl)-1H-pyrazol-1-yl)phenyl)dimethylphosphine oxide (see Example 1(ii) above; 103 mg, 0.354 mmol) in a single portion. The reaction mixture was left to stir at rt overnight. Reaction was repeated twice more and reactions combined. 4-((2-Chloropyrimidin-4-yl)oxy)naphthalen-1-amine (see, for example, Cirillo, P. F. et al., WO 2002/92576, 21 Nov. 2000; 215 mg, 0.793 mmol) was added as a single portion to the combined reaction mixtures and stirring continued at rt for 72 h. The solvent was removed in vacuo to afford a light, brown foam (508 mg). The crude product was purified by chromatography on silica gel (40 g column, 0-10% MeON in DCM) to afford the sub-title compound (215 mg) as an off-white solid.

1H NMR (DMSO-d6) 400 MHz, δ: 9.16 (1H, s) 8.97 (1H, s) 8.66 (1H, d) 8.11 (1H, d) 7.98-7.93 (3H, m) 7.81-7.76 (3H, m) 7.69-7.65 (1H, m) 7.61-7.57 (1H, m) 7.43 (1H, d) 7.27 (1H, d) 6.47 (1H, s) 1.70 (6H, d) 1.30 (9H, s).

LCMS m/z 589 (M+H)⁺ (ES⁺); 587 (M−H)⁻ (ES⁻)

(ii) 1-(4-((2-((1H-Indazol-5-yl)amino)pyrimidin-4-yl)oxy)naphthalen-1-yl)-3-(3-(tert-butyl)-1-(4-(dimethylphosphoryl)phenyl)-1H-pyrazol-5-yl)urea To a solution of the product from step (i) above (101 mg, 0.171 mmol) in THF (2 mL) was added 1H-indazol-5-amine (27.4 mg, 0.206 mmol) and p-TSA monohydrate (65.2 mg, 0.343 mmol) resulting in a lilac suspension. DMF (2 mL) was added and the mixture heated at 60° C. overnight. The reaction was cooled to rt whereupon a further quantity of 1H-indazol-5-amine (11.42 mg, 0.086 mmol) was added. The reaction mixture was then heated at 60° C. for 6 h. A further quantity of 1H-indazol-5-amine (11.42 mg, 0.086 mmol) was added and stirring continued at 60° C. overnight. The reaction mixture was cooled to rt and separated between sodium bicarbonate (15 mL) and EtOAc (20 mL). The aqueous layer was extracted with EtOAc (2×20 mL). The combined organic extracts were washed with water (3×20 mL), brine (20 mL), dried (MgSO₄), filtered and concentrated in vacuo to afford a maroon solid (136 mg). The crude product was purified by chromatography on silica gel (12 g column, 0-10% MeON in DCM) to afford the title compound (42 mg) as a dark pink solid.

1H NMR (DMSO-d6) 400 MHz, δ: 12.81 (1H, s) 9.56 (1H, s) 9.25 (1H, s) 9.04 (1H, s) 8.39 (1H, d) 8.15 (1H, d) 8.06-8.04 (1H, m) 8.00-7.94 (2H, m) 7.85-7.79 (3H, m) 7.66-7.54 (4H, m) 7.43 (1H, d) 7.24 (2H, br s) 6.59 (1H, d) 6.50 (1H, s) 1.70 (6H, d) 1.31 (9H, s).

LCMS m/z 686 (M+H)⁺ (ES⁺)

Example 8

1-(3-(tert-Butyl)-1-(4-(1-oxidophospholan-1-yl)phenyl)-1H-pyrazol-5-yl)-3-(4-((2-(phenylamino)pyrimidin-4-yl)oxy)naphthalen-1-yl)urea

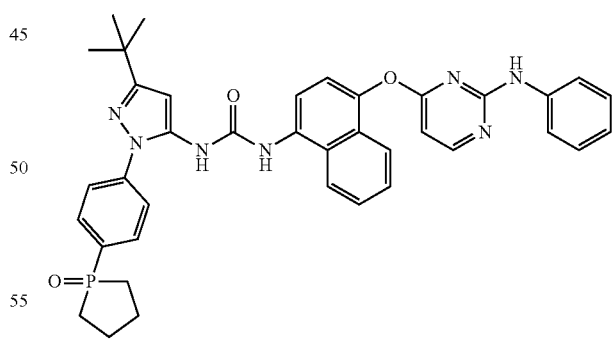

(i) 1-(4-(5-Amino-3-(tert-butyl)-1H-pyrazol-1-yl)phenyl)phospholane 1-oxide 1-(4-Bromophenyl)-3-(tert-butyl)-1H-pyrazol-5-amine (0.5 g, 1.7 mmol), Xantphos (0.098 g, 0.170 mmol), palladium(II) acetate (0.019 g, 0.085 mmol) and K₃PO₄·H₂O (0.397 g, 1.700 mmol) were combined under N₂ in a microwave tube containing a magnetic stirrer. Phospholane 1-oxide (0.425 g, 2.039 mmol) was dissolved in degassed anhydrous DMF (7 mL), reactants were combined under nitrogen and the reaction was heated at 150° C. in a microwave (300 W) for 40 min. The reaction was cooled to ambient temperature and filtered on Glass fibre pad (Whatmans GF/C), solvents removed under reduced pressure. Residue was preadsorbed onto silica (ca. 4 g) and purified by chromatography on the Companion 40 g column, 5% MeOH:DCM to 10% MeOH:DCM to afford the sub-title compound (175 mg) as a beige foam.

1H NMR (400 MHz, DMSO-d6) δ 7.78 (m, 4H), 5.42 (s, 1H), 5.38 (s, 2H), 1.93 (m, 8H), 1.22 (s, 9H).

LCMS m/z 318 (M+H)$^+$ (ES$^+$)

(ii) 1-(3-(tert-Butyl)-1-(4-(1-oxidopholan-1-yl)phenyl)-1H-pyrazol-5-yl)-3-(4-((2-(phenylamino)pyrimidin-4-yl)oxy)naphthalen-1-yl)urea CDI (26.8 mg, 0.165 mmol) was dissolved in DCM (1 mL) and the product from step (i) above (50 mg, 0.158 mmol) added in one portion. Stirred for 16 h, then 4-((4-aminonaphthalen-1-yl)oxy)-N-phenylpyrimidin-2-amine (see Example 1(i) above; 12.93 mg, 0.039 mmol) added and stirring continued for 2 h. Solvent was evaporated and the crude product was purified by chromatography on the Companion (4 g column, DCM to 10% MeOH:DCM) to afford a light tan solid (19 mg), which was purified by recrystallising from MeCN (1 mL) to give the title compound (10 mg).

1H NMR (400 MHz, DMSO-d6) δ 9.52 (s, 1H), 9.24 (s, 1H), 9.01 (s, 1H), 8.40 (d, 1H), 8.11 (d, 1H), 7.91 (m, 3H), 7.81 (dt, 3H), 7.63 (m, 1H), 7.56 (m, 1H), 7.40 (d, 1H), 7.28 (s, 2H), 6.97 (t, 2H), 6.77 (t, 1H), 6.59 (d, 1H), 6.48 (s, 1H), 1.95 (m, 8H), 1.31 (s, 9H).

LCMS m/z 672 (M+H)$^+$ (ES$^+$)

Example 9

Ethyl (4-(3-(tert-butyl)-5-(3-(4-((2-(phenylamino)pyrimidin-4-yl)oxy)naphthalen-1-yl)-ureido)-1H-pyrazol-1-yl)phenyl)(methyl)phosphinate

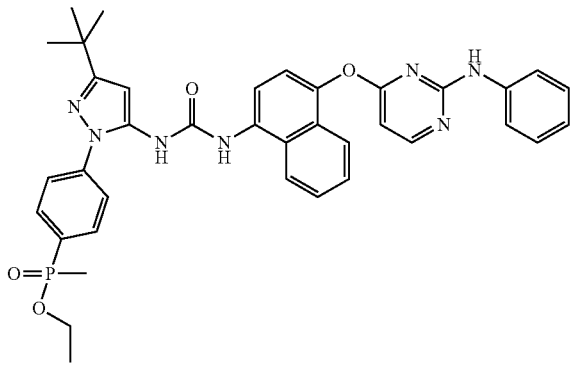 [SMILES: CCOP(C)(=O)c1ccc(-n2nc(C(C)(C)C)cc2NC(=O)Nc2ccc(Oc3ccnc(Nc4ccccc4)n3)c3ccccc23)cc1]

(i) Ethyl (4-(5-amino-3-(tert-butyl)-1H-pyrazol-1-yl)phenyl)(methyl)phosphinate 1-(4-Bromophenyl)-3-(tert-butyl)-1H-pyrazol-5-amine (266 mg, 0.877 mmol), ethyl methyl phosphinate (104 mg, 0.965 mmol) and K$_3$PO$_4$.H$_2$O (505 mg, 2.193 mmol) were stirred in DMF (5 mL) in a microwave vial. The mixture was degassed with nitrogen for 2 minutes before adding palladium(II) acetate (9.85 mg, 0.044 mmol) and Xantphos (30.4 mg, 0.053 mmol). The mixture was heated in the microwave (Smith, 120° C.) for 30 min. This process was done in triplicate. The combined mixtures were diluted with water (50 mL) and extracted with EtOAc (3×40 mL). The combined organic extracts were washed with saturated brine (50 mL), dried (MgSO$_4$) and concentrated. The crude product was purified by chromatography on the Companion (80 g column, CH$_2$Cl$_2$:CH$_3$OH 95:5) to afford the sub-title compound (200 mg) as a dark brown oil.

1H NMR (400 MHz; DMSO-d6) δ 7.86-7.76 (m, 4H), 5.43 (s, 1H), 5.41 (br s, 2H), 4.00-3.87 (m, 1H), 3.84-3.71 (m, 1H), 1.63 (d, 3H), 1.23 (s, 9H), 1.22-1.17 (m, 3H).

LCMS m/z 322 (M+H)$^+$ (ES$^+$)

(ii) Ethyl (4-(3-(tert-butyl)-5-(3-(4-((2-(phenylamino)pyrimidin-4-yl)oxy)naphthalen-1-yl)ureido)-1H-pyrazol-1-yl)phenyl)(methyl)phosphinate The product from step (i) above (210 mg, 0.523 mmol) and CDI (93 mg, 0.575 mmol) were stirred in DCM (5 mL) for 18 h. 4-((4-Aminonaphthalen-1-yl)oxy)-N-phenylpyrimidin-2-amine (see Example 1(i) above; 163 mg, 0.497 mmol) was added and the mixture was stirred at rt for a further 2 h. The mixture was loaded directly onto a silica gel column on the Companion (40 g column, CH$_2$Cl$_2$:$^i$PrOH) to afford the title compound (200 mg) as a tan solid.

1H NMR (400 MHz; DMSO-d6) δ 9.52 (s, 1H), 9.17 (s, 1H), 8.94 (s, 1H), 8.39 (d, 1H), 8.11 (d, 1H), 7.99-7.87 (m, 3H), 7.86-7.77 (m, 3H), 7.68-7.61 (m, 1H), 7.60-7.53 (m, 1H), 7.40 (d, 1H), 7.34-7.20 (m, 2H), 7.03-6.89 (m, 2H), 6.78 (t, 1H), 6.58 (d, 1H), 6.49 (s, 1H), 4.01-3.90 (m, 1H), 3.85-3.74 (m, 1H), 1.69 (d, 3H), 1.31 (s, 9H), 1.21 (t, 3H).

LCMS m/z 676 (M+H)$^+$ (ES$^+$); 674 (M−H)$^-$ (ES$^-$)

Example 10

1-(4-((2-((1H-Indazol-5-yl)amino)pyrimidin-4-yl)oxy)naphthalen-1-yl)-3-(3-(tert-butyl)-1-(3-(dimethylphosphoryl)phenyl)-1H-pyrazol-5-yl)urea

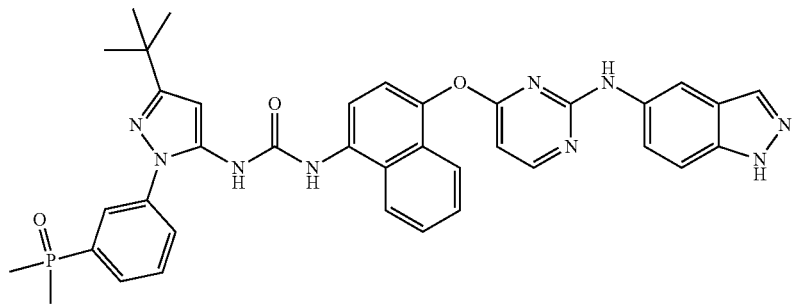 [SMILES: CC(C)(C)c1cc(NC(=O)Nc2ccc(Oc3ccnc(Nc4ccc5[nH]ncc5c4)n3)c3ccccc23)n(-c2cccc(P(C)(C)=O)c2)n1]

(i) 1-(3-(tert-Butyl)-1-(3-(dimethylphosphoryl)phenyl)-1H-pyrazol-5-yl)-3-(4-((2-chloropyrimidin-4-yl)oxy)naphthalen-1-yl)urea CDI (237 mg, 1.459 mmol) was added to a stirred solution of (3-(5-amino-3-(tert-butyl)-1H-pyrazol-1-yl)phenyl)dimethylphosphine oxide (see Example 2(i) above; 425 mg, 1.459 mmol) in DCM (5 mL) at rt. The mixture was stirred for 18 h then a solution of 4-((2-chloropyrimidin-4-yl)oxy)naphthalen-1-amine (see, for example, Cirillo, P. F. et al., WO 2002/92576, 21 Nov. 2000; 340 mg, 1.251 mmol) in THF (2 mL) was added and stirred for 4 h. The solid precipitate was filtered off and washed with DCM (3 mL) to give the sub-title compound as a white solid, 410 mg.

1H NMR (400 MHz; DMSO-d6) δ 9.11 (s, 1H), 8.91 (s, 1H), 8.67 (d, 1H), 8.07 (d, 1H), 7.98 (d, 1H), 7.93 (d, 1H), 7.84-7.78 (m, 3H), 7.75-7.71 (m, 1H), 7.67-7.64 (m, 1H), 7.61-7.57 (m, 1H), 7.43 (d, 1H), 7.28 (d, 1H), 6.46 (s, 1H), 1.71 (d, 6H), 1.31 (s, 9H).

LCMS m/z 589/591 (M+H)$^+$ (ES$^+$)

(ii) 1-(4-((2-((1H-Indazol-5-yl)amino)pyrimidin-4-yl)oxy)naphthalen-1-yl)-3-(3-(tert-butyl)-1-(3-(dimethylphosphoryl)phenyl)-1H-pyrazol-5-yl)urea The product from step (i) above (95 mg, 0.161 mmol) and 1H-indazol-5-amine (43.0 mg, 0.323 mmol) were combined in THF (1 mL), the mixture was stirred for 2 min during which time a precipitate was observed. p-TSA monohydrate (61.4 mg, 0.323 mmol) was added followed by THF (1.5 mL) and the mixture stirred at 60° C. overnight. 1M HCl in isopropanol (484 μL, 0.484 mmol) and isopropanol (1 mL) were added and stirred at 60° C. for 16 h. After this time solvent was removed and the residue partitioned between DCM (10 mL) and sat. aq. NaHCO$_3$ (10 mL). DCM layer concentrated under reduced pressure and purified by preparative HPLC (Waters, Acidic (0.1% Formic acid), Waters X-Select Prep-C18, 5 μm, 19×50 mm column, 20-60% MeCN in Water) followed by purification on a column of SCX (5 g) in MeOH/THF (2 mL). The column was washed with MeOH and then the product was eluted with 0.7 M ammonia in MeOH. The resultant mixture was concentrated in vacuo to afford the title compound (15 mg) as a pale yellow solid.

1H NMR (400 MHz; DMSO-d6) δ 12.80 (s, 1H), 9.54 (br.s, 1H), 9.18 (s, 1H), 8.96 (s, 1H), 8.39 (d, 1H), 8.11 (d, 1H), 8.06-7.96 (m, 2H), 7.87-7.79 (m, 3H), 7.77-7.70 (m, 1H), 7.69-7.49 (m, 4H), 7.42 (d, 1H), 7.34-7.16 (br.s, 2H), 6.58 (d, 1H), 6.48 (s, 1H), 1.71 (d, 6H), 1.31 (s, 9H).

LCMS m/z 686 (M+H)$^+$ (ES$^+$); 684 (M–H)$^-$ (ES$^-$)

Example 11

1-(3-(tert-Butyl)-1-(3-(dimethylphosphoryl)phenyl)-1H-pyrazol-5-yl)-3-(4-((4-((2-oxoindolin-6-yl)amino)pyrimidin-4-yl)oxy)naphthalen-1-yl)urea

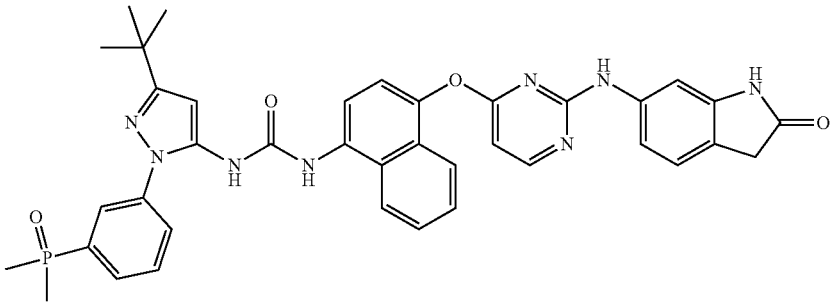 [SMILES: CC(C)(C)c1cc(NC(=O)Nc2ccc(Oc3ccnc(Nc4ccc5c(c4)NC(=O)C5)n3)c3ccccc23)n(-c2cccc(P(C)(C)=O)c2)n1]

1-(3-(tert-Butyl)-1-(3-(dimethylphosphoryl)phenyl)-1H-pyrazol-5-yl)-3-(4-((2-chloropyrimidin-4-yl)oxy)naphthalen-1-yl)urea (see Example 10(i) above; 100 mg, 0.170 mmol) and 6-aminoindolin-2-one (50.3 mg, 0.340 mmol) were combined in THF (2.5 mL) and the mixture stirred for 2 min; p-TSA monohydrate (64.6 mg, 0.340 mmol) was added to the resulting precipitate and the mixture stirred at 60° C. overnight. 1M HCl in IPA (509 μL, 0.509 mmol) was added and stirred at 60° C. over 16 h. After this time solvent was removed and the residue partitioned between DCM (10 mL) and sat. aq. NaHCO$_3$ (10 mL). DCM layer concentrated under reduced pressure and purified by preparative HPLC (Waters, Acidic (0.1% Formic acid), Waters X-Select Prep-C18, 5 μm, 19×50 mm column, 25-70% MeCN in Water) to afford the title compound (40 mg).

1H NMR (400 MHz; DMSO-d6) δ 10.20 (s, 1H), 9.50 (s, 1H), 9.11 (s, 1H), 8.88 (s, 1H), 8.37 (d, 1H), 8.05 (d, 1H), 7.99 (dt, 1H), 7.88 (d, 1H), 7.8-7.77 (m, 3H), 7.76-7.69 (m, 1H), 7.65-7.52 (m, 2H), 7.39 (d, 1H), 7.15 (br. s, 1H), 6.94 (br. d, 1H), 6.79 (br. d, 1H), 6.50-6.46 (m, 2H), 3.31 (s, 2H), 1.71 (d, 6H), 1.31 (s, 9H).

LCMS m/z 701 (M+H)$^+$ (ES$^+$); 699 (M–H)$^-$ (ES$^-$)

Example 12

1-(4-((2-((3-Aminobenzo[d]isoxazol-5-yl)amino)pyrimidin-4-yl)oxy)naphthalen-1-O-3-(3-(tert-butyl)-1-(3-(dimethylphosphoryl)phenyl)-1H-pyrazol-5-yl)urea

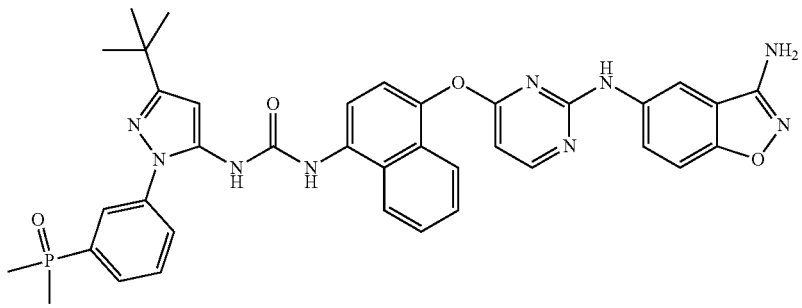 [SMILES: CC(C)(C)c1cc(NC(=O)Nc2ccc(Oc3ccnc(Nc4ccc5onc(N)c5c4)n3)c3ccccc23)n(-c2cccc(P(C)(C)=O)c2)n1]

1-(3-(tert-Butyl)-1-(3-(dimethylphosphoryl)phenyl)-1H-pyrazol-5-yl)-3-(4-((2-chloropyrimidin-4-yl)oxy)naphthalen-1-yl)urea (see Example 10(i) above; 100 mg, 0.170 mmol) and tert-butyl (5-aminobenzo[d]isoxazol-3-yl)carbamate (85 mg, 0.340 mmol) were combined in THF (1 mL) and the mixture stirred for 2 min; p-TSA monohydrate (64.6 mg, 0.340 mmol) was added to the resulting suspension, followed by THF (1.5 mL) and the mixture stirred overnight at 60° C. 1M HCl—IPA (1019 μL, 1.019 mmol) added and stirred reaction at 60° C. over 16 h. After this time solvent was removed and the residue partitioned between DCM (10 mL) and sat. aq. NaHCO₃ (10 mL). DCM layer concentrated under reduced pressure and purified by preparative HPLC (Waters, Acidic (0.1% Formic acid), Waters X-Select Prep-C18, 5 μm, 19×50 mm column, 25-70% MeCN in Water) to afford the title compound (50 mg).

1H NMR (400 MHz; DMSO-d6) δ 9.56 (br.s, 1H), 9.13 (br.s, 1H), 8.93 (br.s, 1H), 8.36 (d, 1H), 8.06-7.97 (m, 2H), 7.91 (br.s, 1H), 7.86 (d, 1H), 7.85-7.77 (m, 3H), 7.75-7.69 (m, 1H), 7.64-7.54 (m, 2H), 7.41 (d, 2H), 7.12 (br.d, 1H), 6.50 (d, 1H), 6.45 (s, 1H), 6.22 (br.s, 2H), 1.70 (d, 6H), 1.31 (s, 9H).

LCMS m/z 702 (M+H)⁺ (ES⁺); 700 (M−H)⁻ (ES⁻)

Example 13

1-(3-(tert-Butyl)-1-(3-(dimethylphosphoryl)phenyl)-1H-pyrazol-5-yl)-3-(4-((2-((7-methyl-1H-indazol-5-yl)amino)pyrimidin-4-yl)oxy)naphthalen-1-yl)urea To a solution of 1-(3-(tert-butyl)-1-(3-(dimethylphosphoryl)phenyl)-1H-pyrazol-5-yl)-3-(4-((2-chloropyrimidin-4-yl)oxy)naphthalen-1-yl)urea (see Example 10(i) above; 69 mg, 0.117 mmol) in isopropanol (1 mL) was added 7-methyl-1H-indazol-5-amine, HCl (43.0 mg, 0.234 mmol) and the mixture warmed to afford almost total dissolution. Isopropanol-HCl (234 μL, 0.234 mmol) was added and the mixture stirred at 60° C. overnight. Reaction was cooled to ambient temperature, solvent removed and then partitioned between EtOAc (10 mL), THF (1 mL) and sat. aq. sodium bicarbonate (10 mL). Organic layer dried over MgSO₄, filtered and solvent removed to afford crude product, 101 mg. The crude product was purified by preparative HPLC (Waters, Acidic (0.1% Formic acid), Waters X-Select Prep-C18, 5 μm, 19×50 mm column, 25-70% MeCN in Water) and then purified on SCX (5 g, loading in MeOH/THF (2 mL)) washed with MeOH (15 mL) and eluted with 0.7 N ammonia in MeOH (10 mL) to afford the title compound (20 mg) as a pale yellow solid.

1H NMR (400 MHz; DMSO-d6) δ 12.89 (s, 1H), 9.46 (br.s, 1H), 9.16 (s, 1H), 8.96 (s, 1H), 8.39 (d, 1H), 8.11 (d, 1H), 8.07-7.97 (m, 2H), 7.88-7.79 (m, 3H), 7.78-7.72 (m, 1H), 7.66-7.52 (m, 3H), 7.42 (d, 1H), 7.39 (br.s, 1H), 7.02 (br.s, 1H), 6.58 (d, 1H), 6.48 (s, 1H), 2.28 (br.s, 3H), 1.72 (d, 6H), 1.32 (s, 9H).

LCMS m/z 700 (M+H)⁺ (ES⁺); 698 (M−H)⁻ (ES⁻)

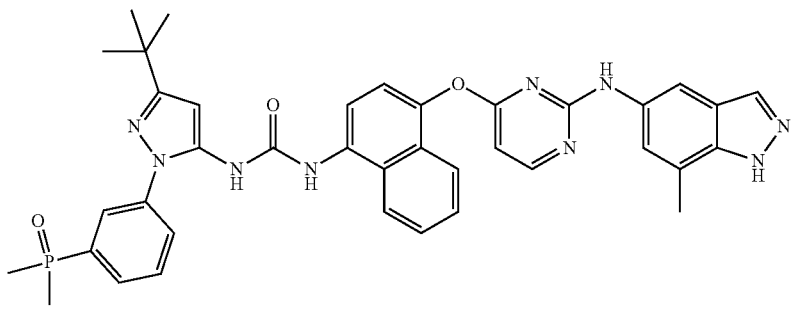 [SMILES: Cc1cc(Nc2nccc(Oc3ccc(NC(=O)Nc4cc(C(C)(C)C)nn4-c4cccc(P(C)(C)=O)c4)c4ccccc34)n2)cc2cn[nH]c12]

Example 14

1-(3-(tert-Butyl)-1-(4-(dimethylphosphoryl)phenyl)-1H-pyrazol-5-yl)-3-(4-((2-((2-oxoindolin-6-yl)amino)pyrimidin-4-yl)oxy)naphthalen-1-yl)urea

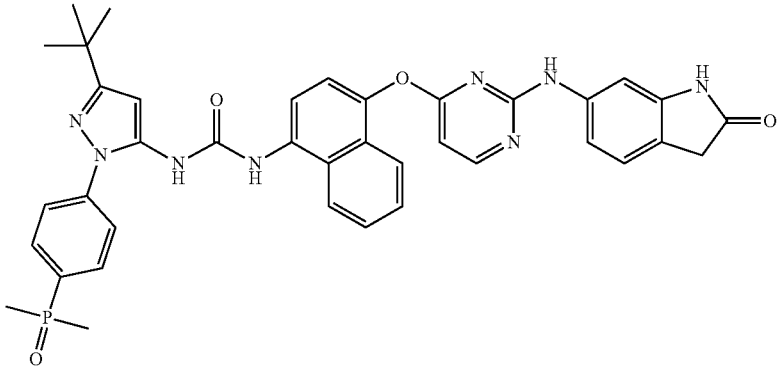 [SMILES: CC(C)(C)c1cc(NC(=O)Nc2ccc(Oc3ccnc(Nc4ccc5c(c4)NC(=O)C5)n3)c3ccccc23)n(-c2ccc(P(C)(C)=O)cc2)n1]

To a stirred solution of 1-(3-(tert-butyl)-1-(4-(dimethylphosphoryl)phenyl)-1H-pyrazol-5-yl)-3-(4-((2-chloropyrimidin-4-yl)oxy)naphthalen-1 yl)urea (see Example 7(i) above; 106 mg, 0.180 mmol) in THF (2 mL) was added p-TSA monohydrate (68.5 mg, 0.360 mmol) then 6-aminoindolin-2-one (53.3 mg, 0.360 mmol). A white precipitate formed causing stirring to stop. DMF (2 mL) was added to solubilise mixture. The reaction was heated at 60° C. overnight. The reaction was cooled to rt and separated between aq sodium bicarbonate (15 mL) and EtOAc (20 mL). The aqueous layer was extracted with EtOAc (2×20 mL). The combined organic extracts were washed with water (3×20 mL), brine (20 mL), dried (MgSO$_4$), filtered and concentrated in vacuo to afford a solid (107 mg). Dissolved in THF then isohexane added to precipitate product. The solid was collected by filtration and washed with isohexane, 90% purity. The solid was dissolved in 1:1 MeOH/THF and dry loaded onto silica then purified by chromatography on silica gel (12 g column, 0-10% MeOH in DCM) to afford a green solid. The solid was dissolved in THF and isohexane added until the product precipitated. The solid was filtered, washed with isohexane and transferred to the vacuum oven overnight to afford the title compound (26 mg) as an off-white solid.

1H NMR (DMSO-d6) 400 MHz, δ: 10.19 (1H, s) 9.50 (1H, s) 9.15 (1H, s) 8.94 (1H, s) 8.37 (1H, d) 8.08 (1H, d) 7.98-7.89 (3H, m) 7.83-7.76 (3H, m) 7.66-7.62 (1H, m) 7.59-7.55 (1H, m) 7.41 (1H, d) 7.15 (1H, br s) 6.95 (1H, br d) 6.79 (1H, br d) 6.50 (1H, s) 6.49 (1H, s) 3.30 (2H, s) 1.70 (6H, d) 1.30 (9H, s).

LCMS m/z 701 (M+H)$^+$ (ES$^+$)

Example 15

1-(3-(tert-Butyl)-1-(4-(dimethylphosphoryl)phenyl)-1H-pyrazol-5-yl)-3-(4-((2-(methyl-(phenyl)amino)pyrimidin-4-yl)oxy)naphthalen-1-yl)urea

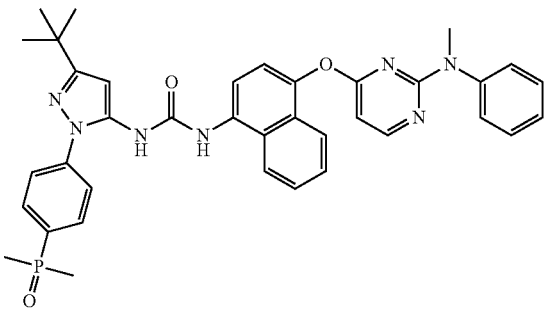 [SMILES: CN(c1ccccc1)c1nccc(Oc2ccc(NC(=O)Nc3cc(C(C)(C)C)nn3-c3ccc(P(C)(C)=O)cc3)c3ccccc23)n1]

To a stirred solution of 1-(3-(tert-butyl)-1-(4-(dimethylphosphoryl)phenyl)-1H-pyrazol-5-yl)-3-(4-((2-chloropyrimidin-4-yl)oxy)naphthalen-1-yl)urea (see Example 7(i) above; 105 mg, 0.178 mmol) in THF (2 mL) was added p-TSA monohydrate (67.8 mg, 0.357 mmol) then N-methylaniline (39.4 µL, 0.357 mmol). DMF (2 mL) was added and the resulting mixture stirred at 60° C. overnight. The reaction was cooled to rt and separated between aq sodium bicarbonate (15 mL) and EtOAc (20 mL). The aqueous layer was extracted with EtOAc (2×20 mL). The combined organic extracts were washed with water (3×20 mL), brine (20 mL), dried (MgSO$_4$), filtered and concentrated in vacuo to afford a pink solid (125 mg). The crude product was purified by chromatography on silica gel (40 g column, 0-10% MeOH in DCM) to afford a cream solid. The crude product was purified by preparative HPLC (Waters, Acidic (0.1% Formic acid), Waters X-Select Prep-C18, 5 µm, 19×50 mm column, 35-65% MeCN in Water) to afford the title compound (51 mg) as a white solid.

1H NMR (DMSO-d6) 400 MHz, δ: 9.14 (1H, s) 8.98 (1H, s) 8.26 (1H, d) 8.07 (1H, d) 7.98-7.93 (2H, m) 7.87 (1H, d) 7.80-7.76 (3H, m) 7.66-7.61 (1H, m) 7.58-7.55 (1H, m) 7.32 (1H, d) 7.19-7.12 (4H, m) 7.07-7.03 (1H, m) 6.47 (1H, s) 6.31 (1H, s) 3.26 (3H, s) 1.70 (6H, d) 1.30 (9H, s).

LCMS m/z 660 (M+H)$^+$ (ES$^+$); 658 (M−H)$^−$ (ES$^−$)

Example 16

3-((4-((4-(3-(3-(tert-Butyl)-1-(3-(dimethylphosphoryl)phenyl)-1H-pyrazol-5-yl)ureido)-naphthalen-1-yl)oxy)pyrimidin-2-yl)amino)-N-(2-morpholinoethyl)benzamide

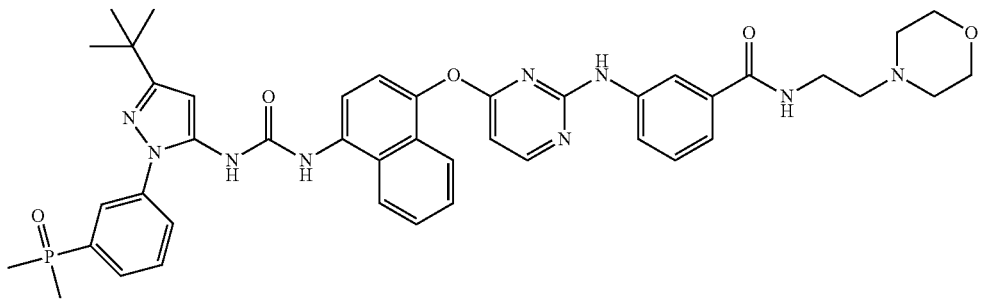 [SMILES: CC(C)(C)c1cc(NC(=O)Nc2ccc(Oc3ccnc(Nc4cccc(C(=O)NCCN5CCOCC5)c4)n3)c3ccccc23)n(-c2cccc(P(C)(C)=O)c2)n1]

To a suspension of 1-(3-(tert-butyl)-1-(3-(dimethylphosphoryl)phenyl)-1H-pyrazol-5-yl)-3-(4-((2-chloropyrimidin-4-yl)oxy)naphthalen-1-yl)urea (see Example 10(i) above; 160 mg, 0.272 mmol) in THF (1 mL) was added p-TSA monohydrate (155 mg, 0.815 mmol). To the resulting solution was added 3-amino-N-(2-morpholinoethyl)benzamide (135 mg, 0.543 mmol) and the resulting suspension was stirred at 50° C. for 18 h. After this time IPA (3 mL), THF (3 mL) was added and the reaction stirred for 2 days at 50° C. DMF (3 mL) was next added and the reaction stirred for a further 24 h at 50° C. Volatiles were removed under reduced pressure and the resulting DMF solution diluted with ethyl acetate (20 mL), washed with sat. aqueous sodium bicarbonate (2×5 mL), brine (5 mL), dried over Na$_2$SO$_4$, filtered and concentrated to afford a yellow solid (210 mg). The crude product was purified by preparative HPLC (Waters, Acidic (0.1% Formic acid), Waters X-Select Prep-C18, 5 μm, 19×50 mm column, 5-95% MeCN in Water) to afford a cream solid which was loaded onto a column of SCX (5 g) in MeOH. The column was washed with MeOH (15 mL) and then the product was eluted with 0.7 M ammonia in MeOH (15 mL). The resultant mixture was concentrated in vacuo to afford the title compound (60 mg) as a cream powder.

1H NMR (400 MHz; DMSO-d6) δ 9.64 (s, 1H), 9.09 (s, 1H), 8.86 (s, 1H), 8.39 (d, 1H), 8.24 (t, 1H), 8.04 (br.d, 1H), 7.99 (dt, 1H), 7.92-7.76 (m, 5H), 7.72 (td, 1H), 7.64-7.52 (m, 2H), 7.44 (br.d, 1H), 7.40 (d, 1H), 7.23 (d, 1H), 6.99 (br.t, 1H), 6.56 (d, 1H), 6.45 (s, 1H), 3.55 (app.t, 4H), 3.38-3.29 (m, 2H), 2.45-2.34 (m, 6H), 1.70 (d, 6H), 1.31 (s, 9H).

LCMS m/z 802 (M+H)$^+$ (ES$^+$); 800 (M−H)$^−$ (ES$^−$)

Example 17

1-(3-(tert-Butyl)-1-(4-(dimethylphosphoryl)phenyl)-1H-pyrazol-5-yl)-3-(4-((2-((3-(2-morpholinoethoxy)phenyl)amino)pyrimidin-4-yl)oxy)naphthalen-1-yl)urea

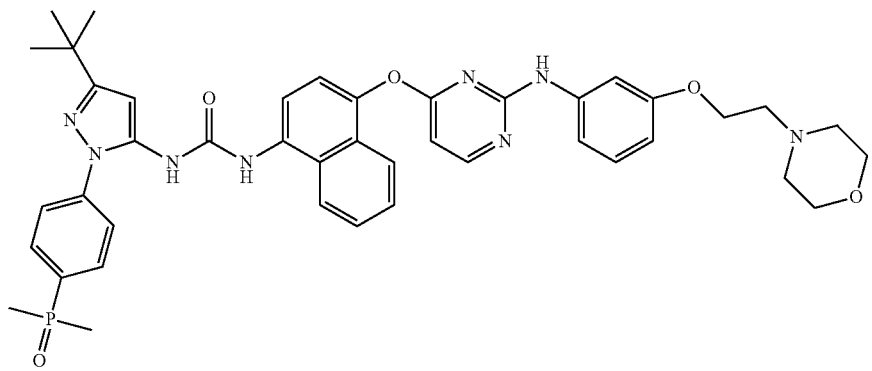 [SMILES: CC(C)(C)c1cc(NC(=O)Nc2ccc(Oc3ccnc(Nc4cccc(OCCN5CCOCC5)c4)n3)c3ccccc23)n(-c2ccc(P(C)(C)=O)cc2)n1]

To a stirred solution of 1-(3-(tert-butyl)-1-(4-(dimethylphosphoryl)phenyl)-1H-pyrazol-5-yl)-3-(4-((2-chloropyrimidin-4-yl)oxy)naphthalen-1-yl)urea (see Example 7(i) above; 101 mg, 0.171 mmol) in THF (2 mL) was added p-TSA monohydrate (65.2 mg, 0.343 mmol) then 3-(2-morpholinoethoxy)aniline (76 mg, 0.343 mmol). DMF (2 mL) was added and the resulting mixture stirred at 60° C. overnight. The reaction was cooled to rt, whereupon p-TSA monohydrate (32.6 mg, 0.171 mmol) was added, followed by 3-(2-morpholinoethoxy)aniline (38.1 mg, 0.171 mmol). The resulting mixture was stirred at 60° C. overnight. The reaction was cooled to rt and separated between aq sodium bicarbonate (15 mL) and EtOAc (20 mL). The aqueous layer was extracted with EtOAc (2×20 mL). The combined organic extracts were washed with water (3×20 mL), brine (20 mL), dried (MgSO₄), filtered and concentrated in vacuo to afford a pink solid (165 mg). The crude product was dissolved in the minimum of DCM and purified by chromatography on silica gel (12 g column, 0-10% MeOH in DCM) to afford a light pink solid which was purified by preparative HPLC (Waters, Basic (0.1% Ammonia), Agilent Prep C-18, 5 μm, 21.2×50 mm column, 25-65% MeCN in Water) to afford the title compound (46 mg) as a white solid.

1H NMR (DMSO-d6) 400 MHz, δ: 9.38 (1H, s) 9.08 (1H, s) 8.88 (1H, s) 8.39 (1H, d) 8.09 (1H, d) 7.97-7.91 (3H, m) 7.83 (1H, d) 7.79-7.76 (2H, m) 7.65-7.61 (1H, m) 7.58-7.54 (1H, m) 7.39 (1H, d) 7.14 (1H, s) 6.97 (1H, d) 6.88 (1H, t) 6.53 (1H, d) 6.47 (1H, s) 6.43-6.41 (1H, m) 3.92 (2H, t) 3.56-3.53 (4H, m) 2.64-2.61 (2H, m) 2.43 (4H, br m) 1.70 (6H, d) 1.31 (9H, s).

LCMS m/z 775 (M+H)⁺ (ES⁺)

Example 18

1-(3-(tert-Butyl)-1-(4-(dimethylphosphoryl)phenyl)-1H-pyrazol-5-yl)-3-(4-((2-((4-((2-hydroxyethyl)thio) phenyl)amino)pyrimidin-4-yl)oxy)naphthalen-1-yl) urea

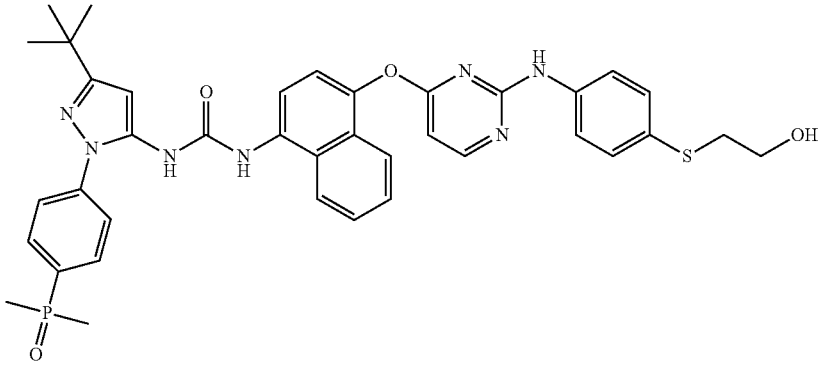 [SMILES: CC(C)(C)c1cc(NC(=O)Nc2ccc(Oc3ccnc(Nc4ccc(SCCO)cc4)n3)c3ccccc23)n(-c2ccc(P(C)(C)=O)cc2)n1]

To a stirred solution of 1-(3-(tert-butyl)-1-(4-(dimethylphosphoryl)phenyl)-1H-pyrazol-5-yl)-3-(4-((2-chloropyrimidin-4-yl)oxy)naphthalen-1-yl)urea (see Example 7(i) above; 100 mg, 0.170 mmol) in THF (2 mL) was added p-TSA monohydrate (64.6 mg, 0.340 mmol) then 2-((4-aminophenyl)thio)ethanol (57.5 mg, 0.340 mmol). The resulting mixture was stirred at 60° C. for 2 h. Stirring continued at 60° C. overnight. The reaction mixture was cooled to rt and separated between aq NaHCO₃ (15 mL) and EtOAc (20 mL). The aqueous layer was extracted with EtOAc (2×20 mL). The combined organic extracts were washed with water (20 mL) then brine (20 mL), dried (MgSO₄), filtered and concentrated in vacuo to afford a pink solid. The crude product was purified by chromatography on silica gel (40 g column, 0-10% MeOH in DCM) to afford a white solid which was purified by preparative HPLC (Waters, Acidic (0.1% Formic acid), Waters X-Select Prep-C18, 5 μm, 19×50 mm column, 25-75% MeCN in Water) to afford the title compound (58 mg) as a white solid.

1H NMR (DMSO-d6) 400 MHz, δ: 9.59 (1H, s) 9.18 (1H, s) 8.98 (1H, s) 8.39 (1H, d) 8.10 (1H, d) 7.99-7.90 (3H, m) 7.82-7.77 (3H, m) 7.65-7.61 (1H, m) 7.58-7.54 (1H, m) 7.41 (1H, d) 7.22 (2H, br s) 7.01 (2H, br d) 6.60 (1H, d) 6.51 (1H, s) 4.83 (1H, t) 3.46-3.41 (2H, m) 2.85 (2H, t) 1.70 (6H, d) 1.30 (9H, s).

LCMS m/z 722 (M+H)⁺ (ES⁺); 720 (M−H)⁻ (ES⁻)

Example 19

(4-(3-(tert-Butyl)-5-(3-(4-((2-(phenylamino)pyrimidin-4-yl)oxy)naphthalen-1-yl)ureido)-1H-pyrazol-1-yl)phenyl)(methyl)phosphinic acid

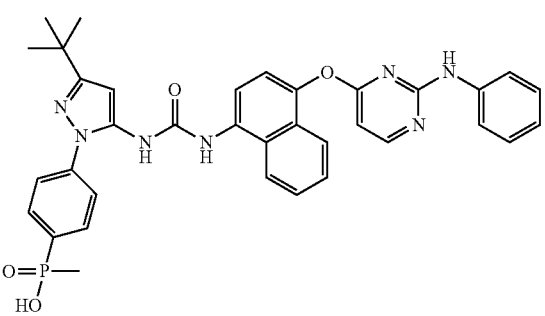 [SMILES: CC(C)(C)c1cc(NC(=O)Nc2ccc(Oc3ccnc(Nc4ccccc4)n3)c3ccccc23)n(-c2ccc(P(C)(=O)O)cc2)n1]

Ethyl (4-(3-(tert-butyl)-5-(3-(4-((2-(phenylamino)pyrimidin-4-yl)oxy)naphthalen-1-yl)-ureido)-1H-pyrazol-1-yl) phenyl)(methyl)phosphinate (145 mg, 0.212 mmol) was stirred in 1,4-dioxane (0.5 mL, 5.85 mmol) and 0.1 M sodium hydroxide (2.124 mL, 0.212 mmol) for 18 h. The mixture was diluted with water (5 mL) and diethyl ether (10 mL). The resulting solid was collected by filtration to give a sticky white paste. The crude product was purified by preparative HPLC (Varian, Acidic (0.1% Formic acid), Agilent Prep C-18, 5 μm, 21.2×50 mm column, 5-95% MeCN in Water) to afford a pink solid. The solid was triturated with acetonitrile to yield the title compound (45 mg) as a pale pink solid.

1H NMR (400 MHz; CDCl₃) δ 9.54 (s, 1H), 9.32 (s, 1H), 9.02 (s, 1H), 8.40 (d, 1H), 8.13 (d, 1H), 7.96-7.83 (m, 3H), 7.86 (d, 1H), 7.77-7.71 (m, 2H), 7.63 (t, 1H), 7.56 (t, 1H), 7.40 (d, 1H), 7.34-7.20 (m, 2H), 6.97 (t, 2H), 6.77 (t, 1H), 6.58 (d, 1H), 6.49 (s, 1H), 1.52 (d, 3H), 1.31 (s, 9H).

LCMS m/z 648 (M+H)⁺ (ES⁺); 646 (M−H)⁻ (ES⁻)

Example 20

1-(4-((2-((3-Aminobenzo[d]isoxazol-5-yl)amino)pyrimidin-4-yl)oxy)naphthalen-1-yl)-3-(3-(tert-butyl)-1-(4-(dimethylphosphoryl)phenyl)-1H-pyrazol-5-yl)urea

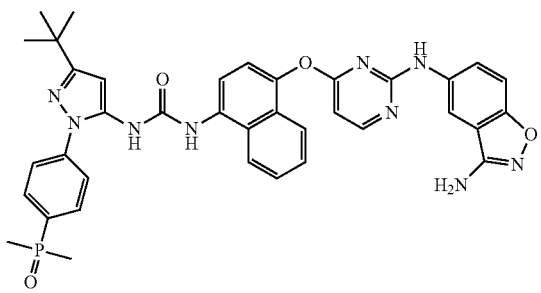 [SMILES: CC(C)(C)c1cc(NC(=O)Nc2ccc(Oc3ccnc(Nc4ccc5onc(N)c5c4)n3)c3ccccc23)n(-c2ccc(P(C)(C)=O)cc2)n1]

To a stirred solution of 1-(3-(tert-butyl)-1-(4-(dimethylphosphoryl)phenyl)-1H-pyrazol-5-yl)-3-(4-((2-chloropyrimidin-4-yl)oxy)naphthalen-1-yl)urea (see Example 7(i) above; 100 mg, 0.170 mmol) in THF (2 mL) was added p-TSA monohydrate (64.6 mg, 0.340 mmol) then tert-butyl (5-aminobenzo[d]isoxazol-3-yl)carbamate (85 mg, 0.340 mmol). DMF (2 mL) was added and the resulting mixture stirred at 60° C. overnight. The reaction was cooled to rt and separated between aq sodium bicarbonate (15 mL) and EtOAc (20 mL). The aqueous layer was extracted with EtOAc (2×20 mL). The combined organic extracts were washed with water (3×20 mL), brine (20 mL), dried (MgSO$_4$), filtered and concentrated in vacuo to afford a pink solid (176 mg), which was dissolved in THF (2 mL) and 1M HCl—IPA (340 μL, 0.340 mmol) added. The mixture was heated at 60° C. for 2 h. HCl—IPA (679 μL, 0.679 mmol) was added and stirring continued at 60° C. overnight. The reaction was cooled to rt and separated between aq sodium bicarbonate (15 mL) and EtOAc (20 mL). The aqueous layer was extracted with EtOAc (2×20 mL). The combined organic extracts were washed with water (3×20 mL), brine (20 mL), dried (MgSO$_4$), filtered and concentrated in vacuo to afford a solid (108 mg) which was purified by chromatography on silica gel (40 g column, 0-10% MeOH in DCM) to afford a light brown solid (42 mg). The crude product was purified by preparative HPLC (Waters, Acidic (0.1% Formic acid), Waters X-Select Prep-C18, 5 μm, 19×50 mm column, 25-65% MeCN in Water) to afford the title compound (18 mg) as an off-white solid.

1H NMR (DMSO-d6) 400 MHz, δ: 9.58 (1H, s) 9.16 (1H, s) 8.97 (1H, s) 8.36 (1H, d) 8.08 (1H, d) 7.98-7.87 (4H, m) 7.83-7.76 (3H, m) 7.66-7.62 (1H, m) 7.60-7.56 (1H, m) 7.43-7.39 (2H, m) 7.13-7.11 (1H, m) 6.50 (1H, d) 6.48 (1H, s) 6.24 (2H, s) 1.70 (6H, d) 1.30 (9H, s).

LCMS m/z 702 (M+H)$^+$ (ES$^+$); 700 (M–H)$^-$ (ES$^-$)

Example 21

1-(3-(tert-Butyl)-1-(4-(dimethylphosphoryl)phenyl)-1H-pyrazol-5-yl)-3-(4-((2-((7-methyl-1H-indazol-5-yl)amino)pyrimidin-4-yl)oxy)naphthalen-1-yl)urea

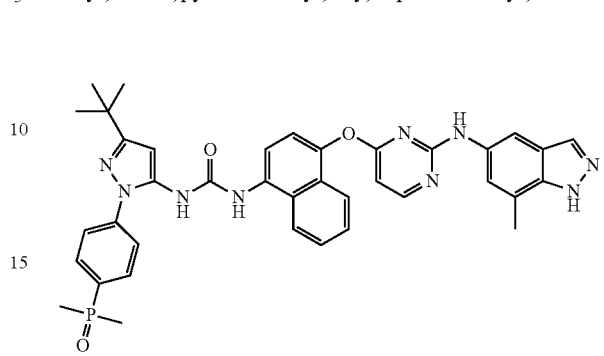

To a stirred solution of 1-(3-(tert-butyl)-1-(4-(dimethylphosphoryl)phenyl)-1H-pyrazol-5-yl)-3-(4-((2-chloropyrimidin-4-yl)oxy)naphthalen-1-yl)urea (see Example 7(i) above; 101 mg, 0.171 mmol) in THF (2 mL) was added p-TSA monohydrate (65.2 mg, 0.343 mmol) then 7-methyl-1H-indazol-5-amine hydrochloride (63.0 mg, 0.343 mmol). The resulting mixture was stirred at 60° C. overnight. DMF (2 mL) was added. Stirring continued at 60° C. overnight. The reaction was cooled to rt and separated between aq sodium bicarbonate (15 mL) and EtOAc (20 mL). The aqueous layer was extracted with EtOAc (2×20 mL). The combined organic extracts were washed with water (3×20 mL), brine (20 mL), dried (MgSO$_4$), filtered and concentrated in vacuo to afford a maroon solid (150 mg). The crude product was purified by chromatography on silica gel (40 g column, 0-10% MeOH in DCM) to afford a burnt orange solid (37 mg). The crude product was purified by preparative HPLC (Gilson, Acidic (0.1% Formic acid), Waters X-Select Prep-C18, 5 μm, 19×50 mm column, 25-75% MeCN in Water) to afford the title compound (18 mg) as a tan solid.

1H NMR (DMSO-d6) 400 MHz, δ: 12.90 (1H, s) 9.48 (1H, br s) 9.29 (1H, s) 9.10 (1H, s) 8.38 (1H, d) 8.15 (1H, d) 8.06-8.04 (1H, m) 7.99-7.94 (2H, m) 7.83-7.77 (3H, m) 7.66-7.54 (4H, m) 7.42 (1H, d) 7.01 (1H, br s) 6.58 (1H, d) 6.49 (1H, s) 2.28 (3H, s) 1.70 (6H, d) 1.31 (9H, s).

LCMS m/z 700 (M+H)$^+$ (ES$^+$); 698 (M–H)$^-$ (ES$^-$)

Example 22

1-(3-(tert-Butyl)-1-(4-(diethylphosphoryl)phenyl)-1H-pyrazol-5-yl)-3-(4-((2-(phenylamino)-pyrimidin-4-yl)oxy)naphthalen-1-yl)urea

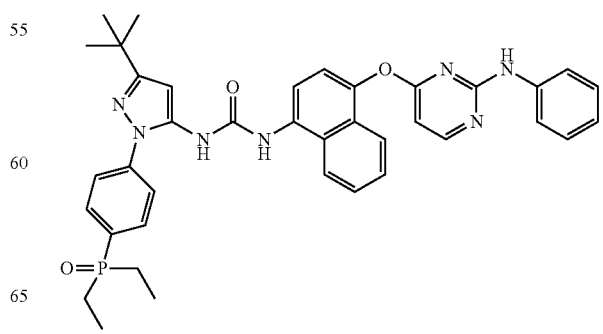

(i) Ethyl 1-(4-bromophenyl)-3-(tert-butyl)-1H-pyrazole-5-carboxylate

Pyridine (1.611 mL, 19.92 mmol) followed by activated 4A molecular sieves (3 g) were added to a stirred mixture of (4-bromophenyl)boronic acid (3 g, 14.94 mmol), ethyl 3-(tert-butyl)-1H-pyrazole-5-carboxylate (1.954 g, 9.96 mmol) and copper (II) acetate (2.71 g, 14.94 mmol) in DCM (50 mL) at rt. The mixture was stirred for 48 h then filtered through Celite, and the cake washed with DCM (300 mL). The filtrate was evaporated under reduced pressure and the crude product was triturated with ether (100 mL) and filtered. The filtrate was evaporated under reduced pressure and the residue purified by chromatography on silica gel (120 g column, 0-10% ether/isohexane) to afford the sub-title compound (3.47 g) as a white solid.

1H NMR (400 MHz; CDCl$_3$) δ 7.56 (d, 2H), 7.32 (d, 2H), 6.89 (s, 1H), 4.24 (q, 2H), 1.35 (s, 9H), 1.28 (t, 3H).

LCMS m/z 351/3 (M+H)$^+$ (ES$^+$)

(ii) Ethyl 3-(tert-butyl)-1-(4-(diethylphosphoryl)phenyl)-1H-pyrazole-5-carboxylate The product from step (i) above (500 mg, 1.424 mmol), Xantphos (82 mg, 0.142 mmol), palladium(II) acetate (15.98 mg, 0.071 mmol) and K$_3$PO$_4$.H$_2$O (332 mg, 1.424 mmol) were combined under N$_2$ in a microwave tube containing a magnetic stirrer. Diethylphosphine oxide (181 mg, 1.708 mmol) was dissolved in degassed anhydrous DMF (40 mL), the reactants were combined under nitrogen and heated at 150° C. in a microwave (300 W) for 40 min. The reaction was cooled to ambient temperature, combined and filtered on Glass fibre pad (Whatmans GF/C), solvents removed under reduced pressure. Residue was preadsorbed onto silica (ca. 5 g) and purified by chromatography on the Companion 40 g column, 0% MeOH:DCM to 10% MeOH:DCM) to afford the sub-title compound (420 mg)

1H NMR (400 MHz, DMSO-d6) δ 7.81 (dd, 2H), 7.60 (dd, 2H), 7.05 (s, 1H), 4.19 (q, 2H), 1.97 (m, 4H), 1.31 (s, 9H), 1.15 (t, 3H), 0.97 (dt, 6H).

LCMS m/z 377 (M+H)$^+$ (ES$^+$)

(iii) 3-(tert-butyl)-1-(4-(diethylphosphoryl)phenyl)-1H-pyrazole-5-carboxylic acid The product from step (ii) above (420 mg, 1.116 mmol) was dissolved in ethanol (5 mL) and NaOH, 2N (837 µL, 1.674 mmol) added. Stirred at rt for 16 h, then the solvent was evaporated and the residue partitioned between EtOAc (20 mL) and water (20 mL). Aqueous separated and acidified with conc. HCl to pH 1. Product was extracted with ethyl acetate (2×20 mL), organics combined, dried (MgSO$_4$) filtered and solvent evaporated to give the sub-title compound (372 mg) as a colourless solid.

1H NMR (400 MHz, DMSO-d6) δ 13.35 (s, 1H), 7.79 (dd, 2H), 7.59 (dd, 2H), 6.99 (s, 1H), 1.96 (m, 4H), 1.30 (s, 9H), 0.96 (dt, 6H).

LCMS m/z 349 (M+H)$^+$ (ES$^+$)

(iv) 1-(3-(tert-Butyl)-1-(4-(diethylphosphoryl)phenyl)-1H-pyrazol-5-yl)-3-(4-((2-(phenylamino)pyrimidin-4-yl)oxy)naphthalen-1-yl)urea DPPA (217 µL, 1.005 mmol) was added to a stirred solution of the product from step (iii) above (350 mg, 1.005 mmol) and Et$_3$N (350 µL, 2.51 mmol) in DMF (4 mL) at 0-5° C. After 30 min the mixture was warmed to rt and stirred for a further 1 h. 4-((4-Aminonaphthalen-1-yl)oxy)-N-phenylpyrimidin-2-amine (see Example 1(i) above; 313 mg, 0.954 mmol) was added and the mixture heated at 100° C. for 1 h, cooled and partitioned between EtOAc (100 mL) and water (50 mL). The organic layer was separated, washed with water (50 mL), 20% w/w brine (50 mL), dried (MgSO$_4$), filtered and evaporated under reduced pressure to a brown solid. The crude product was purified by chromatography on the Companion (40 g column, 0% MeOH:DCM to 5%) to afford the title compound (393 mg) as a pale brown solid.

1H NMR (400 MHz, DMSO-d6) δ 9.54 (s, 1H), 9.19 (s, 1H), 8.93 (s, 1H), 8.39 (d, 1H), 8.11 (d, 1H), 7.88 (m, 3H), 7.80 (m, 3H), 7.63 (m, 1H), 7.56 (m, 1H), 7.39 (d, 1H), 7.27 (s, 2H), 6.96 (t, 2H), 6.77 (t, 1H), 6.58 (d, 1H), 6.48 (s, 1H), 1.94 (m, 4H), 1.30 (s, 9H), 0.95 (dt, 6H).

LCMS m/z 674 (M+H)$^+$ (ES$^+$)

Example 23

1-(3-(tert-Butyl)-1-(3-((dimethylphosphoryl)methyl)phenyl)-1H-pyrazol-5-yl)-3-(4-((2-(phenylamino)pyrimidin-4-yl)oxy)naphthalen-1-yl)urea

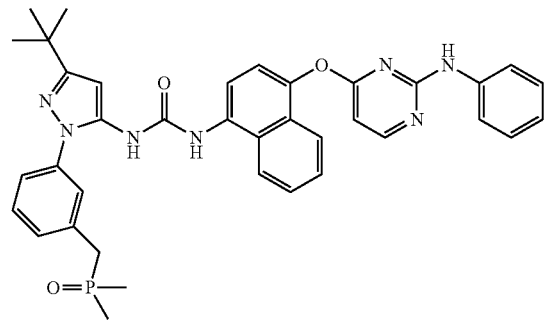 [SMILES: CC(C)(C)c1cc(NC(=O)Nc2ccc(Oc3ccnc(Nc4ccccc4)n3)c3ccccc23)n(-c2cccc(CP(C)(C)=O)c2)n1]

(i) Ethyl 3-(tert-butyl)-1-(3-(hydroxymethyl)phenyl)-1H-pyrazole-5-carboxylate Pyridine (0.759 mL, 9.39 mmol) followed by activated molecular sieves (1 g) were added to a stirred mixture of (3-(hydroxymethyl)phenyl)boronic acid (1.07 g, 7.04 mmol), ethyl 3-(tert-butyl)-1H-pyrazole-5-carboxylate (0.921 g, 4.69 mmol) and copper (II) acetate (1.279 g, 7.04 mmol) in DCM (30 mL) at rt. The mixture was stirred for 18 h, filtered and the filtrate evaporated. Ether (200 mL) was added to the residue, the solid filtered off and the filtrate evaporated under reduced pressure. The residue was purified by chromatography on silica gel (80 g column, 0-40% EtOAc/isohexane) to afford the sub-title compound (1.07 g as a colourless oil.

1H NMR (400 MHz; CDCl$_3$) δ 7.44-7.32 (m, 4H), 6.88 (s, 1H), 4.73 (d, 2H), 4.22 (q, 2H), 1.93 (t, 1H), 1.36 (s, 9H), 1.26 (t, 3H).

LCMS m/z 303 (M+H)$^+$ (ES$^+$)

(ii) Ethyl 3-(tert-butyl)-1-(3-(chloromethyl)phenyl)-1H-pyrazole-5-carboxylate SOCl$_2$ (1.052 mL, 14.42 mmol) was added to a stirred solution of the product from step (i) above (2.18 g, 7.21 mmol) in DCM (20 mL) at rt under N₂. The mixture was stirred for 2 h then the solvent evaporated under reduced pressure. The residue was partitioned between EtOAc (100 mL) and aq NaHCO₃ (100 mL), the organic layer separated, washed with brine, dried (MgSO₄) and evaporated under reduced pressure to give the sub-title compound (2.216 g) as an oil.

1H NMR (CDCl₃) 400 MHz, δ: 7.51-7.37 (m, 4H), 6.90 (s, 1H), 4.63 (s, 2H), 4.23 (q, 2H), 1.36 (s, 9H), 1.24 (t, 3H).

(iii) Ethyl 3-(tert-butyl)-1-(3-((dimethylphosphoryl)methyl)phenyl)-1H-pyrazole-5-carboxylate To a solution of the product from step (ii) above (285 mg, 0.888 mmol) in DMF (5 mL) was added dimethylphosphine oxide (76 mg, 0.977 mmol) and K₃PO₄.H₂O (511 mg, 2.221 mmol). The mixture was purged with nitrogen for 20 min. Palladium(II) acetate (9.97 mg, 0.044 mmol) and xantphos (30.8 mg, 0.053 mmol) were added and the reaction mixture was heated in the microwave (Smith, 120° C.) for 30 min. The mixture was concentrated under reduced pressure and the residue was resuspended in water (10 mL). The suspension was extracted with EtOAc (3×10 mL) and the combined organic phases were concentrated onto loose silica. The silicate was purified by chromatography on the Companion (40 g column, 0-5% CH₃OH:CH₂Cl₂) to afford the sub-title compound (175 mg) as a colourless gum.

1H NMR (400 MHz; CDCl₃) δ 7.45-7.32 (m, 2H), 7.31-7.27 (m, 2H), 6.88 (s, 1H), 4.23 (q, 2H), 3.23 (d, 2H), 1.49 (d, 6H), 1.36 (s, 9H), 1.28 (t, 3H).

LCMS m/z 363 (M+H)⁺ (ES⁺)

(iv) 3-(tert-Butyl)-1-(3-((dimethylphosphoryl)methyl)phenyl)-1H-pyrazole-5-carboxylic acid 1M Sodium hydroxide (0.516 mL, 0.516 mmol) was added to a stirred solution of the product from step (iii) above (170 mg, 0.469 mmol) in THF (1.5 mL) and MeOH (1 mL).

The mixture was stirred at rt overnight. The mixture was diluted with water (10 mL) and concentrated under reduced pressure to remove organic solvents. 1 M hydrogen chloride solution (0.55 mL) was added and the mixture was extracted with ethyl acetate (3×10 mL). The combined organic phases were washed with saturated brine (10 mL), dried (MgSO₄) and concentrated to yield the sub-title compound (142 mg) as a white solid. LCMS m/z 335 (M+H)⁺ (ES⁺); 333 (M−H)⁻ (ES⁻)

(v) 1-(3-(tert-Butyl)-1-(3-((dimethylphosphoryl)methyl)phenyl)-1H-pyrazol-5-yl)-3-(4-((2-(phenylamino)pyrimidin-4-yl)oxy)naphthalen-1-yl)urea DPPA (90 µL, 0.419 mmol) was added to a stirred solution of the product from step (iv) above (140 mg, 0.419 mmol) and Et₃N (146 µL, 1.047 mmol) in DMF (10 mL) under N₂ at 0-5° C. After 30 min the mixture was warmed to rt and stirred for a further 1 h. 4-((4-Aminonaphthalen-1-yl)oxy)-N-phenylpyrimidin-2-amine (see Example 1(i) above; 137 mg, 0.419 mmol) was added and the mixture heated at 100° C. for 1 h. The mixture was diluted with water (10 mL) and extracted with EtOAc (3×30 mL). The organic phases were washed with water (10 mL), brine (10 mL), dried (MgSO₄) and evaporated under reduced pressure. The crude product was purified by chromatography on silica gel (40 g column, 0-5% CH₃OH:CH₂Cl₂) to afford a brown solid. The solid was triturated in acetonitrile to yield the title compound (142 mg) as a pale pink solid.

1H NMR (400 MHz; DMSO-d6) δ 9.53 (s, 1H), 9.51 (s, 1H), 8.97 (s, 1H), 8.39 (d, 1H), 8.22 (d, 1H), 8.00 (d, 1H), 7.81 (d, 1H), 7.68-7.59 (m, 1H), 7.59-7.51 (m, 3H), 7.51-7.44 (m, 1H), 7.40 (d, 1H), 7.37-7.16 (m, 3H), 6.94 (t, 2H), 6.77 (t, 1H), 6.59 (d, 1H), 6.52 (s, 1H), 3.37 (d, 2H), 1.46 (d, 6H), 1.31 (s, 9H).

LCMS m/z 660 (M+H)⁺ (ES⁺); 658 (M−H)⁻ (ES⁻)

Example 24

3-((4-((4-(3-(3-(tert-Butyl)-1-(4-(dimethylphosphoryl)phenyl)-1H-pyrazol-5-yl)ureido)-naphthalen-1-yl)oxy)pyrimidin-2-yl)amino)-N-(2-morpholinoethyl)benzamide

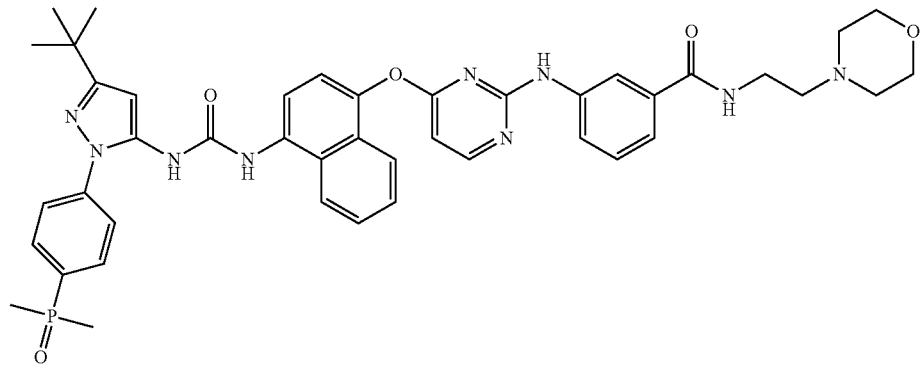 [SMILES: CC(C)(C)c1cc(NC(=O)Nc2ccc(Oc3ccnc(Nc4cccc(C(=O)NCCN5CCOCC5)c4)n3)c3ccccc23)n(-c2ccc(P(C)(C)=O)cc2)n1]

To a stirred solution of 1-(3-(tert-butyl)-1-(4-(dimethylphosphoryl)phenyl)-1H-pyrazol-5-yl)-3-(4-((2-chloropyrimidin-4-yl)oxy)naphthalen-1-yl)urea (see Example 7(i) above; 101 mg, 0.163 mmol) and p-TSA monohydrate (62.0 mg, 0.326 mmol) in THF (2 mL) was added 3-amino-N-(2-morpholinoethyl)benzamide (81 mg, 0.326 mmol). A precipitate formed at rt. The mixture was heated at 60° C. overnight. The reaction was cooled to rt and partitioned between aq sodium bicarbonate solution (20 mL) and EtOAc (20 mL). The aqueous layer was extracted with EtOAc (2×20 mL). The combined organic extracts were washed with water (3×20 mL), brine (20 mL), dried (MgSO₄), filtered and concentrated in vacuo to afford a light pink solid (126 mg). The crude product was purified by chromatography on silica gel (40 g column, 0-10% MeOH/NH₃ in DCM) to afford the title compound (75 mg) as a tan solid.

1H NMR (CDCl₃) 400 MHz, δ: 9.44 (2H, br s) 8.28 (1H, d) 8.17 (2H, t) 7.92-7.88 (3H, m) 7.78 (1H, br s) 7.71-7.66 (2H, m) 7.60-7.58 (1H, m) 7.45-7.41 (1H, m) 7.33-7.26 (3H, m) 7.21-7.18 (2H, m) 6.77 (1H, br t) 6.70 (1H, s) 6.38 (1H, d) 3.69-3.67 (4H, m) 3.50 (2H, q) 2.55 (2H, t) 2.46-2.45 (4H, m) 1.43 (6H, d) 1.37 (9H, s).

LCMS m/z 802 (M+H)⁺ (ES⁺); 800 (M−H)⁻ (ES⁻)

Example 25

1-(3-(tert-Butyl)-1-(4-(dimethylphosphoryl)phenyl)-1H-pyrazol-5-yl)-3-(4-((2-((4-(dimethyl-phosphoryl)phenyl)amino)pyrimidin-4-yl)oxy)naphthalen-1-yl)urea

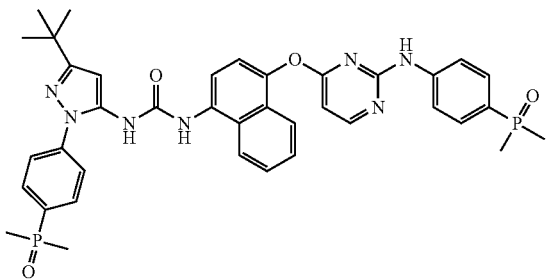

(i) (4-Aminophenyl)dimethylphosphine oxide

To a solution of 4-bromoaniline (250 mg, 1.410 mmol) in DMF (4 mL) was added dimethylphosphine oxide (121 mg, 1.551 mmol), palladium(II) acetate (15.82 mg, 0.070 mmol), Xantphos (48.9 mg, 0.085 mmol) and K₃PO₄ (329 mg, 1.551 mmol) and the mixture purged with N₂ for 20 min. The reaction mixture was heated in the microwave (Smith, 120° C.) for 30 min then filtered through a plug of cotton wool and washed with MeOH. The majority of the solvent was removed in vacuo and the resulting residue diluted with MeOH and loaded onto a column of SCX. The column was washed with MeOH, then the product eluted with NH₃/MeOH. The solvent was removed in vacuo to afford a dark brown oil (172 mg). The crude product was purified by chromatography on silica gel (40 g column, 0-10% MeOH in DCM) to afford the sub-title compound (137 mg) as a light pink solid.

1H NMR (DMSO-d6) 400 MHz, δ: 7.38-7.32 (2H, m) 6.62-6.58 (2H, m) 5.61 (2H, br s) 1.51 (6H, d).

LCMS m/z 170 (M+H)⁺ (ES⁺)

(ii) 1-(3-(tert-Butyl)-1-(4-(dimethylphosphoryl)phenyl)-1H-pyrazol-5-yl)-3-(4-((4-((4-(dimethylphosphoryl)phenyl)amino)pyrimidin-4-yl)oxy)naphthalen-1-yl)urea To a stirred solution of 1-(3-(tert-butyl)-1-(4-(dimethylphosphoryl)phenyl)-1H-pyrazol-5-yl)-3-(4-((2-chloropyrimidin-4-yl)oxy)naphthalen-1-yl)urea (see Example 7(i) above; 100 mg, 0.161 mmol) and p-TSA monohydrate (61.4 mg, 0.323 mmol) in THF (2 mL) was added a solution of the product from step (i) above (54.6 mg, 0.323 mmol) in DMF (1.5 mL). A precipitate formed at rt. The reaction was heated at 60° C. overnight. DMF (4 mL) was added and stirring continued at 60° C. overnight. (4-Aminophenyl)dimethylphosphine oxide (27.3 mg, 0.161 mmol) was added, stirring continued at 60° C. for 3 h then p-TSA monohydrate (30.7 mg, 0.161 mmol) was added and stirring continued at 60° C. overnight. The reaction was cooled to rt and partitioned between aq sodium bicarbonate (15 mL) and EtOAc (20 mL). The aqueous phase was extracted with EtOAc (2×20 mL). The combined organic extracts were washed with water (2×20 mL), brine (20 mL), dried (MgSO₄), filtered and concentrated in vacuo to afford a residue which was purified by chromatography on silica gel (40 g column, 0-10% MeOH/NH₃ in DCM) to afford the title compound (36 mg) an off-white solid.

1H NMR (DMSO-d6) 400 MHz, δ: 9.82 (1H, s) 9.19 (1H, s) 8.97 (1H, s) 8.45 (1H, d) 8.09 (1H, d) 7.99-7.94 (2H, m) 7.89 (1H, d) 7.83-7.77 (3H, m) 7.65-7.60 (1H, m) 7.57-7.53 (1H, m) 7.43 (1H, d) 7.39-7.32 (4H, br m) 6.70 (1H, d) 6.48 (1H, s) 1.71 (6H, d) 1.49 (6H, d) 1.31 (9H, s).

LCMS m/z 722 (M+H)⁺ (ES⁺); 720 (M−H)⁻ (ES⁻)

Example 26

(S)-1-(3-(tert-Butyl)-1-(4-(dimethylphosphoryl)phenyl)-1H-pyrazol-5-yl)-3-(4-((2-(2-(hydroxymethyl)pyrrolidin-1-yl)pyrimidin-4-yl)oxy)naphthalen-1-yl)urea

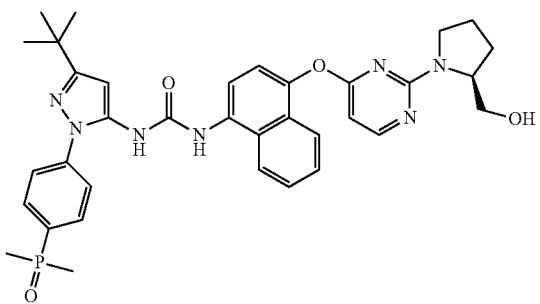 [SMILES: CC(C)(C)c1cc(NC(=O)Nc2ccc(Oc3ccnc(N4CCC[C@H]4CO)n3)c3ccccc23)n(-c2ccc(P(C)(C)=O)cc2)n1]

To a stirred suspension of 1-(3-(tert-butyl)-1-(4-(dimethylphosphoryl)phenyl)-1H-pyrazol-5-yl)-3-(4-((2-chloropyrimidin-4-yl)oxy)naphthalen-1-yl)urea (see Example 7(i) above; 75 mg, 0.121 mmol) n in 1,4-dioxane (2 mL) was added (S)-pyrrolidin-2-ylmethanol (37.7 µL, 0.363 mmol). The resulting mixture was heated at 60° C. for 2 h. The reaction was cooled to rt and the solvent removed in vacuo. The resulting orange oil was partitioned between aq sodium bicarbonate solution (15 mL) and EtOAc (20 mL). The aqueous phase was extracted with EtOAc (2×20 mL). The combined organic extracts were washed with water (20 mL), brine (20 mL), dried (MgSO₄), filtered and concentrated in vacuo to afford an orange solid (76 mg). The crude product was purified by chromatography on silica gel (12 g column, 0-10% MeOH in DCM) to afford the title compound (50 mg) as a tan solid.

1H NMR (DMSO-d6, 333K) 400 MHz, δ: 8.94 (s, 1H) 8.75 (s, 1H) 8.20 (d, 1H) 8.07 (d, 1H) 7.96-7.90 (m, 2H) 7.87-7.83 (m, 2H) 7.79-7.75 (m, 2H) 7.63-7.59 (m, 1H) 7.57-7.53 (m, 1H) 7.33 (d, 1H) 6.43 (s, 1H) 6.13 (d, 1H) 4.39

(br s, 1H) 3.86 (br s, 1H) 3.39 (br s, 1H) 3.26 (br s, 3H) 1.93-1.81 (m, 3H) 1.79-1.68 (m, 7H) 1.32 (s, 9H).
LCMS m/z 654 (M+H)⁺ (ES⁺); 652 (M−H)⁻ (ES⁻)

Example 27

(R)-1-(3-(tert-Butyl)-1-(4-(dimethylphosphoryl)phenyl)-1H-pyrazol-5-yl)-3-(4-((2-(2-(hydroxymethyl)pyrrolidin-1-yl)pyrimidin-4-yl)oxy)naphthalen-1-yl)urea

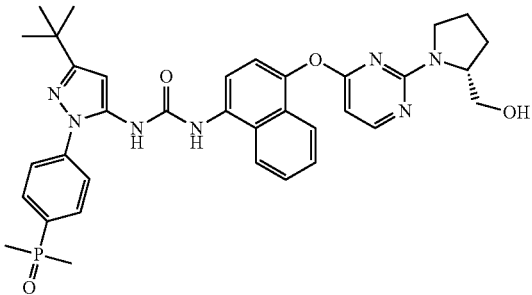 [SMILES: CC(C)(C)c1cc(NC(=O)Nc2ccc(Oc3ccnc(N4CCC[C@@H]4CO)n3)c3ccccc23)n(-c2ccc(P(C)(C)=O)cc2)n1]

To a stirred suspension of 1-(3-(tert-butyl)-1-(4-(dimethylphosphoryl)phenyl)-1H-pyrazol-5-yl)-3-(4-((2-chloropyrimidin-4-yl)oxy)naphthalen-1-yl)urea (see Example 7(i) above; 100 mg, 0.170 mmol) in 1,4-dioxane (3 mL) was added (R)-pyrrolidin-2-ylmethanol (50.8 µL, 0.509 mmol). The resulting mixture was stirred at 60° C. for 2 h. The reaction was cooled to rt and partitioned between aq sodium bicarbonate solution (15 mL) and EtOAc (20 mL). The aqueous phase was extracted with EtOAc (2×20 mL). The combined organic extracts were washed with brine (20 mL), dried (MgSO₄), filtered and concentrated in vacuo to afford a residue (102 mg). The crude product was purified by chromatography on silica gel (40 g column, 0-10% MeOH in DCM) to afford the title compound (82 mg) as an off-white solid.

1H NMR (DMSO-d6, 333K) 400 MHz, δ: 8.95 (s, 1H) 8.76 (s, 1H) 8.21 (d, 1H) 8.07 (d, 1H) 7.97-7.91 (m, 2H) 7.87-7.84 (m, 2H) 7.79-7.7 (m, 2H) 7.64-7.60 (m, 1H) 7.58-7.54 (m, 1H) 7.33 (d, 1H) 6.44 (s, 1H) 6.14 (d, 1H) 4.40 (br s, 1H) 3.87 (br s, 1H) 3.41 (br s, 1H) 3.27 (br s, 3H) 1.94-1.82 (m, 3H) 1.79-1.69 (m, 7H) 1.32 (s, 9H).
LCMS m/z 654 (M+H)⁺ (ES⁺); 652 (M−H)⁻ (ES⁻)

Example 28

1-(3-(tert-Butyl)-1-(4-(dimethylphosphoryl)phenyl)-1H-pyrazol-5-yl)-3-(4-((2-((4-(Pentafluorothio)phenyl)amino)pyrimidin-4-yl)oxy)naphthalen-1-yl)urea

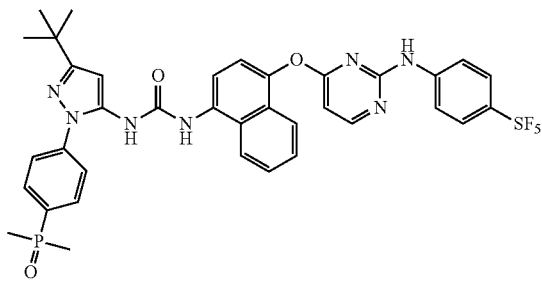

To a stirred solution of 1-(3-(tert-butyl)-1-(4-(dimethylphosphoryl)phenyl)-1H-pyrazol-5-yl)-3-(4-((2-chloropyrimidin-4-yl)oxy)naphthalen-1-yl)urea (see Example 7(i) above; 110 mg, 0.187 mmol) and p-TSA monohydrate (71.0 mg, 0.373 mmol) in THF (2 mL) was added 4-aminophenylsulphur pentafluoride (82 mg, 0.373 mmol). The mixture was heated at 60° C. overnight, 4-aminophenylsulphur pentafluoride (40.9 mg, 0.187 mmol) was added and stirring continued at 60° C. for 2 h. p-TSA monohydrate (71.0 mg, 0.373 mmol) was added followed by 4-aminophenylsulphur pentafluoride (40.9 mg, 0.187 mmol). Stirring continued at 60° C. overnight. The reaction was cooled to rt and partitioned between aq sodium bicarbonate (15 mL) and EtOAc (20 mL). The aqueous phase was extracted with EtOAc (2×20 mL). The combined organic extracts were washed with water (2×20 mL), brine (20 mL), dried (MgSO₄), filtered and concentrated in vacuo to afford an orange oil. The crude product was purified by chromatography on silica gel (40 g column, 0-10% MeOH in DCM) to afford an off-white solid. The crude product was purified by preparative HPLC (Gilson, Acidic (0.1% Formic acid), Waters X-Select Prep-C18, 5 µm, 19×50 mm column, 30-90% MeCN in Water) to afford the title compound (41 mg) as a light tan solid.

1H NMR (DMSO-d6) 400 MHz, δ: 10.07 (s, 1H) 9.22 (s, 1H) 9.05 (s, 1H) 8.49 (d, 1H) 8.11 (d, 1H) 7.99-7.91 (m, 3H) 7.83-7.77 (m, 3H) 7.65-7.61 (m, 1H) 7.58-7.54 (m, 3H) 7.46 (d, 1H) 7.43-7.41 (br m, 2H) 6.78 (d, 1H) 6.52 (s, 1H) 1.71 (d, 6H) 1.30 (s, 9H).
LCMS m/z 772 (M+H)⁺ (ES⁺); 770 (M−H)⁻ (ES⁻)

Example 29

1-(3-(tert-Butyl)-1-(4-(dimethylphosphoryl)phenyl)-1H-pyrazol-5-yl)-3-(4-((2-(phenylthio)-pyrimidin-4-yl)oxy)naphthalen-1-yl)urea

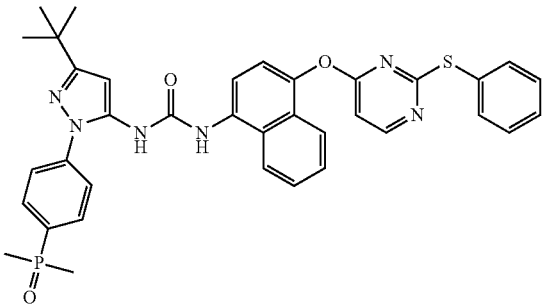 [SMILES: CC(C)(C)c1cc(NC(=O)Nc2ccc(Oc3ccnc(Sc4ccccc4)n3)c3ccccc23)n(-c2ccc(P(C)(C)=O)cc2)n1]

(i) 4-((2-(Phenylthio)pyrimidin-4-yl)oxy)naphthalen-1-amine

To a stirred solution of 4-((2-chloropyrimidin-4-yl)oxy)naphthalen-1-amine (see, for example, Cirillo, P. F. et al., WO 2002/92576, 21 Nov. 2000; 352 mg, 1.296 mmol) in THF (15 mL) was added sodium thiophenoxide (514 mg, 3.89 mmol). The reaction mixture was stirred at rt overnight. The crude reaction mixture was combined with a 50 mg scale reaction. The reaction mixture was separated between water (40 mL) and EtOAc (40 mL). The aqueous layer was extracted with EtOAc (3×40 mL). The combined organic extracts were dried (MgSO₄), filtered and concentrated in vacuo to afford a red oil. The crude product was purified by chromatography on silica gel (40 g column, 0-100% EtOAc in isohexane) to afford a light brown foam which was triturated with diethyl ether/isohexane to afford the sub-title compound (264 mg) as a buff solid.

1H NMR (DMSO) 400 MHz, δ: 8.40 (1H, d) 8.16-8.12 (1H, m) 7.53-7.50 (1H, m) 7.45-7.41 (2H, m) 7.40-7.32 (3H, m) 7.28-7.24 (2H, m) 7.03 (1H, d) 6.71 (1H, d) 6.61 (1H, d) 5.82 (2H, s).

LCMS m/z 346 (M+H)$^+$ (ES$^+$)

(ii) Ethyl 3-(tert-butyl)-1-(4-(dimethylphosphoryl) phenyl)-1H-pyrazole-5-carboxylate A mixture of ethyl 1-(4-bromophenyl)-3-(tert-butyl)-1H-pyrazole-5-carboxylate (see Example 22(i) above; 500 mg, 1.424 mmol), dimethylphosphine oxide (148 mg, 1.708 mmol), Xantphos (82 mg, 0.142 mmol), palladium (II) acetate (15.98 mg, 0.071 mmol) and $K_3PO_4.H_2O$ (349 mg, 1.495 mmol) in DMF (6 mL) was degassed with nitrogen for 15 min. The reaction mixture was heated in the microwave (Smith, 140° C., 200 W) for 40 min. Reaction was repeated a further 3 times, then the combined reactions were partitioned between EtOAc (200 mL) and water (200 mL). The organic phase was separated, washed with brine (200 mL), dried (MgSO$_4$) and evaporated under reduced pressure. The crude product was purified by chromatography on silica gel (120 g column, 0-5% MeOH/DCM) to afford the sub-title compound (1.033 g) as a gum. LCMS m/z 349 (M+H)$^+$ (ES$^+$)

(iii) 3-(tert-Butyl)-1-(4-(dimethylphosphoryl)phenyl)-1H-pyrazole-5-carboxylic acid Aq. 1M NaOH (6.03 mL, 6.03 mmol) was added to a stirred solution of the product from step (ii) above (1 g, 2.009 mmol) in EtOH (15 mL) at rt. The mixture was stirred for 3 h then the solvent evaporated under reduced pressure. The residue was partitioned between water (40 mL) and DCM (40 mL), the aqueous layer was separated, acidified to pH 1 with 1M HCl and extracted with DCM (50 mL). The DCM layer was washed with brine (20 mL), dried (MgSO$_4$) and evaporated under reduced pressure to give the sub-title compound (644 mg) as a foam.

LCMS m/z 321 (M+H)$^+$ (ES$^+$); 319 (M–H)$^-$ (ES$^-$)

(iv) 1-(3-(tert-Butyl)-1-(4-(dimethylphosphoryl) phenyl)-1H-pyrazol-5-yl)-3-(4-((2-(phenylthio) pyrimidin-4-yl)oxy)naphthalen-1-yl)urea To a stirred solution of the product from step (iii) above (130 mg, 0.373 mmol) and triethylamine (130 μL, 0.933 mmol) in DMF (2 mL) at 0-5° C., was added DPPA (84 μL, 0.392 mmol). After 30 min the ice bath was removed and the reaction allowed to warm to rt. Stirring continued at rt for 1 h, then the product from step (i) above (129 mg, 0.373 mmol) was added and the mixture heated at 100° C. for 1 h. The reaction mixture was partitioned between EtOAc (30 mL) and water (30 mL). The organic layer was washed with water (30 mL), brine (30 mL), dried (MgSO$_4$), filtered and concentrated in vacuo to afford an orange solid. The crude product was purified by preparative HPLC (Gilson, Acidic (0.1% Formic acid), Waters X-Select Prep-C18, 5 μm, 19×50 mm column, 25-65% MeCN in Water) to afford the title compound (44 mg) as a white solid. 1H NMR (DMSO) 400 MHz, δ: 9.13 (s, 1H) 8.97 (s, 1H) 8.49 (d, 1H) 8.08 (d, 1H) 7.98-7.94 (m, 2H) 7.85 (d, 1H) 7.80-7.77 (m, 2H) 7.72-7.70 (m, 1H) 7.67-7.63 (m, 1H) 7.57-7.53 (m, 1H) 7.31-7.23 (m, 4H) 7.19-7.15 (m, 2H) 6.94 (d, 1H) 6.49 (s, 1H) 1.69 (d, 6H) 1.31 (s, 9H).

LCMS m/z 663 (M+H)$^+$ (ES$^+$); 661 (M–H)$^-$ (ES$^-$)

Example 30

1-(3-(tert-Butyl)-1-(4-(dimethylphosphoryl)phenyl)-1H-pyrazol-5-yl)-3-(4-((2-((3-hydroxy-propyl)(methyl)amino)pyrimidin-4-yl)oxy)naphthalen-1-yl) urea

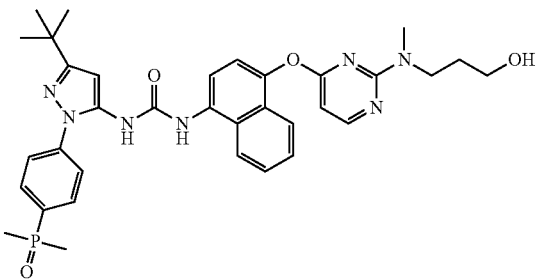 [SMILES: CN(CCCO)c1nccc(Oc2ccc(NC(=O)Nc3cc(C(C)(C)C)nn3-c3ccc(P(C)(C)=O)cc3)c3ccccc23)n1]

To a stirred suspension of 1-(3-(tert-butyl)-1-(4-(dimethylphosphoryl)phenyl)-1H-pyrazol-5-yl)-3-(4-((2-chloropyrimidin-4-yl)oxy)naphthalen-1-yl)urea (see Example 7(i) above; 100 mg, 0.170 mmol) in 1,4-dioxane (3 mL) was added 3-(methylamino)propan-1-ol (51.6 μL, 0.509 mmol). The resulting mixture was stirred at 60° C. for 2 h. The reaction was cooled to rt and partitioned between aq sodium bicarbonate solution (15 mL) and EtOAc (20 mL). The aqueous phase was extracted with EtOAc (2×20 mL). The combined organic extracts were washed with brine (20 mL), dried (MgSO$_4$), filtered and concentrated in vacuo to afford a residue (123 mg). The crude product was purified by chromatography on silica gel (40 g column, 0-10% MeOH in DCM) to afford the title compound (65 mg) as a white solid.

1H NMR (DMSO-d6, 333K) 400 MHz, δ: 8.95 (s, 1H) 8.76 (s, 1H) 8.22 (d, 1H) 8.07 (d, 1H) 7.96-7.91 (m, 2H) 7.87 (d, 1H) 7.82 (d, 1H) 7.78-7.76 (m, 2H) 7.63-7.59 (m, 1H) 7.56-7.52 (m, 1H) 7.32 (d, 1H) 6.44 (s, 1H) 6.16 (d, 1H) 4.12 (br s, 1H) 3.35 (br s, 2H) 3.20 (br s, 2H) 2.90 (s, 3H) 1.70 (d, 6H) 1.47 (br s, 2H) 1.32 (s, 9H).

LCMS m/z 642 (M+H)$^+$ (ES$^+$); 640 (M–H)$^-$ (ES$^-$)

Example 31

1-(3-(tert-Butyl)-1-(4-(dimethylphosphoryl)phenyl)-1H-pyrazol-5-yl)-3-(4-((2-((3-hydroxy-propyl)amino)pyrimidin-4-yl)oxy)naphthalen-1-yl)urea

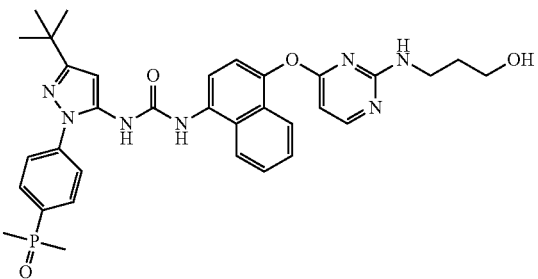 [SMILES: CC(C)(C)c1cc(NC(=O)Nc2ccc(Oc3ccnc(NCCCO)n3)c3ccccc23)n(-c2ccc(P(C)(C)=O)cc2)n1]

To a stirred suspension of 1-(3-(tert-butyl)-1-(4-(dimethylphosphoryl)phenyl)-1H-pyrazol-5-yl)-3-(4-((2-chloropyrimidin-4-yl)oxy)naphthalen-1-yl)urea (see Example 7(i) above; 100 mg, 0.170 mmol) in 1,4-dioxane (3 mL) was added 3-aminopropan-1-ol (38.3 mg, 0.509 mmol). The resulting mixture was stirred at 60° C. for 2 h. Stirring continued at 60° C. overnight. 3-Aminopropan-1-ol (38.3 mg, 0.509 mmol) was added and stirring continued at 60° C. overnight. The reaction was cooled to rt and the solvent removed in vacuo. The resulting oil was partitioned between aq sodium bicarbonate solution (15 mL) and EtOAc (20 mL). The aqueous phase was extracted with EtOAc (2×20 mL). The combined organic extracts were washed with brine (20 mL), dried (MgSO$_4$), filtered and concentrated in vacuo to afford an orange solid (89 mg). The crude product was purified by chromatography on silica gel (12 g column, 0-10% MeOH in DCM) to afford the title compound (34 mg) as a light tan solid.

1H NMR (DMSO-d6, 353K) 400 MHz, δ: 8.86 (s, 1H) 8.67 (s, 1H) 8.16 (d, 1H) 8.06 (d, 1H) 7.95-7.89 (m, 2H) 7.85-7.83 (m, 1H) 7.8 (d, 1H) 7.79-7.75 (m, 2H) 7.63-7.59 (m, 1H) 7.57-7.53 (m, 1H) 7.29 (d, 1H) 6.73-6.69 (br m, 1H) 6.42 (s, 1H) 6.15 (d, 1H) 4.04 (br s, 1H) 3.37-3.34 (m, 2H) 3.20-3.15 (m, 2H) 1.70 (d, 6H) 1.58-1.52 (m, 2H) 1.33 (s, 9H).

LCMS m/z 628 (M+H)$^+$ (ES$^+$); 626 (M−H)$^−$ (ES$^−$)

Example 32

1-(3-(tert-Butyl)-1-(3-((dimethylphosphoryl)methyl)phenyl)-1H-pyrazol-5-yl)-3-(4-((2-((7-methyl-1H-indazol-5-yl)amino)pyrimidin-4-yl)oxy)naphthalen-1-yl)urea

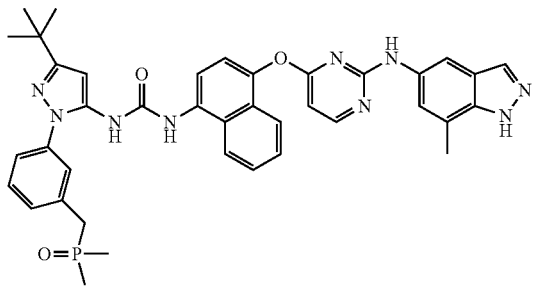 [SMILES: Cc1cc(Nc2nccc(Oc3ccc(NC(=O)Nc4cc(C(C)(C)C)nn4-c4cccc(CP(C)(C)=O)c4)c4ccccc34)n2)cc2cn[nH]c12]

(i) 1-(3-(tert-Butyl)-1-(3-((dimethylphosphoryl)methyl)phenyl)-1H-pyrazol-5-yl)-3-(4-((2-chloropyrimidin-4-yl)oxy)naphthalen-1-yl)urea DPPA (418 μL, 1.939 mmol) was added to a stirred solution of 3-(tert-butyl)-1-(3-((dimethylphosphoryl)methyl)phenyl)-1H-pyrazole-5-carboxylic acid (see Example 23(iv) above; 630 mg, 1.847 mmol) and Et$_3$N (643 μL, 4.62 mmol) in DMF (12 mL) at 0-5° C. under N$_2$. The solution was warmed to rt, stirred for 1 h then 4-((2-chloropyrimidin-4-yl)oxy)naphthalen-1-amine (see, for example, Cirillo, P. F. et al., WO 2002/92576, 21 Nov. 2000; 502 mg, 1.847 mmol) was added and heated at 100° C. for 1 h. The mixture was cooled, partitioned between EtOAc (150 mL) and water (100 mL), the organic layer was separated, washed with water (100 mL), brine (100 mL), dried (MgSO$_4$) and evaporated under reduced pressure. The crude product was purified by chromatography on silica gel (80 g column, EtOAc, solid loaded) to afford the sub-title compound (535 mg) as a solid.

1H NMR (DMSO-d6) 400 MHz, δ: 9.51 (s, 1H), 9.00 (s, 1H), 8.66 (d, 1H), 8.24 (d, 1H), 8.01 (d, 1H), 7.80 (d, 1H), 7.69-7.66 (m, 1H), 7.61-7.46 (m, 4H), 7.43 (d, 1H), 7.32 (brd, 1H), 7.28 (d, 1H), 6.50 (s, 1H), 3.37 (d, 2H), 1.46 (d, 6H), 1.31 (s, 9H).

LCMS m/z 603/5 (M+H)$^+$ (ES$^+$)

(ii) 1-(3-(tert-Butyl)-1-(3-((dimethylphosphoryl)methyl)phenyl)-1H-pyrazol-5-yl)-3-(4-((2-((7-methyl-1H-indazol-5-yl)amino)pyrimidin-4-yl)oxy)naphthalen-1-yl)urea A mixture of the product from step (i) above (200 mg, 0.332 mmol), 7-methyl-1H-indazol-5-amine hydrochloride (122 mg, 0.663 mmol) and p-TSA monohydrate (32 mg, 0.168 mmol) in THF (1 mL) and DMF (1 mL) was heated at 70° C. (bath temperature) for 22 h. The mixture was partitioned between EtOAc (60 mL) and aq NaHCO$_3$ (20 mL), the organic layer separated, washed with water (2×40 mL), dried (MgSO$_4$) and evaporated under reduced pressure. The crude product was purified by chromatography on silica gel (40 g column, 0-5% MeOH/DCM) to afford the product (90 mg). Further purification by preparative HPLC (Waters, Acidic (0.1% Formic acid), Waters X-Select Prep-C18, 5 μm, 19×50 mm column, 35-60% MeCN in Water) gave the title compound (24 mg) as a white solid.

1H NMR (DMSO-d6) 400 MHz, δ: 12.84 (s, 1H), 9.58 (s, 1H), 9.44 (s, 1H), 9.06 (s, 1H), 8.38 (d, 1H), 8.28 (d, 1H), 8.11 (d, 1H), 7.80 (d, 1H), 7.65-7.32 (m, 9H), 7.02 (s, 1H), 6.58 (d, 1H), 6.53 (s, 1H), 3.39 (d, 2H), 2.28 (s, 3H), 1.46 (d, 6H), 1.32 (s, 9H).

LCMS m/z 714 (M+H)$^+$ (ES$^+$)

Example 33

1-(3-(tert-Butyl)-1-(3-((dimethylphosphoryl)methyl)phenyl)-1H-pyrazol-5-yl)-3-(4-((2-((2-oxoindolin-6-yl)amino)pyrimidin-4-yl)oxy)naphthalen-1-yl)urea

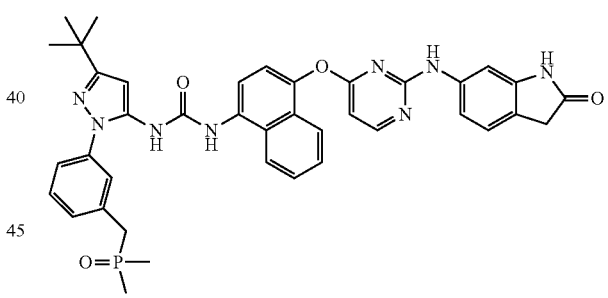

A mixture of 1-(3-(tert-butyl)-1-(3-((dimethylphosphoryl)methyl)phenyl)-1H-pyrazol-5-yl)-3-(4-((2-chloropyrimidin-4-yl)oxy)naphthalen-1-yl)urea (see Example 32(i) above; 160 mg, 0.265 mmol), 6-aminoindolin-2-one (79 mg, 0.531 mmol) and p-TSA monohydrate (25 mg, 0.131 mmol) in THF (1 mL) and DMF (1 mL) was heated at 70° C. (bath temperature) for 22 h. The mixture was partitioned between EtOAc (60 mL) and aq NaHCO$_3$ (20 mL), the organic layer separated, washed with water (2×40 mL), dried (MgSO$_4$) and evaporated under reduced pressure. The residue was triturated with MeCN, the solid filtered and purified by chromatography on silica gel (12 g column, 0-5% MeOH/DCM, solid loaded) to afford the title compound (65 mg) as a light purple solid.

1H NMR (DMSO-d6) 400 MHz, δ: 10.18 (s, 1H), 9.48 (d, 2H), 8.95 (s, 1H), 8.38 (d, 1H), 8.21 (d, 1H), 7.98 (d, 1H), 7.83 (d, 1H), 7.66-7.47 (m, 5H), 7.41 (d, 1H), 7.33 (d, 1H), 7.16 (s, 1H), 6.96 (d, 1H), 6.80 (d, 1H), 6.54 (s, 1H), 6.50 (d, 1H), 3.38 (d, 2H), 3.31 (s, 2H), 1.47 (d, 6H), 1.31 (s, 9H).

LCMS m/z 715 (M+H)$^+$ (ES$^+$)

Example 34

1-(3-(tert-Butyl)-1-(3-((dimethylphosphoryl)methyl)phenyl)-1H-pyrazol-5-yl)-3-(4-((2-((3-(2-morpholinoethoxy)phenyl)amino)pyrimidin-4-yl)oxy)naphthalen-1-yl)urea

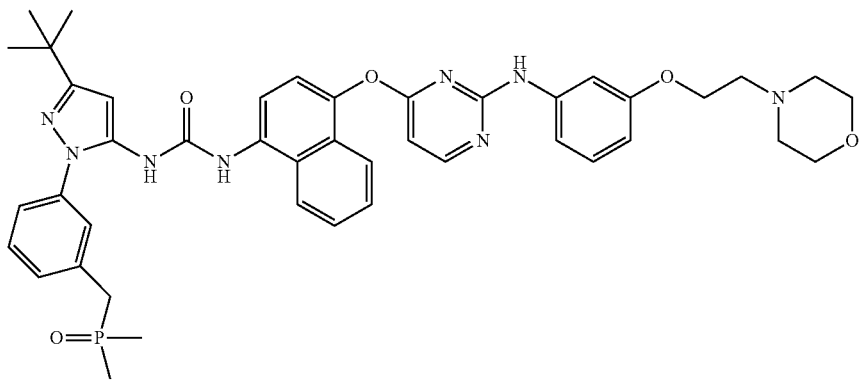 [SMILES: CC(C)(C)c1cc(NC(=O)Nc2ccc(Oc3ccnc(Nc4cccc(OCCN5CCOCC5)c4)n3)c3ccccc23)n(-c2cccc(CP(C)(C)=O)c2)n1]

A mixture of 1-(3-(tert-butyl)-1-(3-((dimethylphosphoryl)methyl)phenyl)-1H-pyrazol-5-yl)-3-(4-((2-chloropyrimidin-4-yl)oxy)naphthalen-1-yl)urea (see Example 32(i) above; 160 mg, 0.265 mmol), 3-(2-morpholinoethoxy) aniline (118 mg, 0.531 mmol) and p-TSA monohydrate (51 mg, 0.268 mmol) in THF (1 mL) and DMF (1 mL) was heated at 70° C. (bath temperature) for 2 h. A further portion of p-TSA monohydrate (100 mg) was added and heated for a further 20 h. The mixture was partitioned between EtOAc (60 mL) and aq. NaHCO$_3$ (20 mL), the organic layer separated, washed with water (2×40 mL), dried (MgSO$_4$) and evaporated under reduced pressure. The crude product was purified by chromatography on silica gel (40 g column, 0-5% MeOH/DCM) to afford the product (145 mg). Further purification by preparative HPLC (Waters, Acidic (0.1% Formic acid), Waters X-Select Prep-C18, 5 μm, 19×50 mm column, 20-50% MeCN in Water) gave the formate salt which was loaded onto a column of SCX in MeOH. The column was washed with MeOH and then the product was eluted with 0.7 M ammonia in MeOH. The resultant mixture was concentrated in vacuo to afford the title compound (63 mg) as a white solid.

1H NMR (DMSO-d6) 400 MHz, δ: 9.50 (s, 1H), 9.48 (s, 1H), 8.98 (s, 1H), 8.40 (d, 1H), 8.22 (d, 1H), 8.02 (d, 1H), 7.82 (d, 1H), 7.66-7.47 (m, 5H), 7.41 (d, 1H), 7.32 (d, 1H), 7.12 br s, 1H), 6.98-6.84 (m, 2H), 6.56 (d, 1H), 6.52 (s, 1H), 6.41 (d, 1H), 3.90 (br s, 2H), 3.53 (br s, 4H), 3.38 (d, 2H), 2.60 (br s, 2H), 2.40 (br s, 4H), 1.46 (d, 6H), 1.31 (s, 9H).

LCMS m/z 789 (M+H)$^+$ (ES$^+$)

Example 35

1-(1-(3-((Dimethylphosphoryl)methyl)phenyl)-3-(trimethylsilyl)-1H-pyrazol-5-yl)-3-(4-((2-(phenylamino)pyrimidin-4-yl)oxy)naphthalen-1-yl)urea

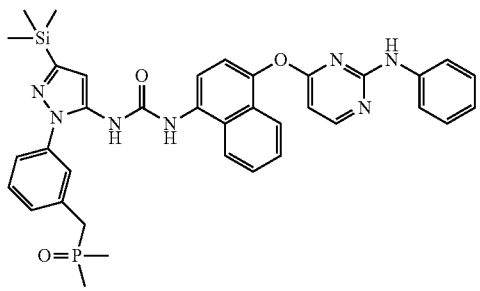 [SMILES: C[Si](C)(C)c1cc(NC(=O)Nc2ccc(Oc3ccnc(Nc4ccccc4)n3)c3ccccc23)n(-c2cccc(CP(C)(C)=O)c2)n1]

(i) Ethyl 1-(3-(hydroxymethyl)phenyl)-3-(trimethylsilyl)-1H-pyrazole-5-carboxylate Pyridine (4.88 mL, 60.3 mmol) followed by activated 4A molecular sieves (6.4 g) were added to a stirred mixture of ethyl 3-(trimethylsilyl)-1H-pyrazole-5-carboxylate (see, for example, *Bioorg. & Med. Chem. Lett.*, 17(2), 354-357 (2007); 6.4 g, 30.1 mmol), (3-(hydroxymethyl)phenyl)boronic acid (6.87 g, 45.2 mmol) and copper (II) acetate (8.21 g, 45.2 mmol) in DCM (150 mL) at rt. The mixture was stirred at rt overnight. Stirring continued at rt overnight (open flask), filtered through Celite and the filtrate concentrated in vacuo. Ether (300 mL) was added to the residue, the solid filtered and the filtrate concentrated in vacuo to afford a green oil (10.8 g). The crude product was purified by chromatography on silica gel (220 g column, 0-100% EtOAc in isohexane) to afford the sub-title compound (6.29 g) as an oil.

1H NMR (DMSO) 400 MHz, δ: 7.44-7.35 (m, 3H) 7.29-7.26 (m, 1H) 7.20 (s, 1H) 5.34 (t, 1H) 4.57 (d, 2H) 4.17 (q, 2H) 1.16 (t, 3H) 0.28 (s, 9H).

LCMS m/z 319 (M+H)$^+$ (ES$^+$)

(ii) Ethyl 1-(3-(chloromethyl)phenyl)-3-(trimethylsilyl)-1H-pyrazole-5-carboxylate To a stirred solution of the product from step (i) above (2.02 g, 5.71 mmol) in DCM (20 mL) under N$_2$, was added thionyl chloride (0.833 mL, 11.42 mmol). The resulting solution was stirred at rt for 2 h. The solvent was removed in vacuo. The crude product was purified by chromatography on silica gel (80 g column, 0-40% EtOAc in isohexane) to afford the sub-title compound (1.76 g) as an oil.

1H NMR (DMSO) 400 MHz, δ: 7.55-7.47 (m, 3H) 7.43-7.40 (m, 1H) 7.22 (s, 1H) 4.84 (s, 2H) 4.17 (q, 2H) 1.15 (t, 3H) 0.29 (s, 9H).

LCMS m/z 337 (M+H)$^+$ (ES$^+$)

(iii) Ethyl 1-(3-((dimethylphosphoryl)methyl)phenyl)-3-(trimethylsilyl)-1H-pyrazole-5-carboxylate A suspension of the product from step (ii) above (500 mg, 1.484 mmol), Xantphos (51.5 mg, 0.089 mmol), palladium (II) acetate (16.66 mg, 0.074 mmol), K$_3$PO$_4$ (347 mg, 1.633 mmol) and dimethylphosphine oxide (150 mg, 1.633 mmol) in DMF (8 mL) was purged with nitrogen with sonication for 30 min. The reaction mixture was heated in the microwave (CEM, 120° C.) for 30 min. Repeated in duplicate. The combined reaction mixtures were diluted with EtOAc (50 mL) and filtered. The filtrate was washed with water (2×150 mL), brine (100 mL), dried (MgSO$_4$), filtered and concentrated in vacuo to afford a brown oil. The crude product was purified by chromatography on silica gel (80 g column, 0-10% MeOH in DCM) to afford the sub-title compound (128 mg) as an oil.

1H NMR (DMSO) 400 MHz, δ: 7.45-7.41 (m, 1H) 7.34-7.31 (m, 3H) 7.20 (s, 1H) 4.17 (q, 2H) 3.23 (d, 2H) 1.35 (d, 6H) 1.16 (t, 3H) 0.28 (s, 9H).

LCMS m/z 379 (M+H)+ (ES+)

(iv) 1-(3-((Dimethylphosphoryl)methyl)phenyl)-3-(trimethylsilyl)-1H-pyrazole-5-carboxylic acid To a stirred solution of the product from step (iii) above (120 mg, 0.317 mmol) in EtOH (2 mL) was added 1M sodium hydroxide (634 μL, 0.634 mmol). The resulting mixture was stirred at rt overnight. The solvent was removed in vacuo and the resulting residue partitioned between 1M HCl (5 mL) and EtOAc (15 mL). The organic layer was washed with brine (10 mL), dried (MgSO4), filtered and concentrated in vacuo to afford the sub-title compound (106 mg) as a solid.

1H NMR (DMSO) 400 MHz, δ: 13.24 (br s, 1H) 7.44-7.40 (m, 1H) 7.32-7.30 (m, 3H) 7.14 (s, 1H) 3.23 (d, 2H) 1.35 (d, 6H) 0.28 (s, 9H).

LCMS m/z 351 (M+H)+ (ES+); 349 (M−H)− (ES−)

(v) 1-(1-(3-((Dimethylphosphoryl)methyl)phenyl)-3-(trimethylsilyl)-1H-pyrazol-5-yl)-3-(4-((2-(phenylamino)pyrimidin-4-yl)oxy)naphthalen-1-yl)urea To a stirred solution of the product from step (iv) above (92 mg, 0.263 mmol) and triethylamine (91 μL, 0.656 mmol) in 1,4-dioxane (1.5 mL) at 0-5° C. was added DPPA (59.4 μL, 0.276 mmol). After stirring at 0-5° C. for 30 mins, the reaction was allowed to warm to rt and then stirred at rt for 1 h. 4-((4-Aminonaphthalen-1-yl)oxy)-N-phenylpyrimidin-2-amine (see Example 1(i) above; 86 mg, 0.263 mmol) was added in a single portion and the reaction heated at 100° C. for 1 h. The reaction was cooled to rt and the solvent removed in vacuo. The residue was partitioned between EtOAc (100 mL) and water (50 mL). The organic layer was washed with brine (50 mL), dried (MgSO4), filtered and concentrated in vacuo to afford a brown solid. The crude product was purified by chromatography on silica gel (40 g column, 0-10% MeOH) to afford a solid (143 mg) at 81% purity. The solid was triturated with ether to afford the title compound (23 mg) as a light tan solid.

1H NMR (DMSO) 400 MHz, δ: 9.49 (s, 1H) 9.48 (s, 1H) 8.95 (s, 1H) 8.39 (d, 1H) 8.21 (d, 1H) 7.98 (d, 1H) 7.81 (d, 1H) 7.65-7.49 (m, 5H) 7.40-7.35 (m, 2H) 7.28-7.26 (br m, 2H) 6.96 (t, 2H) 6.76 (t, 1H) 6.70 (s, 1H) 6.58 (d, 1H) 3.38 (d, 2H) 1.46 (d, 6H) 0.28 (s, 9H).

LCMS m/z 676 (M+H)+ (ES+); 674 (M−H)− (ES−)

Example 36

1-(3-(tert-Butyl)-1-(3-((diethylphosphoryl)methyl)phenyl)-1H-pyrazol-5-yl)-3-(4-((2-((7-methyl-1H-indazol-5-yl)amino)pyrimidin-4-yl)oxy)naphthalen-1-yl)urea

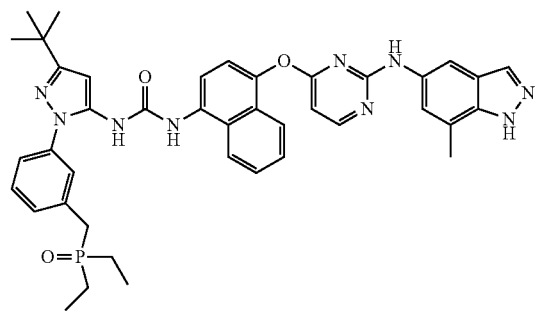 [SMILES: CCP(=O)(CC)Cc1cccc(-n2nc(C(C)(C)C)cc2NC(=O)Nc2ccc(Oc3ccnc(Nc4cc(C)c5[nH]ncc5c4)n3)c3ccccc23)c1]

(i) Ethyl 3-(tert-butyl)-1-(3-((diethylphosphoryl)methyl)phenyl)-1H-pyrazole-5-carboxylate A suspension of ethyl 3-(tert-butyl)-1-(3-(chloromethyl)phenyl)-1H-pyrazole-5-carboxylate (see Example 23(ii) above; 435 mg, 1.356 mmol), diethylphosphine oxide (178 μL, 1.627 mmol), K3PO4 (317 mg, 1.492 mmol), Xantphos (47.1 mg, 0.081 mmol) and Pd(OAc)2 (15.22 mg, 0.068 mmol) in anhydrous DMF was degassed for 20 min and then heated at 120° C. in the Smith Microwave. Reaction performed in duplicate. After this time the reaction was cooled to ambient temperature and partitioned between ethyl acetate (30 mL) and water (15 mL) and the organic layer washed with brine (2×10 mL), dried over MgSO4, filtered and concentrated under reduced pressure to afford a dark brown oil. The crude product was purified by chromatography on the Companion (40 g column, 0-5% MeOH in DCM) to afford the sub-title compound (146 mg) as a pale yellow foam.

1H NMR (400 MHz; DMSO-d6) δ 7.43-7.37 (m, 1H), 7.35-7.26 (m, 3H), 6.98 (s, 1H), 4.17 (q, 2H), 3.19 (d, 2H), 1.67-1.52 (m, 4H), 1.30 (s, 9H), 1.17 (t, 3H), 1.00 (dt, 6H).

LCMS m/z 391 (M+H)+ (ES+)

(ii) 3-(tert-Butyl)-1-(3-((diethylphosphoryl)methyl)phenyl)-1H-pyrazole-5-carboxylic acid To a stirred solution of the product from step (i) above (142 mg, 0.364 mmol) in EtOH (2.5 mL) was added 1M sodium hydroxide (727 μL, 0.727 mmol). The resulting mixture was stirred at rt overnight. The solvent was removed in vacuo and the resulting yellow solid partitioned between 1M HCl (5 mL) and EtOAc (20 mL). The organic layer was washed with brine (15 mL), dried (MgSO4), filtered and concentrated in vacuo to afford the sub-title compound (114 mg) as a white solid.

1H NMR (DMSO-d6) 400 MHz, δ: 13.22 (br s, 1H) 7.41-7.37 (m, 1H) 7.31-7.27 (m, 3H) 6.93 (s, 1H) 3.19 (d, 2H) 1.66-1.53 (m, 4H) 1.29 (s, 9H) 1.00 (dt, 6H)

LCMS m/z 363 (M+H)+ (ES+); 361 (M−H)− (ES−)

(iii) 1-(3-(tert-Butyl)-1-(3-((diethylphosphoryl)methyl)phenyl)-1H-pyrazol-5-yl)-3-(4-((2-chloropyrimidin-4-yl)oxy)naphthalen-1-yl)urea To a stirred solution of the product from step (ii) above (110 mg, 0.304 mmol) and triethylamine (106 µL, 0.759 mmol) in 1,4-dioxane (2 mL) at 0-5° C. was added DPPA (68.7 µL, 0.319 mmol). After stirring at 0-5° C. for 30 min, the reaction was allowed to warm to rt and then stirred at rt for 1 h. 4-((2-Chloropyrimidin-4-yl)oxy)naphthalen-1-amine (see, for example, Cirillo, P. F. et al., WO 2002/92576, 21 Nov. 2000; 82 mg, 0.304 mmol) was added as a single portion and the reaction heated at 100° C. for 1 h. The reaction was cooled to rt and the solvent removed in vacuo. The resulting residue was partitioned between EtOAc (100 mL) and water (50 mL). The organic layer was washed with brine (50 mL), dried (MgSO$_4$), filtered and concentrated in vacuo to afford a pink foam. The crude product was purified by chromatography on silica gel (40 g column, 0-10% MeOH in DCM) to afford the sub-title compound (74 mg) as a pale pink solid.

1H NMR (DMSO-d6, 353K) 400 MHz, δ: 9.44 (s, 1H) 8.89 (s, 1H) 8.63 (d, 1H) 8.28-8.27 (m, 1H) 8.01 (d, 1H) 7.83-7.81 (m, 1H) 7.64-7.46 (m, 5H) 7.40 (d, 1H) 7.35-7.33 (m, 1H) 7.17 (d, 1H) 6.51 (s, 1H) 3.35 (d, 2H) 1.81-1.68 (m, 4H) 1.33 (s, 9H) 1.03 (dt, 6H).

LCMS m/z 631/633 (M+H)$^+$ (ES$^+$)

(iv) 1-(3-(tert-Butyl)-1-(3-((diethylphosphoryl)methyl)phenyl)-1H-pyrazol-5-yl)-3-(4-((2-((7-methyl-1H-indazol-5-yl)amino)pyrimidin-4-yl)oxy)naphthalen-1-yl)urea To a stirred solution of the product from step (iii) above (70 mg, 0.111 mmol) in THF/DMF (3 mL, 1:1) was added p-TSA monohydrate (42.2 mg, 0.222 mmol) followed by 7-methyl-1H-indazol-5-amine hydrochloride (40.7 mg, 0.222 mmol). The resulting mixture was stirred at 60° C. overnight. The reaction was cooled to rt then partitioned between EtOAc (20 mL) and sat. NaHCO$_3$ solution (15 mL). The aqueous layer was extracted with EtOAc (2×20 mL). The combined organic extracts were washed with water (2×20 mL), brine (20 mL), dried (MgSO$_4$), filtered and concentrated in vacuo to afford a solid. The crude product was purified by chromatography on silica gel (40 g column, 0-10% MeOH in DCM) to afford an off-white solid (40 mg). The crude product was purified by preparative HPLC (Waters, Acidic (0.1% Formic acid), Waters X-Select Prep-C18, 5 µm, 19×50 mm column, 40-65% MeCN in Water) to afford the title compound (25 mg) as a white solid.

1H NMR (DMSO-d6) 400 MHz, δ: 12.83 (s, 1H) 9.68 (s, 1H) 9.43 (s, 1H) 9.14 (s, 1H) 8.38 (d, 1H) 8.30 (d, 1H) 8.13 (d, 1H) 7.84-7.81 (m, 1H) 7.62-7.53 (m, 5H) 7.50-7.48 (m, 1H) 7.43-7.34 (m, 3H) 7.02 (s, 1H) 6.58 (d, 1H) 6.54 (s, 1H) 3.37 (d, 2H) 2.27 (s, 3H) 1.79-1.64 (m, 4H) 1.31 (s, 9H) 0.97 (dt, 6H).

LCMS m/z 742 (M+H)$^+$ (ES$^+$); 740 (M−H)$^-$ (ES$^-$)

Example 37

1-(1-(3-((Dimethylphosphoryl)methyl)phenyl)-3-isopropyl-1H-pyrazol-5-yl)-3-(4-((2-((7-methyl-1H-indazol-5-yl)amino)pyrimidin-4-yl)oxy)naphthalen-1-yl)urea

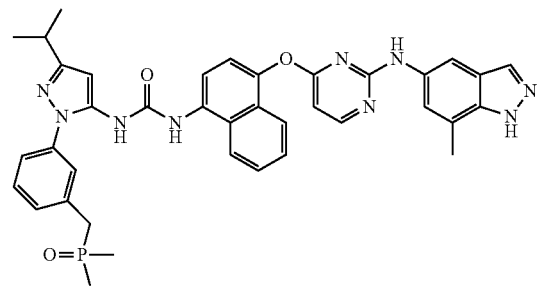 [SMILES: Cc1cc(Nc2nccc(Oc3ccc(NC(=O)Nc4cc(C(C)C)nn4-c4cccc(CP(C)(C)=O)c4)c4ccccc34)n2)cc2cn[nH]c12]

(i) Ethyl 1-(3-(hydroxymethyl)phenyl)-3-isopropyl-1H-pyrazole-5-carboxylate Pyridine (4.44 mL, 54.9 mmol) followed by activated 4A molecular sieves (5 g) were added to a stirred mixture of (3-(hydroxymethyl)phenyl)boronic acid (6.25 g, 41.2 mmol), ethyl 3-isopropyl-1H-pyrazole-5-carboxylate (5 g, 27.4 mmol) and copper (II) acetate (7.48 g, 41.2 mmol) in DCM (150 mL) at rt. open to the air. The mixture was stirred for 5 days, filtered and the filtrate evaporated. Ether (200 mL) was added to the residue, the solid filtered off and the filtrate evaporated under reduced pressure. The crude product was purified by chromatography on silica gel (120 g column, 0-60% ether/isohexane) to afford the sub-title compound (3.23 g) as a yellow oil.

1H NMR (CDCl$_3$) 400 MHz, δ: 7.44-7.31 (m, 4H), 6.85 (s, 1H), 4.73 (s, 2H), 4.23 (q, 2H), 3.07 (sept, 1H), 1.32 (d, 6H), 1.26 (t, 3H).

LCMS m/z 289 (M+H)$^+$ (ES$^+$)

(ii) Ethyl 1-(3-(chloromethyl)phenyl)-3-isopropyl-1H-pyrazole-5-carboxylate To a stirred solution of the product from step (i) above (2.10 g, 6.19 mmol) in DCM (20 mL) was added thionyl chloride (0.904 mL, 12.38 mmol). The resulting solution was stirred at rt for 2 h. The solvent was removed in vacuo and the resulting oil partitioned between EtOAc (120 mL) and saturated NaHCO$_3$ solution (100 mL). The organic layer was washed with brine (100 mL), dried (MgSO$_4$), filtered and concentrated in vacuo to afford an orange oil. The crude product was purified by chromatography on silica gel (80 g column, 0-20% EtOAc in isohexane) to afford the sub-title compound (1.58 g) as a yellow oil.

1H NMR (DMSO-d6) 400 MHz, δ: 7.52-7.45 (m, 3H) 7.41-7.38 (m, 1H) 6.97 (s, 1H) 4.83 (s, 2H) 4.17 (q, 2H) 3.03-2.93 (m, 1H) 1.25 (d, 6H) 1.15 (t, 3H).

LCMS m/z 307 (M+H)$^+$ (ES$^+$)

(iii) Ethyl 1-(3-((dimethylphosphoryl)methyl)phenyl)-3-isopropyl-1H-pyrazole-5-carboxylate A stirred suspension of the product from step (ii) above (480 mg, 1.565 mmol), Xantphos (54.3 mg, 0.094 mmol), palladium(II) acetate (17.56 mg, 0.078 mmol), K$_3$PO$_4$ (365 mg, 1.721 mmol) and dimethylphosphine oxide (149 mg, 1.721 mmol) in DMF (3 mL) was purged with N₂ with sonication for 20 min. The reaction mixture was heated in the microwave (CEM, 120° C.) for 30 min. Reaction performed in triplicate. The reaction mixture was partitioned between DCM (300 mL) and water (300 mL). The organic layer was washed with water (300 mL), brine (300 mL), dried (MgSO₄), filtered and concentrated in vacuo to afford a brown oil. The crude product was purified by chromatography on silica gel (80 g column, 0-10% MeOH in DCM) to afford the sub-title compound (959 mg) as a brown solid.

1H NMR (DMSO-d6) 400 MHz, δ: 7.43-7.39 (m, 1H) 7.33-7.28 (m, 3H) 6.94 (s, 1H) 4.17 (q, 2H) 3.22 (d, 2H) 3.03-2.93 (m, 1H) 1.35 (d, 6H) 1.25 (d, 6H) 1.16 (t, 3H).

LCMS m/z 349 (M+H)⁺ (ES⁺)

(iv) 1-(3-((Dimethylphosphoryl)methyl)phenyl)-3-isopropyl-1H-pyrazole-5-carboxylic acid To a stirred solution of the product from step (iii) above (955 mg, 2.74 mmol) in EtOH (16 mL) was added 1M sodium hydroxide (5483 μL, 5.48 mmol). The resulting mixture was stirred at rt for 2 h. The solvent was removed in vacuo and the resulting residue partitioned between 1M HCl (35 mL) and EtOAc (140 mL). The organic layer was washed with brine (100 mL), dried (MgSO₄), filtered and concentrated in vacuo to afford the sub-title compound (645 mg) as a pale, yellow solid.

1H NMR (DMSO-d6) 400 MHz, δ: 13.21 (br s, 1H) 7.41-7.38 (m, 1H) 7.30-7.28 (m, 3H) 6.88 (s, 1H) 3.21 (d, 2H) 3.02-2.91 (m, 1H) 1.35 (d, 6H) 1.25 (d, 6H).

LCMS m/z 321 (M+H)⁺ (ES⁺); 319 (M−H)⁻ (ES⁻)

(v) 1-(4-((2-Chloropyrimidin-4-yl)oxy)naphthalen-1-yl)-3-(1-(3-((dimethylphosphoryl)-methyl)phenyl)-3-isopropyl-1H-pyrazol-5-yl)urea To a stirred solution of the product from step (iv) above (518 mg, 1.569 mmol) and triethylamine (547 μL, 3.92 mmol) in 1,4-dioxane (10 mL) at 0-5° C. was added DPPA (355 μL, 1.647 mmol). After stirring at 0-5° C. for 30 min, the reaction was allowed to warm to rt and then stirred at rt for 1 h. 4-((2-chloropyrimidin-4-yl)oxy)naphthalen-1-amine (see, for example, Cirillo, P. F. et al., WO 2002/92576, 21 Nov. 2000; 426 mg, 1.569 mmol) was added as a single portion and the reaction heated at 100° C. for 1 h. The reaction mixture was cooled to rt and the solvent removed in vacuo. The resulting brown oil was partitioned between EtOAc (200 mL) and water (100 mL). The aqueous phase was extracted with EtOAc (200 mL). The combined organic extracts were washed with brine (200 mL), dried (MgSO₄), filtered and concentrated in vacuo to afford a solid. The crude product was purified by chromatography on silica gel (80 g column, 0-10% MeOH in DCM) to afford the sub-title compound (362 mg) as a pale pink solid.

1H NMR (DMSO-d6) 400 MHz, δ: 9.51 (s, 1H) 9.00 (s, 1H) 8.66 (d, 1H) 8.24 (d, 1H) 8.00 (d, 1H) 7.80-7.78 (m, 1H) 7.69-7.64 (m, 1H) 7.61-7.52 (m, 3H) 7.48-7.46 (m, 1H) 7.42 (d, 1H) 7.32-7.30 (m, 1H) 7.27 (d, 1H) 6.46 (s, 1H) 3.37 (d, 2H) 2.97-2.87 (m, 1H) 1.46 (d, 6H) 1.26 (d, 6H).

LCMS m/z 589 (M)⁺ (ES+)

(vi) 1-(1-(3-((Dimethylphosphoryl)methyl)phenyl)-3-isopropyl-1H-pyrazol-5-yl)-3-(4-((2-((7-methyl-1H-indazol-5-yl)amino)pyrimidin-4-yl)oxy)naphthalen-1-yl)urea To a stirred solution of the product from step (v) above (181 mg, 0.307 mmol) in THF/DMF (4 mL, 1:1) was added p-TSA monohydrate (117 mg, 0.615 mmol) followed by 7-methyl-1H-indazol-5-amine hydrochloride (113 mg, 0.615 mmol). The resulting mixture was heated at 60° C. overnight. The reaction was cooled to rt then partitioned between EtOAc (50 mL) and sat. NaHCO₃ solution (30 mL). The product crashed out in the organic layer. The layers were separated and the organic layer concentrated in vacuo. The crude product was purified by chromatography on silica gel (80 g column, 0-10% MeOH in DCM) to afford a brown solid (81 mg), which was triturated with MeCN to afford the title compound (52 mg) as a buff solid.

1H NMR (DMSO-d6) 400 MHz, δ: 12.85 (s, 1H) 9.57 (s, 1H) 9.46 (s, 1H) 9.06 (s, 1H) 8.39 (d, 1H) 8.27 (d, 1H) 8.11 (d, 1H) 7.83-7.81 (m, 1H) 7.65-7.48 (m, 6H) 7.43-7.32 (m, 3H) 7.01 (s, 1H) 6.59 (d, 1H) 6.49 (s, 1H) 3.39 (d, 2H) 2.96-2.89 (m, 1H) 2.27 (s, 3H) 1.46 (d, 6H) 1.26 (d, 6H).

LCMS m/z 700 (M+H)⁺ (ES⁺); 698 (M−H)⁻ (ES⁻)

Example 38

3-((4-((4-(3-(1-(3-((Dimethylphosphoryl)methyl)phenyl)-3-isopropyl-1H-pyrazol-5-yl)-ureido)naphthalen-1-yl)oxy)pyrimidin-2-yl)amino)-5-methoxy-N-(2-morpholinoethyl)-benzamide

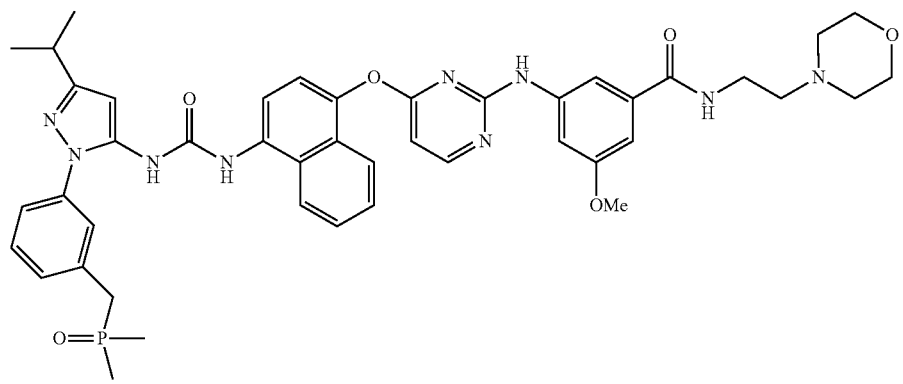 [SMILES: COc1cc(Nc2nccc(Oc3ccc(NC(=O)Nc4cc(C(C)C)nn4-c4cccc(CP(C)(C)=O)c4)c4ccccc34)n2)cc(C(=O)NCCN2CCOCC2)c1]

(i) 3-Amino-5-methoxy-N-(2-morpholinoethyl)benzamide

To a stirred mixture of 3-amino-5-methoxybenzoic acid (5.20 g, 31.1 mmol), Et₃N (4.50 mL, 32.3 mmol) and 2-morpholinoethanamine (4.23 mL, 32.3 mmol) in THF (150 mL) and DMF (4 mL) was added HATU (14.72 g, 38.7 mmol) and the reaction stirred at ambient temperature overnight. After this time the mixture was taken up in ethyl acetate (300 mL) and washed with sat NaHCO₃(aq) (2×100 mL). The aqueous was back extracted with further ethyl acetate (4×50 mL) and organics combined, dried over MgSO₄, filtered and concentrated under reduced pressure. Trituration with isohexanes (100 mL) afforded a pale orange gum (15 g). The crude product was purified by chromatography on the Companion (220 g column, 0-60% IPA in DCM). Fractions were combined as two separate batches to afford the sub-title compound (5.35 g) as an orange solid.

1H NMR (400 MHz; CDCl₃) δ: 6.69-6.64 (m, 3H), 6.35 (t, 1H), 3.81 (br.s, 2H), 3.81 (s, 3H), 3.73 (m, 4H), 3.53 (dd, 2H), 2.62-2.57 (m, 2H), 2.53-2.49 (m, 4H).

LCMS m/z 280 (M+H)⁺ (ES⁺)

(ii) 3-((4-((4-(3-(1-(3-((Dimethylphosphoryl)methyl)phenyl)-3-isopropyl-1H-pyrazol-5-yl)-ureido)naphthalen-1-yl)oxy)pyrimidin-2-yl)amino)-5-methoxy-N-(2-morpholinoethyl)-benzamide To a stirred solution of 1-(4-((2-chloropyrimidin-4-yl)oxy)naphthalen-1-yl)-3-(1-(3-((dimethylphosphoryl)methyl)phenyl)-3-isopropyl-1H-pyrazol-5-yl)urea (see Example 37(v) above; 181 mg, 0.307 mmol) in THF/DMF (4 mL, 1:1) was added p-TSA monohydrate (117 mg, 0.615 mmol) followed by the product from step (i) above (181 mg, 0.615 mmol). The resulting mixture was heated at 60° C. overnight. The reaction was cooled to rt then partitioned between EtOAc (50 mL) and sat. NaHCO₃ solution (30 mL). An emulsion formed initially. The layers were allowed to slowly separate and the organic layer concentrated in vacuo. The crude product was purified by chromatography on silica gel (80 g column, 0-10% MeOH in DCM) to afford a pink solid. Trituration of the solid with MeCN afforded the title compound (40 mg) as a white solid.

1H NMR (DMSO-d6) 400 MHz, δ: 9.60 (s, 1H) 9.45 (s, 1H) 8.98 (s, 1H) 8.41 (d, 1H) 8.21-8.18 (m, 2H) 7.99 (d, 1H) 7.83-7.81 (m, 1H) 7.65-7.52 (m, 5H) 7.48-7.46 (m, 1H) 7.40 (d, 1H) 7.32-7.31 (m, 2H) 6.85-6.84 (br m, 1H) 6.54 (d, 1H) 6.46 (s, 1H) 3.56-3.54 (m, 7H) 3.37 (d, 2H), 2H under water peak at 3.33 ppm, 2.95-2.88 (m, 1H) 2.44-2.38 (m, 6H) 1.46 (d, 6H) 1.26 (d, 6H).

LCMS m/z 832 (M+H)⁺ (ES⁺); 830 (M−H)⁻ (ES⁻)

Example 39

1-(1-(3-((Dimethylphosphoryl)methyl)phenyl)-3-isopropyl-1H-pyrazol-5-yl)-3-(4-((2-((3-methoxy-5-(2-morpholinoethoxy)phenyl)amino)pyrimidin-4-yl)oxy)naphthalen-1-yl)urea

(i) 3-Methoxy-5-(2-morpholinoethoxy)aniline

To a stirred suspension of 3-amino-5-methoxyphenol (205 mg, 1.473 mmol) and K₂CO₃ (1018 mg, 7.37 mmol) in pyridine/DMF (2 mL, 1:3) was added 4-(2-chloroethyl)morpholine hydrochloride (274 mg, 1.473 mmol). The resulting mixture was heated at 60° C. overnight. The reaction was cooled to rt, filtered and concentrated in vacuo to afford a brown oil (850 mg). The crude product was purified by chromatography on silica gel (40 g column, 0-10% MeOH in DCM) to afford the sub-title compound (201 mg) as a sticky orange oil.

1H NMR (DMSO-d6) 400 MHz, δ: 5.75-5.73 (m, 2H) 5.67 (t, 1H) 5.05 (s, 2H) 3.94 (t, 2H) 3.61 (s, 3H) 3.58-3.55 (m, 4H) 2.62 (t, 2H) 2.45-2.43 (m, 4H).

LCMS m/z 253 (M+H)⁺ (ES⁺)

(ii) 1-(1-(3-((Dimethylphosphoryl)methyl)phenyl)-3-isopropyl-1H-pyrazol-5-yl)-3-(4-((2-((3-methoxy-5-(2-morpholinoethoxy)phenyl)amino)pyrimidin-4-yl)oxy)naphthalene-1-yl)urea To a stirred solution of 1-(4-((2-chloropyrimidin-4-yl)oxy)naphthalen-1-yl)-3-(1-(3-((dimethylphosphoryl)methyl)phenyl)-3-isopropyl-1H-pyrazol-5-yl)urea (see Example 37(v) above; 150 mg, 0.255 mmol) in THF/DMF (4 mL, 1:1) was added p-TSA monohydrate (72.7 mg, 0.382 mmol) followed by the product from step (i) above (110 mg, 0.382 mmol). The resulting mixture was heated at 60° C. overnight. DMF (2 mL) was added and the reaction mixture stirred at 60° C. for 48 h. The reaction was cooled to rt and partitioned between EtOAc (40 mL) and sat. NaHCO₃ (25 mL). The aqueous phase was extracted with EtOAc (2×40 mL). The combined organic extracts were washed with water (3×50 mL), brine (100 mL), dried (MgSO₄), filtered and concentrated in vacuo to afford an orange solid. The crude product was purified by chromatography on silica gel (80 g column, 0-10% MeOH in DCM) to afford a light brown foam (87 mg). Trituration of the foam with MeCN afforded the title compound (47 mg) as an off-white solid.

1H NMR (DMSO-d6) 400 MHz, δ: 9.48 (s, 1H) 9.41 (s, 1H) 9.00 (s, 1H) 8.40 (d, 1H) 8.21 (d, 1H) 8.01 (d, 1H) 7.83-7.81 (m, 1H) 7.65-7.52 (m, 4H) 7.48-7.46 (m, 1H) 7.39 (d, 1H) 7.33-7.31 (m, 1H) 6.79-6.77 (m, 2H) 6.54 (d, 1H) 6.46 (s, 1H) 6.02-6.01 (m, 1H) 3.87 (t, 2H) 3.54-3.51 (m, 4H) 3.48 (s, 3H) 3.37 (d, 2H) 2.95-2.88 (m, 1H) 2.58 (t, 2H) 2.40-2.38 (m, 4H) 1.46 (d, 6H) 1.25 (d, 6H).

LCMS m/z 805 (M+H)⁺ (ES⁺); 803 (M−H)⁻ (ES⁻)

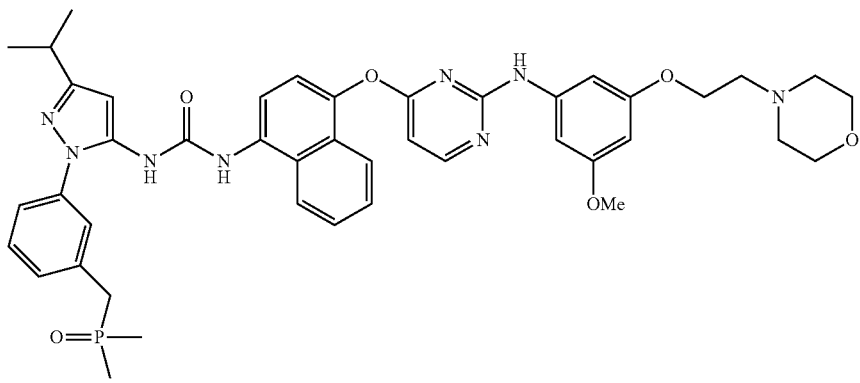

Example 40

1-(1-(3-((dimethylphosphoryl)methyl)phenyl)-3-isopropyl-1H-pyrazol-5-yl)-3-(4-((2-((2-methoxyphenyl)amino)pyrimidin-4-yl)oxy)naphthalen-1-yl)urea

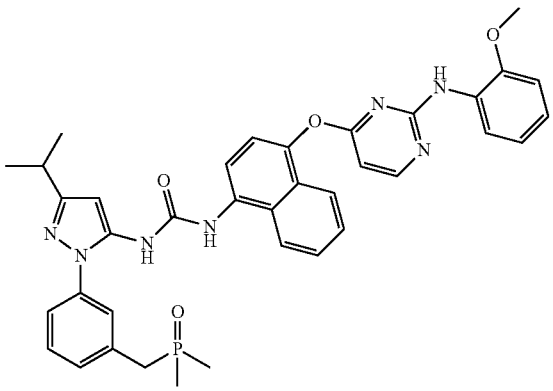 [SMILES: COc1ccccc1Nc1nccc(Oc2ccc(NC(=O)Nc3cc(C(C)C)nn3-c3cccc(CP(C)(C)=O)c3)c3ccccc23)n1]

To a stirred solution of 1-(4-((2-chloropyrimidin-4-yl)oxy)naphthalen-1-yl)-3-(1-(3-((dimethylphosphoryl)methyl)phenyl)-3-isopropyl-1H-pyrazol-5-yl)urea (see Example 37(v) above; 151 mg, 0.256 mmol) in THF/DMF (4 mL, 1:1) was added p-TSA monohydrate (98 mg, 0.513 mmol) followed by 2-methoxyaniline (57.8 μL, 0.513 mmol). The resulting solution was heated at 60° C. overnight. The reaction was cooled to rt then partitioned between EtOAc (40 mL) and sat. NaHCO₃ solution (25 mL). The aqueous phase was extracted with EtOAc (40 mL). The combined organic extracts were washed with water (3×50 mL), brine (50 mL), dried (MgSO₄), filtered and concentrated in vacuo to afford a dark pink solid. The crude product was purified by chromatography on silica gel (40 g column, 0-10% MeOH in DCM) to afford a light pink solid which was triturated with MeCN afforded a white solid (63 mg) at 90% purity. The crude product was purified by preparative HPLC (Waters, Acidic (0.1% Formic acid), Waters X-Select Prep-C18, 5 μm, 19×50 mm column, 35-60% MeCN in Water) to afford the title compound (32 mg) as a white solid.

1H NMR (DMSO-d6) 400 MHz, δ: 9.52 (s, 1H) 8.99 (s, 1H) 8.37 (d, 1H) 8.23 (d, 1H) 8.00 (d, 1H) 7.87 (s, 1H) 7.81-7.79 (m, 1H) 7.65-7.61 (m, 1H) 7.58-7.53 (m, 3H) 7.49-7.46 (m, 1H) 7.45-7.35 (m, 2H) 7.33-7.31 (m, 1H) 6.92-6.89 (m, 1H) 6.87-6.82 (m, 1H) 6.57 (d, 1H) 6.52-6.48 (m, 1H) 6.47 (s, 1H) 3.75 (s, 3H) 3.38 (d, 2H) 2.96-2.89 (m, 1H) 1.46 (d, 6H) 1.26 (d, 6H).

LCMS m/z 676 (M+H)⁺ (ES⁺); 674 (M−H)⁻ (ES⁻)

Example 41

1-(3-(tert-Butyl)-1-(3-((dimethylphosphoryl)methyl)phenyl)-1H-pyrazol-5-yl)-3-(4-((2-(phenylamino)pyridin-4-yl)oxy)naphthalen-1-yl)urea

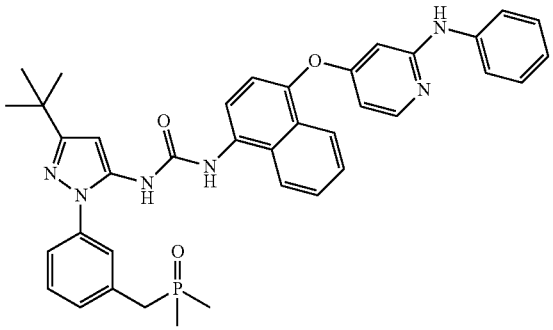 [SMILES: CC(C)(C)c1cc(NC(=O)Nc2ccc(Oc3ccnc(Nc4ccccc4)c3)c3ccccc23)n(-c2cccc(CP(C)(C)=O)c2)n1]

(i) 4-((4-Aminonaphthalen-1-yl)oxy)-N-phenylpyridin-2-amine

A mixture of 4-((2-chloropyridin-4-yl)oxy)naphthalen-1-amine (see, for example, Ito, K. et al., WO 2010/112936, 7 Oct. 2010; 600 mg, 2.216 mmol), aniline (619 mg, 6.65 mmol) and 4M HCl in dioxane (831 μL, 3.32 mmol) in NMP (6 mL) was heated at 140° C. for 18 h. The mixture was partitioned between EtOAc (150 mL) and aq. NaHCO₃ solution (50 mL), the organic layer separated, washed with 20% brine (100 mL), dried (MgSO₄) and evaporated under reduced pressure. The crude product was purified by chromatography on silica gel (80 g column, 0-30% EtOAc/isohexane) to afford a solid which was triturated with ether/isohexane, filtered and dried to afford the sub-title compound (328 mg).

1H NMR (400 MHz; CDCl₃) δ 7.97 (d, 1H), 7.87-7.83 (m, 2H), 7.54-7.46 (m, 2H), 7.28-7.21 (m, 4H), 7.05-6.99 (m, 2H), 6.90 (s, 1H), 6.74 (d, 1H), 6.38 (d, 1H), 6.31-6.29 (m, 1H), 4.11 (brs, 2H).

LCMS m/z 328 (M+H)⁺ (ES⁺)

(ii) 1-(3-(tert-Butyl)-1-(3-((dimethylphosphoryl)methyl)phenyl)-1H-pyrazol-5-yl)-3-(4-((2-(phenylamino)pyridin-4-yl)oxy)naphthalen-1-yl)urea DPPA (92 μL, 0.426 mmol) was added to a stirred solution of 3-(tert-butyl)-1-(3-((dimethylphosphoryl)methyl)phenyl)-1H-pyrazole-5-carboxylic acid (see Example 23(iv) above 95 mg, 0.284 mmol) and triethylamine (99 μL, 0.710 mmol) in DMF (2 mL) under N₂ at rt for 50 min. The product from step (i) above (140 mg, 0.426 mmol) was added and the mixture heated at 100° C. for 2 h. The mixture was diluted with water (6 mL) and extracted with EtOAc (3×6 mL). The combined organic phases were washed with saturated brine (10 mL), dried (MgSO₄) and concentrated under reduced pressure. The crude product was purified by chromatography on the Companion (40 g column, EtOAc) to afford a white solid.

The solid was purified further by chromatography on the Companion (12 g column, 0-5% MeOH/DCM) to afford the title compound (22 mg) as a colourless glass.

1H NMR (DMSO-d6) 400 MHz, δ: 9.29 (s, 1H), 8.78 (s, 1H), 8.65 (s, 1H), 8.24 (d, 1H), 8.07 (d, 1H), 7.97 (d, 1H), 7.92 (dd, 1H), 7.67-7.46 (m, 7H), 7.35-7.30 (m, 1H), 7.30 (d, 1H), 7.23-7.17 (m, 2H), 6.90-6.82 (m, 1H), 6.49 (s, 1H), 6.48 (dd, 1H), 6.22 (d, 1H), 3.37 (d, 2H), 1.47 (d, 6H), 1.34 (s, 9H).

LCMS m/z 659 (M+H)⁺ (ES⁺); 657 (M−H)⁻ (ES⁻)

Example 42

1-(1-(3-((Dimethylphosphoryl)methyl)phenyl)-3-isopropyl-1H-pyrazol-5-yl)-3-(4-((2-(phenylamino)pyridin-4-yl)oxy)naphthalen-1-yl)urea

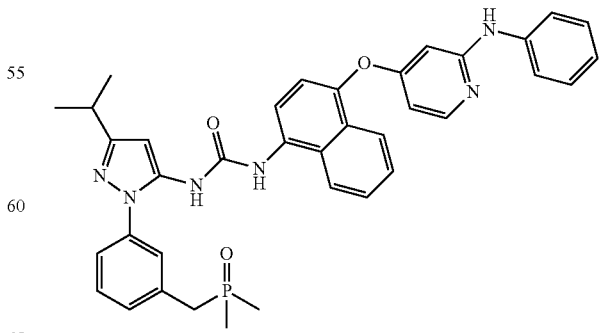

DPPA (92 μL, 0.427 mmol) was added to a stirred solution of 1-(3-((dimethylphosphoryl)methyl)phenyl)-3-isopropyl- 1H-pyrazole-5-carboxylic acid (see Example 37(iv) above; 95 mg, 0.285 mmol) and triethylamine (99 μL, 0.712 mmol) in DMF (2 mL) under $N_2$ at rt for 50 min. 4-((4-Aminonaphthalen-1-yl)oxy)-N-phenylpyridin-2-amine (see Example 41(i) above; 140 mg, 0.427 mmol) was added and the mixture heated at 100° C. for 2 h. The mixture was diluted with water (10 mL) and the precipitate was collected by filtration. The solid was triturated in acetonitrile and collected by filtration. The solid was triturated two further times in methanol and collected by filtration to afford the title compound (75 mg, 0.113 mmol, 39.6% yield) as a solid.

1H NMR (DMSO-d6) 400 MHz, δ: 9.49 (s, 1H), 8.98 (s, 1H), 8.91 (s, 1H), 8.23 (d, 1H), 8.07 (d, 1H), 8.02 (d, 1H), 7.89-7.83 (m, 1H), 7.71-7.63 (m, 1H), 7.63-7.51 (m, 5H), 7.51-7.44 (m, 1H), 7.37 (d, 1H), 7.35-7.29 (m, 1H), 7.23-7.15 (m, 2H), 6.87-6.80 (m, 1H), 6.55 (dd, 1H), 6.47 (s, 1H), 6.07 (d, 1H), 3.37 (d, 2H), 2.93 (hept, 1H), 1.46 (d, 6H), 1.26 (d, 6H)

LCMS m/z 645 (M+H)$^+$ (ES$^+$); 643 (M−H)$^-$ (ES$^-$)

Example 43

3-((4-((4-(3-(1-(3-((Dimethylphosphoryl)methyl)phenyl)-3-isopropyl-1H-pyrazol-5-yl)ureido)naphthalen-1-yl)oxy)pyrimidin-2-yl)amino)-5-ethynyl-N-(2-morpholinoethyl)benzamide was purified by chromatography on the Companion (40 g column, 2% MeOH:DCM to 5%) to afford the sub-title compound (1.4 g) as a yellow crystalline solid.

1H NMR (400 MHz, DMSO) δ 8.28 (t, 1H), 7.06 (t, 1H), 6.98 (dd, 1H), 6.85 (t, 1H), 5.58 (s, 2H), 3.57 (t, 4H), 3.33 (m, 2H), 2.41 (m, 6H).

LCMS m/z 328/330 (M+H)$^+$ (ES$^+$)

(ii) 3-Amino-N-(2-morpholinoethyl)-5-((triisopropylsilyl)ethynyl)benzamide

Pd(PPh$_3$)$_4$ (176 mg, 0.152 mmol) was added to a degassed suspension of the product from step (i) above (500 mg, 1.523 mmol), copper(I) iodide (29.0 mg, 0.152 mmol), and ethynyltriisopropylsilane (0.513 mL, 2.285 mmol) in TEA (3 mL) and DMF (3 mL), heated at 80° C. (block temp.) for 1 h then cooled, filtered on Celite and solvents evaporated. The crude product was purified by chromatography on the Companion (12 g column, 5% MeOH:DCM to 10%) to afford the sub-title compound (600 mg) as a pale yellow gum.

1H NMR (400 MHz, CDCl$_3$) δ 11.05 (s, 1H), 7.16 (t, 1H), 7.13 (t, 1H), 6.90 (dd, 1H), 3.83 (s, 2H), 3.77 (t, 4H), 3.56 (q, 2H), 2.65 (s, 2H), 2.57 (s, 4H), 1.13 (s, 21H).

LCMS m/z 430 (M+H)$^+$ (ES$^+$)

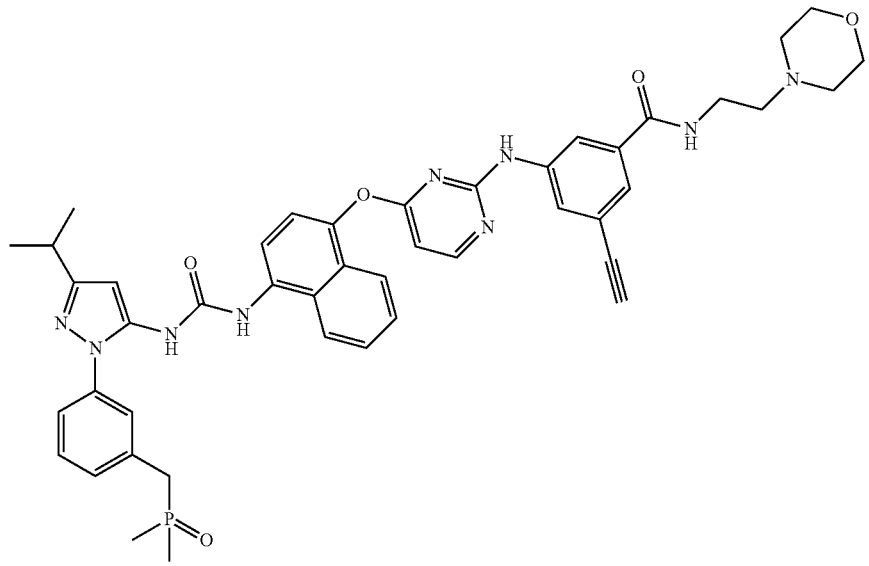 [SMILES: C#Cc1cc(Nc2nccc(Oc3ccc(NC(=O)Nc4cc(C(C)C)nn4-c4cccc(CP(C)(C)=O)c4)c4ccccc34)n2)cc(C(=O)NCCN2CCOCC2)c1]

(i) 3-Amino-5-bromo-N-(2-morpholinoethyl)benzamide

2-Morpholinoethanamine (0.911 mL, 6.94 mmol) was added to an ice cold suspension of T3P (2.76 mL, 4.63 mmol), 3-amino-5-bromobenzoic acid (1 g, 4.63 mmol) and TEA (1.936 mL, 13.89 mmol) in DCM (20 mL). Allowed to warm to room temperature and stirred overnight. More T3P (2.76 mL, 4.63 mmol) and 2-morpholinoethanamine (0.911 mL, 6.94 mmol) were added and stirred for a further 1 h. Partitioned with saturated NaHCO$_3$ solution (20 mL), the aqueous layer separated and partitioned with fresh DCM (20 mL). The organics separated, bulked and partitioned with 20% w/w NaCl solution. Organic layer separated, dried (MgSO$_4$) filtered and solvent evaporated. The crude product (iii) 3-Amino-5-ethynyl-N-(2-morpholinoethyl)benzamide The product from step (ii) above (500 mg, 1.164 mmol) was dissolved in THF (5 mL) and TBAF (1164 μL, 1.164 mmol) added and stirred for 1 h. TBAF (1164 μL, 1.164 mmol) added again and stirred for 30 min. Reaction partitioned between water (10 mL) and ethyl acetate (10 mL), organic layer separated and washed with 20% w/w NaCl solution. Organic layer separated, dried (MgSO$_4$) filtered and evaporated. The crude product was purified by chromatography on the Companion (12 g column, 2% MeOH:DCM to 5%) to afford the sub-title compound (260 mg) as a colourless gum.

1H NMR (400 MHz, CDCl₃) δ 7.15 (m, 2H), 6.91 (dd, 1H), 6.67 (s, 1H), 3.85 (s, 2H), 3.74 (t, 4H), 3.53 (q, 2H), 3.07 (s, 1H), 2.59 (t, 2H), 2.51 (t, 4H).

LCMS m/z 274 (M+H)⁺ (ES⁺)

(iv) 3-((4-((4-(3-(1-(3-((Dimethylphosphoryl) methyl)phenyl)-3-isopropyl-1H-pyrazol-5-yl)ureido) naphthalen-1-yl)oxy)pyrimidin-2-yl)amino)-5-ethynyl-N-(2-morpholinoethyl)benzamide A mixture of 1-(4-((2-chloropyrimidin-4-yl)oxy)naphthalen-1-yl)-3-(1-(3-((dimethyl-phosphoryl)methyl)phenyl)-3-isopropyl-1H-pyrazol-5-yl)urea (see Example 37(v) above; 200 mg, 0.340 mmol), the product from step (iii) above (144 mg, 0.526 mmol) and pTSA monohydrate (129 mg, 0.679 mmol) was heated to 70° C. in DMF (2 mL) for 18 h. The mixture was diluted with water (10 mL) and saturated sodium hydrogen carbonate solution (10 mL). The precipitate was collected by filtration and washed with water (15 mL) to yield a dark solid. The crude product was purified by chromatography on the Companion (40 g column, DCM:MeOH:ammonia, 90:9:1) to afford a pink solid. The solid was triturated in acetonitrile to afford the title compound (125 mg) as a pale pink solid.

1H NMR (DMSO-d6) 400 MHz, δ: 9.77 (s, 1H), 9.44 (s, 1H), 8.97 (s, 1H), 8.44 (d, 1H), 8.37 (dd, 1H), 8.20 (d, 1H), 8.05 (s, 1H), 7.99 (d, 1H), 7.85 (s, 1H), 7.82 (dd, 1H), 7.66-7.51 (m, 4H), 7.51-7.40 (m, 3H), 7.35-7.30 (m, 1H), 6.57 (d, 1H), 6.47 (s, 1H), 4.12 (s, 1H), 3.61-3.51 (m, 4H), 3.38 (d, 2H), 3.37-3.30 (m, 2H), 2.93 (septet, 1H), 2.47-2.34 (m, 6H), 1.46 (d, 6H), 1.26 (d, 6H).

LCMS m/z 826 (M+H)+ (ES+); 824 (M⁻H)⁻ (ES⁻).

Example 44

1-(3-(tert-Butyl)-1-(3-((1-oxidophospholan-1-yl) methyl)phenyl)-1H-pyrazol-5-yl)-3-(4-((2-(phenylamino)pyridin-4-yl)oxy)naphthalen-1-yl)urea

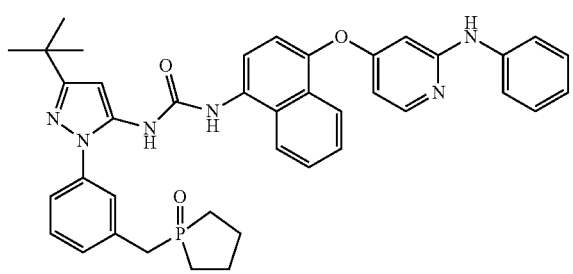 [SMILES: CC(C)(C)c1cc(NC(=O)Nc2ccc(Oc3ccnc(Nc4ccccc4)c3)c3ccccc23)n(-c2cccc(CP3(=O)CCCC3)c2)n1]

(i) Ethyl 3-(tert-butyl)-1-(3-((1-oxidophospholan-1-yl)methyl)phenyl)-1H-pyrazole-5-carboxylate A suspension of ethyl 3-(tert-butyl)-1-(3-(chloromethyl) phenyl)-1H-pyrazole-5-carboxylate (see Example 23(ii) above; 0.5 g, 1.481 mmol), xantphos (0.051 g, 0.089 mmol), palladium(II) acetate (0.017 g, 0.074 mmol), K₃PO₄ (0.346 g, 1.629 mmol) and phospholane 1-oxide (0.308 g, 2.96 mmol) in DMF (5 mL) was purged with N₂ with sonication for 20 mins. The reaction mixture was heated at 120° C. for 1 h. The reaction was cooled to rt then partitioned between EtOAc (50 mL) and water (50 mL). The organic layer was washed with water (50 mL), 20% NaCl solution (50 mL), dried (MgSO₄), filtered and concentrated in vacuo to afford brown gum. The crude product was purified by chromatography on silica gel (40 g column, 2% MeOH:DCM to 8%) to afford the sub-title compound (185 mg) as a colourless gum.

1H NMR (400 MHz, CDCl₃) δ 7.45-7.30 (m, 4H), 6.87 (s, 1H), 4.22 (q, 2H), 3.32 (d, 2H), 2.05-1.68 (m, 6H), 1.66-1.52 (m, 2H), 1.36 (s, 9H), 1.27 (t, 3H).

LCMS m/z 389 (M+H)+ (ES+)

(ii) 3-(tert-Butyl)-1-(3-((1-oxidophospholan-1-yl) methyl)phenyl)-1H-pyrazole-5-carboxylic acid The product from step (i) above (165 mg, 0.425 mmol) was dissolved in ethanol (2 mL) and 2 M NaOH (255 μL, 0.510 mmol) added and stirred for 4 h. Solvents were evaporated and the residue partitioned between water (5 mL) and EtOAc (5 mL), aqueous layer separated and acidified to pH 1 with conc. HCl. The product was extracted into EtOAc (5 mL). Organic layer separated, dried (MgSO₄) filtered and solvent evaporated to the sub-title compound (150 mg) as a colourless gum.

1H NMR (400 MHz, DMSO) δ 13.17 (s, 1H), 7.44-7.34 (m, 3H), 7.33-7.24 (m, 1H), 6.93 (s, 1H), 3.34 (d, 2H), 1.90-1.73 (m, 4H), 1.63 (dt, 2H), 1.55-1.40 (m, 2H), 1.30 (s, 9H).

LCMS m/z 361 (M+H)⁺ (ES⁺); 359 (M–H)⁻ (ES⁻)

(iii) 1-(3-(tert-Butyl)-1-(3-((1-oxidophospholan-1-yl)methyl)phenyl)-1H-pyrazol-5-yl)-3-(4-((2-(phenylamino)pyridin-4-yl)oxy)naphthalen-1-yl)urea DPPA (90 μL, 0.416 mmol) was added to a solution of the product from step (ii) above (150 mg, 0.416 mmol) and TEA (145 μL, 1.041 mmol) in DMF (3 mL). Stirred at rt for 1 h before addition of 4-((4-aminonaphthalen-1-yl)oxy)-N-phenylpyridin-2-amine (see Example 41(i) above; 129 mg, 0.395 mmol). Heated at 100° C. for 2 h. Cooled and partitioned between 20% w/w NaCl solution (30 mL) and EtOAc (30 mL), the organic layer separated, dried (MgSO₄) filtered and evaporated. The crude product was preabsorbed onto silica (4 g) and purified by chromatography on silica gel (40 g column, 2% to 8% MeOH in DCM) to afford a pale beige solid. Trituration with MeCN (3 mL) afforded the title compound (140 mg) as a colourless solid.

1H NMR (400 MHz, DMSO) δ 9.40 (s, 1H), 8.94 (s, 1H), 8.90 (s, 1H), 8.22 (d, 1H), 8.08 (d, 1H), 8.04 (d, 1H), 7.86 (dd, 1H), 7.71-7.50 (m, 6H), 7.51-7.44 (m, 1H), 7.44-7.39 (m, 1H), 7.36 (d, 1H), 7.28-7.12 (m, 2H), 6.84 (tt, 1H), 6.60-6.52 (m, 1H), 6.50 (s, 1H), 6.09 (d, 1H), 3.46 (d, 2H), 1.98-1.66 (m, 6H), 1.64-1.45 (m, 2H), 1.31 (s, 9H).

LCMS m/z 685 (M+H)+ (ES+).

Example 45

1-(1-(3-((Dimethylphosphoryl)methyl)phenyl)-3-isopropyl-1H-pyrazol-5-yl)-3-(4-((2-((3-methoxy-5-(2-(2-(2-methoxyethoxy)ethoxy)ethoxy)phenyl)amino)pyrimidin-4-yl)oxy)naphthalen-1-yl)urea

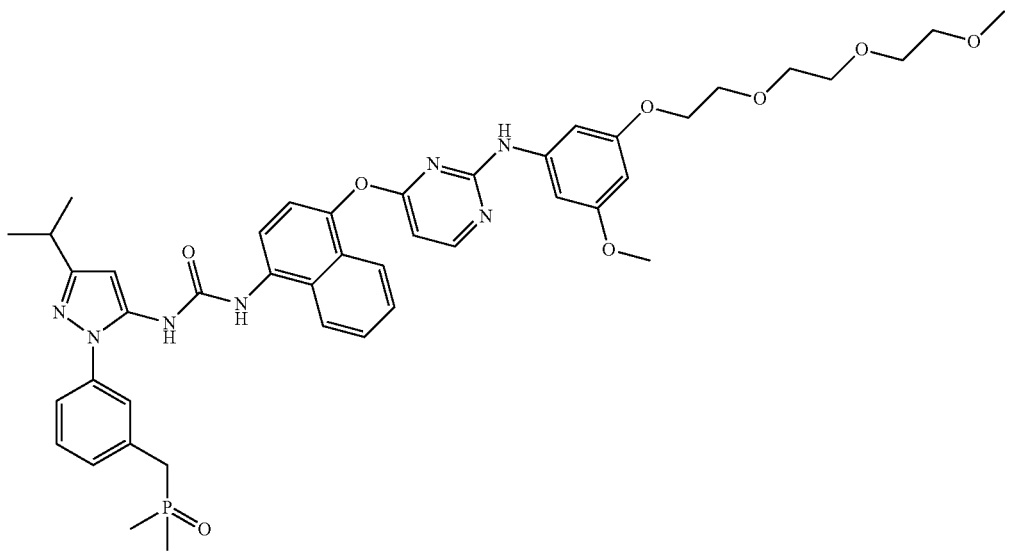 [SMILES: COCCOCCOCCOc1cc(Nc2nccc(Oc3ccc(NC(=O)Nc4cc(C(C)C)nn4-c4cccc(CP(C)(C)=O)c4)c4ccccc34)n2)cc(OC)c1]

(i) 3-Methoxy-5-(2-(2-(2-methoxyethoxy)ethoxy)ethoxy)aniline

3-Amino-5-methoxyphenol (500 mg, 3.59 mmol) and $K_2CO_3$ (2483 mg, 17.97 mmol) were stirred in N,N-dimethylformamide:pyridine (3:1, 5 mL) at rt. 1-Bromo-2-(2-(2-methoxyethoxy)ethoxy)ethane (938 mg, 4.13 mmol) was added and the mixture was heated to 60° C. overnight. Sodium iodide (539 mg, 3.59 mmol) was added and the mixture was heated to 90° C. for 2 h. The mixture was diluted with water (75 mL) and extracted with ethyl acetate (3×50 mL). The combined organic phases were washed with saturated brine (3×50 mL), dried ($MgSO_4$) and concentrated under reduced pressure. The crude product was purified by chromatography on the Companion (40 g column, $Et_2O$, then EtOAc) to afford the sub-title compound (728 mg) as a brown oil.

1H NMR (DMSO-d6) 400 MHz, δ: 5.77-5.73 (m, 2H), 5.69 (t, 1H), 5.05 (s, 2H), 3.97-3.91 (m, 2H), 3.71-3.66 (m, 2H), 3.63 (s, 3H), 3.59-3.55 (m, 2H), 3.55-3.50 (m, 4H), 3.46-3.41 (m, 2H), 3.25 (s, 3H).

(ii) 1-(1-(3-((Dimethylphosphoryl)methyl)phenyl)-3-isopropyl-1H-pyrazol-5-yl)-3-(4-((2-((3-methoxy-5-(2-(2-(2-methoxyethoxy)ethoxy)ethoxy)phenyl)amino)pyrimidin-4-yl)oxy)-naphthalen-1-yl)urea A mixture of 1-(4-((2-chloropyrimidin-4-yl)oxy)naphthalen-1-yl)-3-(1-(3-((dimethyl-phosphoryl)methyl)phenyl)-3-isopropyl-1H-pyrazol-5-yl)urea (see Example 37(v) above; 150 mg, 0.255 mmol), the product from step (i) above (113 mg, 0.395 mmol) and pTSA monohydrate (24.22 mg, 0.127 mmol) was heated to 70° C. in DMF (2 mL) for 18 h. The mixture was diluted with water (15 mL), saturated $NaHCO_3$ solution (15 mL) and extracted with ethyl acetate (3×15 mL). The combined organic phases were washed with saturated brine (25 mL), dried ($MgSO_4$) and concentrated under reduced pressure. The crude product was purified by chromatography on the Companion (40 g column, EtOAc, then DCM:MeOH:ammonia 90:9:1) to afford a brown oil. The brown oil was purified further by chromatography on the Companion (40 g column, 0-100% acetone in toluene) to afford a brown oil. The brown oil was further purified by preparative HPLC (Waters, Acidic (0.1% Formic acid), Waters X-Select Prep-C18, 5 μm, 19×50 mm column, 25-70% MeCN in Water) to afford the title compound (41 mg) as a cream glass.

1H NMR (DMSO-d6) 400 MHz, δ: 9.51 (s, 1H), 9.43 (s, 1H), 9.04 (s, 1H), 8.41 (d, 1H), 8.22 (d, 1H), 8.00 (d, 1H), 7.86-7.79 (m, 1H), 7.68-7.61 (m, 1H), 7.61-7.51 (m, 3H), 7.51-7.44 (m, 1H), 7.40 (d, 1H), 7.35-7.28 (m, 1H), 6.86-6.74 (m, 2H), 6.54 (d, 1H), 6.46 (s, 1H), 6.03 (dd, 1H), 3.90-3.82 (m, 2H), 3.64-3.61 (m, 2H), 3.55-3.52 (m, 2H), 3.52-3.45 (m, 7H), 3.41-3.37 (m, 2H), 3.33 (d, 2H), 3.22 (s, 3H), 2.93 (septet, 1H), 1.46 (d, 6H), 1.26 (d, 6H).

LCMS m/z 838 $(M+H)^+$ $(ES^+)$; 836 $(M-H)^-$ $(ES^-)$

Example 46

1-(4-((2-((3-(Cyclopropylsulfonyl)-5-methoxyphenyl)amino)pyrimidin-4-yl)oxy)naphthalen-1-yl)-3-(1-(3-((dimethylphosphoryl)methyl)phenyl)-3-isopropyl-1H-pyrazol-5-yl)urea

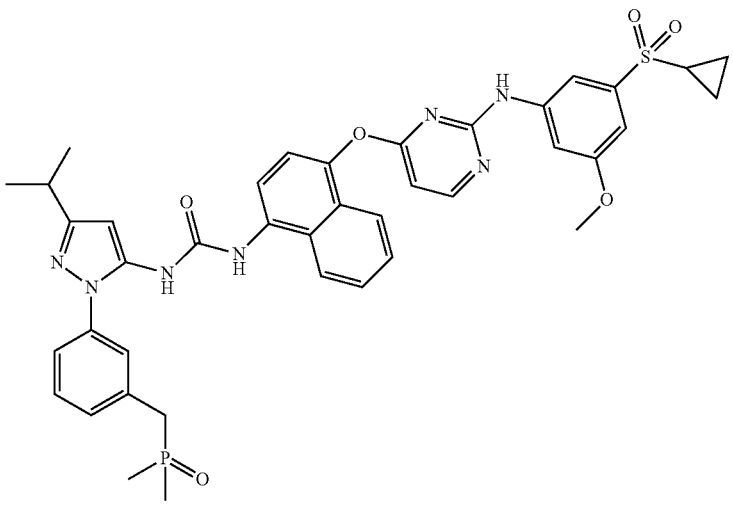 [SMILES: COc1cc(Nc2nccc(Oc3ccc(NC(=O)Nc4cc(C(C)C)nn4-c4cccc(CP(C)(C)=O)c4)c4ccccc34)n2)cc(S(=O)(=O)C2CC2)c1]

(i) 1-(Cyclopropylsulfonyl)-3-methoxy-5-nitrobenzene

A mixture of 1-bromo-3-methoxy-5-nitrobenzene (830 mg, 3.58 mmol), sodium cyclopropanesulfinate (550 mg, 4.29 mmol), copper(I) iodide (70 mg, 0.368 mmol), L-proline (82 mg, 0.715 mmol) and NaOH (29 mg, 0.725 mmol) in DMSO (5 mL) was heated at 95° C. for 18 h. The mixture was partitioned between EtOAc (100 mL) and water (100 mL), the organic layer separated, washed with water (100 mL), dried (MgSO$_4$) and evaporated under reduced pressure. The crude product was purified by chromatography on silica gel (40 g column, 0-50% EtOAc/isohexane) to afford the sub-title compound (453 mg) as a solid.

1H NMR (400 MHz; CDCl$_3$) δ 8.30 (s, 1H), 7.95 (s, 1H), 7.74 (s, 1H), 3.99 (s, 3H), 2.54-2.47 (m, 1H), 1.44-1.39 (m, 2H), 1.13-1.07 (m, 2H).

(ii) 3-(Cyclopropylsulfonyl)-5-methoxyaniline

The product from step (i) above (450 mg, 1.749 mmol) was dissolved in ethanol (8 mL) and iron powder (977 mg, 17.49 mmol) added followed by a solution of ammonium chloride (936 mg, 17.49 mmol) in water (4 mL). Heated at 60° C. in a sonic bath for 1 h. Filtered on glass fibre pad (Whatman GF/A) and solvent evaporated until a thick beige precipitate formed which was filtered and washed with water. Oven dried to give the sub-title compound (337 mg) as a pale yellow solid.

1H NMR (400 MHz, DMSO) δ 6.66 (t, 1H), 6.49 (t, 1H), 6.39 (t, 1H), 5.68 (s, 2H), 3.74 (s, 3H), 2.77-2.72 (m, 1H), 1.23-0.83 (m, 4H).

LCMS m/z 228 (M+H)$^+$ (ES$^+$)

(iii) 1-(4-((2-((3-(Cyclopropylsulfonyl)-5-methoxyphenyl)amino)pyrimidin-4-yl)oxy)naphthalen-1-yl)-3-(1-(3-((dimethylphosphoryl)methyl)phenyl)-3-isopropyl-1H-pyrazol-5-yl)urea A mixture of 1-(4-((2-chloropyrimidin-4-yl)oxy)naphthalen-1-yl)-3-(1-(3-((dimethyl-phosphoryl)methyl)phenyl)-3-isopropyl-1H-pyrazol-5-yl)urea (see Example 37(v) above; 150 mg, 0.255 mmol), the product from step (ii) above (72.3 mg, 0.318 mmol) and pTSA monohydrate (24.22 mg, 0.127 mmol) was heated to 70° C. in DMF (2 mL) for 18 h. The mixture was cooled and triethylamine (0.15 mL) was added. The mixture was then added to vigorously stirred water (25 mL) and the resulting precipitate collected by filtration. The solid was purified by chromatography on the Companion (40 g column, EtOAc:DCM:MeOH:NH$_3$, 100:0:0:0→0:90:9:1) to afford a pink solid. The solid was triturated in acetonitrile to yield the title compound (18 mg) as a white solid.

1H NMR (DMSO-d6) 400 MHz, δ: 9.58 (s, 1H), 9.47 (s, 1H), 8.99 (s, 1H), 8.47 (d, 1H), 8.22 (d, 1H), 8.01 (d, 1H), 7.84-7.79 (m, 1H), 7.78-7.69 (m, 1H), 7.68-7.61 (m, 1H), 7.61-7.45 (m, 5H), 7.41 (d, 1H), 7.35-7.29 (m, 1H), 6.86 (dd, 1H), 6.64 (d, 1H), 6.47 (s, 1H), 3.62 (s, 3H), 3.37 (d, 2H), 2.93 (septet, 1H), 2.78-2.69 (m, 1H), 1.46 (d, 6H), 1.26 (d, 6H), 1.10-0.95 (m, 4H).

LCMS m/z 780 (M+H)$^+$ (ES$^+$); 778 (M−H)$^−$ (ES$^−$)

Example 47

3-((4-((4-(3-(3-(tert-Butyl)-1-(3-((dimethylphosphoryl)methyl)phenyl)-1H-pyrazol-5-yl)ureido)naphthalen-1-yl)oxy)pyrimidin-2-yl)amino)-5-methoxy-N-(2-morpholinoethyl)-benzamide

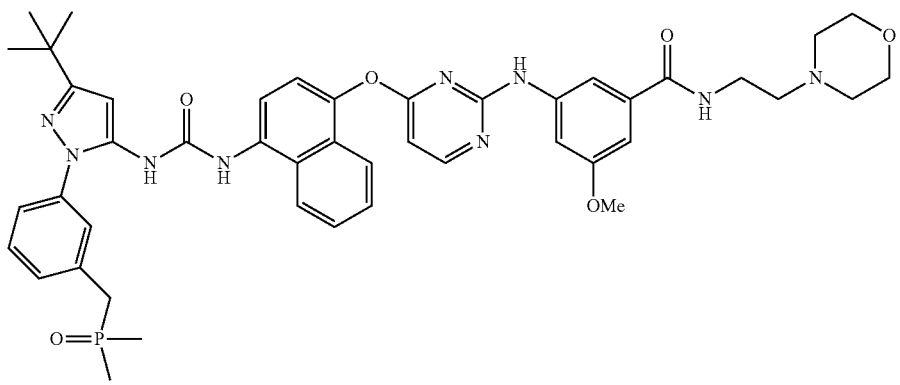 [SMILES: COc1cc(Nc2nccc(Oc3ccc(NC(=O)Nc4cc(C(C)(C)C)nn4-c4cccc(CP(C)(C)=O)c4)c4ccccc34)n2)cc(C(=O)NCCN2CCOCC2)c1]

A suspension of 1-(3-(tert-butyl)-1-(3-((dimethylphosphoryl)methyl)phenyl)-1H-pyrazol-5-yl)-3-(4-((2-chloropyrimidin-4-yl)oxy)naphthalen-1-yl)urea (see Example 32(i) above; 150 mg, 0.249 mmol), 3-amino-5-methoxy-N-(2-morpholinoethyl)benzamide (see Example 38(i) above; 146 mg, 0.497 mmol) and p-TSA monohydrate (95 mg, 0.497 mmol) in THF/DMF (6 mL, 1:2) was heated at 60° C. overnight. The reaction was cooled to rt and partitioned between EtOAc (40 mL) and sat. aq. NaHCO₃ (30 mL). The aqueous layer was extracted with EtOAc (2×40 mL). The combined organic extracts were washed with water (2×50 mL), brine (2×50 mL), dried (MgSO₄), filtered and concentrated in vacuo to afford a foam. The crude product was purified by chromatography on silica gel (40 g column, 0-10% MeOH) to afford a cream solid, which was triturated with diethyl ether then MeCN to afford the title compound (99 mg) as a white solid. 1H NMR (DMSO-d6) 400 MHz, δ: 9.59 (s, 1H), 9.44 (s, 1H), 8.95 (s, 1H), 8.41 (d, 1H), 8.21-8.17 (m, 2H), 7.99 (d, 1H), 7.83-7.81 (m, 1H), 7.65-7.61 (m, 1H), 7.59-7.52 (m, 4H), 7.48-7.46 (m, 1H), 7.40 (d, 1H), 7.34-7.30 (m, 2H), 6.85-6.84 (br m, 1H), 6.54 (d, 1H), 6.50 (s, 1H), 3.58-3.52 (br m, 7H), 3.37 (d, 2H), 2H under water peak at 3.32 ppm, 2.44-2.36 (br m, 6H), 1.46 (d, 6H), 1.31 (s, 9H).

LCMS m/z 846 (M+H)+ (ES+); 844 (M−H)− (ES−)

Example 48

1-(1-(3-((Dimethylphosphoryl)methyl)phenyl)-3-isopropyl-1H-pyrazol-5-yl)-3-(4-((2-((3-(2-morpholinoethoxy)-5-(trifluoromethoxy)phenyl)amino)pyrimidin-4-yl)oxy)naphthalen-1-yl)urea

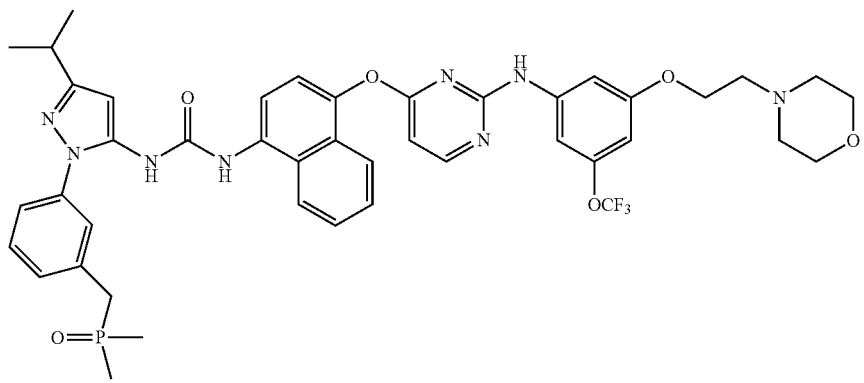 [SMILES: CC(C)c1cc(NC(=O)Nc2ccc(Oc3ccnc(Nc4cc(OCCN5CCOCC5)cc(OC(F)(F)F)c4)n3)c3ccccc23)n(-c2cccc(CP(C)(C)=O)c2)n1]

(i) Methyl 3-(2-morpholinoethoxy)-5-(trifluoromethoxy)benzoate

To solution of methyl 3-hydroxy-5-(trifluoromethoxy)benzoate (1.13 g, 4.79 mmol) in acetonitrile (15 mL) was added 4-(2-chloroethyl)morpholine, HCl (0.979 g, 5.26 mmol) and K₂CO₃ (1.455 g, 10.53 mmol) and the reaction heated at 60° C. over 20 h. The reaction diluted with ethyl acetate (100 mL) and washed with 1 M aqueous KOH (20 mL), 50% brine (20 mL), brine (20 mL), dried over Na₂SO₄, filtered and concentrated under reduced pressure to afford the sub-title compound (1.625 g) as a clear yellow oil.

1H NMR (400 MHz; DMSO-d6) δ 7.50-7.48 (m, 1H), 7.41-7.39 (m, 1H), 7.30-7.28 (m, 1H), 4.20 (t, 2H), 3.87 (s, 3H), 3.59-3.55 (m, 4H), 2.70 (t, 2H), 2.49-2.45 (m, 4H).

(ii) 3-(2-Morpholinoethoxy)-5-(trifluoromethoxy)benzoic acid

To a solution of the product from step (i) above (1.6 g, 4.35 mmol) in methanol (10 mL) and THF (1 mL) was added 2 M aqueous NaOH (3.48 mL, 6.96 mmol) and the reaction stirred at ambient temperature over 16 h. After this time, solvent was removed under reduced pressure, coevaporated with acetonitrile (20 mL) and then the crude product was loaded onto a column of SCX (20 g) in acetonitrile-water 90-10. The column was washed with acetonitrile (100 mL) and then the product was eluted with 90:10 acetonitrile: aqueous ammonia. The resultant mixture was concentrated in vacuo to afford the sub-title compound (1.503 g) as a clear, pale orange oil.

1H NMR (400 MHz; DMSO-d6) δ: 7.49-7.47 (m, 1H), 7.39-7.36 (m, 1H), 7.09-7.07 (1H, m), 4.20 (t, 2H), 3.61-3.56 (4H, m), 2.73 (t, 2H), 2.51-2.49 (m, 4H).

LCMS m/z 336 (M+H)+ (ES+); 334 (M−H)− (ES−)

(iii) tert-Butyl (3-(2-morpholinoethoxy)-5-(trifluoromethoxy)phenyl)carbamate

DPPA (0.771 mL, 3.58 mmol) was added to a stirred solution of the product from step (ii) above (800 mg, 2.386 mmol) and triethylamine (0.998 mL, 7.16 mmol) in tert-butanol (10 mL) and heated to reflux for 18 h. The mixture was cooled, water (50 mL) added and extracted with ethyl acetate (3×50 mL). The combined organic phases were washed with saturated brine (25 mL), dried (MgSO4) and concentrated under reduced pressure. The crude product was purified by chromatography on the Companion (40 g column, EtOAc) to afford the sub-title compound (586 mg).

1H NMR (DMSO-d6) 400 MHz, δ: 9.61 (s, 1H), 7.13 (s, 1H), 7.06 (s, 1H), 6.55 (s, 1H), 4.06 (t, 2H), 3.62-3.52 (m, 4H), 2.67 (t, 2H), 2.49-2.42 (m, 4H), 1.48 (s, 9H).

LCMS m/z 407 (M+H)+ (ES+); 405 (M−H)− (ES−)

(iv) 3-(2-Morpholinoethoxy)-5-(trifluoromethoxy) aniline, HCl

The product from step (iii) above (580 mg, 1.356 mmol) was stirred in 5 M HCl solution in isopropanol (5 mL) at rt for 18 h. The volatiles were removed under reduced pressure and the residue was co-evaporated with acetonitrile ×3 to yield the sub-title compound (520 mg) as a white foam.

LCMS m/z 307 (M+H)+ (ES+) (90% purity)

(v) 1-(1-(3-((Dimethylphosphoryl)methyl)phenyl)-3-isopropyl-1H-pyrazol-5-yl)-3-(4-((2-((3-(2-morpholinoethoxy)-5-(trifluoromethoxy)phenyl)amino) pyrimidin-4-yl)oxy)naphthalen-1-yl)urea A mixture of 1-(4-((2-chloropyrimidin-4-yl)oxy)naphthalen-1-yl)-3-(1-(3-((dimethyl-phosphoryl)methyl)phenyl)-3-isopropyl-1H-pyrazol-5-yl)urea (see Example 37(v) above; 395 mg, 0.671 mmol), the product from step (iv) above (230 mg, 0.671 mmol) and p-TSA monohydrate (65 mg, 0.342 mmol) in DMF (3 mL) were heated at 60° C. for 18 h. The mixture was cooled, aq. Sat. NaHCO3 (6 mL) added and the precipitate filtered. The solid was partitioned between EtOAc (150 mL) and water (50 mL), the organic layer separated, dried (MgSO4) and evaporated under reduced pressure. The crude product was purified by chromatography on silica gel (40 g column, 0-5% MeOH/DCM) to afford a foam which was triturated with MeOH (4 mL), filtered and dried under vacuum to afford the title compound (101 mg).

1H NMR (400 MHz; DMSO-d6) δ 9.73 (s, 1H), 9.48 (s, 1H), 9.00 (s, 1H), 8.46 (d, 1H), 8.23 (d, 1H), 8.04 (d, 1H), 7.81 (d, 1H), 7.66-7.53 (m, 4H), 7.47 (d, 1H), 7.42 (d, 1H), 7.32 (d, 1H), 7.20 (br s, 2H), 6.64 (d, 1H), 6.47 (s, 1H), 6.42 (s, 1H), 3.94 (t, 2H), 3.54-3.52 (m, 4H), 3.38 (d, 2H), 2.93 (septet, 1H), 2.60 (t, 2H), 2.40 (br m, 4H), 1.46 (d, 6H), 1.26 (d, 6H).

LCMS m/z 859 (M+H)+ (ES+)

Example 49

1-(1-(3-((Dimethylphosphoryl)methyl)phenyl)-3-isopropyl-1H-pyrazol-5-yl)-3-(4-((2-((3-(2-morpholinoethoxy)-5-(trifluoromethyl)phenyl)amino) pyrimidin-4-yl)oxy)naphthalen-1-yl)urea

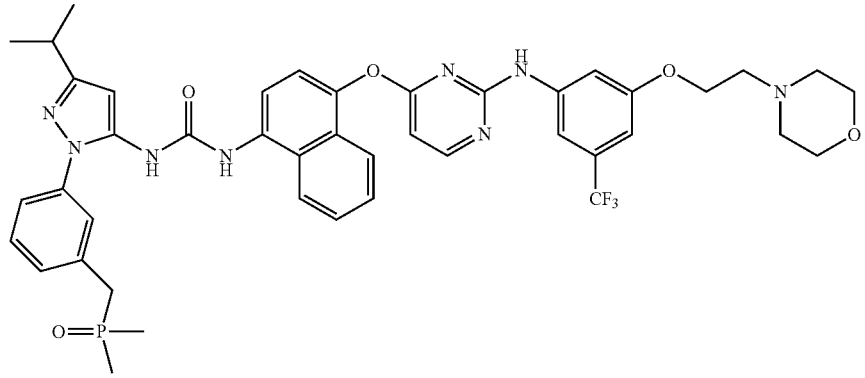 [SMILES: CC(C)c1cc(NC(=O)Nc2ccc(Oc3ccnc(Nc4cc(OCCN5CCOCC5)cc(C(F)(F)F)c4)n3)c3ccccc23)n(-c2cccc(CP(C)(C)=O)c2)n1]

A mixture of 1-(4-((2-chloropyrimidin-4-yl)oxy)naphthalen-1-yl)-3-(1-(3-((dimethyl-phosphoryl)methyl)phenyl)-3-isopropyl-1H-pyrazol-5-yl)urea (see Example 37(v) above; 150 mg, 0.255 mmol), 3-(2-morpholinoethoxy)-5-(trifluoromethyl)aniline (see, for example, Adams, Ruth S. et al. WO 2006/076706, 20 Jul. 2006; 92 mg, 0.318 mmol) and p-TSA monohydrate (85 mg, 0.446 mmol) was heated to 70° C. in DMF (2 mL) for 18 h. The mixture was cooled and triethylamine (0.15 mL) was added. The mixture was then added to vigorously stirred water (25 mL) and the resulting precipitate collected by filtration. The solid was purified by chromatography on the Companion (40 g column, EtOAc:DCM:MeOH:NH3, 100:0:0:0→0:90:9:1) to afford a pink solid. The solid was triturated in diethyl ether then recrystallised from acetonitrile to yield the title compound (32 mg) as a pale pink solid.

1H NMR (DMSO-d6) 400 MHz, δ: 9.77 (s, 1H), 9.48 (s, 1H), 9.00 (s, 1H), 8.47 (d, 1H), 8.23 (d, 1H), 8.01 (d, 1H), 7.85-7.78 (m, 1H), 7.67-7.61 (m, 1H), 7.60-7.45 (m, 6H), 7.41 (d, 1H), 7.35-7.29 (m, 1H), 6.76-6.72 (m, 1H), 6.63 (d, 1H), 6.47 (s, 1H), 4.00 (t, 2H), 3.57-3.48 (m, 4H), 3.38 (d, 2H), 2.93 (hept, 1H), 2.62 (t, 2H), 2.44-2.37 (m, 4H), 1.47 (d, 6H), 1.26 (d, 6H).

LCMS m/z 843 (M+H)+ (ES+); 841 (M−H)− (ES−)

Example 50

3-((4-((4-(3-(1-(3-((Dimethylphosphoryl)methyl)phenyl)-3-isopropyl-1H-pyrazol-5-yl)-ureido)naphthalen-1-yl)oxy)pyridin-2-yl)amino)-5-methoxy-N-(2-morpholinoethyl)-benzamide

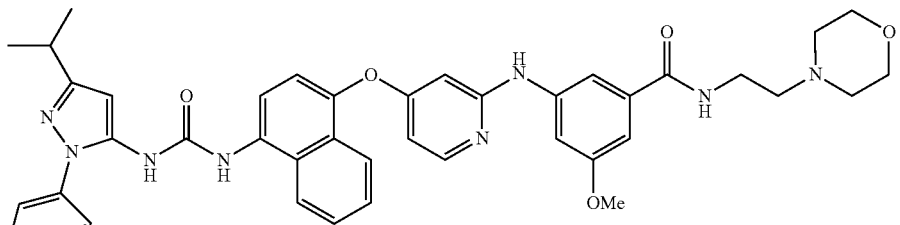

(i) 3-((4-((4-Aminonaphthalen-1-yl)oxy)pyridin-2-yl)amino)-5-methoxy-N-(2-morpholinoethyl)benzamide A mixture of 4-((2-chloropyridin-4-yl)oxy)naphthalen-1-amine (see, for example, Ito, K. et al., WO 2010/112936, 7 Oct. 2010; 400 mg, 1.478 mmol), 3-amino-5-methoxy-N-(2-morpholinoethyl)benzamide (see Example 38(i) above; 825 mg, 2.96 mmol) and 4M HCl in dioxane (1108 μL, 4.43 mmol) in NMP (5 mL) was heated at 140° C. for 18 h. The mixture was partitioned between EtOAc (150 mL) and aq. NaHCO3 solution (50 mL), the organic layer separated, washed with 20% brine (100 mL), dried (MgSO4) and evaporated under reduced pressure. The crude product was purified by chromatography on silica gel (80 g column, 0-10% MeOH/DCM) to afford the sub-title compound (216 mg).

LCMS m/z 514 (M+H)+ (ES+) (80% purity)

(ii) 3-((4-((4-(3-(1-(3-((Dimethylphosphoryl)methyl)phenyl)-3-isopropyl-1H-pyrazol-5-yl)ureido)naphthalen-1-yl)oxy)pyridin-2-yl)amino)-5-methoxy-N-(2-morpholinoethyl)benzamide DPPA (78 μL, 0.360 mmol) was added to a stirred solution of 1-(3-((dimethylphosphoryl)methyl)phenyl)-3-isopropyl-1H-pyrazole-5-carboxylic acid (see Example 37(iv) above; 105 mg, 0.327 mmol) and Et3N (114 μL, 0.818 mmol) in DMF (1.5 mL) at 0-5° under N2. The mixture was warmed to rt and stirred for 1 h. A solution of the product from step (i) above (210 mg, 0.327 mmol) in DMF (1 mL) was added and the mixture heated at 100° C. for 1.5 h, cooled and partitioned between EtOAc (50 mL) and water (50 mL). The organic layer was separated, washed with water, dried (MgSO4) and evaporated under reduced pressure. The crude product was purified by chromatography on silica gel (40 g column, 0-8% MeOH/DCM) to afford a solid which was slurried with MeCN. The solid was filtered, washed with MeCN then dried to afford the title compound (47 mg).

1H NMR (400 MHz; DMSO-d6) δ 9.49 (s, 1H), 9.06 (s, 1H), 8.98 (s, 1H), 8.25-8.21 (m, 2H), 8.10 (d, 1H), 8.03 (d, 1H), 7.86 (d, 1H), 7.69-7.65 (m, 1H), 7.59-7.47 (m, 6H), 7.37 (d, 1H), 7.32 (brd, 1H), 6.85 (s, 1H), 6.58 (dd, 1H), 6.47 (s, 1H), 6.12 (d, 1H), 3.74 (s, 3H), 3.58-3.55 (m, 4H), 3.39-3.30 (m, 4H), 2.93 (septet, 1H), 2.46-2.38 (m, 6H), 1.46 (d, 6H), 1.26 (d, 6H).

LCMS m/z 831 (M+H)+ (ES+)

Example 51

1-(1-(3-((Dimethylphosphoryl)methyl)phenyl)-3-isopropyl-1H-pyrazol-5-yl)-3-(4-((2-((3-methoxy-5-(2-morpholinoethoxy)phenyl)amino)pyridin-4-yl)oxy)naphthalen-1-yl)urea

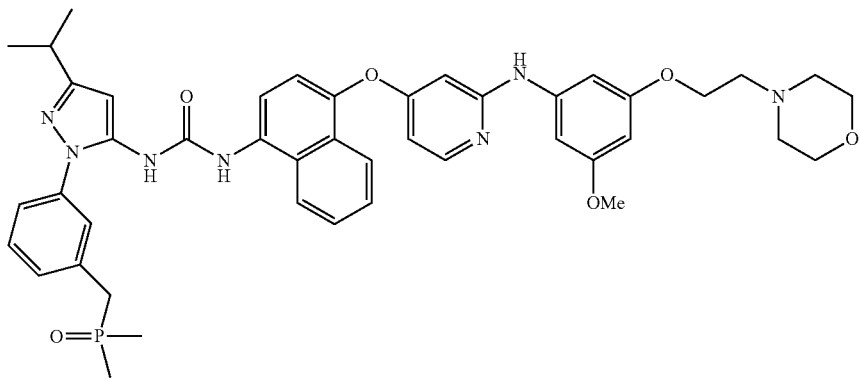

(i) 4-((4-Aminonaphthalen-1-yl)oxy)-N-(3-methoxy-5-(2-morpholinoethoxy)phenyl)pyridin-2-amine A mixture of 4-((2-chloropyridin-4-yl)oxy)naphthalen-1-amine (see, for example, Ito, K. et al., WO 2010/112936, 7 Oct. 2010; 300 mg, 1.108 mmol), 3-methoxy-5-(2-morpholinoethoxy)aniline (see Example 39(i) above; 559 mg, 2.216 mmol) and 4M HCl in dioxane (831 µL, 3.32 mmol) in NMP (4 mL) was heated at 140° C. for 18 h. The mixture was partitioned between EtOAc (100 mL) and aq. NaHCO$_3$ solution (50 mL), the organic layer separated, washed with water (50 mL), dried (MgSO$_4$) and evaporated under reduced pressure. The crude product was purified by chromatography on silica gel (40 g column, 0-10% MeOH/DCM) to afford the sub-title compound (206 mg) as a light tan foam.

1H NMR (400 MHz; CDCl$_3$) δ 8.00 (d, 1H), 7.87-7.83 (m, 2H), 7.51-7.45 (m, 2H), 7.05 (d, 1H), 6.78 (s, 1H), 6.75 (d, 1H), 6.40-6.35 (m, 4H), 6.72 (t, 1H), 3.99 (t, 2H), 3.76-3.74 (m, 4H), 3.63 (s, 3H), 2.78 (t, 2H), 2.60-2.58 (m, 4H).

LCMS m/z 487 (M+H)+ (ES+)

(ii) 1-(1-(3-((Dimethylphosphoryl)methyl)phenyl)-3-isopropyl-1H-pyrazol-5-yl)-3-(4-((2-((3-methoxy-5-(2-morpholinoethoxy)phenyl)amino)pyridin-4-yl)oxy)naphthalen-1-yl)urea DPPA (97 µL, 0.452 mmol)) was added to a stirred solution of 1-(3-((dimethylphosphoryl)methyl)phenyl)-3-isopropyl-1H-pyrazole-5-carboxylic acid (see Example 37(iv) above; 132 mg, 0.411 mmol) and Et$_3$N (143 µL, 1.028 mmol) in DMF (1.5 mL) at 0-5° under N$_2$. The mixture was warmed to rt and stirred for 1 h. A solution of the product from step (i) above (200 mg, 0.411 mmol) in DMF (1 mL) was added and the mixture heated at 100° C. for 1.5 h, cooled and partitioned between EtOAc (50 mL) and water (50 mL). The organic layer was separated, washed with water, dried (MgSO4) and evaporated under reduced pressure. The crude product was purified by chromatography on silica gel (40 g column, 0-7% MeOH/DCM) to afford a solid which was slurried with MeCN. The solid was filtered, washed with MeCN then dried to afford the title compound (128 mg).

1H NMR (400 MHz; DMSO-d6) δ 9.49 (s, 1H), 8.98 (s, 1H), 8.86 (s, 1H), 8.24 (d, 1H), 8.10 (d, 1H), 8.02 (d, 1H), 7.85 (d, 1H), 7.68-7.47 (m, 5H), 7.36 (d, 1H), 7.32 (brd, 1H), 6.90-6.89 (t, 1H), 6.78 (t, 1H), 6.56 (dd, 1H), 6.47 (s, 1H), 6.06 (d, 1H), 6.03 (t, 1H), 3.98 (t, 2H), 3.65 (s, 3H), 3.58-3.56 (m, 4H), 3.38 (d, 2H), 2.93 (septet, 1H), 2.65 (t, 2H), 2.46-2.44 (m, 4H), 1.46 (d, 6H), 1.26 (d, 6H).

LCMS m/z 804 (M+H)+ (ES+)

Example 52

1-(4-((2-((3-(2,5,8,11-Tetraoxatridecan-13-yloxy)-5-methoxyphenyl)amino)pyrimidin-4-yl)oxy)naphthalen-1-yl)-3-(1-(3-((dimethylphosphoryl)methyl)phenyl)-3-isopropyl-1H-pyrazol-5-yl)urea

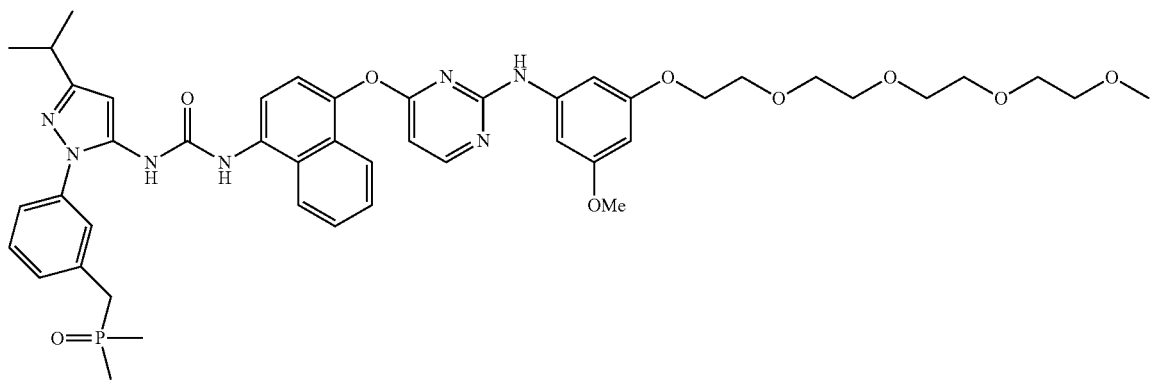 [SMILES: COCCOCCOCCOCCOc1cc(Nc2nccc(Oc3ccc(NC(=O)Nc4cc(C(C)C)nn4-c4cccc(CP(C)(C)=O)c4)c4ccccc34)n2)cc(OC)c1]

(i) 3-(2,5,8,11-Tetraoxatridecan-13-yloxy)-5-methoxyaniline

3-Amino-5-methoxyphenol (500 mg, 3.59 mmol) and K$_2$CO$_3$ (2483 mg, 17.97 mmol) were stirred in N,N-dimethylformamide:pyridine (3:1, 5 mL) at rt. 13-Bromo-2,5,8,11-tetraoxatridecane (1120 mg, 4.13 mmol) was added and the mixture was heated to 60° C. overnight. Sodium iodide (539 mg, 3.59 mmol) was added and the mixture was heated to 90° C. for 2 h. The mixture was diluted with water (75 mL) and extracted with ethyl acetate (3×50 mL). The combined organic phases were washed with saturated brine (3×50 mL), dried (MgSO$_4$) and concentrated under reduced pressure. The crude product was purified by chromatography on the Companion (40 g column, Et$_2$O, then EtOAc) to afford the sub-title compound (820 mg) as a brown oil.

1H NMR (DMSO-d6) 400 MHz, δ: 5.77-5.73 (m, 2H), 5.69 (t, 1H), 5.05 (s, 2H), 3.97-3.91 (m, 2H), 3.71-3.66 (m, 2H), 3.63 (s, 3H), 3.60-3.49 (m, 10H), 3.46-3.41 (m, 2H), 3.24 (s, 3H).

(ii) 1-(4-((2-((3-(2,5,8,11-Tetraoxatridecan-13-yloxy)-5-methoxyphenyl)amino)pyrimidin-4-yl)oxy)naphthalen-1-yl)-3-(1-(3-((dimethylphosphoryl)methyl)phenyl)-3-isopropyl-1H-pyrazol-5-yl)urea p-TSA monohydrate (153 mg, 0.806 mmol) was added to a stirred solution of 1-(4-((2-chloropyrimidin-4-yl)oxy)naphthalen-1-yl)-3-(1-(3-((dimethylphosphoryl)methyl)phenyl)-3-isopropyl-1H-pyrazol-5-yl)urea (see Example 37(v) above; 250 mg, 0.403 mmol) and the product from step (i) above (280 mg, 0.806 mmol) in THF/DMF (6 mL, 1:1). The resulting mixture was heated at 60° C. overnight. The reaction was cooled to rt and partitioned between EtOAc (50 mL) and sat. aq. NaHCO$_3$ (40 mL). The aqueous layer was extracted with EtOAc (2×50 mL). The combined organic extracts were washed with water (2×75 mL) then brine (100 mL), dried (MgSO$_4$), filtered and concentrated to afford an oil. The crude product was purified by chromatography on silica gel (80 g column, 0-5% MeOH in DCM) to afford an orange oil which was triturated with Et$_2$O (×2) to afford the title compound (118 mg) as a white solid.

1H NMR (CDCl$_3$) 400 MHz, δ: 9.53 (s, 1H), 8.83 (s, 1H), 8.29-8.24 (m, 2H), 8.08 (d, 1H), 7.89-7.86 (m, 1H), 7.65-7.61 (m, 1H), 7.53-7.48 (m, 2H), 7.45-7.40 (m, 2H), 7.26 (d, 1H), 7.13-7.09 (m, 1H), 6.95 (s, 1H), 6.74-6.73 (m, 1H), 6.70 (s, 1H), 6.66-6.65 (m, 1H), 6.31 (d, 1H), 6.08 (t, 1H), 3.97-3.95 (m, 2H), 3.77-3.74 (m, 2H), 3.67-3.58 (m, 10H), 3.55 (s, 3H), 3.50-3.47 (m, 2H), 3.32 (s, 3H), 3.23 (d, 2H), 3.07-2.96 (m, 1H), 1.53 (d, 6H), 1.32 (d, 6H).

LCMS m/z 882 (M+H)+ (ES+); 880 (M-H)- (ES-)

Example 53

1-(1-(3-((Dimethylphosphoryl)methyl)phenyl)-3-isopropyl-1H-pyrazol-5-yl)-3-(4-((2-((3-(methylsulfonyl)-5-(2-morpholinoethoxy)phenyl)amino)pyrimidin-4-yl)oxy)naphthalen-1-yl)urea

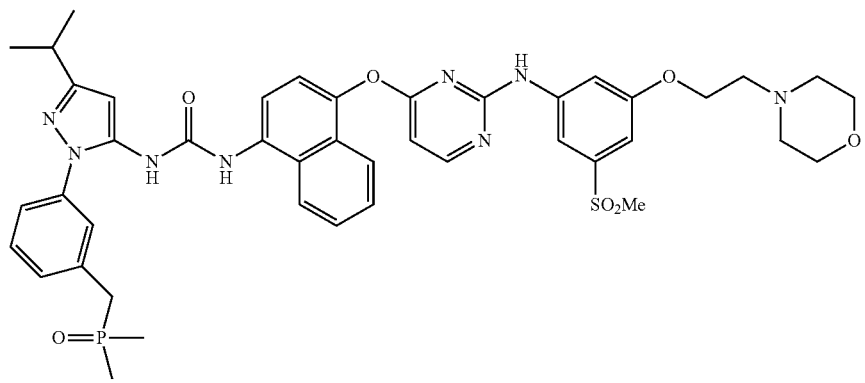 [SMILES: CC(C)c1cc(NC(=O)Nc2ccc(Oc3ccnc(Nc4cc(OCCN5CCOCC5)cc(S(C)(=O)=O)c4)n3)c3ccccc23)n(-c2cccc(CP(C)(C)=O)c2)n1]

(i) 4-(2-(3-(Methylsulfonyl)-5-nitrophenoxy)ethyl)morpholine 3-(Methylsulfonyl)-5-nitrophenol (270 mg, 1.243 mmol), 4-(2-chloroethyl)morpholine, HCl (243 mg, 1.305 mmol), K$_2$CO$_3$ (430 mg, 3.11 mmol) and NaI (18.63 mg, 0.124 mmol) were suspended in MeCN (5 mL) and heated at reflux for 16 h then cooled, filtered and partitioned between water (20 mL) and EtOAc (20 mL). Organic layer was separated, dried (MgSO$_4$), filtered and solvent evaporated to a brown oil. The crude product was purified by chromatography on silica gel (40 g column, 2% MeOH:DCM to 5%)) to afford the sub-title compound (363 mg) as a thick yellow oil.

1H NMR (400 MHz, DMSO-d6) δ 8.21 (dd, 1H), 8.07 (t, 1H), 7.92 (dd, 1H), 4.35 (t, 2H), 3.58 (t, 4H), 3.38 (s, 3H), 2.75 (t, 2H), 2.56-2.44 (m, 4H).

(ii) 3-(Methylsulfonyl)-5-(2-morpholinoethoxy)aniline

The product from step (i) above (363 mg, 1.099 mmol) was dissolved in ethanol (3 mL) and Pd—C, 10% (58.5 mg, 0.055 mmol) added. Stirred under hydrogen for 1 h then filtered and solvents evaporated to give the sub-title compound (300 mg) as a colourless oil.

1H NMR (400 MHz, DMSO-d6) δ 6.69 (t, 1H), 6.55 (dd, 1H), 6.39 (t, 1H), 5.66 (s, 2H), 4.06 (t, 2H), 3.58 (t, 4H), 3.11 (s, 3H), 2.68 (t, 2H), 2.47 (t, 4H).

LCMS m/z 301 (M+H)+ (ES+)

(iii) 1-(1-(3-((Dimethylphosphoryl)methyl)phenyl)-3-isopropyl-1H-pyrazol-5-yl)-3-(4-((2-((3-(methylsulfonyl)-5-(2-morpholinoethoxy)phenyl)amino)pyrimidin-4-yl)oxy)naphthalen-1-yl)urea 1-(4-((2-Chloropyrimidin-4-yl)oxy)naphthalen-1-yl)-3-(1-(3-((dimethylphosphoryl)methyl)-phenyl)-3-isopropyl- 1H-pyrazol-5-yl)urea (see Example 37(v) above; 150 mg, 0.255 mmol) was dissolved in DMF (3 mL) and added to the product from step (ii) above (126 mg, 0.419 mmol) and p-TSA monohydrate (121 mg, 0.637 mmol). Stirred at 70° C. (block temperature) for 7 h then poured into sat. NaHCO$_3$ solution (20 mL) and the product extracted with EtOAc (2×20 mL). Organics bulked and washed with 20% w/w brine solution (20 mL), separated, dried (MgSO$_4$), filtered and evaporated to a yellow solid. The crude product was purified by chromatography on silica gel (12 g column, 2% MeOH:DCM to 8%) to afford 100 mg of a pale beige foam. Triturated with diethyl ether (2 mL) then recrystallised twice from MeCN (2 mL) to afford the title compound (50 mg) as a colourless solid.

1H NMR (400 MHz, DMSO-d6) δ 9.84 (s, 1H), 9.49 (s, 1H), 8.99 (s, 1H), 8.47 (d, 1H), 8.22 (d, 1H), 8.02 (d, 1H), 7.90-7.73 (m, 2H), 7.70-7.39 (m, 7H), 7.33 (d, 1H), 6.97 (t, 1H), 6.62 (d, 1H), 6.47 (s, 1H), 4.02 (t, 2H), 3.62-3.47 (m, 4H), 3.38 (d, 2H), 3.11 (s, 3H), 3.01-2.87 (m, 1H), 2.64 (t, 2H), 2.42 (t, 4H), 1.47 (d, 6H), 1.26 (d, 6H).

LCMS m/z 853 (M+H)+ (ES+); 851 (M−H)− (ES−)

Example 54

1-(1-(3-((Dimethylphosphoryl)methyl)phenyl)-3-isopropyl-1H-pyrazol-5-yl)-3-(5-((2-((3-methoxy-5-(2-morpholinoethoxy)phenyl)amino)pyrimidin-4-yl)oxy)quinolin-8-yl)urea

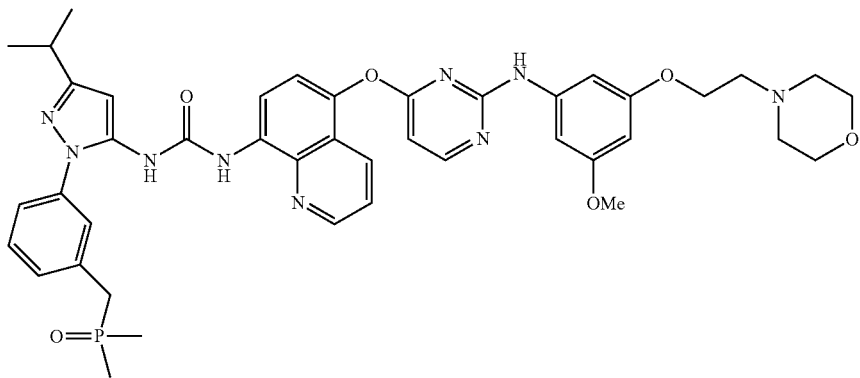

(i) 5-((2-chloropyrimidin-4-yl)oxy)-8-nitroquinoline

DBU (1.110 mL, 7.36 mmol) was added over 5 min to a stirred mixture of 8-nitroquinolin-5-ol (1 g, 5.26 mmol) in MeCN (20 mL) at 0-5° C. After stirring for 10 min, 2,4-dichloropyrimidine (0.838 g, 5.63 mmol) was added, the mixture stirred at rt for 2 h then heated at 60° C. for 2 h. A further portions of DBU (1.110 mL, 7.36 mmol) and 2,4-dichloropyrimidine (0.838 g, 5.63 mmol) were added, heated at 60° C. for a further 2 h then partitioned between ether (100 mL) and water (100 mL). The organic layer was separated, washed with water, dried (MgSO$_4$) and evaporated under reduced pressure. The crude product was purified by chromatography on silica gel (40 g column, 0-100% EtOAc/isohexane) to afford the subtitle compound (880 mg) as a yellow solid.

1H NMR (DMSO-d6) 400 MHz, δ: 9.13 (dd, 1H), 8.76 (d, 1H), 8.50 (dd, 1H), 8.44 (d, 1H), 7.80-7.76 (m, 2H), 7.48 (d, 1H).

LCMS m/z 303/305 (M+H)+ (ES+)

(ii) 5-((2-Chloropyrimidin-4-yl)oxy)quinolin-8-amine

To a partially dissolved suspension of NH$_4$Cl (68.5 mg, 1.280 mmol) in IPA (90 mL) was added the product from step (i) above (775 mg, 2.56 mmol) and a mixture of Fe powder (1430 mg, 25.6 mmol) in water (5 mL). The mixture was heated at reflux for 16 h after which time the mixture was filtered and then the crude product was purified by chromatography on the Companion (40 g column, 0-5% methanol in DCM) to afford the sub-title compound (700 mg) as a pale yellow-brown powder.

1H NMR (400 MHz; DMSO-d6) δ: 8.80 (dd, 1H), 8.60 (d, 1H), 8.03 (dd, 1H), 7.50 (dd, 1H), 7.25 (d, 1H), 7.14 (d, 1H), 6.87 (d, 1H), 6.06 (br.s, 2H).

LCMS m/z 272/4 (M+H)+ (ES+); 270/2 (M−H)− (ES−)

(iii) 1-(5-((2-Chloropyrimidin-4-yl)oxy)quinolin-8-yl)-3-(1-(3-((dimethylphosphoryl)methyl) phenyl)-3-isopropyl-1H-pyrazol-5-yl)urea To a solution of 1-(3-((dimethylphosphoryl)methyl)phenyl)-3-isopropyl-1H-pyrazole-5-carboxylic acid (see Example 37(iv) above; 464 mg, 1.449 mmol) in anhydrous dioxane (5 mL) was added DPPA (468 μL, 2.173 mmol) and Et$_3$N (606 μL, 4.35 mmol) and the reaction heated at 100° C. for 60 minutes prior to the addition of the product from step (ii) above (395 mg, 1.449 mmol) and dioxane (2.5 mL). The reaction was heated for a further 20 h. Volatiles were removed under reduced pressure and the crude material was purified by chromatography on the Companion (40 g column, 1-7% MeOH in DCM) to afford the sub-title compound (94 mg) as a pale brown oil.

LCMS m/z 591 (M+H)+ (ES+); 589 (M−H)− (ES−)

(iv) 1-(1-(3-((Dimethylphosphoryl)methyl)phenyl)-3-isopropyl-1H-pyrazol-5-yl)-3-(5-((2-((3-methoxy-5-(2-morpholinoethoxy)phenyl)amino)pyrimidin-4-yl)oxy)quinolin-8-yl)urea To a solution of the product from step (iii) above (94 mg, 0.143 mmol) and 3-methoxy-5-(2-morpholinoethoxy)aniline (see Example 39(i) above; 54.3 mg, 0.215 mmol) in DMF (1 mL) and THF (0.5 mL) was added p-TSA monohydrate (68.2 mg, 0.358 mmol) and the reaction heated at 70° C. for 16 h. After this time the reaction mixture was diluted with ethyl acetate (30 mL) and washed with sat. aqueous sodium bicarbonate (10 mL), half saturated brine (10 mL) and brine (10 mL) and then dried over sodium sulfate, filtered and evaporated to afford a brown oil. The crude product was purified by chromatography on the Companion (12 g column, 1-9% 0.7M NH$_3$/MeOH in DCM) then purified by preparative HPLC (Waters, Acidic (0.1% Formic acid), Waters X-Select Prep-C18, 5 μm, 19×50 mm column, 20-50% MeCN in Water) to afford the title compound, 0.5 Formic Acid (29 mg) as a pale cream solid.

1H NMR (400 MHz; DMSO-d6) δ: 10.03 (s, 1H), 9.67 (s, 1H), 9.39 (s, 1H), 8.92 (dd, 1H), 8.56 (d, 1H), 8.41 (d, 1H), 8.21 (dd, 1H), 8.18 (0.5H), 7.62 (dd, 1H), 7.51-7.41 (m, 4H), 7.32-7.21 (m, 1H), 6.67 (br.d, 2H), 6.59 (d, 1H), 6.42 (s, 1H), 6.00 (t, 1H), 3.84 (t, 2H), 3.55-3.50 (m, 4H), 3.48 (s, 3H), 3.25 (d, 2H), 2.96-2.86 (m, 1H), 2.58 (t, 2H), 2.42-2.36 (m, 4H), 1.37 (d, 6H), 1.26 (d, 6H).

LCMS m/z 806 (M+H)+ (ES+); 804 (M−H)− (ES−)

Example 55

1-(4-((2-((3-(2,5,8,11,14-Pentaoxahexadecan-16-yloxy)-5-methoxyphenyl)amino)-pyrimidin-4-yl)oxy)naphthalen-1-yl)-3-(1-(3-((dimethylphosphoryl)methyl)phenyl)-3-isopropyl-1H-pyrazol-5-yl)urea

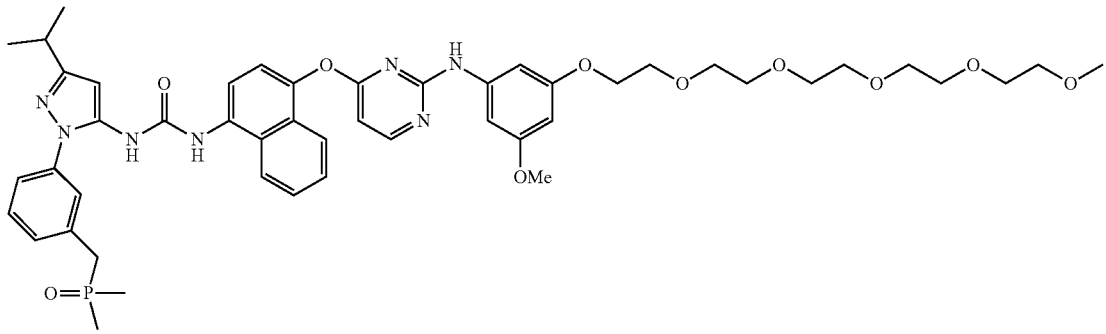 [SMILES: COCCOCCOCCOCCOCCOc1cc(Nc2nccc(Oc3ccc(NC(=O)Nc4cc(C(C)C)nn4-c4cccc(CP(C)(C)=O)c4)c4ccccc34)n2)cc(OC)c1]

(i) 3-(2,5,8,11,14-Pentaoxahexadecan-16-yloxy)-5-methoxyaniline

DIAD (419 μL, 2.156 mmol) added to a suspension of 3-amino-5-methoxyphenol (200 mg, 1.437 mmol), PPh₃ (565 mg, 2.156 mmol) and 2,5,8,11,14-pentaoxahexadecan-16-ol (504 μL, 2.156 mmol) in THF (5 mL). Stirred at rt for 16 h then cooled and partitioned between water (20 mL) and ethyl acetate (20 mL). Organic layer was separated, dried (MgSO₄), filtered and solvent evaporated to give a brown oil. The crude product was purified by chromatography on silica gel (40 g column, 1% MeOH:DCM to 5%) to afford a pale brown residue which was purified by chromatography on silica gel (12 g column, 50% EtOAc:isohexane to 100%) to afford the sub-title compound (350 mg) as a clear colourless oil.

1H NMR (400 MHz, CDCl₃) δ 5.93 (t, 1H), 5.89 (t, 1H), 5.86 (t, 1H), 4.11-4.02 (m, 2H), 3.86-3.77 (m, 2H), 3.76-3.60 (m, 17H), 3.57-3.52 (m, 2H), 3.38 (s, 3H).

(ii) 1-(4-((2-((3-(2,5,8,11,14-Pentaoxahexadecan-16-yloxy)-5-methoxyphenyl)amino)-pyrimidin-4-yl)oxy)naphthalen-1-yl)-3-(1-(3-((dimethylphosphoryl)methyl)phenyl)-3-isopropyl-1H-pyrazol-5-yl)urea 1-(4-((2-Chloropyrimidin-4-yl)oxy)naphthalen-1-yl)-3-(1-(3-((dimethylphosphoryl)methyl)-phenyl)-3-isopropyl-1H-pyrazol-5-yl)urea (see Example 37(v) above; 146 mg, 0.248 mmol) was dissolved in DMF (3 mL) and added to the product from step (i) above (185 mg, 0.496 mmol) and p-TSA monohydrate (23.57 mg, 0.124 mmol). Stirred at 70° C. (block temperature) for 7 h. then poured into sat. aq. NaHCO₃ solution (20 mL) and the product extracted with EtOAc (2×20 mL). Organics bulked and washed with 20% w/w brine solution (20 mL), separated, dried (MgSO₄), filtered and evaporated to a yellow solid. The crude product was purified by chromatography on silica gel (12 g column, 2% MeOH:DCM to 8%) to afford a brown gum which was stirred in diethyl ether (3 mL) overnight to give a pale pink solid. Triturated 3 more times with diethyl ether (3 mL) afforded the title compound (138 mg).

1H NMR (400 MHz, DMSO-d6) δ 9.47 (s, 1H), 9.41 (s, 1H), 8.98 (s, 1H), 8.41 (d, 1H), 8.22 (d, 1H), 8.01 (d, 1H), 7.83 (d, 1H), 7.68-7.51 (m, 4H), 7.51-7.44 (m, 1H), 7.40 (d, 1H), 7.35-7.29 (m, 1H), 6.88-6.75 (m, 2H), 6.54 (d, 1H), 6.47 (s, 1H), 6.03 (t, 1H), 3.87 (dd, 2H), 3.69-3.61 (m, 2H), 3.58-3.44 (m, 17H), 3.44-3.35 (m, 4H), 3.22 (s, 3H), 2.93 (hept, 1H), 1.47 (d, 6H), 1.26 (d, 6H).

LCMS m/z 926 (M+H)+ (ES+)

Example 56

1-(1-(3-((Dimethylphosphoryl)methyl)phenyl)-3-isopropyl-1H-pyrazol-5-yl)-3-(4-((2-((3-ethynyl-5-(2-morpholinoethoxy)phenyl)amino)pyrimidin-4-yl)oxy)naphthalen-1-yl)urea

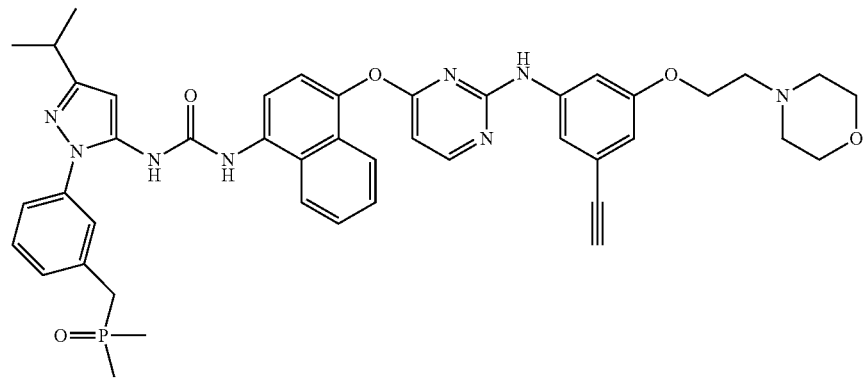 [SMILES: C#Cc1cc(Nc2nccc(Oc3ccc(NC(=O)Nc4cc(C(C)C)nn4-c4cccc(CP(C)(C)=O)c4)c4ccccc34)n2)cc(OCCN2CCOCC2)c1]

(i) 4-(2-(3-Bromo-5-nitrophenoxy)ethyl)morpholine 4-(2-Chloroethyl)morpholine, HCl (357 mg, 1.917 mmol) was added to a stirred suspension of 3-bromo-5-nitrophenol (380 mg, 1.743 mmol), $K_2CO_3$ (964 mg, 6.97 mmol) and NaI (26.1 mg, 0.174 mmol) in N,N-dimethylformamide. Stirred at 80° C. for 2 h then the mixture was diluted with 20% sodium chloride solution (50 mL) and extracted with ethyl acetate (3×50 mL). The combined organic phases were washed with saturated brine (50 mL), dried ($MgSO_4$) and concentrated to yield the sub-title compound (790 mg) as a brown oil which was used in the next stage without further purification. LCMS m/z 331, 333 (M+H)+ (ES+)

(ii) 4-(2-(3-Nitro-5-((triisopropylsilyl)ethynyl)phenoxy)ethyl)morpholine $(PPh_3)_2Pd(II)Cl_2$ (178 mg, 0.254 mmol) was added to a degassed suspension of the product from step (i) above (1400 mg, 2.54 mmol), Cu(I)I (48.3 mg, 0.254 mmol), and ethynyltriisopropylsilane (711 µL, 3.17 mmol) in diethylamine (8 mL) and N,N-dimethylformamide (8 mL). The mixture was heated at 80° C. (block temp.) for 1 h. The solvents were evaporated and the residue was resuspended in 20% sodium chloride solution. The suspension was extracted with ethyl acetate (3×50 mL) and the combined organic phases were washed with saturated brine (50 mL), dried ($MgSO_4$) and concentrated under reduced pressure. The crude product was purified by chromatography on the Companion (80 g column, EtOAc) to afford the sub-title compound (1.04 g) as a brown oil.
LCMS m/z 433 (M+H)+ (ES+)

(iii) 4-(2-(3-Ethynyl-5-nitrophenoxy)ethyl)morpholine

The product from step (ii) above (1.04 g, 2.404 mmol) and 1.0 M TBAF in THF (2.76 mL, 2.76 mmol) were stirred in tetrahydrofuran (10 mL) at rt overnight. The mixture was diluted with water (25 mL) and extracted with ethyl acetate (3×25 mL). The combined organic phases were washed with saturated brine (50 mL), dried ($MgSO_4$) and concentrated under reduced pressure. The crude product was triturated in 2-propanol and collected by filtration. The filter cake was washed with iso-hexane to yield the sub-title compound (528 mg).
1H NMR (DMSO-d6) 400 MHz, δ: 7.82 (dd, 1H), 7.78 (dd, 1H), 7.53 (dd, 1H), 4.49 (s, 1H), 4.25 (t, 2H), 3.62-3.54 (m, 4H), 2.71 (t, 2H), 2.43-2.51 (m, 4H).
LCMS m/z 277 (M+H)+ (ES+)

(iv) 3-Ethynyl-5-(2-morpholinoethoxy)aniline

The product from step (iii) above (525 mg, 1.862 mmol), $NH_4Cl$ (149 mg, 2.79 mmol) and Fe powder (1040 mg, 18.62 mmol) were stirred in ethanol (7 mL) and water (1 mL) at reflux for 2 h. The mixture was cooled and filtered. The filtrate was concentrated under reduced pressure and the residue was partitioned between ethyl acetate (25 mL) and saturated sodium hydrogen carbonate solution (25 mL). The organic phase was dried ($MgSO_4$) and concentrated to yield a brown oil. The crude product was purified by chromatography on the Companion (12 g column, EtOAc:MeOH:NH4OH [90:4.5:0.5]) to afford the sub-title compound (275 mg) as a yellow oil.

1H NMR (DMSO-d6) 400 MHz, δ: 6.27 (dd, 1H), 6.18 (dd, 1H), 6.17 (dd, 1H), 5.23 (br s, 2H), 3.98 (t, 2H), 3.96 (s, 1H), 3.60-3.54 (m, 4H), 2.64 (t, 2H), 2.48-2.42 (m, 4H).
LCMS m/z 247 (M+H)+ (ES+)

(v) tert-Butyl (4-((2-((3-ethynyl-5-(2-morpholinoethoxy)phenyl)amino)pyrimidin-4-yl)oxy)naphthalen-1-yl)carbamate $Pd_2dba_3$ (32.0 mg, 0.035 mmol) and BINAP (43.5 mg, 0.070 mmol) were stirred in butyl acetate (1 mL) for 10 minutes under $N_2$, using a heat gun to aid dissolution. In a separate vessel, purged with $N_2$, caesium carbonate (342 mg, 1.049 mmol), the product from step (iv) above (172 mg, 0.699 mmol) and tert-butyl (4-((2-chloropyrimidin-4-yl)oxy)naphthalen-1-yl)carbamate (see, for example, Ito, K. et al., WO 2010/067130, 17 Jun. 2010; 260 mg, 0.699 mmol) were stirred in butyl acetate (5 mL). The catalyst solution was added to the main reaction mixture and the whole was heated to 90° C. for 9 h. The mixture was diluted with ethyl acetate (10 mL) and water (10 mL) was added. The organic phase was separated and the aqueous layer was extracted with further portions of ethyl acetate (2×10 mL). The combined organic phases were washed with saturated brine solution (10 mL), dried ($MgSO_4$) and concentrated onto silica. The silicate was purified by chromatography on the Companion (12 g column, 0-8% MeOH (1% $NH_3$)/DCM) to afford the sub-title compound (260 mg) as a sticky orange gum.
LCMS m/z 582 (M+H)+ (ES+); 580 (M-H)- (ES-)

(vi) 4-((4-Aminonaphthalen-1-yl)oxy)-N-(3-ethynyl-5-(2-morpholinoethoxy)phenyl)-pyrimidin-2-amine TFA (344 µL, 4.47 mmol) was added to a solution of the product from step (v) above (260 mg, 0.447 mmol) in DCM (1 mL) and the mixture was stirred at rt overnight. The volatiles were removed under reduced pressure and the residue was loaded onto SCX. The resin was washed with methanol (3×10 mL), then eluted into fractions using 1% ammonia in methanol (3×10 mL). Fractions containing product were combined and concentrated under reduced pressure to yield the sub-title compound (210 mg) as a brown gum.
LCMS m/z 482 (M+H)+ (ES+); 480 (M-H)- (ES-)

(vii) 1-(1-(3-((Dimethylphosphoryl)methyl)phenyl)-3-isopropyl-1H-pyrazol-5-yl)-3-(4-((2-((3-ethynyl-5-(2-morpholinoethoxy)phenyl)amino)pyrimidin-4-yl)oxy)naphthalen-1-yl)urea DPPA (105 µL, 0.486 mmol) was added to a stirred solution of 1-(3-((dimethylphosphoryl)methyl)phenyl)-3-isopropyl-1H-pyrazole-5-carboxylic acid (see Example 37(iv) above; 108 mg, 0.324 mmol) and triethylamine (113 µL, 0.809 mmol) in DMF (2 mL) under $N_2$ at 0° C. The mixture was allowed to warm to rt then stirred for 40 min then the product from step (vi) above (246 mg, 0.486 mmol) was added and the mixture heated at 100° C. for 1 h. The mixture was added to vigorously stirred water (15 mL) and the precipitate was collected by filtration. The solid was purified by chromatography on the Companion (40 g column, 0-5% MeOH (1% $NH_3$)/DCM) to afford a dark red-brown solid. The solid was triturated in acetone to yield the title compound (25 mg) as a grey solid.

1H NMR (DMSO-d6) 400 MHz, δ:9.57 (s, 1H), 9.46 (s, 1H), 8.98 (s, 1H), 8.43 (d, 1H), 8.22 (d, 1H), 8.20 (d, 1H), 7.85-7.79 (m, 1H), 7.67-7.61 (m, 1H) 7.61-7.51 (m, 3H), 7.51-7.45 (m, 1H), 7.36-7.25 (m, 3H), 6.57 (d, 1H), 6.56-6.53 (m, 1H), 6.47 (s, 1H), 4.01 (s, 1H), 3.93 (t, 2H), 3.57-3.48 (m, 4H), 3.38 (d, 2H), 2.93 (hept, 1H), 2.60 (t, 2H), 2.44-2.36 (m, 4H), 1.46 (d, 6H), 1.26 (d, 6H).

LCMS m/z 799 (M+H)+ (ES+); 797 (M-H)- (ES-)

Example 57

1-(4-((2-((3-cyano-5-(2-morpholinoethoxy)phenyl)amino)pyrimidin-4-yl)oxy)-naphthalen-1-yl)-3-(1-(3-((dimethylphosphoryl)methyl)phenyl)-3-isopropyl-1H-pyrazol-5-yl)urea

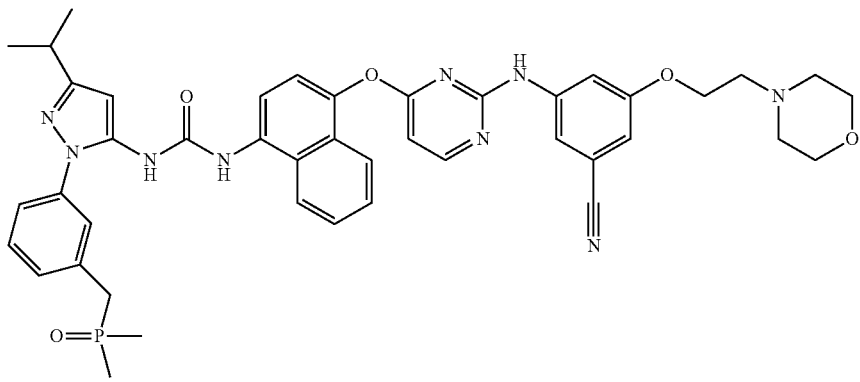 [SMILES: CC(C)c1cc(NC(=O)Nc2ccc(Oc3ccnc(Nc4cc(C#N)cc(OCCN5CCOCC5)c4)n3)c3ccccc23)n(-c2cccc(CP(C)(C)=O)c2)n1]

(i) 3-(2-Morpholinoethoxy)-5-nitrobenzonitrile

3-Hydroxy-5-nitrobenzonitrile (1.0 g, 6.09 mmol), K₂CO₃ (1.684 g, 12.19 mmol) and NaI (0.091 g, 0.609 mmol) were stirred in acetonitrile (15 mL) at rt. 4-(2-Chloroethyl)morpholine hydrochloride (1.247 g, 6.70 mmol) was added and the mixture was heated to reflux overnight. The mixture was diluted with water (50 mL) and extracted with ethyl acetate (3×50 mL). The combined organic phases were washed with saturated brine (50 mL), dried (MgSO₄) and concentrated. The crude product was purified by chromatography on the Companion (40 g column, EtOAc) to afford the sub-title compound (1.52 g) as a sticky yellow oil.

1H NMR (DMSO-d6) 400 MHz, δ: 8.30 (dd, 1H), 8.05 (dd, 1H), 7.98 (dd, 1H), 4.30 (t, 2H), 3.62-3.53 (m, 4H), 2.73 (t, 2H), 2.52-2.43 (m, 4H).

LCMS 278 (M+H)+ (ES+)

(ii) 3-Amino-5-(2-morpholinoethoxy)benzonitrile

The product from step (i) above (1.5 g, 5.41 mmol), NH₄Cl (0.434 g, 8.11 mmol) and Fe powder (3.02 g, 54.1 mmol) were stirred in ethanol (20 mL) and water (4 mL) at reflux for 2 h. The mixture was cooled and filtered. The filtrate was concentrated under reduced pressure and the residue was partitioned between ethyl acetate (50 mL) and saturated sodium hydrogen carbonate solution (25 mL). The organic phase was dried (MgSO₄) and concentrated to yield the sub-title compound (1.38 g) as a yellow oil.

1H NMR (DMSO-d6) 400 MHz, δ: 6.52-6.44 (m, 2H), 6.41 (dd, 1H), 5.59 (br s, 2H), 4.03 (t, 2H), 3.61-3.52 (m, 4H), 2.65 (t, 2H), 2.48-2.42 (m, 4H).

LCMS, m/z 248 (M+H)+ (ES+)

(iii) tert-Butyl (4-((2-((3-cyano-5-(2-morpholinoethoxy)phenyl)amino)pyrimidin-4-yl)oxy)-naphthalen-1-yl)carbamate Pd₂dba₃ (64.6 mg, 0.071 mmol) and BINAP (88 mg, 0.141 mmol) were stirred in butyl acetate (1 mL) for 10 minutes under N₂, using a heat gun to aid dissolution. In a separate vessel, purged with N₂, caesium carbonate (690 mg, 2.118 mmol), the product from step (ii) above (349 mg, 1.412 mmol) and tert-butyl (4-((2-chloropyrimidin-4-yl)oxy)naphthalen-1-yl)carbamate (see, for example, Ito, K. et al., WO 2010/067130, 17 Jun. 2010; 525 mg, 1.412 mmol) were stirred in butyl acetate (7 mL). The catalyst solution was added to the main reaction mixture and the whole was heated to 90° C. for 3 h. The mixture was diluted with ethyl acetate (10 mL) and water (10 mL) was added. The organic phase was separated and the aqueous layer was extracted with further portions of ethyl acetate (2×10 mL). The combined organic phases were washed with saturated brine solution (10 mL), dried (MgSO₄) and concentrated onto silica. The silicate was purified by chromatography on the Companion (12 g column, 0-8% MeOH (1% NH₃)/DCM) to afford the sub-title compound (680 mg) as a sticky orange gum.

LCMS m/z 583 (M+H)+ (ES+); 581 (M-H)- (ES-)

(iv) 3-((4-((4-Aminonaphthalen-1-yl)oxy)pyrimidin-2-yl)amino)-5-(2-morpholinoethoxy)-benzonitrile TFA (899 μL, 11.67 mmol) was added to a solution of the product from step (iii) above (680 mg, 1.167 mmol) in DCM (1 mL) and the mixture was stirred at rt overnight. The volatiles were removed under reduced pressure and the residue was loaded onto SCX. The resin was washed with methanol (3×20 mL), then eluted into fractions using 1% ammonia in methanol (3×20 mL). Fractions containing product were combined and concentrated under reduced pressure to yield the sub-title compound (558 mg) as a tan foam.

1H NMR (DMSO-d6) 400 MHz, δ: 9.77 (s, 1H), 8.39 (s, 1H), 8.17-8.11 (m, 1H), 7.68-7.54 (m, 3H), 7.48-7.38 (m, 2H), 7.14 (d, 1H), 6.97-6.94 (m, 1H), 6.71 (d, 1H), 6.44 (d, 1H), 5.76 (s, 2H), 4.03 (t, 2H), 3.60-3.52 (m, 4H), 2.65 (t, 2H), 2.48-2.40 (m, 4H).

LCMS m/z 483 (M+H)+ (ES+); 481 (M-H)- (ES-)

(v) 1-(4-((2-((3-Cyano-5-(2-morpholinoethoxy)phenyl)amino)pyrimidin-4-yl)oxy)-naphthalen-1-yl)-3-(1-(3-((dimethylphosphoryl)methyl)phenyl)-3-isopropyl-1H-pyrazol-5-yl)urea DPPA (105 µL, 0.486 mmol) was added to a stirred solution of 1-(3-((dimethylphosphoryl)methyl)phenyl)-3-isopropyl-1H-pyrazole-5-carboxylic acid (see Example 37(iv) above; 108 mg, 0.324 mmol) and triethylamine (113 µL, 0.809 mmol) in DMF (2 mL) under $N_2$ at 0° C. The mixture was allowed to warm to rt then stirred for 40 min. The product from step (iv) above (276 mg, 0.486 mmol) was added and the mixture heated at 100° C. for 1 h. The mixture was diluted with methanol (10 mL) and added slowly to vigorously stirred water (50 mL). The precipitate was collected by filtration then purified by chromatography on the Companion (40 g column, 0-5% MeOH (1% $NH_3$)/DCM) to afford a brown solid. The solid was triturated with diethyl ether to afford the title compound (60 mg) as a tan solid.

1H NMR (DMSO-d6) 400 MHz, δ: 9.80 (s, 1H), 9.44 (s, 1H), 9.00 (s, 1H), 8.48 (s, 1H), 8.22 (d, 1H), 8.03 (d, 1H), 7.81 (d, 1H), 7.67-7.60 (m, 1H), 7.60-7.44 (m, 6H), 7.42 (d, 1H), 7.35-7.29 (m, 1H), 6.95-6.90 (m, 1H), 6.66 (d, 1H), 6.46 (s, 1H), 4.00 (t, 2H), 3.57-3.48 (m, 4H), 3.37 (d, 2H), 2.93 (hept, 1H), 2.62 (t, 2H), 2.45-2.35 (m, 4H), 1.46 (d, 6H), 1.26 (d, 6H).

LCMS m/z 800 (M+H)+ (ES+)

Example 58

3-((4-((4-(3-(3-(tert-Butyl)-1-(3-((dimethylphosphoryl)methyl)phenyl)-1H-pyrazol-5-yl)-ureido)naphthalen-1-yl)oxy)pyrimidin-2-yl)amino)-N-(2-morpholinoethyl)-5-(trifluoromethyl)benzamide The aqueous was separated and re-partitioned with fresh DCM (20 mL). The combined organics were washed with 20% w/w NaCl soln. (20 mL), dried ($MgSO_4$) filtered and concentrated in vacuo. The crude product was purified by chromatography on the Companion 40 g column, 2% MeOH:DCM to 5%) to afford the sub-title compound (1.43 g) as a yellow oil.

1H NMR (400 MHz; $CDCl_3$) δ 8.44 (t, 1H), 7.25 (m, 1H), 7.22 (m, 1H), 6.96 (s, 1H), 5.78 (s, 2H), 3.57 (t, 4H), 3.36 (q, 2H), 2.40-2.45 (m, 6H).

LCMS m/z 318.0 (M+H)+ (ES+)

(ii) 3-((4-((4-(3-(3-(tert-Butyl)-1-(3-((dimethylphosphoryl)methyl)phenyl)-1H-pyrazol-5-yl)-ureido)naphthalen-1-yl)oxy)pyrimidin-2-yl)amino)-N-(2-morpholinoethyl)-5-(trifluoromethyl)benzamide A suspension of 1-(3-(tert-butyl)-1-(3-((dimethylphosphoryl)methyl)phenyl)-1H-pyrazol-5-yl)-3-(4-((2-chloropyrimidin-4-yl)oxy)naphthalen-1-yl)urea (see Example 32(i) above; 150 mg, 0.249 mmol), 3-amino-N-(2-morpholinoethyl)-5-(trifluoromethyl)benzamide (see step (i) above; 158 mg, 0.497 mmol) and p-TSA monohydrate (95 mg, 0.497 mmol) in THF/DMF (6 mL, 1:2) was heated at 60° C. for 72 h. The reaction was cooled to rt and partitioned between EtOAc (40 mL) and sat. aq. $NaHCO_3$ (30 mL). The aqueous layer was extracted with EtOAc (2×40 mL). The combined organic extracts were washed with water (2×50 mL), brine (2×50 mL), dried ($MgSO_4$), filtered and concentrated in vacuo. The crude product was purified by chromatography on silica gel (40 g column, 0-10% MeOH) then triturated with diethyl ether to afford a pink solid (100 mg). The material was further purified by prep-HPLC affording the

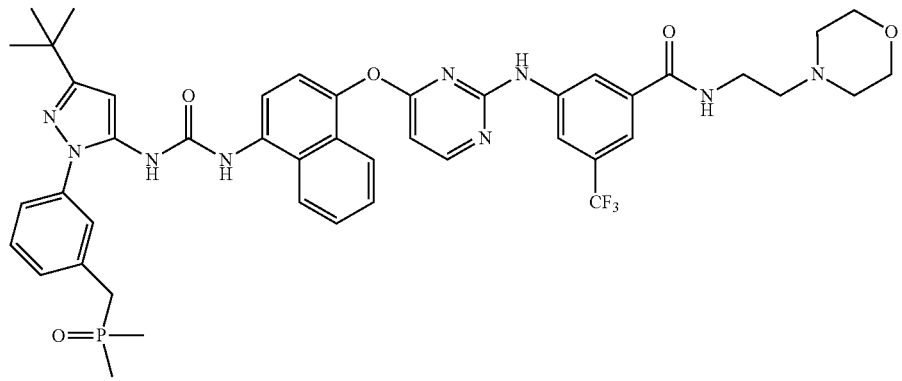 [SMILES: CC(C)(C)c1cc(NC(=O)Nc2ccc(Oc3ccnc(Nc4cc(C(=O)NCCN5CCOCC5)cc(C(F)(F)F)c4)n3)c3ccccc23)n(-c2cccc(CP(C)(C)=O)c2)n1]

(i) 3-Amino-N-(2-morpholinoethyl)-5-(trifluoromethyl)benzamide

To a stirred solution of 3-amino-5-(trifluoromethyl)benzoic acid (1.0 g, 4.87 mmol), 2-morpholinoethanamine (1.280 mL 9.75 mmol) and triethylamine (2.038 mL, 14.62 mmol) in DCM (20 mL) was added T3P (50 Wt % in EtOAc, 4.35 mL, 7.31 mmol) carefully, maintaining a temperature below 35° C. The reaction was stirred at rt for 1 h. The mixture was partitioned with sat. $NaHCO_3$ soln. (20 mL).

title compound, 0.31 Formic Acid (45 mg) as a pale yellow solid.

1H NMR (400 MHz; DMSO-d6) δ 9.99 (s, 1H), 9.48 (s, 1H), 9.02 (s, 1H), 8.54 (t, 1H), 8.48 (d, 1H), 8.28 (s, 1H), 8.21 (d, 1H), 8.11 (s, 1H), 7.98 (d, 1H), 7.82 (d, 1H), 7.62-7.66 (m, 2H), 7.53-7.59 (m, 3H), 7.48 (d, 1H), 7.42 (d, 1H), 7.32 (d, 1H), 6.65 (d, 1H), 6.50 (s, 1H), 3.55 (t, 4H), 3.38-3.39 (m, 4H), 2.40-2.46 (m, 6H), 1.46 (d, 6H), 1.31 (s, 9H).

LCMS m/z 442 $(M+2H)^{2+}$ (ES+)

Example 59

3-((4-((4-(3-(3-(tert-Butyl)-1-(3-((dimethylphosphoryl)methyl)phenyl)-1H-pyrazol-5-yl)-ureido)naphthalen-1-yl)oxy)pyrimidin-2-yl)amino)-N-(2-morpholinoethyl)-5-(trifluoromethoxy)benzamide

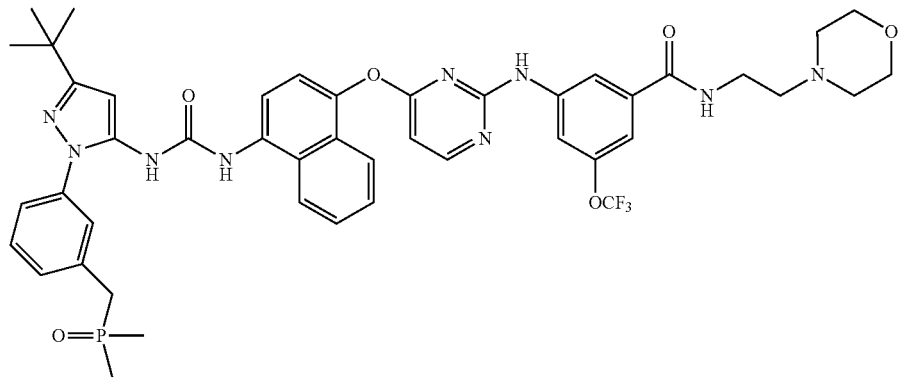 [SMILES: CC(C)(C)c1cc(NC(=O)Nc2ccc(Oc3ccnc(Nc4cc(OC(F)(F)F)cc(C(=O)NCCN5CCOCC5)c4)n3)c3ccccc23)n(-c2cccc(CP(C)(C)=O)c2)n1]

(i) 3-Amino-5-(trifluoromethoxy)benzoic acid

A mixture of 3-bromo-5-(trifluoromethoxy)benzoic acid (0.5 g, 1.754 mmol), sodium azide (0.303 g, 4.66 mmol), N1,N2-dimethylethane-1,2-diamine (0.062 g, 0.702 mmol), copper(I) iodide (0.067 g, 0.351 mmol) and $K_3PO_4$ (0.819 g, 3.86 mmol) in DMF (5 mL) was heated at 135° C. for 18 h. The mixture was cooled, EtOAc (20 mL) and Celite (2 g) was added then filtered. The filtrate was evaporated under reduced pressure to give a black oil. Repeat in duplicate. The crude product was loaded onto a column of SAX (Discovery® DSC-SAX, a polymer-bound quaternary amine) in MeOH. The column was washed with MeOH and then the product was eluted with 5% AcOH in MeOH. The resultant mixture was concentrated in vacuo then loaded onto a column of SCX in MeOH. The column was washed with MeOH and then the product was eluted with 0.7 M ammonia in MeOH. The resultant mixture was concentrated in vacuo to afford the sub-title compound (450 mg) as a yellow powder.

1H NMR (400 MHz; DMSO-d6) δ 7.15 (s, 1H), 6.87 (s, 1H), 6.57 (s, 1H), 5.63 (br s, 2H)

LCMS m/z 222 (M+H)+ (ES+); 220 (M−H)− (ES−)

(ii) 3-Amino-N-(2-morpholinoethyl)-5-(trifluoromethoxy)benzamide

T3P (50% Wt in EtOAc, 1.8 mL, 3.02 mmol) was added over 1 min to a solution of 3-amino-5-(trifluoromethoxy)benzoic acid (see step (i) above; 440 mg, 1.990 mmol), 2-morpholinoethanamine (520 μL, 3.96 mmol) and TEA (0.83 mL, 5.95 mmol) in DCM (10 mL). The mixture was stirred at rt for 1 h then partitioned with sat. aq $NaHCO_3$ solution (20 mL) and DCM (30 mL). The organic layer was separated, washed with brine (20 mL), dried ($MgSO_4$) and evaporated under reduced pressure. The crude product was purified by chromatography on silica gel (40 g column, 0-5% MeOH/DCM) to afford the sub-title compound (520 mg) as a white solid.

1H NMR (400 MHz; $CDCl_3$) δ 7.03 (s, 1H), 6.88 (s, 1H), 6.71 (s, 1H), 6.63 (s, 1H), 3.98 (s, 2H), 3.74-3.72 (m, 4H), 3.55-3.50 (m, 2H), 2.60 (t, 2H), 2.52-2.50 (m, 4H).

LCMS m/z 334 (M+H)+ (ES+)

(iii) 3-((4-((4-(3-(3-(tert-Butyl)-1-(3-((dimethylphosphoryl)methyl)phenyl)-1H-pyrazol-5-yl)-ureido)naphthalen-1-yl)oxy)pyrimidin-2-yl)amino)-N-(2-morpholinoethyl)-5-(trifluoromethoxy)benzamide A mixture of 1-(3-(tert-butyl)-1-(3-((dimethylphosphoryl)methyl)phenyl)-1H-pyrazol-5-yl)-3-(4-((2-chloropyrimidin-4-yl)oxy)naphthalen-1-yl)urea (see Example 32(i) above; 150 mg, 0.249 mmol), the product from step (ii) above (166 mg, 0.497 mmol) and p-TSA monohydrate (62 mg, 0.326 mmol) in DMF (3 mL) were heated at 60° C. for 18 h. A further portion of p-TSA monohydrate (62 mg, 0.326 mmol) was added and the mixture heated for a further 18 h. The mixture was cooled, aq. sat. $NaHCO_3$ (10 mL) added and the solid filtered, washed with water (10 mL) then water/MeOH (1:1, 20 mL). The crude product was purified by chromatography on silica gel (40 g column, 0-10% MeOH/DCM) to give a solid which was triturated with isohexane/ether/EtOAc to afford the title compound (52 mg) as a solid.

1H NMR (400 MHz; DMSO-d6) δ 9.96 (s, 1H), 9.44 (s, 1H), 8.98 (s, 1H), 8.47 (d, 1H), 8.41 (t, 1H), 8.22 (d, 1H), 8.02 (d, 1H), 7.97 (s, 1H), 7.81 (d, 1H), 7.76 (s, 1H), 7.66-7.47 (m, 5H), 7.42 (d, 1H), 7.32 (d, 1H), 7.22 (s, 1H), 6.65 (d, 1H), 6.50 (s, 1H), 3.56-3.54 (m, 4H), 3.38 (d, 2H), 2.45-2.39 (m, 6H), 1.46 (d, 6H), 1.31 (s, 9H). (2H under $H_2O$ peak).

LCMS m/z 900 (M+H)+ (ES+)

Example 60

1-(3-(tert-Butyl)-1-(3-((dimethylphosphoryl)methyl)phenyl)-1H-pyrazol-5-yl)-3-(4-((2-((3-methoxy-5-(2-(2-(2-methoxyethoxy)ethoxy)ethoxy)phenyl)amino)pyrimidin-4-yl)oxy)-naphthalen-1-yl)urea

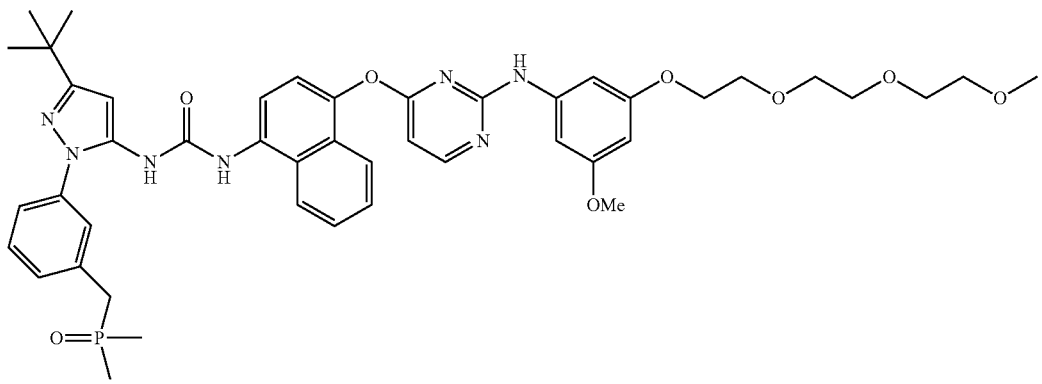 [SMILES: COCCOCCOCCOc1cc(Nc2nccc(Oc3ccc(NC(=O)Nc4cc(C(C)(C)C)nn4-c4cccc(CP(C)(C)=O)c4)c4ccccc34)n2)cc(OC)c1]

1-(3-(tert-Butyl)-1-(3-((dimethylphosphoryl)methyl)phenyl)-1H-pyrazol-5-yl)-3-(4-((2-chloropyrimidin-4-yl)oxy)naphthalen-1-yl)urea (see Example 32(i) above; 145 mg, 0.240 mmol) was dissolved in DMF (3 mL) and added to 3-methoxy-5-(2-(2-(2-methoxyethoxy)ethoxy)ethoxy)aniline (see Example 45(i) above; 135 mg, 0.473 mmol) and p-TSA monohydrate (23 mg, 0.121 mmol). Stirred at 70° C. (block temperature) for 7 h then poured into sat. NaHCO₃ solution (20 mL) and the product extracted with EtOAc (2×20 mL). Organics were bulked, washed with 20% w/w brine solution (20 mL), dried (MgSO₄), filtered and evaporated to a brown gum. The crude product was purified by chromatography on silica gel (40 g column, 2% MeOH:DCM to 8%) then crystallised from MeCN (2 mL) to afford the title compound (90 mg) as a colourless solid.

1H NMR (400 MHz, DMSO-d6) δ 9.46 (s, 1H), 9.43 (s, 1H), 8.97 (s, 1H), 8.41 (d, 1H), 8.21 (d, 1H), 8.01 (d, 1H), 7.83 (d, 1H), 7.68-7.50 (m, 4H), 7.50-7.44 (m, 1H), 7.40 (d, 1H), 7.36-7.27 (m, 1H), 6.91-6.71 (m, 2H), 6.54 (d, 1H), 6.51 (s, 1H), 6.03 (t, 1H), 3.94-3.78 (m, 2H), 3.72-3.60 (m, 2H), 3.59-3.44 (m, 9H), 3.44-3.37 (m, 3H), 3.36 (s, 1H), 3.21 (s, 3H), 1.46 (d, 6H), 1.31 (s, 9H).

LCMS m/z 852 (M+H)+ (ES+)

Example 61

1-(3-(tert-Butyl)-1-(3-((dimethylphosphoryl)methyl)phenyl)-1H-pyrazol-5-yl)-3-(4-((2-((3-(2-morpholinoethoxy)-5-(trifluoromethyl)phenyl)amino)pyrimidin-4-yl)oxy)naphthalen-1-yl)urea

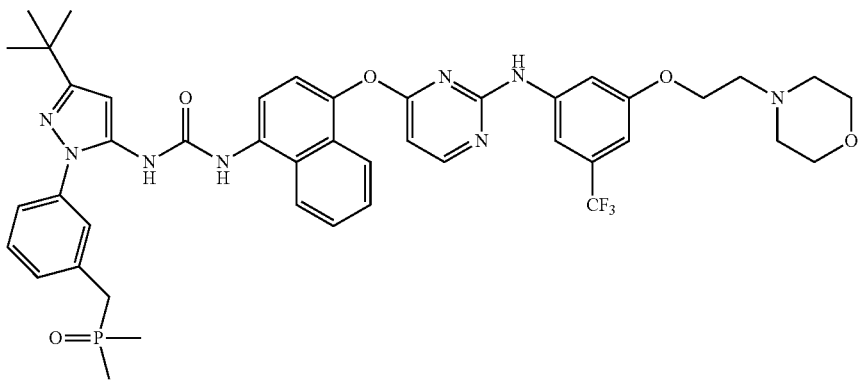 [SMILES: CC(C)(C)c1cc(NC(=O)Nc2ccc(Oc3ccnc(Nc4cc(OCCN5CCOCC5)cc(C(F)(F)F)c4)n3)c3ccccc23)n(-c2cccc(CP(C)(C)=O)c2)n1]

A solution of 3-(2-morpholinoethoxy)-5-(trifluoromethyl)aniline (see, for example, Adams, Ruth S. et al. WO 2006/076706, 20 Jul. 2006; 136 mg, 0.450 mmol) in DMF (1 mL) was added to a stirred suspension of 1-(3-(tert-butyl)-1-(3-((dimethylphosphoryl)methyl)-phenyl)-1H-pyrazol-5-yl)-3-(4-((2-chloropyrimidin-4-yl)oxy)naphthalen-1-yl)urea (see Example 32(i) above; 181 mg, 0.300 mmol) in THF/DMF (6 mL, 1:1), followed by p-TSA monohydrate (29 mg, 0.152 mmol). The resulting suspension was heated at 60° C. overnight. A further quantity of p-TSA monohydrate (52 mg, 0.302 mmol) was added and stirring continued at 60° C. for 72 h. The reaction was cooled to rt and partitioned between sat. aq. NaHCO₃ (30 mL) and EtOAc (40 mL). The aqueous phase was back extracted with EtOAc (2×40 mL). The combined organic extracts were washed with water (3×50 mL), brine (50 mL), dried (MgSO$_4$), filtered and concentrated in vacuo to afford an orange oil (360 mg). The crude product was purified by chromatography on silica gel (40 g column, 0-5% MeOH in DCM) then triturated with diethyl ether, filtered and washed with fresh diethyl ether to afford the title compound (43 mg) as an off-white solid.

1H NMR (DMSO-d6) 400 MHz, δ: 9.80 (s, 1H), 9.49 (s, 1H), 9.02 (s, 1H), 8.47 (d, 1H), 8.22 (d, 1H), 8.00 (d, 1H), 7.81 (d, 1H), 7.65-7.46 (m, 7H), 7.41 (d, 1H), 7.32-7.30 (br m, 1H), 6.74 (br s, 1H), 6.63 (d, 1H), 6.50 (s, 1H), 4.11-3.87 (br m, 2H), 3.63-3.41 (br m, 4H), 3.37 (d, 2H), 2.69-2.52 (br m, 2H), 2.47-2.32 (br m, 4H), 1.46 (d, 6H), 1.30 (s, 9H).

LCMS m/z 857 (M+H)+ (ES+); 855 (M−H)− (ES−)

Biological Testing: Experimental Methods

Enzyme Inhibition Assays

The enzyme inhibitory activities of compounds disclosed herein are determined by FRET using synthetic peptides labelled with both donor and acceptor fluorophores (Z-LYTE, Invitrogen Ltd., Paisley, UK).

p38 MAPKα Enzyme Inhibition

The following two assay variants can be used for determination of p38 MAPKα inhibition.

Method 1

The inhibitory activities of test compounds against the p38 MAPKα isoform (MAPK14: Invitrogen), are evaluated indirectly by determining the level of activation/phosphorylation of the down-stream molecule, MAPKAP-K2. The p38 MAPKα protein (80 ng/mL, 2.5 μL) is mixed with the test compound (2.5 μL of either 4 μg/mL, 0.4 μg/mL, 0.04 μg/mL or 0.004 μg/mL) for 2 hr at RT. The mix solution (2.5 μL) of the p38a inactive target MAPKAP-K2 (Invitrogen, 600 ng/mL) and FRET peptide (8 μM; a phosphorylation target for MAPKAP-K2) is then added and the kinase reaction is initiated by adding ATP (40 μM, 2.5 μL). The mixture is incubated for 1 hr at RT. Development reagent (protease, 5 μL) is added for 1 hr prior to detection in a fluorescence microplate reader (Varioskan® Flash, ThermoFisher Scientific).

Method 2 This method follows the same steps as Method 1 above, but utilises a higher concentration of the p38 MAPKα protein (2.5 μL of 200 ng/mL protein instead of 2.5 μL of 80 ng/mL protein) for mixing with the test compound.

p38 MAPKγ Enzyme Inhibition

The inhibitory activities of compounds of the invention against p38MAPKγ (MAPK12: Invitrogen), are evaluated in a similar fashion to that described hereinabove. The enzyme (800 ng/mL, 2.5 μL) is incubated with the test compound (2.5 μL at either 4 μg/mL, 0.4 μg/mL, 0.04 μg/mL, or 0.004 μg/mL) for 2 hr at RT. The FRET peptides (8 μM, 2.5 μL), and appropriate ATP solution (2.5 μL, 400 μM) is then added to the enzymes/compound mixtures and incubated for 1 hr. Development reagent (protease, 5 μL) is added for 1 hr prior to detection in a fluorescence microplate reader (Varioskan® Flash, Thermo Scientific).

c-Src and Syk Enzyme Inhibition

The inhibitory activities of compounds of the invention against c-Src and Syk enzymes (Invitrogen), are evaluated in a similar fashion to that described hereinabove. The relevant enzyme (3000 ng/mL or 2000 ng/mL respectively, 2.5 μL) is incubated with the test compound (either 4 μg/mL, 0.4 μg/mL, 0.04 μg/mL, or 0.004 μg/mL, 2.5 μL each) for 2 hr at RT. The FRET peptides (8 μM. 2.5 μL), and appropriate ATP solutions (2.5 μL, 800 μM for c-Src, and 60 μM ATP for Syk) are then added to the enzymes/compound mixtures and incubated for 1 hr. Development reagent (protease, 5 μL) is added for 1 hr prior to detection in a fluorescence microplate reader (Varioskan® Flash, ThermoFisher Scientific).

GSK 3α Enzyme Inhibition

The following two assay variants can be used for determination of GSK 3α inhibition.

Method 1

The inhibitory activities of compounds of the invention against the GSK 3α enzyme isoform (Invitrogen), are evaluated by determining the level of activation/phosphorylation of the target peptide. The GSK3-α protein (500 ng/mL, 2.5 μL) is mixed with the test compound (2.5 μL at either 4 μg/mL, 0.4 μg/mL, 0.04 μg/mL, or 0.004 μg/mL) for 2 hr at RT. The FRET peptide (8 μM, 2.5 μL), which is a phosphorylation target for GSK3α, and ATP (40 μM, 2.5 μL) are then added to the enzyme/compound mixture and the resulting mixture incubated for 1 hr. Development reagent (protease, 5 μL) is added for 1 hr prior to detection in a fluorescence microplate reader (Varioskan® Flash, ThermoFisher Scientific).

In all cases, the site-specific protease cleaves non-phosphorylated peptide only and eliminates the FRET signal. Phosphorylation levels of each reaction are calculated using the ratio of coumarin emission (donor) over fluorescein emission (acceptor), for which high ratios indicate high phosphorylation and low ratios indicate low phosphorylation levels. The percentage inhibition of each reaction is calculated relative to non-inhibited control and the 50% inhibitory concentration (IC$_{50}$ value) is then calculated from the concentration-response curve.

Method 2

This method follows the same steps as Method 1 above, but utilises a shorter period of mixing of the test compound (105 minutes instead of 2 hours) with the GSK3-α protein.

Cellular Assays

The compounds of the invention were studied using one or more of the following assays.

(a) LPS-Induced TNFα/IL-8 Release in d-U937 Cells

U937 cells, a human monocytic cell line, are differentiated to macrophage-type cells by incubation with phorbol myristate acetate (PMA; 100 ng/mL) for 48 to 72 hr. Cells are pre-incubated with final concentrations of test compound for 2 hr and are then stimulated with 0.1 μg/mL of LPS (from *E. Coli*: O111:B4, Sigma) for 4 hr. The supernatant is collected for determination of TNFα and IL-8 concentrations by sandwich ELISA (Duo-set, R&D systems). The inhibition of TNFα production is calculated as a percentage of that achieved by 10 μg/mL of BIRB796 at each concentration of test compound by comparison against vehicle control. The relative 50% effective concentration (REC$_{50}$) is determined from the resultant concentration-response curve. The inhibition of IL-8 production is calculated at each concentration of test compound by comparison with vehicle control. The 50% inhibitory concentration (IC$_{50}$) is determined from the resultant concentration-response curve.

(b) LPS-Induced TNFα/IL-8 Release in PBMC Cells

Peripheral blood mononuclear cells (PBMCs) from healthy subjects are separated from whole blood using a density gradient (Lymphoprep, Axis-Shield Healthcare). The PBMCs are seeded in 96 well plates and treated with compounds at the desired concentration for 2 hours before addition of 1 ng/mL LPS (*Escherichia Coli* 0111:B4 from Sigma Aldrich) for 24 hours under normal tissue culture conditions (37° C., 5% CO$_2$). The supernatant is harvested for determination of IL-8 and TNFα concentrations by sandwich ELISA (Duo-set, R&D systems) and read on the fluorescence microplate reader (Varioskan® Flash, Thermo- Fisher Scientific). The concentration at 50% inhibition ($IC_{50}$) of IL-8 and TNFα production is calculated from the dose response curve.

(c) IL-2 and IFN Gamma Release in CD3/CD28 Stimulated PBMC Cells

PBMCs from healthy subjects are separated from whole blood using a density gradient (Lymphoprep, Axis-Shield Healthcare). Cells are added to a 96 well plate pre-coated with a mixture of CD3/CD38 monoclonal antibodies (0.3 μg/mL eBioscience and 3 μg/mL BD Pharmingen respectively). Compound at the desired concentration is then added to the wells and the plate left for 3 days under normal tissue culture conditions. Supernatants are harvested and IL-2 and IFN gamma release determined by Sandwich ELISA (Duo-set, R&D System). The $IC_{50}$ is determined from the dose response curve.

(d) IL-1β-Induced IL-8 Release in HT29 Cells

HT29 cells, a human colon adenocarcinoma cell line, are plated in a 96 well plate (24 hrs) and pre-treated with compounds at the desired concentration for 2 hours before addition of 5 ng/mL of IL-1β (Abcam) for 24 hours. Supernatants are harvested for IL-8 quantification by Sandwich ELISA (Duo-set, R&D System). The $IC_{50}$ is determined from the dose response curve.

(e) LPS-Induced IL-8 and TNFα Release in Primary Macrophages

PBMCs from healthy subjects are separated from whole blood using a density gradient (Lymphoprep, Axis-Shield Healthcare). Cells are incubated for 2 hrs and non-adherent cells removed by washing. To differentiate the cells to macrophages the cells are incubated with 5 ng/mL of GM-CSF (Peprotech) for 7 days under normal tissue culture conditions. Compounds are then added to the cells at the desired concentration for a 2 hour pre-treatment before stimulation with 10 ng/mL LPS for 24 hours. Supernatants are harvested and IL-8 and TNFα release determined by Sandwich ELISA (Duo-set, R&D System). The $IC_{50}$ is determined from the dose response curve.

(f) Poly I:C-Induced ICAM-1 Expression in BEAS2B Cells

Poly I:C is used in these studies as a simple, RNA virus mimic. Poly I:C-Oligofectamine mixture (1 μg/mL Poly I:C, ±2% Oligofectamine, 25 μL; Invivogen Ltd., San Diego, Calif., and Invitrogen, Carlsbad, Calif., respectively) is transfected into BEAS2B cells (human bronchial epithelial cells, ATCC). Cells are pre-incubated with final concentrations of test compounds for 2 hr and the level of ICAM1 expression on the cell surface is determined by cell-based ELISA. At a time point 18 hr after poly I:C transfection, cells are fixed with 4% formaldehyde in PBS and then endogenous peroxidase is quenched by the addition of washing buffer (100 μL, 0.05% Tween in PBS: PBS-Tween) containing 0.1% sodium azide and 1% hydrogen peroxide. Cells are washed with wash-buffer (3×200 μL) and after blocking the wells with 5% milk in PBS-Tween (100 μL) for 1 hr, the cells are incubated with anti-human ICAM-1 antibody (50 μL; Cell Signalling Technology, Danvers, Mass.) in 1% BSA PBS overnight at 4° C.

The cells are washed with PBS-Tween (3×200 μL) and incubated with the secondary antibody (100 μL; HRP-conjugated anti-rabbit IgG, Dako Ltd., Glostrup, Denmark). The cells are then incubated with of substrate (50 μL) for 2-20 min, followed by the addition of stop solution (50 μL, 1N $H_2SO_4$). The ICAM-1 signal is detected by reading the absorbance at 450 nm against a reference wavelength of 655 nm using a spectrophotometer. The cells are then washed with PBS-Tween (3×200 μL) and total cell numbers in each well are determined by reading absorbance at 595 nm after Crystal Violet staining (50 μL of a 2% solution in PBS) and elution by 1% SDS solution (100 μL) in distilled water. The measured OD 450-655 readings are corrected for cell number by dividing with the OD595 reading in each well. The inhibition of ICAM-1 expression is calculated at each concentration of test compound by comparison with vehicle control. The 50% inhibitory concentration ($IC_{50}$) is determined from the resultant concentration-response curve.

(g) Cell Mitosis Assay

Peripheral blood mononucleocytes (PBMCs) from healthy subjects are separated from whole blood (Quintiles, London, UK) using a density gradient (Histopaque®-1077, Sigma-Aldrich, Poole, UK). The PBMCs (3 million cells per sample) are subsequently treated with 2% PHA (phytohaemagglutinin, Sigma-Aldrich, Poole, UK) for 48 hr, followed by a 20 hr exposure to varying concentrations of test compounds. At 2 hr before collection, PBMCs are treated with demecolcine (0.1 μg/mL; Invitrogen, Paisley, UK) to arrest cells in metaphase. To observe mitotic cells, PBMCs are permeabilised and fixed by adding Intraprep (50 μL; Beckman Coulter, France), and stained with anti-phospho-histone 3 (0.26 ng/L; #9701; Cell Signalling, Danvers, Mass.) and propidium iodide (1 mg/mL; Sigma-Aldrich, Poole, UK) as previously described (Muehlbauer P. A. and Schuler M. J., *Mutation Research*, 2003, 537:117-130). Fluorescence is observed using an ATTUNE flow cytometer (Invitrogen, Paisley, UK), gating for lymphocytes. The percentage inhibition of mitosis is calculated for each treatment relative to vehicle (0.5% DMSO) treatment.

(h) Rhinovirus-Induced IL-8 Release and ICAM-1 Expression

Human rhinovirus RV16 is obtained from the American Type Culture Collection (Manassas, Va.). Viral stocks are generated by infecting Hela cells with HRV until 80% of the cells are cytopathic.

BEAS2B cells are infected with HRV at an MOI of 5 and incubated for 2 hr at 33° C. with gentle shaking for to promote absorption. The cells are then washed with PBS, fresh media added and the cells are incubated for a further 72 hr. The supernatant is collected for assay of IL-8 concentrations using a Duoset ELISA development kit (R&D systems, Minneapolis, Minn.).

The level of ICAM1 expressing cell surface is determined by cell-based ELISA. At 72 hr after infection, cells are fixed with 4% formaldehyde in PBS. After quenching endogenous peroxidase by adding 0.1% sodium azide and 1% hydrogen peroxide, wells are washed with wash-buffer (0.05% Tween in PBS: PBS-Tween). After blocking well with 5% milk in PBS-Tween for 1 hr, the cells are incubated with anti-human ICAM-1 antibody in 5% BSA PBS-Tween (1:500) overnight. Wells are washed with PBS-Tween and incubated with the secondary antibody (HRP-conjugated anti-rabbit IgG, Dako Ltd.). The ICAM-1 signal is detected by adding substrate and reading at 450 nm with a reference wavelength of 655 nm using a spectrophotometer. The wells are then washed with PBS-Tween and total cell numbers in each well are determined by reading absorbance at 595 nm after Crystal Violet staining and elution by 1% SDS solution. The measured $OD_{450-655}$ readings are corrected for cell number by dividing with the $OD_{595}$ reading in each well. Compounds are added 2 hr before HRV infection and 2 hr after infection when non-infected HRV is washed out.

(i) Assessment of HRV16 Induced CPE in MRCS

MRC-5 cells are infected with HRV16 at an MOI of 1 in DMEM containing 5% FCS and 1.5 mM $MgCl_2$, followed by incubation for 1 hr at 33° C. to promote adsorption. The supernatants are aspirated, and then fresh media added followed by incubation for 4 days. Where appropriate, cells are pre-incubated with compound or DMSO for 2 hr, and the compounds and DMSO added again after washout of the virus.

Supernatants are aspirated and incubated with methylene blue solution (100 μL, 2% formaldehyde, 10% methanol and 0.175% Methylene Blue) for 2 hr at RT. After washing, 1% SDS in distilled water (100 μL) is added to each well, and the plates are shaken lightly for 1-2 hr prior to reading the absorbance at 660 nm. The percentage inhibition for each well is calculated. The $IC_{50}$ value is calculated from the concentration-response curve generated by the serial dilutions of the test compounds.

(j) In Vitro RSV Virus Load in Primary Bronchial Epithelial Cells

Normal human bronchial epithelial cells (NHBEC) grown in 96 well plates are infected with RSV A2 (Strain A2, HPA, Salisbury, UK) at an MOI of 0.001 in the LHC8 Media: RPMI-1640 (50:50) containing 15 mM magnesium chloride and incubated for 1 hr at 37° C. for adsorption. The cells are then washed with PBS (3×200 μL), fresh media (200 μL) is added and incubation continued for 4 days. Where appropriate, cells are pre-incubated with the compound or DMSO for 2 hr, and then added again after washout of the virus.

The cells are fixed with 4% formaldehyde in PBS solution (50 μL) for 20 min, washed with WB (3×200 μL), (washing buffer, PBS including 0.5% BSA and 0.05% Tween-20) and incubated with blocking solution (5% condensed milk in PBS) for 1 hr. Cells are then washed with WB (3×200 μL) and incubated for 1 hr at RT with anti-RSV (2F7) F-fusion protein antibody (40 μL; mouse monoclonal, lot 798760, Cat. No.ab43812, Abcam) in 5% BSA in PBS-tween. After washing, cells are incubated with an HRP-conjugated secondary antibody solution (50 μL) in 5% BSA in PBS-Tween (lot 00053170, Cat.No. P0447, Dako) and then TMB substrate added (50 μL; substrate reagent pack, lot 269472, Cat. No. DY999, R&D Systems, Inc.). This reaction is stopped by the addition of 2N $H_2SO_4$ (50 μL) and the resultant signal is determined colourimetrically (OD: 450 nm with a reference wavelength of 655 nm) in a microplate reader (Varioskan® Flash, ThermoFisher Scientific).

Cells are then washed and a 2.5% crystal violet solution (50 μL; lot 8656, Cat. No. PL7000, Pro-Lab Diagnostics) is applied for 30 min. After washing with WB, 1% SDS in distilled water (100 μL) is added to each well, and plates are shaken lightly on the shaker for 1 hr prior to reading the absorbance at 595 nm. The measured $OD_{450-655}$ readings are corrected to the cell number by dividing the $OD_{450-655}$ by the $OD_{595}$ readings. The percentage inhibition for each well is calculated and the $IC_{50}$ value is calculated from the concentration-response curve generated from the serial dilutions of compound.

(k) Cell Viability Assay: MTT Assay

Differentiated U937 cells are pre-incubated with each test compound (final concentration 1 μg/mL or 10 μg/mL in 200 μL media indicated below) under two protocols: the first for 4 hr in 5% FCS RPMI1640 media and the second in 10% FCS RPMI1640 media for 24 h. The supernatant is replaced with new media (200 μL) and MTT stock solution (10 μL, 5 mg/mL) is added to each well. After incubation for 1 hr the media are removed, DMSO (200 μL) is added to each well and the plates are shaken lightly for 1 hr prior to reading the absorbance at 550 nm. The percentage loss of cell viability is calculated for each well relative to vehicle (0.5% DMSO) treatment. Consequently an apparent increase in cell viability for drug treatment relative to vehicle is tabulated as a negative percentage.

(l) Human Biopsy Assay

Intestinal mucosa biopsies are obtained from the inflamed regions of the colon of IBD patients. The biopsy material is cut into small pieces (2-3 mm) and placed on steel grids in an organ culture chamber at 37° C. in a 5% $CO_2$/95% $O_2$ atmosphere in serum-free media. DMSO control or test compounds at the desired concentration are added to the tissue and incubated for 24 hr in the organ culture chamber. The supernatant is harvested for determination of IL-6, IL-8, IL-1β and TNFα levels by R&D ELISA. Percentage inhibition of cytokine release by the test compounds is calculated relative to the cytokine release determined for the DMSO control (100%).

(m) Accumulation of β Catenin in d-U937 Cells

U937 cells, a human monocytic cell line, are differentiated into macrophage-type cells by incubation with PMA; (100 ng/mL) for between 48 to 72 hr. The cells are then incubated with either final concentrations of test compound or vehicle for 18 hr. The induction of β-catenin by the test compounds is stopped by replacing the media with 4% formaldehyde solution. Endogenous peroxide activity is neutralised by incubating with quenching buffer (100 μL, 0.1% sodium azide, 1% $H_2O_2$ in PBS with 0.05% Tween-20) for 20 min. The cells are washed with washing buffer (200 μL; PBS containing 0.05% Tween-20) and incubated with blocking solution (200 μL; 5% milk in PBS) for 1 hr, re-washed with washing buffer (200 μL) and then incubated overnight with anti-β-catenin antibody solution (50 μL) in 1% BSA/PBS (BD, Oxford, UK).

After washing with washing buffer (3×200 μL; PBS containing 0.05% Tween-20), cells are incubated with an HRP-conjugated secondary antibody solution (100 μL) in 1% BSA/PBS (Dako, Cambridge, UK) and the resultant signal is determined colourimetrically (OD: 450 nm with a reference wavelength of 655 nm) using TMB substrate (50 μL; R&D Systems, Abingdon, UK). This reaction is stopped by addition of 1N $H_2SO_4$ solution (50 μL). Cells are then washed with washing buffer and 2% crystal violet solution (50 μL) is applied for 30 min. After washing with washing buffer (3×200 μL), 1% SDS (100 μL) is added to each well and the plates are shaken lightly for 1 hr prior to measuring the absorbance at 595 nm (Varioskan® Flash, Thermo-Fisher Scientific).

The measured $OD_{450-655}$ readings are corrected for cell number by dividing the $OD_{450-655}$ by the $OD_{595}$ readings. The percentage induction for each well is calculated relative to vehicle, and the ratio of induction normalised in comparison with the induction produced by a standard control comprising of N-(4-(4-(3-(3-tert-butyl-1-p-tolyl-1H-pyrazol-5-yl)ureido)naphthalen-1-yloxy)pyridin-2-yl)-2-methoxyacetamide (1 μg/mL) which is defined as unity. A signal less than 0.15 of that observed for the standard control is designated as "-ve".

(n) T Cell Proliferation

PBMCs from healthy subjects are separated from whole blood using a density gradient (Lymphoprep, Axis-Shield Healthcare). The lymphocyte fraction is first enriched for CD4+ T cells by negative magnetic cell sorting as per the manufacturer's instructions (Miltenyi Biotec 130-091-155). Nave CD4+ T cells are then separated using positive magnetic selection of CD45RA+ cells using microbeads as per the manufacturer's instructions (130-045-901). Cells are plated at $2\times10^5$ cells per well in 100 μL RPMI/10% FBS on 96 well flat bottomed plate (Corning Costar). 25 μL of test compound are diluted to the appropriate concentration (8× final conc.) in normal medium and added to duplicate wells on the plate to achieve a dose response range of 0.03 ng/mL-250 ng/mL. DMSO is added as a negative control. Plates are allowed to pre-incubate for 2 hours before stimulation with 1 µg/mL anti-CD3 (OKT3; eBioscience). After 72 h, the medium in each well is replaced with 150 µL of fresh medium containing 10 µM BrdU (Roche). After 16 h, the supernatant is removed, the plate is dried and the cells fixed by adding 100 µL of fix/denature solution to each well for 20 min as per the manufacturer's instructions (Roche). Plates are washed once with PBS before addition of the anti-BrdU detection antibody and incubated for 90 mins at room temperature. Plates are then washed gently 3× with the wash buffer supplied and developed by addition of 100 µL of substrate solution. The reaction is stopped by addition of 50 µL of 1 M $H_2SO_4$, and read for absorbance at 450 nm on a plate reader (Varioskan® Flash, ThermoFisher Scientific). The $IC_{50}$ is determined from the dose response curve.

(o) IL-2 and IFNγ Release in CD3/CD28 Stimulated LPMC Cells from IBD Patients

Lamina propria mononuclear cells (LPMCs) are isolated and purified from inflamed IBD mucosa of surgical specimens or from normal mucosa of surgical specimens as follows: The mucosa is removed from the deeper layers of the surgical specimens with a scalpel and cut in fragments 3-4 mm size. The epithelium is removed by washing the tissue fragments three times with 1 mM EDTA (Sigma-Aldrich, Poole, UK) in HBSS (Sigma-Aldrich) with agitation using a magnetic stirrer, discarding the supernatant after each wash. The sample is subsequently treated with type 1A collagenase (1 mg/mL; Sigma-Aldrich) for 1 h with stirring at 37° C. The resulting cell suspension is then filtered using a 100 µm cell strainer, washed twice, resuspended in RPMI-1640 medium (Sigma-Aldrich) containing 10% fetal calf serum, 100 U/mL penicillin and 100 µg/mL streptomycin, and used for cell culture.

Freshly isolated LPMCs ($2\times10^5$ cells/well) are stimulated with 1 µg/mL α-CD3/α-CD28 for 48 h in the presence of either DMSO control or appropriate concentrations of compound. After 48 h, the supernatant is removed and assayed for the presence of TNFα and IFNγ by R&D ELISA. Percentage inhibition of cytokine release by the test compounds is calculated relative to the cytokine release determined for the DMSO control (100%).

(p) Inhibition of Cytokine Release from Myofibroblasts Isolated from IBD Patients Myofibroblasts from inflamed IBD mucosa are isolated as follows:

The mucosa is dissected and discarded and 1 mm-sized mucosal samples are cultured at 37° C. in a humidified $CO_2$ incubator in Dulbecco's modified Eagle's medium (DMEM, Sigma-Aldrich) supplemented with 20% FBS, 1% non-essential amino acids (Invitrogen, Paisley, UK), 100 U/mL penicillin, 100 µg/mL streptomycin, 50 µg/mL gentamycin, and 1 µg/mL amphotericin (Sigma-Aldrich). Established colonies of myofibroblasts are seeded into 25-cm² culture flasks and cultured in DMEM supplemented with 20% FBS and antibiotics to at least passage 4 to provide a sufficient quantity for use in stimulation experiments.

Subconfluent monolayers of myofibroblasts are then seeded in 12-well plates at $3\times10^5$ cells per well are starved in serum-free medium for 24 h at 37° C., 5% $CO_2$ before being cultured for 24 h in the presence of either DMSO control or appropriate concentrations of compound. After 24 h the supernatant is removed and assayed for the presence of IL-8 and IL-6 by R&D ELISA. Percentage inhibition of cytokine release by the test compounds is calculated relative to the cytokine release determined for the DMSO control (100%).

(q) Human Neutrophil Degranulation

Neutrophils are isolated from human peripheral blood as follows:

Blood is collected by venepuncture and anti-coagulated by addition of 1:1 EDTA: sterile phosphate buffered saline (PBS, no Ca+/Mg+). Dextran (3% w/v) is added (1 part dextran solution to 4 parts blood) and the blood allowed to stand for approximately 20 minutes at rt. The supernatant is carefully layered on a density gradient (Lymphoprep, Axis-Shield Healthcare) and centrifuged (15 mins, 2000 rpm, no brake). The supernatant is aspirated off and the cell pellet is re-suspended in sterile saline (0.2%) for no longer than 60 seconds (to lyse contaminating red blood cells). 10 times volume of PBS is then added and the cells centrifuged (5 mins, 1200 rpm). Cells are re-suspended in HBSS+ (Hanks buffered salt solution (without phenol red) containing cytochalasin B (5 µg/mL) and 1 mM $CaCl_2$) to achieve $5\times10^6$ cells/mL.

$5\times10^4$ cells are added to each well of a V-bottom 96 well plate and incubated (30 mins, 37° C.) with the appropriate concentration of test compound (0.3-1000 ng/mL) or vehicle (DMSO, 0.5% final conc). Degranulation is stimulated by addition of fMLP (final conc 1 µM) which after a further incubation (30 mins, 37° C.) the cells are removed by centrifugation (5 mins, 1500 rpm) and the supernatants transferred to a flat bottom 96 well plate. An equal volume of tetramethylbenzidine (TMB) is added and after 10 mins the reaction terminated by addition of an equal volume of sulphuric acid (0.5 M) and absorbance read at 450 nm (background at 655 nm subtracted). The 50% inhibitory concentration ($IC_{50}$) is determined from the resultant concentration-response curve.

(r) Cell Cytotoxicity Assay $5\times10^4$ TK6 cells (lymphoblastic T cell line) are added to the appropriate number of wells of a 96 well plate in 195 µL of media (RPMI supplemented with 10% foetal bovine serum). 5 µL of DMSO control (final concentration 0.5% v/v) or test compound (final concentration either 5 or 1 µg/mL) is added to the wells and incubated at 37° C., 5% $CO_2$. After 24 hours, the plate is centrifuged at 1300 rpm for 3 minutes and the supernatant discarded. Cells are then resuspended in 7.5 µg/mL propidium iodide (PI) in PBS. After 15 minutes, cells are analysed by flow cytometry (BD accuri). The % viability is calculated as the % of cells that are PI negative in the test wells normalised to the DMSO control.

In Vivo Screening: Pharmacodynamics and Anti-Inflammatory Activity (i) LPS-Induced Neutrophil Accumulation in Mice Non-fasted Balb/c mice are dosed by the intra tracheal route with either vehicle, or the test substance at the indicated times (within the range 2-8 hr) before stimulation of the inflammatory response by application of an LPS challenge. At T=0, mice are placed into an exposure chamber and exposed to LPS (7.0 mL, 0.5 mg/mL solution in PBS) for 30 min. After a further 8 hr the animals are anesthetized, their tracheas cannulated and BALF extracted by infusing and then withdrawing from their lungs 1.0 mL of PBS via the tracheal catheter. Total and differential white cell counts in the BALF samples are measured using a Neubaur haemocytometer. Cytospin smears of the BALF samples are prepared by centrifugation at 200 rpm for 5 min at RT and stained using a DiffQuik stain system (Dade Behring). Cells are counted using oil immersion microscopy. Data for neutrophil numbers in BAL are shown as mean±S.E.M. (standard error of the mean). The percentage inhibition of neutrophil accumulation is calculated for each treatment relative to vehicle treatment.

(ii) Cigarette Smoke Model

A/J mice (males, 5 weeks old) are exposed to cigarette smoke (4% cigarette smoke, diluted with air) for 30 min/day for 11 days using a Tobacco Smoke Inhalation Experiment System for small animals (Model SIS-CS; Sibata Scientific Technology, Tokyo, Japan). Test substances are administered intra-nasally (35 µL of solution in 50% DMSO/PBS) once daily for 3 days after the final cigarette smoke exposure. At 12 hr after the last dosing, each of the animals is anesthetized, the trachea cannulated and bronchoalveolar lavage fluid (BALF) is collected. The numbers of alveolar macrophages and neutrophils are determined by FACS analysis (EPICS® ALTRA II, Beckman Coulter, Inc., Fullerton, Calif., USA) using anti-mouse MOMA2 antibody (macrophage) or anti-mouse 7/4 antibody (neutrophil).

(iii) DSS-Induced Colitis in Mice

Non-fasted, 10-12 week old, male BDF1 mice are dosed by oral gavage twice daily with either vehicle, reference item (5-ASA) or test compound one day before (Day −1) stimulation of the inflammatory response by treatment with dextran sodium sulphate (DSS). On Day 0 of the study DSS (5% w/v) is administered in the drinking water followed by BID dosing of the vehicle (5 mL/kg), reference (100 mg/kg) or test compound (5 mg/kg) for 7 days. The drinking water with DSS is replenished every 3 days. During the study animals are weighed every day and stool observations are made and recorded as a score, based on stool consistency. At the time of sacrifice on Day +6 the large intestine is removed and the length and weight are recorded. Sections of the colon are taken for either MPO analysis to determine neutrophil infiltration or for histopathology scoring to determine disease severity.

(iv) TNBS-Induced Colitis in Mice

Non-fasted, 10-12 week old, male BDF1 mice are dosed by oral gavage twice daily with either vehicle (5 mL/kg), reference item (Budesonide 2.5 mg/kg) or test compound (1 or 5 mg/kg) one day before (Day −1) stimulation of the inflammatory response by treatment with 2,4,6-trinitrobenzenesuiphonic acid (TNBS) (15 mg/mL in 50% ethanol/50% saline). On Day 0 of the study TNBS (200 µL) is administered intra-colonically via a plastic catheter followed by BID dosing of the vehicle, reference or test compound for 2 or 4 days. During the study animals are weighed every day and stool observations are made and recorded as a score, based on stool consistency. At the time of sacrifice on Day 2 (or Day 4) the large intestine is removed and the length and weight recorded. Sections of the colon are taken for either MPO analysis to determine neutrophil infiltration or for histopathology involving scoring to determine disease severity.

(v) Adoptive Transfer in Mice

On Study day 0, female Balb/C mice are terminated and spleens obtained for CD45RB$^{high}$ cell isolation (Using SCID IBD cell Separation protocol). Approximately 4×10$^5$ cells/mL CD45RB$^{high}$ cells are then injected IP (100 µL/mouse) into female SCID animals. On study day 14, mice are weighed and randomized into treatment groups based on body weight. On Day 21 compounds are administered BID, via oral gavage, in a peanut oil vehicle at the dose levels outlined below and a dose volume of 5 mL/kg. Treatment continues until study day 42, at which point the animals are necropsied 4 hours after administration. The colon length and weight is recorded and used as a secondary endpoint in the study as a measurement of colon oedema. The colon is then divided into six cross-sections, four of which are used for histopathology scoring (primary endpoint) and two are homogenised for cytokine analysis. Data shown is the % inhibition of the induction window between nave animals and vehicle animals, where higher inhibition implies closer to the non-diseased, nave, phenotype.

Summary of In Vitro and In Vivo Screening Results

TABLE 1

Results from in vitro p38 MAPKα (Method 2), c-Src, Syk and GSKSα (Method 2) inhibition assays

| Test Compound Example No. | IC50 Values for Enzyme Inhibition (nM) | | | |
|---|---|---|---|---|
| | p38 MAPKα | c-Src | Syk | GSK3α |
| 1 | 8 | 15 | 34 | 1,282 |
| 2 | — | — | — | 647 |
| 3 | — | — | — | 16 |
| 4 | — | 12 | — | 220 |
| 5 | — | — | — | 429 |
| 6 | — | — | — | 183 |
| 7 | — | — | — | 486 |
| 8 | — | — | — | 849 |
| 9 | — | — | — | 1,445 |
| 10 | — | — | — | 684 |
| 11 | — | — | — | 205 |
| 12 | — | — | — | 73 |
| 13 | — | — | — | 208 |
| 14 | — | — | — | 294 |
| 15 | 56 | >1,000 | >1,000 | >10,000 |
| 16 | — | — | — | 72 |
| 17 | — | — | — | 74 |
| 18 | — | — | — | 168 |
| 19 | — | — | — | 76 |
| 20 | — | — | — | 68 |
| 21 | 44 | 1 | 2 | 761 |
| 22 | 67 | 9 | 200 | 818 |
| 23 | 265 | 40 | 97 | 1,644 |
| 24 | — | — | — | 293 |
| 25 | — | — | — | 163 |
| 26 | — | — | — | 8,131 |
| 27 | — | — | — | 979 |
| 28 | >1,000 | 372 | 884 | >10,000 |
| 29 | 149 | >1,000 | >1,000 | >10,000 |
| 30 | 27 | 795 | >1,000 | >10,000 |
| 31 | — | — | — | 211 |
| 32 | 60 | 5 | 5 | 1,315 |
| 33 | — | — | — | 326 |
| 34 | — | — | — | 324 |
| 35 | — | — | — | 1,273 |
| 36 | 159 | 8 | 9 | 3,414 |
| 37 | 70 | 10 | 5 | 4,859 |
| 38 | 10 | 2 | 3 | 1,249 |
| 39 | 13 | 3 | 1 | 2,233 |
| 40 | — | — | — | 8,916 |
| 41 | 357 | 56 | 96 | 4,303 |
| 42 | — | 47 | 63 | 6,982 |
| 43 | — | — | — | 174 |
| 44 | 201 | — | — | 8,039 |
| 45 | 21 | — | — | 1,126 |
| 46 | — | — | — | 1,595 |
| 47 | — | — | — | 406 |
| 48 | 231 | 87 | 232 | >10,000 |
| 49 | 202 | 95 | 219 | >10,000 |
| 50 | 24 | — | — | 2,091 |
| 51 | 58 | 8 | — | 2,806 |
| 52 | 18 | 3 | 4 | 1,192 |
| 53 | — | — | — | 188 |
| 54 | — | — | — | >10,000 |
| 55 | — | — | — | 1,668 |
| 56 | — | — | — | 788 |
| 57 | 21 | 9 | 7 | 1246 |
| 58 | 84 | 7 | 12 | 689 |
| 59 | 81 | 7 | 18 | 1239 |
| 60 | 71 | 2 | 8 | 1096 |
| 61 | 303 | 14 | 24 | 4187 |

TABLE 2

Test Compound IC$_{50}$ Values for Inhibition of Cytokine Release (nM)

| Example No. | dU937 cells | | PBMCs | | | | HT29 cells |
|---|---|---|---|---|---|---|---|
| | IL-8 | TNFα | IL-8 | TNFα | IL-2 | IFNγ | IL-8 |
| 1 | 4.9 | 2.0 | 6.9 | 1.3 | — | — | — |
| 2 | 9.4 | 3.6 | — | 4.3 | — | — | — |
| 3 | 8.6 | 3.6 | — | 2.5 | — | — | — |
| 4 | — | 19.2 | 58.9 | 20.8 | — | — | — |
| 5 | — | — | 16.3 | 4.3 | — | — | — |
| 6 | — | — | 6.4 | 2.5 | — | — | — |
| 7 | — | — | 6.7 | 2.5 | — | — | — |
| 8 | — | — | 17.2 | 4.8 | — | — | — |
| 9 | — | — | 24.0 | 6.2 | — | — | — |
| 10 | — | — | 13.7 | 4.0 | — | — | — |
| 11 | — | — | 16.2 | 2.7 | — | — | — |
| 12 | — | — | 8.5 | 1.8 | — | — | — |
| 13 | — | — | 3.4 | 1.7 | — | — | — |
| 14 | — | — | 13.2 | 4.0 | — | — | — |
| 15 | 397.5 | 182.3 | 680 | 200.3 | — | — | 632.0 |
| 16 | — | — | 8.3 | 4.3 | — | — | — |
| 17 | — | — | 5.4 | 1.8 | — | — | — |
| 18 | — | — | 7.2 | 2.9 | — | — | — |
| 19 | — | — | 407.4 | — | — | — | — |
| 20 | — | — | 9.0 | — | — | — | — |
| 21 | — | — | 3.4 | — | — | — | — |
| 22 | — | — | 32.8 | — | — | — | — |
| 23 | 2.2 | 1.4 | 7.5 | — | 42.7 | — | 13.5 |
| 24 | — | — | 26.3 | — | — | — | — |
| 25 | — | — | 14.4 | — | — | — | — |
| 26 | — | — | 188.7 | — | — | — | — |
| 27 | — | — | 209.3 | — | — | — | — |
| 28 | — | — | 214.0 | — | — | — | — |
| 29 | — | — | 149.8 | — | — | — | — |
| 30 | — | — | 280.5 | — | — | — | — |
| 31 | — | — | 90.2 | — | — | — | — |
| 32 | — | — | 1.3 | — | 4.2 | 2.3 | 1.9 |
| 33 | — | — | 2.4 | — | — | — | — |
| 34 | — | — | 1.1 | — | — | — | — |
| 35 | — | — | 7.6 | — | 76.8 | — | — |
| 36 | — | — | 3.5 | — | — | — | — |
| 37 | — | — | 3.0 | — | — | — | — |
| 38 | 2.9 | 1.6 | 3.8 | — | 9.2 | — | 27.0 |
| 39 | — | 0.5 | 1.2 | — | — | — | 4.6 |
| 40 | — | — | 103.9 | — | — | — | — |
| 41 | — | — | 2.8 | — | 56.4 | — | 4.7 |
| 42 | — | — | 5.5 | — | — | — | 5.6 |
| 43 | — | — | 1.6 | — | — | — | — |
| 44 | — | — | 4.0 | — | — | — | 7.1 |
| 45 | — | 3.9 | 3.3 | — | 19.3 | — | 6.5 |
| 46 | — | — | 5.9 | — | — | — | — |
| 47 | — | — | 0.8 | — | — | — | — |
| 48 | — | — | 1.5 | — | 53.4 | — | 4.3 |
| 49 | — | — | 1.4 | — | 45.6 | 5.1 | 3.8 |
| 50 | — | — | 1.0 | — | 16.1 | — | — |
| 51 | — | — | 0.5 | — | 6.1 | — | — |
| 52 | — | — | 3.3 | — | 11.6 | — | — |
| 53 | — | — | 2.0 | — | — | — | — |
| 54 | — | — | 27.4 | — | — | — | — |
| 55 | — | — | 5.4 | — | — | — | — |
| 56 | — | — | 1.7 | — | — | — | — |
| 57 | — | — | 2.7 | — | 10.5 | — | — |
| 58 | — | — | 1.4 | — | 62.1 | 4.8 | — |
| 59 | 0.9 | — | 0.8 | — | 75.1 | 2.5 | 1.9 |
| 60 | 0.4 | 0.2 | 0.9 | 0.6 | 16.0 | 1.9 | 0.8 |
| 61 | — | — | 2.3 | — | 50.7 | 3.3 | 2.6 |

Results from cellular assays in d-U937 cells, PBMCs and HT29 cells (the protocols for which are described by assays (a) to (d) above).

As illustrated in Table 3 below, the compounds of Examples 32 and 60 were also screened in in vivo assay (iv) above, as conducted over 2 days. Histopathology analysis revealed that the compounds of Examples 32 and 60 displayed significant activity in this in vivo model of colonic inflammation. In particular, these compounds, when dosed orally at 5 mg/kg, demonstrated marked improvements in ulcer grade and epithelial repair compared to the vehicle control. In addition, the compounds of Examples 32 and 60 produced a marked reduction in inflammatory cell infiltrate in the reticular and laminar propria zone.

TABLE 3

Summary of results from studies on TNBS-induced colitis in mice.

| Experiment no. | Treatment group | n | TNBS | |
|---|---|---|---|---|
| | | | Ulcer grade | LP inflammation |
| 1 | Non-diseased | 6 | 0.0 ± 0.0 | 0.3 ± 0.2 |
| 1 | TNBS + Vehicle | 24 | 3.6 ± 0.3 | 3.9 ± 0.3 |
| 1 | TNBS + Example 32 (5 mg/kg) | 12 | 3.3 ± 0.4 | 2.7 ± 0.4 |
| 2 | Non-diseased | 6 | 0.0 ± 0.0 | 0.2 ± 0.2 |
| 2 | TNBS + Vehicle | 24 | 4.4 ± 0.2 | 4.5 ± 0.2 |
| 2 | TNBS + Example 60 (5 mg/kg) | 12 | 3.6 ± 0.4 | 2.8 ± 0.4 |

As illustrated in Table 4 below, the compound of Example 60 was also screened in cellular assay (I), i.e., the ex-vivo human biopsy model described above, where it demonstrated significant anti-inflammatory effects in biopsies from ulcerative colitis (UC) patients. In contrast to healthy volunteers, intestinal mucosal biopsies from UC patients have been shown to spontaneously release pro-inflammatory cytokines in vitro (Onken, J. E. et al., *J Clin Immunol,* 2008, 126(3): 345-352). Thus, the compound of Example 60 significantly inhibited cytokine (IL-1b, IL-6 and IL-8) release compared to the DMSO control when incubated, at 1 μg/mL, for 24 hours with biopsies from ulcerative colitis patients.

TABLE 4

Summary of results from assays using intestinal mucosa biopsies from the inflamed regions of the colon of various patients suffering from ulcerative colitis (a form of IBD).

| Treatment group | Cytokine release from biopsies of UC patients | | | | | |
|---|---|---|---|---|---|---|
| | n | IL-1b release | n | IL-6 release | n | IL-8 release |
| DMSO control | | 100% | | 100% | | 100% |
| Example 60 (1 μg/ml) | 2 | 1 ± 2 | 4 | 0 ± 0 | 4 | 2 ± 4 |

ABBREVIATIONS

AcOH glacial acetic acid
aq aqueous
ATP adenosine-5'-triphosphate
BALF bronchoalveolar lavage fluid
br broad
BSA bovine serum albumin
CatCart® catalytic cartridge
CDI 1,1-carbonyl-diimidazole
Conc concentrated
COPD chronic obstructive pulmonary disease
CV column volumes
d doublet
DCM dichloromethane
DMA dimethylacetamide
DMF dimethylformamide
DMSO dimethyl sulfoxide
d-U937 cells PMA differentiated U-937 cells
DPPA diphenylphosphoryl azide
(ES$^+$) electrospray ionization, positive mode
Et ethyl Et₃N triethylamine
ether diethyl ether
EtOAc ethyl acetate
EtOH ethanol
Et₂O diethyl ether
FCS foetal calf serum
FRET fluorescence resonance energy transfer
GSK3α glycogen synthase kinase 3α
HATU 0-(7-azabenzotriazol-1-yl)-N,N,N',N'-tetramethyl-uronium hexafluorophosphate
HBEC primary human bronchial epithelial cells
HPLC high performance liquid chromatography
hr or H hour(s)
HRP horseradish peroxidise
HRV human rhinovirus
ICAM-1 inter-cellular adhesion molecule 1
IPA Iso-propyl alcohol
JNK c-Jun N-terminal kinase
LC liquid chromatography
LPS lipopolysaccharide
m multiplet
(M+H)⁺ protonated molecular ion
MAPK mitogen-activated protein kinases
MAPKAP-K2 mitogen-activated protein kinase-activated protein kinase-2
Me methyl
MeCN acetonitrile
MeOH methanol
MHz megahertz
min minute(s)
MMAD mass median aerodynamic diameter
MOI multiplicity of infection
MTT 3-(4,5-dimethylthiazol-2-yl)-2,5-diphenyltetrazolium bromide
MS mass spectrometry
m/z: mass-to-charge ratio
NBS N-bromosuccinimide
NMP N-methylpyrrolidone
NMR nuclear magnetic resonance (spectroscopy)
PBMC peripheral blood mononuclear cell
PBS phosphate buffered saline
Ph phenyl
PHA phytohaemagglutinin
PMA phorbol myristate acetate
p-TsOH or p-TSA 4-methylbenzenesulfonic acid (para-toluenesulfonic acid)
q quartet
rt room temperature
RP HPLC reverse phase high performance liquid chromatography
RSV respiratory syncytial virus
s singlet
sat saturated
SCX solid supported cation exchange (resin)
SDS sodium dodecyl sulphate
S_NAr nucleophilic aromatic substitution
t triplet
T3P 1-propanephosphonic acid cyclic anhydride
TBAF tetra-n-butylammonium fluoride
TBDMS tert-butyldimethylsilyl
TCID₅₀ 50% tissue culture infectious dose
TEA triethylamine
TFA trifluoroacetic acid
THF tetrahydrofuran
TNFα tumor necrosis factor alpha Prefixes n-, s-, i-, t- and tert-have their usual meanings: normal, secondary, iso, and tertiary.

What is claimed is:
1. A compound of formula I,

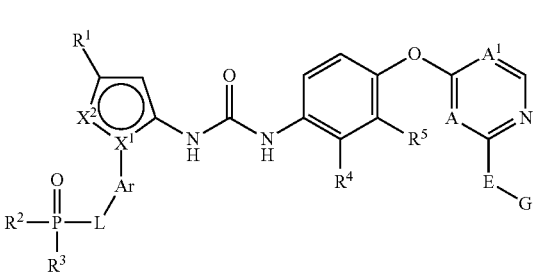

wherein
R¹ represents $C_{2-6}$ alkyl, Si(R$^{1a}$)(R$^{1b}$)(R$^{1c}$), $C_{3-7}$ cycloalkyl, phenyl or a 5- or 6-membered heteroaryl group containing one or more heteroatoms selected from the group consisting of N, O and S, which alkyl, cycloalkyl, phenyl and heteroaryl groups are optionally substituted by one or more substituents selected from the group consisting of halo, $C_{1-4}$ alkyl, $C_{2-3}$ alkynyl, $C_{3-4}$ cycloalkyl, $C_{1-4}$ haloalkyl, $C_{1-4}$ alkoxy, hydroxy, amino and cyano;
R$^{1a}$ and R$^{1b}$ independently represent $C_{1-4}$ alkyl or $C_{3-6}$ cycloalkyl, or R$^{1a}$ and R$^{1b}$ together combine to form $C_{2-6}$ alkylene;
R$^{1c}$ represents $C_{1-2}$ alkyl;
X¹ and X² are both N, or X$^i$ is C and X² is either O or S;
Ar is phenyl or a 5- or 6-membered heteroaryl group containing one or more heteroatoms selected from the group consisting of N, O and S, which phenyl and heteroaryl groups are optionally substituted by one or more substituents selected from the group consisting of halo, $C_{1-4}$ alkyl, $C_{1-4}$ haloalkyl, $C_{1-4}$ alkoxy, hydroxy, amino and cyano;
L is a direct bond or $C_{1-2}$ alkylene;
R² represents $C_{1-4}$ alkyl;
R³ represents $C_{1-4}$ alkyl, $C_{3-6}$ cycloalkyl, $C_{1-4}$ alkoxy or hydroxy;
or R² and R³ together combine to form $C_{3-6}$ alkylene;
R⁴ and R⁵ are each independently $C_{1-3}$ alkyl, $C_{1-3}$ haloalkyl, cyano or halo,
or R⁴ and R⁵ together combine to form $C_{3-5}$ alkylene or $C_{3-5}$ alkenylene, which latter two groups are optionally substituted by one or more substituents selected from the group consisting of $C_{1-3}$ alkyl, $C_{1-3}$ haloalkyl, cyano and halo,
or R⁴ and R⁵, together with the C-atoms to which they are attached, form a fused phenyl or Het¹ ring, which latter two rings are optionally substituted by one or more substituents selected from the group consisting of $C_{1-3}$ alkyl, $C_{1-3}$ haloalkyl, cyano and halo;
Het¹ represents a 5- to 7-membered heterocyclic group that is fully saturated, partially unsaturated or fully aromatic, which heterocyclic group contains one or more heteroatoms selected from the group consisting of N, O and S;
one of A and A¹ represents N and the other represents CH,
or both A and A¹ represent CH;

E represents N(G$^1$), O or S;

G represents
phenyl optionally substituted by one or more Y$^1$,
Het$^2$ optionally substituted by one or more Y$^2$,
R$^{6a}$ or
C(O)R$^{6b}$;

G$^1$ represents H or C$_{1-3}$ alkyl;

or G and G$^1$ together combine to form C$_{3-6}$ alkylene optionally substituted by one or more substituents selected from the group consisting of halo, hydroxy and C$_{1-3}$ alkyl, which latter group is optionally substituted by one or more halo atoms or by hydroxy;

each Y$^1$ is independently selected from the group consisting of
halo, hydroxy, cyano, SF$_5$, —OC(O)NH$_2$,
P(O)R$^{6c}$R$^{6d}$,
E$^1$-N(R$^{6e}$)R$^{6f}$,
E$^2$-S(O)$_2$R$^{6g}$,
E$^3$-[CH$_2$(CH$_2$)$_{0-1}$CH$_2$—O]$_{2-8}$—R$^{6h}$,
—C≡C—R$^{6i}$,
—N=S(O)R$^{6j}$R$^{6k}$,
Het$^a$, and
C$_{1-6}$ alkyl, C$_{3-6}$ cycloalkyl, C$_{1-6}$ alkoxy, C$_{3-6}$ cycloalkoxy, —S(O)$_{0-1}$—C$_{1-6}$ alkyl and —S(O)$_{0-1}$—C$_{3-6}$ cycloalkyl which latter six groups are optionally substituted by one or more substituents selected from the group consisting of halo, hydroxy, C$_{1-3}$ alkyl, C$_{1-3}$ alkoxy and C$_{3-6}$ cycloalkyl;

each Y$^2$ independently represents oxo or Y$^1$;

E$^1$ represents
a direct bond,
—C(O)—
—[C(O)]$_p$—C$_{1-8}$ alkylene,
—C(O)NR$^{7a}$—CH$_2$—[C$_{1-7}$ alkylene]-,
-Q$^1$-CH$_2$—[C$_{1-5}$ alkylene]-,
the alkylene parts of which latter four groups are optionally substituted by one or more substituents selected from the group consisting of halo, C$_{1-3}$ alkyl and hydroxy;

E$^2$ represents
a direct bond,
—O—,
—NH—
C$_{1-6}$ alkylene or
-Q$^2$-CH$_2$—[C$_{1-5}$ alkylene]-,
the alkylene parts of which latter two groups are optionally substituted by one or more substituents selected from the group consisting of halo, C$_{1-3}$ alkyl and hydroxy;

E$^3$ represents —O— or S(O)$_{0-2}$;

Q$^1$ and Q$^2$ independently represent O or S(O)$_{0-2}$;

p represents 0 or 1;

R$^{6a}$ represents C$_{1-8}$ alkyl, wherein one or two non-adjacent C-atoms of the alkyl group, that are not linked directly to E, are optionally replaced by heteroatoms independently selected from the group consisting of O and N and/or wherein the alkyl group is substituted by one or more R$^8$ substituents;

R$^{6b}$ represents C$_{1-8}$ alkyl, wherein one C-atom of the alkyl group is, or two non-adjacent C-atoms of the alkyl group are, optionally replaced by heteroatoms independently selected from the group consisting of O and N and/or wherein the alkyl group is substituted by one or more R$^8$ substituents;

R$^{6c}$ and R$^{6d}$ independently represent C$_{1-3}$ alkyl or C$_{1-3}$ alkoxy, or R$^{6c}$ and R$^{6d}$ together combine to form C$_{4-6}$ alkylene;

R$^{6e}$ and R$^{6f}$ independently represent H or C$_{1-8}$ alkyl, which latter group is optionally substituted by R$^{7b}$ and/or one or more substituents selected from the group consisting of halo and hydroxy or R$^{6e}$ and R$^{6f}$, together with the N-atom to which they are attached, form a 4- to 7-membered heterocyclic group that is fully saturated, partially unsaturated or fully aromatic and which heterocyclic group contains one N atom (the atom to which R$^{6e}$ and R$^{6f}$ are attached) and, optionally, one or more further heteroatoms selected from the group consisting of O, S and N, and which heterocyclic group is optionally substituted by one or more substituents selected from the group consisting of halo, hydroxy, oxo, C$_{1-4}$ alkyl and C$_{1-4}$ alkoxy;

R$^{6g}$ represents C$_{1-6}$ alkyl, C$_{3-6}$ cycloalkyl or phenyl, which latter three groups are optionally substituted by one or more substituents selected from the group consisting of halo, hydroxy, C$_{1-3}$ alkyl, C$_{1-3}$ alkoxy and C$_{3-6}$ cycloalkyl;

R$^{6h}$, R$^{6i}$, R$^{6j}$ and R$^{6k}$ independently represent C$_{1-4}$ alkyl optionally substituted by one or more halo atoms, or R$^{6h}$ and R$^{6i}$ independently represent H;

R$^{7a}$ represents H or C$_{1-3}$ alkyl optionally substituted by one or more halo atoms;

R$^{7b}$ represents C$_{1-4}$ alkoxy, S—C$_{1-4}$ alkyl, phenyl or Het$^4$, which latter two groups are optionally substituted by one or more substituents selected from the group consisting of halo, C$_{1-4}$ alkyl, C$_{1-4}$ haloalkyl, C$_{1-4}$ alkoxy, hydroxy, amino and cyano;

R$^8$ represents, independently on each occurrence, halo, hydroxy, C$_{1-4}$ alkoxy, oxo, C$_{3-8}$ cycloalkyl, Het$^3$ or phenyl, which latter three groups are optionally substituted by one or more substituents selected from the group consisting of halo, C$_{1-4}$ alkyl, C$_{1-4}$ haloalkyl, C$_{1-4}$ alkoxy, hydroxy, amino and cyano;

Het$^2$ represents a 5- to 10-membered heteroaromatic group, which group is monocyclic or bicyclic and contains at least one carbocyclic or heterocyclic ring that is fully aromatic, and which group contains one or more heteroatoms selected from the group consisting of N, O and S;

Het$^3$ and Het$^4$ independently represent 4- to 10-membered heterocyclic groups that are fully saturated, partially unsaturated or fully aromatic, which heterocyclic groups contain one or more heteroatoms selected from the group consisting of N, O and S; and Het$^a$ represents a 5- or 6-membered heterocyclic group that is fully saturated, partially unsaturated or fully aromatic, which group contains one or more heteroatoms selected from the group consisting of N, O and S, and which group is optionally substituted by one or more substituents selected from the group consisting of halo, hydroxy, C$_{1-3}$ alkyl, C$_{1-3}$ alkoxy and C$_{3-6}$ cycloalkyl;

or a pharmaceutically acceptable salt, solvate or isotopic derivative thereof.

2. A compound as claimed in claim 1 which is a compound of formula Ia,

Ia

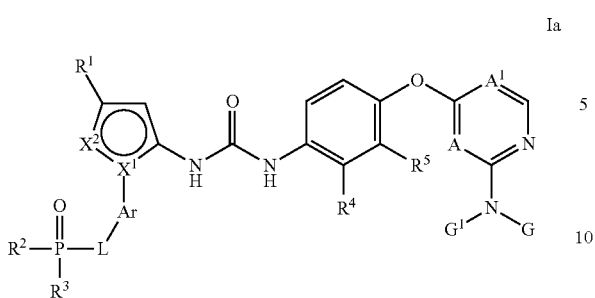

wherein R¹ to R⁵, X¹, X², Ar, L, A, A¹, E and G are as defined in claim 1,
or a pharmaceutically acceptable salt, solvate or isotopic derivative thereof.

3. A compound as claimed in claim 1 which is a compound of formula Ib,

Ib

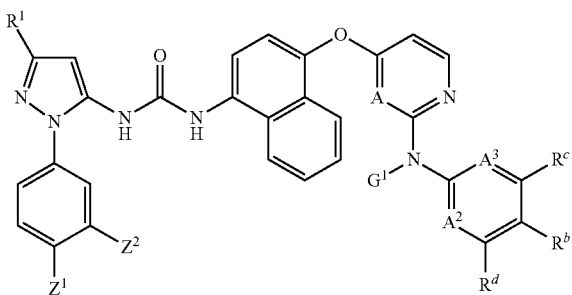

wherein
one of Z¹ and Z² represents the structural fragment

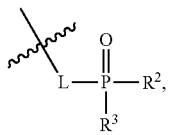

and the other of Z¹ and Z² represents H;
R¹ represents $C_{1-4}$ alkyl or $Si(CH_3)_3$;
R² and R³ independently represent $C_{1-2}$ alkyl or $C_{1-2}$ alkoxy;
or R² and R³ together combine to form $C_{3-6}$ alkylene;
L is a direct bond or, particularly, —$CH_2$—;
A represents CH or N;
G¹ represents H or methyl;
A² and A³ both represent $C(R^a)$, or one of A² and A³ represents N and the other represents $C(R^a)$;
$R^a$, $R^b$, $R^c$ and $R^d$ independently represent H, halo, hydroxy, cyano, $P(O)R^{6c}R^{6d}$, $SF_5$, —C≡CH, —O—$CH_2CH_2$—$N(R^{6e})R^{6f}$, —C(O)$NHC_{1-2}$ alkyl, —C(O)$NHCH_2CH_2$—$N(R^{6e})R^{6f}$, —$S(O)_2R^{6g}$, —O—$[CH_2CH_2O]_{2-7}$—$CH_3$, —S—$C_{1-4}$ alkyl, —S—$C_{2-4}$ hydroxyalkyl, $C_{1-4}$ hydroxyalkyl, $C_{1-4}$ alkyl or $C_{1-4}$ alkoxy, which latter two groups are optionally substituted by one or more halo atoms;
or $R^b$ and $R^c$, together with the C-atoms to which they are attached, form a fused, 5- or 6-membered aromatic, heteroaromatic or heterocyclic ring, which ring:

(i) when heteroaromatic or heterocyclic contains one to three heteroatoms selected from the group consisting of N, O and S; and
(ii) is optionally substituted by one or more substituents selected from the group consisting of H, halo, hydroxy, oxo, amino, $C_{1-2}$ alkyl and $C_{1-2}$ alkoxy, which latter two groups are optionally substituted by one or more halo atoms;

$R^{6c}$ and $R^{6d}$ both represent methyl;
$R^{6e}$ and $R^{6f}$ both represent $C_{1-2}$ alkyl or, together with the N-atom to which they are attached, form a 5- or 6-membered heterocyclic group that is fully saturated and which heterocyclic group contains one N atom (the atom to which $R^{6e}$ and $R^{6f}$ are attached) and, optionally, one further heteroatom selected from the group consisting of O, S and N, and which heterocyclic group is optionally substituted by one or more substituents selected from the group consisting of halo, hydroxy, oxo, $C_{1-4}$ alkyl and $C_{1-4}$ alkoxy; and $R^{6g}$ represents $C_{1-2}$ alkyl or cyclopropyl, which latter two groups are optionally substituted by one or more halo atoms, or a pharmaceutically acceptable salt, solvate or isotopic derivative thereof.

4. A compound as claimed in claim 3, which is a compound of formula Ic,

Ic

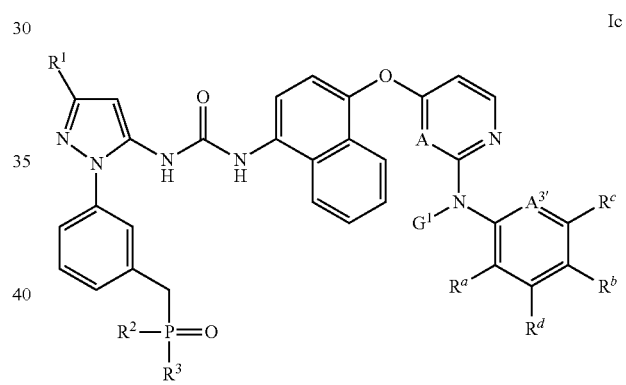

or a pharmaceutically acceptable salt, solvate or isotopic derivative thereof,
wherein R¹ to R³, A, G¹ and $R^a$ to $R^d$ are as defined in claim 3 and $A^{3'}$ represents CH or N.

5. A compound as claimed in claim 3, which is a compound of formula Id, Ie or If Id

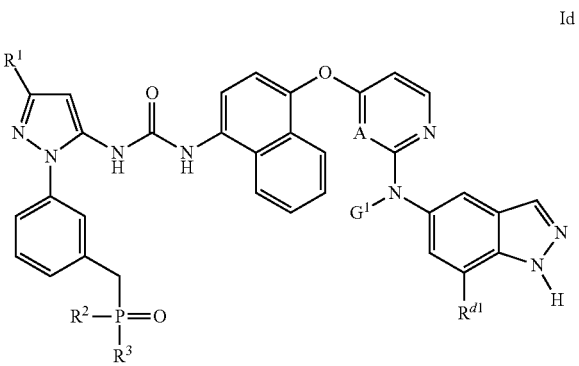

133
-continued

Ie

[Structure Ie: pyrazole-urea-naphthalene-oxy-pyrimidine scaffold with R¹, R², R³, A, G¹, Rᵃ², R^{b2}, R^{c2}, R^{d2}, A³']

If

[Structure If: similar scaffold with oxoindoline group]

or a pharmaceutically acceptable salt, solvate or isotopic derivative thereof,
wherein:
$R^1$ to $R^3$, A and $G^1$ are as defined in claim 3;
$R^{d1}$ as defined above for $R^d$ in claim 3;
$R^{a2}$ are as defined above for $R^a$ to $R^d$, respectively, in claim 3; and
$A^{3'}$ represents CH or N.

6. A compound as claimed in claim 1, wherein $R^1$ represents $C_{3-4}$ alkyl.

7. A compound as claimed in claim 1, wherein $R^2$ and $R^3$ independently represent $C_{1-2}$ alkyl, or together form $C_4$ alkylene.

8. A compound as claimed in claim 1, wherein $G^1$ represents H.

9. A compound as claimed in claim 5, wherein:
(i) $R^{a2}$, $R^{b2}$, $R^{c2}$ and $R^{d2}$ are all H;
(ii) one of $R^{c2}$ and $R^{d2}$ is —O—CH$_2$CH$_2$—N($R^{6e}$)$R^{6f}$, —C(O)NHCH$_2$CH$_2$—N($R^{6e}$)$R^{6f}$ or —O—[CH$_2$CH$_2$O]$_{2-7}$—CH$_3$, and the other three of $R^{a2}$, $R^{b2}$, $R^{c2}$ and $R^{d2}$ are H; or
(iii) one of $R^{c2}$ and $R^{d2}$ is —C≡CH, —CH$_3$ cyano, —CF$_3$, —OCH$_3$ or —OCF$_3$, the other of $R^{c2}$ and $R^{d2}$ is —C(O)NHCH$_2$CH$_2$—N($R^{6e}$)$R^{6f}$, —O—CH$_2$CH$_2$—N($R^{6e}$)$R^{6f}$, —S(O)$_2$$R^{6g}$ or —O—[CH$_2$CH$_2$O]$_{2-7}$—CH$_3$, and $R^{a2}$ and $R^{b2}$ are both H.

10. A compound as claimed in claim 3, wherein $R^b$ is P(O)$R^{6c}R^{6d}$, SF$_5$ or —S—CH$_2$CH$_2$—OH, and $R^a$, $R^c$ and $R^d$ are all H.

11. A compound as claimed in claim 5, wherein $R^{d1}$ is H or methyl.

12. A compound as claimed in claim 1, wherein $R^{6c}$ and $R^{6d}$ are both methyl.

13. A compound as claimed in claim 1, wherein N($R^{6e}$)$R^{6f}$ represents morpholin-4-yl.

14. A compound as claimed in claim 1, which compound is selected from the group consisting of:

1-(3-(tert-Butyl)-1-(4-(dimethylphosphoryl)phenyl)-1H-pyrazol-5-yl)-3-(4-((2-(phenylamino) pyrimidin-4-yl)oxy)naphthalen-1-yl)urea;
1-(3-(tert-Butyl)-1-(3-(dimethylphosphoryl)phenyl)-1H-pyrazol-5-yl)-3-(4-((2-(phenylamino)pyrimidin-4-yl)oxy)naphthalen-1-yl)urea;
N-(4-((4-(3-(3-(tert-Butyl)-1-(4-(dimethylphosphoryl)phenyl)-1H-pyrazol-5-yl)ureido)naphthalen-1-yl)oxy)pyridin-2-yl)-2-methoxyacetamide;
1-(1-(4-(Dimethylphosphoryl)phenyl)-3-isopropyl-1H-pyrazol-5-yl)-3-(4-((2-(phenylamino) pyrimidin-4-yl)oxy)naphthalen-1-yl)urea;
1-(1-(4-(Dimethylphosphoryl)phenyl)-3-(trimethylsilyl)-1H-pyrazol-5-yl)-3-(4-((2-(phenylamino) pyrimidin-4-yl)oxy)naphthalen-1-yl)urea;
1-(3-(tert-Butyl)-1-(4-((dimethylphosphoryl)methyl)phenyl)-1H-pyrazol-5-yl)-3-(4-((2-(phenylamino)pyrimidin-4-yl)oxy)naphthalen-1-yl)urea;
1-(4-((2-((1H-Indazol-5-yl)amino)pyrimidin-4-yl)oxy)naphthalen-1-yl)-3-(3-(tert-butyl)-1-(4-(dimethylphosphoryl)phenyl)-1H-pyrazol-5-yl)urea;
1-(3-(tert-Butyl)-1-(4-(1-oxidophospholan-1-yl)phenyl)-1H-pyrazol-5-yl)-3-(4-((2-(phenylamino)pyrimidin-4-yl)oxy)naphthalen-1-yl)urea;
Ethyl (4-(3-(tert-butyl)-5-(3-(4-((2-(phenylamino)pyrimidin-4-yl)oxy)naphthalen-1-yl)ureido)-1H-pyrazol-1-yl)phenyl)(methyl)phosphinate;
1-(4-((2-((1H-Indazol-5-yl)amino)pyrimidin-4-yl)oxy)naphthalen-1-yl)-3-(3-(tert-butyl)-1-(3-(dimethylphosphoryl)phenyl)-1H-pyrazol-5-yl)urea;
1-(3-(tert-Butyl)-1-(3-(dimethylphosphoryl)phenyl)-1H-pyrazol-5-yl)-3-(4-((2-((2-oxoindolin-6-yl)amino)pyrimidin-4-yl)oxy)naphthalen-1-yl)urea;
1-(4-((2-((3-Aminobenzo[d]isoxazol-5-yl)amino)pyrimidin-4-yl)oxy)naphthalen-1-yl)-3-(3-(tert-butyl)-1-(3-(dimethylphosphoryl)phenyl)-1H-pyrazol-5-yl)urea;
1-(3-(tert-Butyl)-1-(3-(dimethylphosphoryl)phenyl)-1H-pyrazol-5-yl)-3-(4-((2-((7-methyl-1H-indazol-5-yl)amino)pyrimidin-4-yl)oxy)naphthalen-1-yl)urea;
1-(3-(tert-Butyl)-1-(4-(dimethylphosphoryl)phenyl)-1H-pyrazol-5-yl)-3-(4-((2-((2-oxoindolin-6-yl)amino)pyrimidin-4-yl)oxy)naphthalen-1-yl)urea;
1-(3-(tert-Butyl)-1-(4-(dimethylphosphoryl)phenyl)-1H-pyrazol-5-yl)-3-(4-((2-(methyl(phenyl) amino)pyrimidin-4-yl)oxy)naphthalen-1-yl)urea;
3-((4-((4-(3-(3-(tert-Butyl)-1-(3-(dimethylphosphoryl)phenyl)-1H-pyrazol-5-yl)ureido)naphthalen-1-yl)oxy)pyrimidin-2-yl)amino)-N-(2-morpholinoethyl)benzamide;
1-(3-(tert-Butyl)-1-(4-(dimethylphosphoryl)phenyl)-1H-pyrazol-5-yl)-3-(4-((2-((3-(2-morpholinoethoxy)phenyl)amino)pyrimidin-4-yl)oxy)naphthalen-1-yl)urea;
1-(3-(tert-Butyl)-1-(4-(dimethylphosphoryl)phenyl)-1H-pyrazol-5-yl)-3-(4-((2-((4-((2-hydroxyethyl)thio)phenyl)amino)pyrimidin-4-yl)oxy)naphthalen-1-yl)urea;
(4-(3-(tert-Butyl)-5-(3-(4-((2-(phenylamino)pyrimidin-4-yl)oxy)naphthalen-1-yl)ureido)-1H-pyrazol-1-yl)phenyl)(methyl)phosphinic acid;
1-(4-((2-((3-Aminobenzo[d]isoxazol-5-yl)amino)pyrimidin-4-yl)oxy)naphthalen-1-yl)-3-(3-(tert-butyl)-1-(4-(dimethylphosphoryl)phenyl)-1H-pyrazol-5-yl)urea;
1-(3-(tert-Butyl)-1-(4-(dimethylphosphoryl)phenyl)-1H-pyrazol-5-yl)-3-(4-((2-((7-methyl-1H-indazol-5-yl)amino)pyrimidin-4-yl)oxy)naphthalen-1-yl)urea;
1-(3-(tert-Butyl)-1-(4-(diethylphosphoryl)phenyl)-1H-pyrazol-5-yl)-3-(4-((2-(phenylamino) pyrimidin-4-yl)oxy)naphthalen-1-yl)urea;

1-(3-(tert-Butyl)-1-(3-((dimethylphosphoryl)methyl)phenyl)-1H-pyrazol-5-yl)-3-(4-((2-(phenylamino)pyrimidin-4-yl)oxy)naphthalen-1-yl)urea;
3-((4-((4-(3-(3-(tert-Butyl)-1-(4-(dimethylphosphoryl)phenyl)-1H-pyrazol-5-yl)ureido)naphthalen-1-yl)oxy)pyrimidin-2-yl)amino)-N-(2-morpholinoethyl)benzamide;
1-(3-(tert-Butyl)-1-(4-(dimethylphosphoryl)phenyl)-1H-pyrazol-5-yl)-3-(4-((2-((4-(dimethylphosphoryl)phenyl)amino)pyrimidin-4-yl)oxy)naphthalen-1-yl)urea;
(S)-1-(3-(tert-Butyl)-1-(4-(dimethylphosphoryl)phenyl)-1H-pyrazol-5-yl)-3-(4-((2-(2-(hydroxymethyl)pyrrolidin-1-yl)pyrimidin-4-yl)oxy)naphthalen-1-yl)urea;
(R)-1-(3-(tert-Butyl)-1-(4-(dimethylphosphoryl)phenyl)-1H-pyrazol-5-yl)-3-(4-((2-(2-(hydroxymethyl)pyrrolidin-1-yl)pyrimidin-4-yl)oxy)naphthalen-1-yl)urea;
1-(3-(tert-Butyl)-1-(4-(dimethylphosphoryl)phenyl)-1H-pyrazol-5-yl)-3-(4-((2-((4-(pentafluorothio)phenyl)amino)pyrimidin-4-yl)oxy)naphthalen-1-yl)urea;
1-(3-(tert-Butyl)-1-(4-(dimethylphosphoryl)phenyl)-1H-pyrazol-5-yl)-3-(4-((2-(phenylthio)pyrimidin-4-yl)oxy)naphthalen-1-yl)urea;
1-(3-(tert-Butyl)-1-(4-(dimethylphosphoryl)phenyl)-1H-pyrazol-5-yl)-3-(4-((2-((3-hydroxypropyl)(methyl)amino)pyrimidin-4-yl)oxy)naphthalen-1-yl)urea;
1-(3-(tert-Butyl)-1-(4-(dimethylphosphoryl)phenyl)-1H-pyrazol-5-yl)-3-(4-((2-((3-hydroxypropyl)amino)pyrimidin-4-yl)oxy)naphthalen-1-yl)urea;
1-(3-(tert-Butyl)-1-(3-((dimethylphosphoryl)methyl)phenyl)-1H-pyrazol-5-yl)-3-(4-((2-((7-methyl-1H-indazol-5-yl)amino)pyrimidin-4-yl)oxy)naphthalen-1-yl)urea;
1-(3-(tert-Butyl)-1-(3-((dimethylphosphoryl)methyl)phenyl)-1H-pyrazol-5-yl)-3-(4-((2-((2-oxoindolin-6-yl)amino)pyrimidin-4-yl)oxy)naphthalen-1-yl)urea;
1-(3-(tert-Butyl)-1-(3-((dimethylphosphoryl)methyl)phenyl)-1H-pyrazol-5-yl)-3-(4-((2-((3-(2-morpholinoethoxy)phenyl)amino)pyrimidin-4-yl)oxy)naphthalen-1-yl)urea;
1-(1-(3-((Dimethylphosphoryl)methyl)phenyl)-3-(trimethylsilyl)-1H-pyrazol-5-yl)-3-(4-((2-(phenylamino)pyrimidin-4-yl)oxy)naphthalen-1-yl)urea;
1-(3-(tert-Butyl)-1-(3-((diethylphosphoryl)methyl)phenyl)-1H-pyrazol-5-yl)-3-(4-((2-((7-methyl-1H-indazol-5-yl)amino)pyrimidin-4-yl)oxy)naphthalen-1-yl)urea;
1-(1-(3-((Dimethylphosphoryl)methyl)phenyl)-3-isopropyl-1H-pyrazol-5-yl)-3-(4-((2-((7-methyl-1H-indazol-5-yl)amino)pyrimidin-4-yl)oxy)naphthalen-1-yl)urea;
3-((4-((4-(3-(1-(3-((Dimethylphosphoryl)methyl)phenyl)-3-isopropyl-1H-pyrazol-5-yl)ureido)naphthalen-1-yl)oxy)pyrimidin-2-yl)amino)-5-methoxy-N-(2-morpholino ethyl)benzamide;
1-(1-(3-((Dimethylphosphoryl)methyl)phenyl)-3-isopropyl-1H-pyrazol-5-yl)-3-(4-((2-((3-methoxy-5-(2-morpholinoethoxy)phenyl)amino)pyrimidin-4-yl)oxy)naphthalen-1-yl)urea;
1-(1-(3-((dimethylphosphoryl)methyl)phenyl)-3-isopropyl-1H-pyrazol-5-yl)-3-(4-((2-((2-methoxyphenyl)amino)pyrimidin-4-yl)oxy)naphthalen-1-yl)urea;
1-(3-(tert-butyl)-1-(3-((dimethylphosphoryl)methyl)phenyl)-1H-pyrazol-5-yl)-3-(4-((2-(phenylamino)pyridin-4-yl)oxy)naphthalen-1-yl)urea;
1-(1-(3-((dimethylphosphoryl)methyl)phenyl)-3-isopropyl-1H-pyrazol-5-yl)-3-(4-((2-(phenylamino)pyridin-4-yl)oxy)naphthalen-1-yl)urea;
3-((4-((4-(3-(1-(3-((Dimethylphosphoryl)methyl)phenyl)-3-isopropyl-1H-pyrazol-5-yl)ureido)naphthalen-1-yl)oxy)pyrimidin-2-yl)amino)-5-ethynyl-N-(2-morpholinoethyl) benzamide;
1-(3-(tert-Butyl)-1-(3-((1-oxidophospholan-1-yl)methyl)phenyl)-1H-pyrazol-5-yl)-3-(4-((2-(phenylamino)pyridin-4-yl)oxy)naphthalen-1-yl)urea;
1-(1-(3-((Dimethylphosphoryl)methyl)phenyl)-3-isopropyl-1H-pyrazol-5-yl)-3-(4-((2-((3-methoxy-5-(2-(2-(2-methoxyethoxy)ethoxy)ethoxy)phenyl)amino)pyrimidin-4-yl)oxy)naphthalen-1-yl)urea; 1-(4-((2-((3-(Cyclopropylsulfonyl)-5-methoxyphenyl)amino)pyrimidin-4-yl)oxy)naphthalen-1-yl)-3-(1-(3-((dimethylphosphoryl)methyl)phenyl)-3-isopropyl-1H-pyrazol-5-yl)urea;
3-((4-((4-(3-(3-(tert-butyl)-1-(3-((dimethylphosphoryl)methyl)phenyl)-1H-pyrazol-5-yl)ureido)naphthalen-1-yl)oxy)pyrimidin-2-yl)amino)-5-methoxy-N-(2-morpholinoethyl)-benzamide;
1-(1-(3-((dimethylphosphoryl)methyl)phenyl)-3-isopropyl-1H-pyrazol-5-yl)-3-(4-((2-((3-(2-morpholinoethoxy)-5-(trifluoromethoxy)phenyl)amino)pyrimidin-4-yl)oxy)naphthalen-1-yl)urea;
1-(1-(3-((dimethylphosphoryl)methyl)phenyl)-3-isopropyl-1H-pyrazol-5-yl)-3-(4-((2-((3-(2-morpholinoethoxy)-5-(trifluoromethyl)phenyl)amino)pyrimidin-4-yl)oxy)naphthalen-1-yl)urea;
3-((4-((4-(3-(1-(3-((dimethylphosphoryl)methyl)phenyl)-3-isopropyl-1H-pyrazol-5-yl)ureido)naphthalen-1-yl)oxy)pyridin-2-yl)amino)-5-methoxy-N-(2-morpholinoethyl)-benzamide;
1-(1-(3-((dimethylphosphoryl)methyl)phenyl)-3-isopropyl-1H-pyrazol-5-yl)-3-(4-((2-((3-methoxy-5-(2-morpholinoethoxy)phenyl)amino)pyridin-4-yl)oxy)naphthalen-1-yl)urea;
1-(4-((2-((3-(2,5,8,11-tetraoxatridecan-13-yloxy)-5-methoxyphenyl)amino)pyrimidin-4-yl)oxy)naphthalen-1-yl)-3-(1-(3-((dimethylphosphoryl)methyl)phenyl)-3-isopropyl-1H-pyrazol-5-yl)urea;
1-(1-(3-((dimethylphosphoryl)methyl)phenyl)-3-isopropyl-1H-pyrazol-5-yl)-3-(4-((2-((3-(methylsulfonyl)-5-(2-morpholinoethoxy)phenyl)amino)pyrimidin-4-yl)oxy)naphthalen-1-yl)urea;
1-(1-(3-((dimethylphosphoryl)methyl)phenyl)-3-isopropyl-1H-pyrazol-5-yl)-3-(5-((2-((3-methoxy-5-(2-morpholinoethoxy)phenyl)amino)pyrimidin-4-yl)oxy)quinolin-8-yl)urea;
1-(4-((2-((3-(2,5,8,11,14-pentaoxahexadecan-16-yloxy)-5-methoxyphenyl)amino)-pyrimidin-4-yl)oxy)naphthalen-1-yl)-3-(1-(3-((dimethylphosphoryl)methyl)phenyl)-3-isopropyl-1H-pyrazol-5-yl)urea;
1-(1-(3-((dimethylphosphoryl)methyl)phenyl)-3-isopropyl-1H-pyrazol-5-yl)-3-(4-((2-((3-ethynyl-5-(2-morpholinoethoxy)phenyl)amino)pyrimidin-4-yl)oxy)naphthalen-1-yl)urea;
1-(4-((2-((3-cyano-5-(2-morpholinoethoxy)phenyl)amino)pyrimidin-4-yl)oxy)naphthalen-1-yl)-3-(1-(3-((dimethylphosphoryl)methyl)phenyl)-3-isopropyl-1H-pyrazol-5-yl)urea;
3-((4-((4-(3-(3-(tert-butyl)-1-(3-((dimethylphosphoryl)methyl)phenyl)-1H-pyrazol-5-yl)-ureido)naphthalen-1-yl)oxy)pyrimidin-2-yl)amino)-N-(2-morpholinoethyl)-5-(trifluoromethyl)benzamide;
3-((4-((4-(3-(3-(tert-butyl)-1-(3-((dimethylphosphoryl)methyl)phenyl)-1H-pyrazol-5-yl)-ureido)naphthalen-1-yl)oxy)pyrimidin-2-yl)amino)-N-(2-morpholinoethyl)-5-(trifluoromethoxy)benzamide;

1-(3-(tert-butyl)-1-(3-((dimethylphosphoryl)methyl)phenyl)-1H-pyrazol-5-yl)-3-(4-((2-((3-methoxy-5-(2-(2-methoxyethoxy)ethoxy)ethoxy)phenyl)amino)pyrimidin-4-yl)oxy)-naphthalen-1-yl)urea; and 1-(3-(tert-Butyl)-1-(3-((dimethylphosphoryl)methyl)phenyl)-1H-pyrazol-5-yl)-3-(4-((2-((3-(2-morpholinoethoxy)-5-(trifluoromethyl)phenyl)amino)pyrimidin-4-yl)oxy)naphthalen-1-yl)urea, or a pharmaceutically acceptable salt, solvate or isotopic derivative thereof.

15. A compound as claimed in claim 1, which compound is 1-(3-(tert-butyl)-1-(3-((dimethylphosphoryl)methyl)phenyl)-1H-pyrazol-5-yl)-3-(4-((2-((3-methoxy-5-(2-(2-methoxyethoxy)ethoxy)ethoxy)phenyl)amino)pyrimidin-4-yl)oxy)-naphthalen-1-yl)urea or a pharmaceutically acceptable salt, solvate or isotopic derivative thereof.

16. A pharmaceutical formulation comprising a compound as defined in claim 1, or pharmaceutically acceptable salt, solvate or isotopic derivative thereof, in admixture with a pharmaceutically acceptable adjuvant, diluent or carrier.

17. A combination product comprising
(A) a compound as defined in claim 1, or pharmaceutically acceptable salt, solvate or isotopic derivative thereof, and
(B) another therapeutic agent,
wherein each of components (A) and (B) is formulated in admixture with a pharmaceutically-acceptable adjuvant, diluent or carrier.

18. A method of treating inflammation, said method comprising administering to a subject an effective amount of a compound as defined in claim 1, or a pharmaceutically acceptable salt, solvate or isotopic derivative thereof, wherein the inflammation is a component in a disease is selected from the group consisting of cystic fibrosis, pulmonary hypertension, lung sarcoidosis, idiopathic pulmonary fibrosis, Chronic Obstructive Pulmonary Disease (COPD), chronic bronchitis, emphysema, asthma, paediatric asthma, atopic dermatitis, allergic dermatitis, contact dermatitis or psoriasis, allergic rhinitis, rhinitis, sinusitis, conjunctivitis, allergic conjunctivitis, keratoconjunctivitis sicca (dry eye), glaucoma, diabetic retinopathy, macular oedema, diabetic macular oedema, central retinal vein occlusion (CRVO), dry and/or wet age related macular degeneration (AMD), post-operative cataract inflammation, uveitis, posterior uveitis, anterior uveitis, pan uveitis, corneal graft and limbal cell transplant rejection, gluten sensitive enteropathy (coeliac disease), eosinophilic esophagitis, intestinal graft versus host disease, Crohn's disease and ulcerative colitis.

19. The method according to claim 18, wherein the disease is asthma or COPD.

20. The method according to claim 18, wherein the disease is uveitis, Crohn's disease or ulcerative colitis.

21. A process for the preparation of a compound of formula I according to claim 1, which process comprises:
(a) reaction of a compound of formula II,

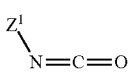

with a compound of formula III,

wherein one of $Z^1$ and $Z^2$ is a structural fragment of formula IV

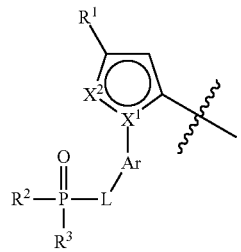

and the other of $Z^1$ and $Z^2$ is a structural fragment of formula V

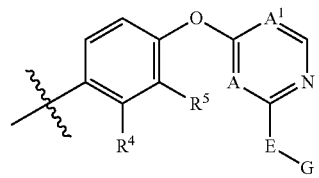

where E, L, Ar, $X^1$, $X^2$, $R^1$ to $R^5$, A, $A^1$, G and $G^1$ are as defined in claim 1;

(b) reaction of a compound of formula IIa,

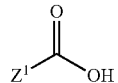

wherein $Z^1$ is as defined above, with a suitable azide-forming agent in the presence of an amine base and an organic solvent,
which reaction is followed, without isolation, by thermal rearrangement of the intermediate acyl azide (of formula $Z^1$—C(O)—$N_3$) to provide, in situ, a compound of formula II, which compound is then reacted with a compound of formula III as defined above;

(c) reaction of a compound of formula IIb,

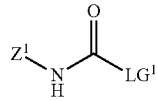

wherein $LG^1$ represents a suitable leaving group and $Z^1$ is as defined above, with a compound of formula III, as defined above;

(d) reaction of a compound of formula VI,

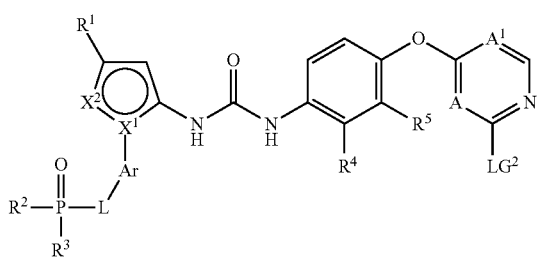

wherein $LG^2$ represents a suitable leaving group and L, Ar, $X^1$, $X^2$, $R^1$ to $R^5$, A and $A^1$ are as defined in claim 1 with a compound of formula VII,

wherein G and E are as defined in claim 1, or (e) deprotection of an protected derivative of a compound of formula I, wherein the protected derivative bears a protecting group on an O- or N-atom of the compound of formula I.

22. A method of treating inflammation, said method comprising administering to a subject an effective amount of a pharmaceutical formulation as defined in claim 16, wherein the inflammation is a component in a disease is selected from the group consisting of cystic fibrosis, pulmonary hypertension, lung sarcoidosis, idiopathic pulmonary fibrosis, Chronic Obstructive Pulmonary Disease (COPD), chronic bronchitis, emphysema, asthma, paediatric asthma, atopic dermatitis, allergic dermatitis, contact dermatitis or psoriasis, allergic rhinitis, rhinitis, sinusitis, conjunctivitis, allergic conjunctivitis, keratoconjunctivitis sicca (dry eye), glaucoma, diabetic retinopathy, macular oedema, diabetic macular oedema, central retinal vein occlusion (CRVO), dry and/or wet age related macular degeneration (AMD), post-operative cataract inflammation, uveitis, posterior uveitis, anterior uveitis, pan uveitis, corneal graft and limbal cell transplant rejection, gluten sensitive enteropathy (coeliac disease), eosinophilic esophagitis, intestinal graft versus host disease, Crohn's disease and ulcerative colitis.

23. A method of treating inflammation, said method comprising administering to a subject an effective amount of a combination product as defined claim 17, wherein the inflammation is a component in a disease is selected from the group consisting of cystic fibrosis, pulmonary hypertension, lung sarcoidosis, idiopathic pulmonary fibrosis, Chronic Obstructive Pulmonary Disease (COPD), chronic bronchitis, emphysema, asthma, paediatric asthma, atopic dermatitis, allergic dermatitis, contact dermatitis or psoriasis, allergic rhinitis, rhinitis, sinusitis, conjunctivitis, allergic conjunctivitis, keratoconjunctivitis sicca (dry eye), glaucoma, diabetic retinopathy, macular oedema, diabetic macular oedema, central retinal vein occlusion (CRVO), dry and/or wet age related macular degeneration (AMD), post-operative cataract inflammation, uveitis, posterior uveitis, anterior uveitis, pan uveitis, corneal graft and limbal cell transplant rejection, gluten sensitive enteropathy (coeliac disease), eosinophilic esophagitis, intestinal graft versus host disease, Crohn's disease and ulcerative colitis.

* * * * *